(12) United States Patent
Kim et al.

(10) Patent No.: US 10,011,608 B2
(45) Date of Patent: Jul. 3, 2018

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si, Chungcheongnam-do (KR)

(72) Inventors: Wonsam Kim, Hwaseong-si (KR); Yuri Kim, Wonju-si (KR); Seunghoon Hahn, Cheonan-si (KR); HyunJu Song, Seoul (KR); Junghwan Park, Hwaseong-si (KR); Sunhee Lee, Cheonan-si (KR); Jungwook Lee, Gunsan-si (KR)

(73) Assignee: DUK SAN NEOLUX CO., LTD., Cheonan-si, Chungcheon (KR)

( * ) Notice: Subject to any disclaimer, the term of this patent is extended or adjusted under 35 U.S.C. 154(b) by 0 days.

(21) Appl. No.: 15/327,440

(22) PCT Filed: Jul. 17, 2015

(86) PCT No.: PCT/KR2015/007475
§ 371 (c)(1),
(2) Date: Jan. 19, 2017

(87) PCT Pub. No.: WO2016/013817
PCT Pub. Date: Jan. 28, 2016

(65) Prior Publication Data
US 2017/0166581 A1    Jun. 15, 2017

(30) Foreign Application Priority Data
Jul. 21, 2014 (KR) ........................ 10-2014-0091615

(51) Int. Cl.
*C07D 405/04*    (2006.01)
*C07D 495/04*    (2006.01)
*C07D 493/04*    (2006.01)
*H01L 51/50*    (2006.01)
*H01L 51/00*    (2006.01)

(52) U.S. Cl.
CPC ......... *C07D 495/04* (2013.01); *C07D 493/04* (2013.01); *H01L 51/50* (2013.01); *H01L 51/0003* (2013.01); *H01L 51/0005* (2013.01)

(58) Field of Classification Search
CPC .................................................. C07D 495/04
USPC ........................................................ 549/50
See application file for complete search history.

(56) References Cited

U.S. PATENT DOCUMENTS 9,331,288 B2 *    5/2016    Park ..................... C07D 491/04
9,570,689 B2 *    2/2017    Park .................... H01L 51/0071

FOREIGN PATENT DOCUMENTS

| CN | 103467447 A | 12/2013 |
| KR | 10-1144358 B1 | 5/2012 |
| KR | 10-2013-0127563 A | 11/2013 |
| KR | 10-2014-0034711 A | 3/2014 |
| KR | 10-2014-0049530 A | 4/2014 |

OTHER PUBLICATIONS

Dorwald F. A. Side Reactions in Organic Synthesis, 2005, Wiley: VCH, Weinheim p. IX of Preface p. 1-15.*

* cited by examiner

*Primary Examiner* — Nizal S Chandrakumar
(74) *Attorney, Agent, or Firm* — Vorys, Sater, Seymour & Pease LLP; Mih Suhn Koh

(57) ABSTRACT

Provided are a compound of Formula 1 and an organic electric element including a first electrode, a second electrode, and an organic material layer between the first electrode and the second electrode and comprising the compound, the element showing decreased driving voltage, improved luminescent efficiency, stability, and life span.

11 Claims, 1 Drawing Sheet

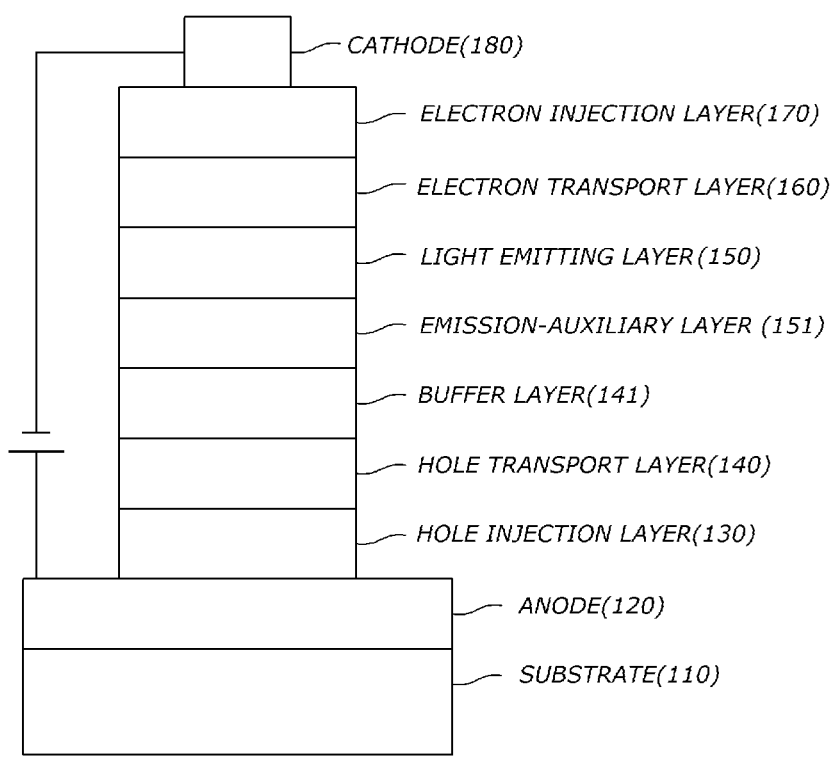

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This patent application claims benefit under 35 U.S.C. 119, 120, 121, or 365, and is a National Stage entry from International Application No. PCT/KR2015/007475, filed Jul. 17, 2015, which claims priority to Korean Patent Application No. 10-2014-0091615 filed on Jul. 21, 2014, the contents of which are hereby incorporated by reference for all purposes as if fully set forth herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. Here, in many cases, the organic material layer may have a multi-layered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more and more as size of display becomes larger and larger in the portable display market. Therefore, the power consumption is a very important factor in the portable display with a limited power source of the battery, and efficiency and life span issue also be solved. The most problematic issues in an organic electric element are life span and efficiency, and the situation is such that this life span or efficiency issue must be solved as displays become larger and larger.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Therefore it is required to develop a light emitting material that has high thermal stability and can achieve efficiently a charge balance in the light-emitting layer. In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a strong need to develop new host materials for an organic material layer.

SUMMARY

In order to solve one or more of the above-mentioned problems occurring in the prior art, an aspect of the present invention provides a compound capable of lowering the driving voltage, and improving luminous efficiency, color purity and life span of an organic electric element, an organic electric element using the same, and an electronic device including the organic electric element.

In accordance with an aspect of the present invention, there is provided a compound represented by Formula below.

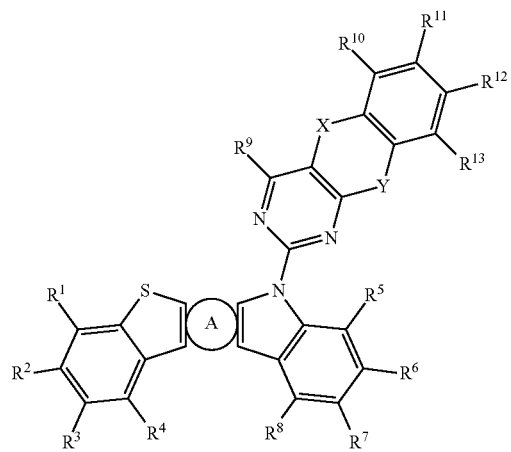

In another aspect of the present invention, there are provided an organic electric element using the compound represented by Formula above and an electronic device including the organic electric element.

By employing the compound according to embodiments of the present invention, an organic electric element according to one or more embodiments of the present invention not only can have a low driving voltage but also significantly improved luminous efficiency, color purity and life span.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine, chlorine, bromine, or iodine.

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "alkenyl" or "alkynyl" as used herein has, but not limited to, double or triple bonds of 2 to 60 carbon atoms, and includes a linear alkyl group, or a branched chain alkyl group, Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below. Also, "substituted fluorenyl group" or "substituted fluorenylene group" means, functional group which at least any one of R, R' and R" is a functional group other than hydrogen and spiro compound which R and R' can be linked together with the carbon to which they are attached to form spiro compound.

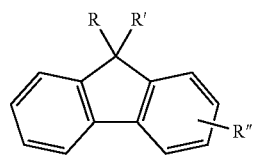

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

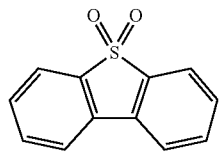 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an aryl alkoxy means an alkoxy substituted with an aryl, an alkoxyl carbonyl means a carbonyl substituted with an alkoxyl, and an aryl carbonyl alkenyl also means an alkenyl substitutes with an aryl carbonyl, wherein the aryl carbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Otherwise specified, the Formulas used in the present invention are as defined in the index definition of the substituent of the following Formula.

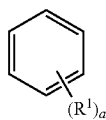

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different each other, and are linked to the benzene ring as follows. when a is an integer of 4 to 6, the substituents $R^1$s are linked to carbon atom of the benzene ring in a similar manner to that. Meanwhile, hydrogen atoms linked to carbon constituting the benzene ring may not be represented as usual.

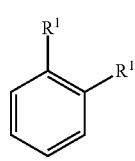

(a-2)

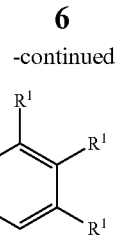

(a-3)

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound may be used as material of a hole injection layer 130, a hole transport layer 140, an electron transport layer 160, an electron injection layer 170, a light emitting layer 150, a capping layer, an emission-auxiliary layer and the like. For example, the inventive compound may be used as a host material of a light emitting layer 150.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

[Formula 1]

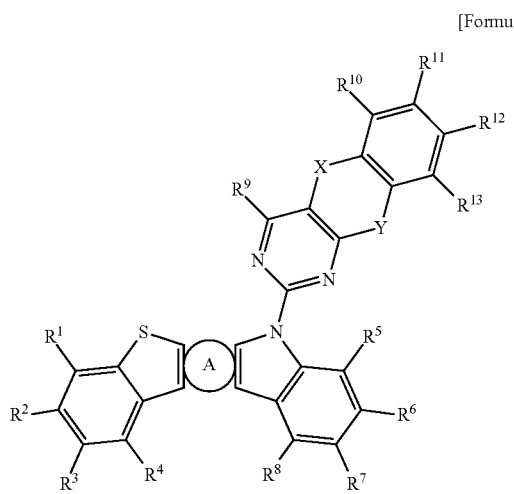

In Formula 1, each symbol may be defined as follows.
In Formula 1, A is a benzene ring. Preferably, the benzene ring represented by A ring may be bonded to a benzothiophene derivative and a indole derivative on both sides thereof to form a heterocyclic ring in which five rings are bonded to each other.

In Formula 1, X and Y are each independently a single bond, O, S or Se, and it is preferable that X and Y are not single bonds at the same time.

i) $R^1$ to $R^{13}$ are each independently selected from the group consisting of hydrogen, deuterium; halogen; a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R^a$)($R^b$), and ii) adjacent groups among $R^1$s to $R^{13}$s may be linked to form an aromatic ring or an heteroaromatic ring, and $R^1$ to $R^{13}$ not forming a ring are the same as defined in i) above, wherein the formed aromatic ring or heteroaromatic ring may be a monocyclic or polycyclic ring.

Preferably, $R^1$ to $R^{13}$ are each independently hydrogen, a $C_6$-$C_{18}$ aryl group or a $C_3$-$C_{12}$ heterocyclic group and so on, more preferably, a $C_6$, $C_{10}$, $C_{12}$ or $C_{18}$ aryl group, or a $C_{12}$ heterocyclic group, and for example, hydrogen, phenyl unsubstituted or substituted with deuterium, naphthyl, biphenyl, terphenyl, dibenzothiophene, dibenzofuran or carbazole unsubstituted or substituted with phenyl and so on.

Preferably, $R^1$ to $R^{13}$ may be each substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

L' is selected from the group consisting of a single bond; a $C_6$-$C_{60}$ arylene group; a fluorenylene group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si and P.

$R^a$ and $R^b$ are each independently selected from the group consisting of a $C_6$-$C_{60}$ aryl group; a fluorenyl group; a fused ring formed by a $C_3$-$C_{60}$ aliphatic ring and a $C_6$-$C_{60}$ aromatic ring; and a $C_2$-$C_{60}$ heterocyclic group containing at least one heteroatom selected from the group consisting of O, N, S, Si and P.

Preferably, L', $R^a$ and $R^b$ may be each substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

Preferably, the above Formula 1 is represented by Formula 2 or Formula 3 below, wherein Formula 1 may be represented by Formula 2 where Y is a single bond and X is not a single bond, and Formula 1 may be represented by Formula 3 where X is a single bond and Y is not a single bond.

<Formula 2>
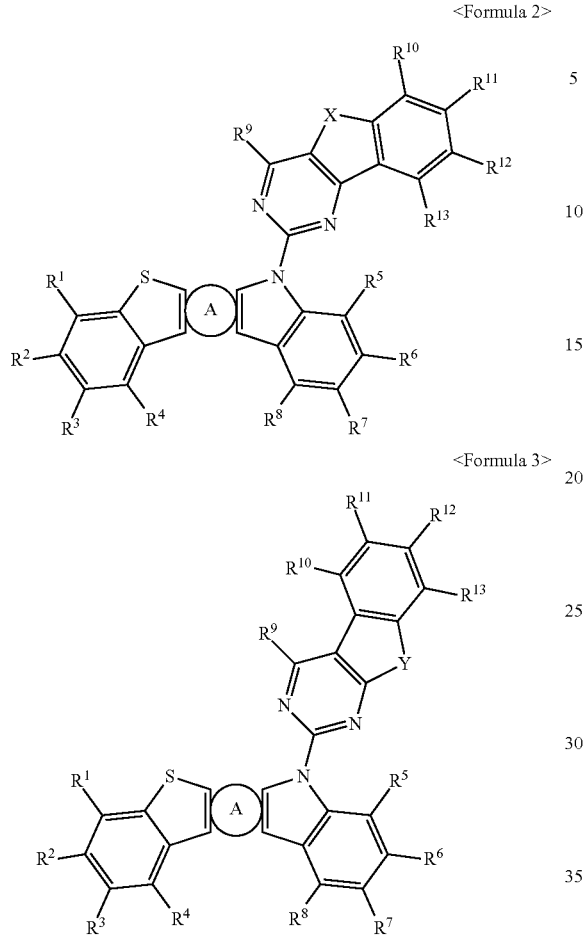
<Formula 3>
<Formula 5>
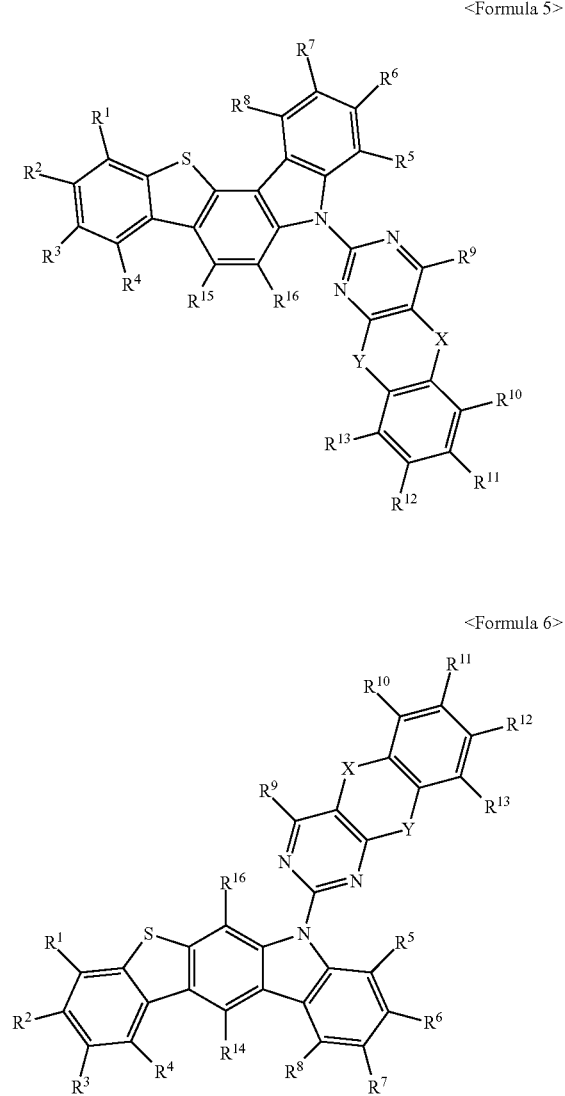
<Formula 6>
In Formulas 2 and 3, A, X, Y, and $R^1$ to $R^{13}$ are each the same as defined in Formula 1.
Preferably, the above Formula 1 may be represented by any one of the following Formulas 4 and 9.
<Formula 4>
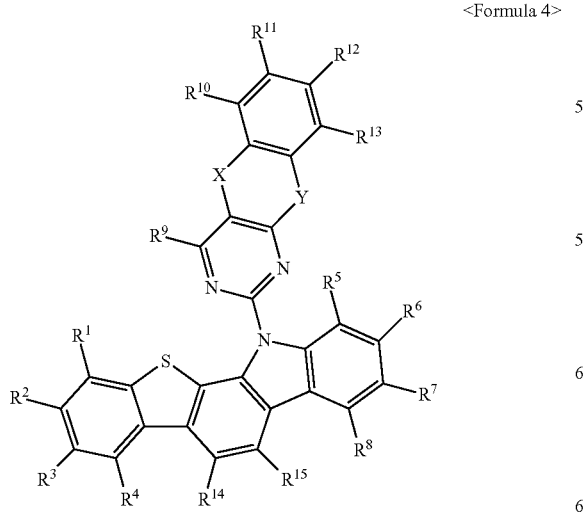
<Formula 7>
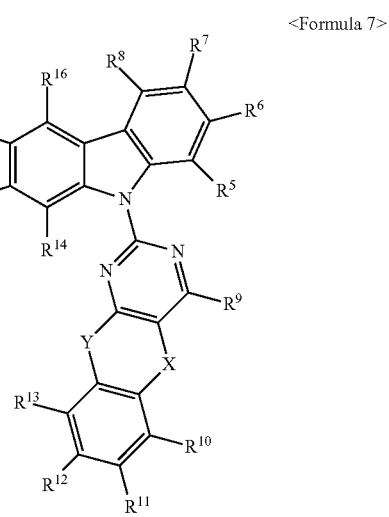

-continued

<Formula 8>

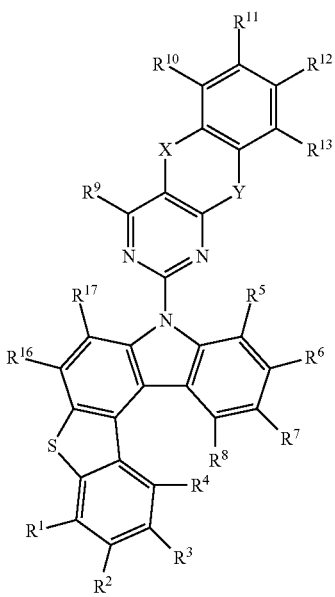

<Formula 9>

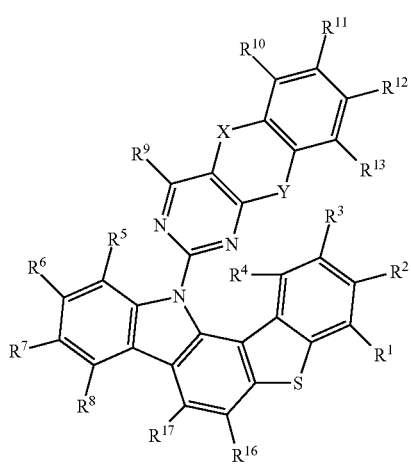

In Formulas 4 to 9, X, Y, and $R^1$ to $R^{13}$ are each the same as defined in Formula 1.

In Formulas 4 to 9, i) $R^{14}$ to $R^{17}$ are each independently selected from the group consisting of hydrogen, deuterium; halogen; a $C_6$-$C_{60}$ aryl group; a fluorenyl group; a $C_2$-$C_{60}$ heterocyclic group containing at least one heteroatom selected from the group consisting of O, N, S, Si and P; a fused ring formed by a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R^a$)($R^b$), and ii) adjacent groups among $R^{14}$s to $R^{17}$s may be linked to form an aromatic ring or an heteroaromatic ring, and $R^{14}$ to $R^{17}$ not forming a ring are the same as defined in i) above, wherein the formed aromatic ring or heteroaromatic ring may be a monocyclic or polycyclic ring.

Preferably, $R^{14}$ to $R^{17}$ may be each substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

The above L', $R^a$ and $R^b$ are each the same as defined in Formula 1.

Specially, compound represented by Formula 1 above may be any one of compounds below.

2-1

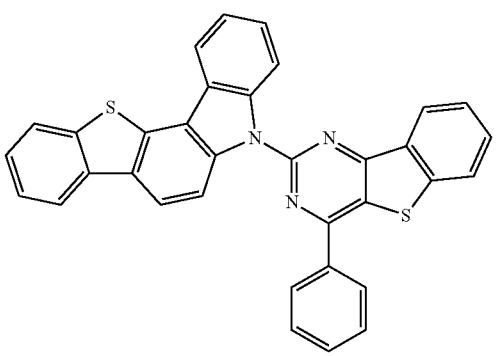

2-2

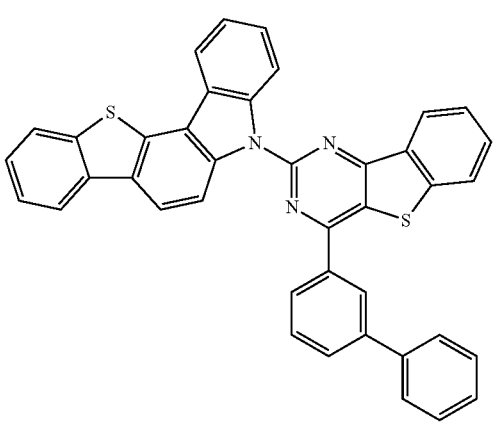

2-3

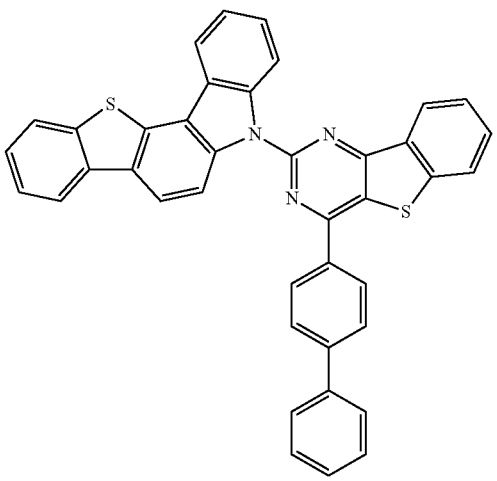

2-4
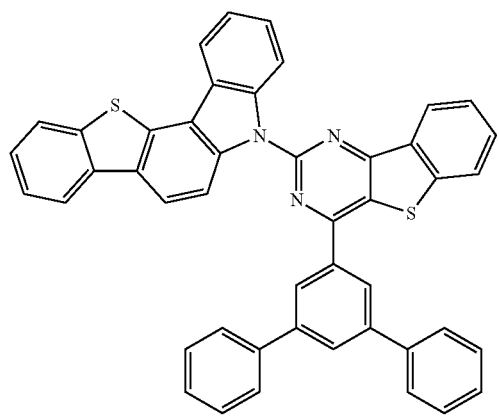
2-5
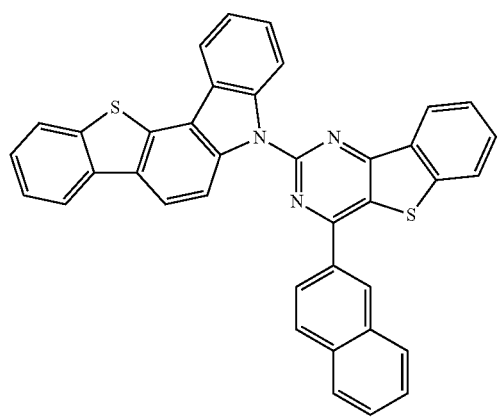
2-6
2-7
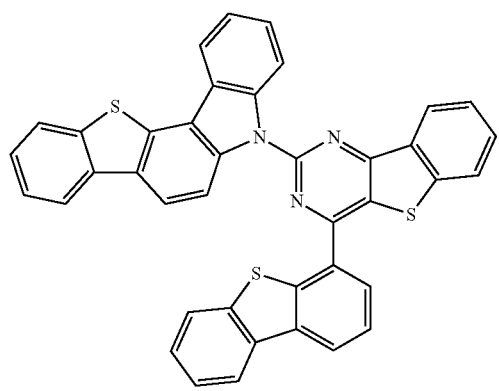
2-8
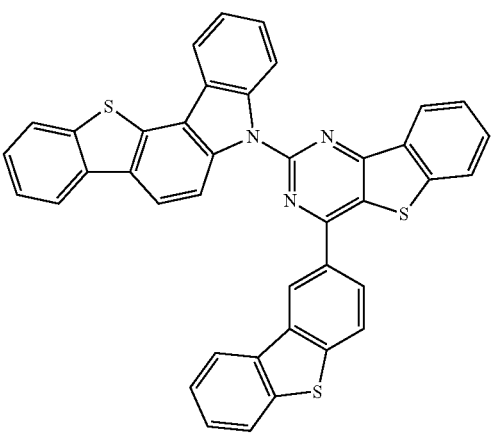
2-9
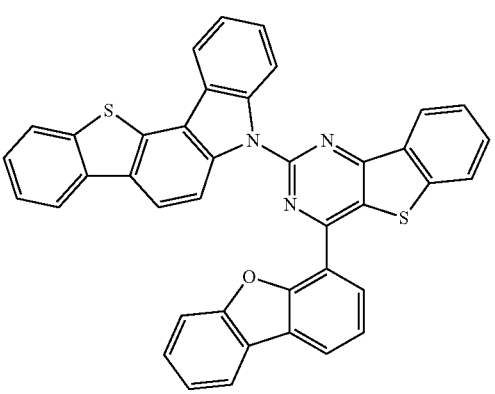
2-10
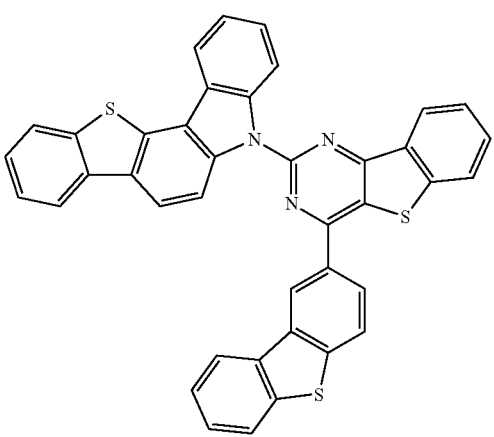

2-11
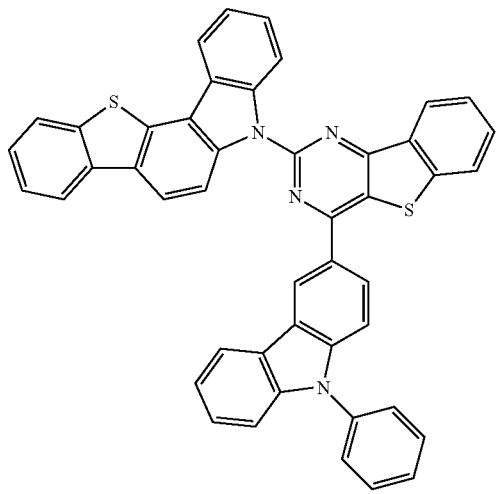
2-12
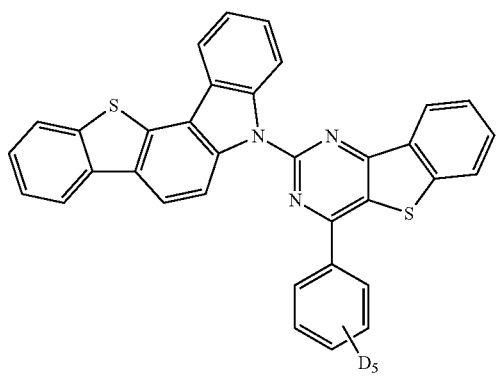
3-1
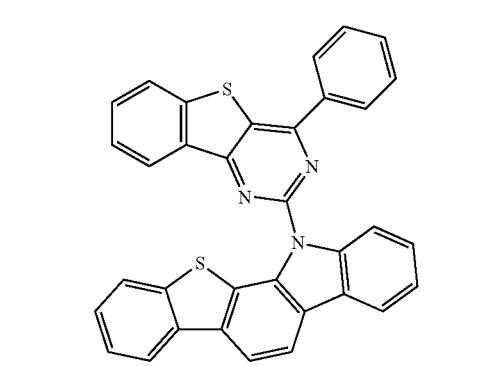
3-2
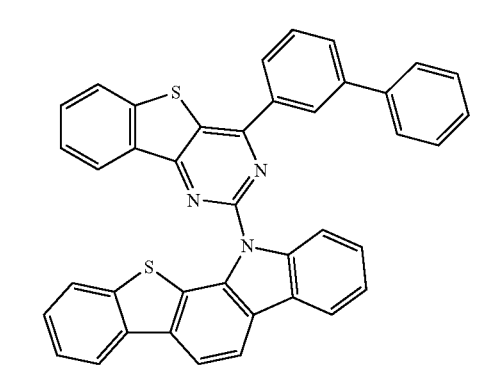
3-3
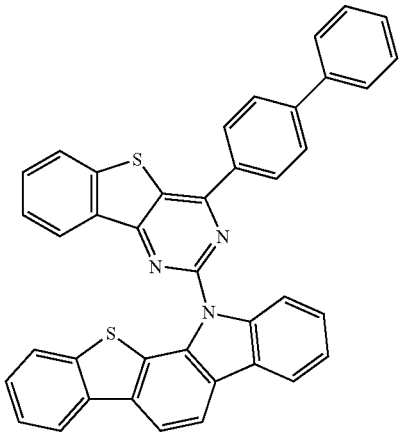
3-4
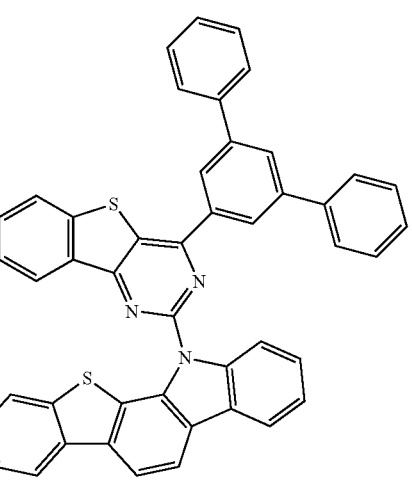
3-5
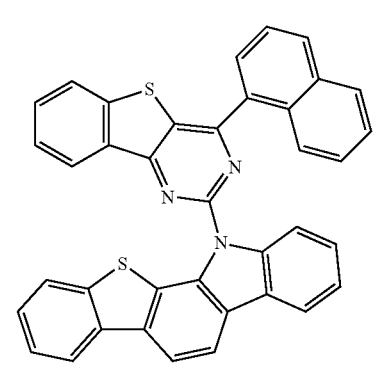
3-6
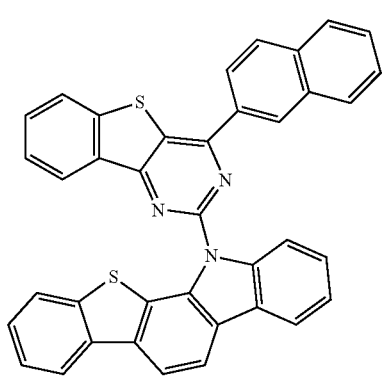

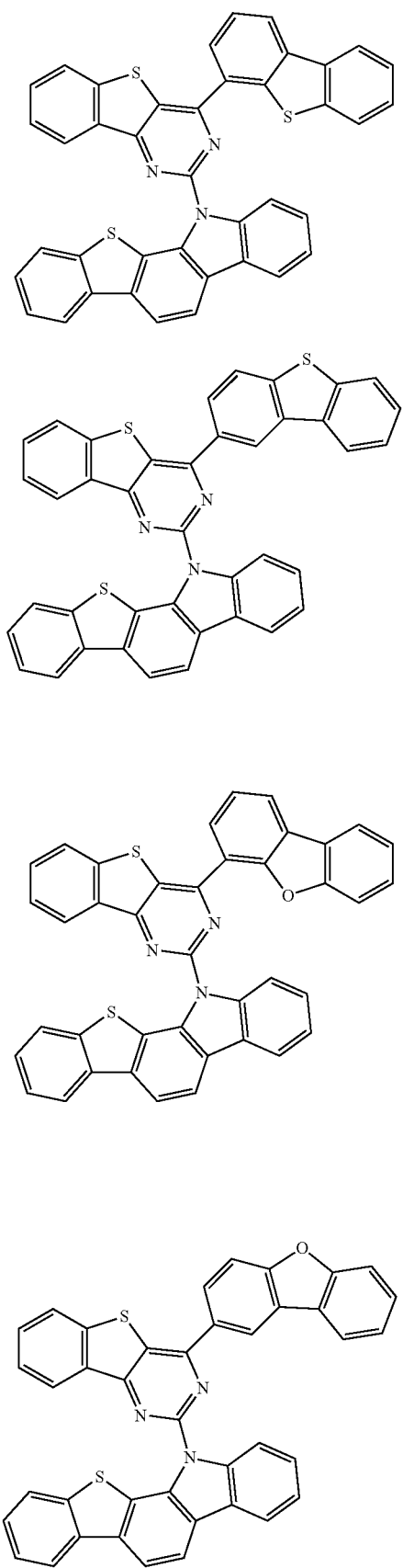
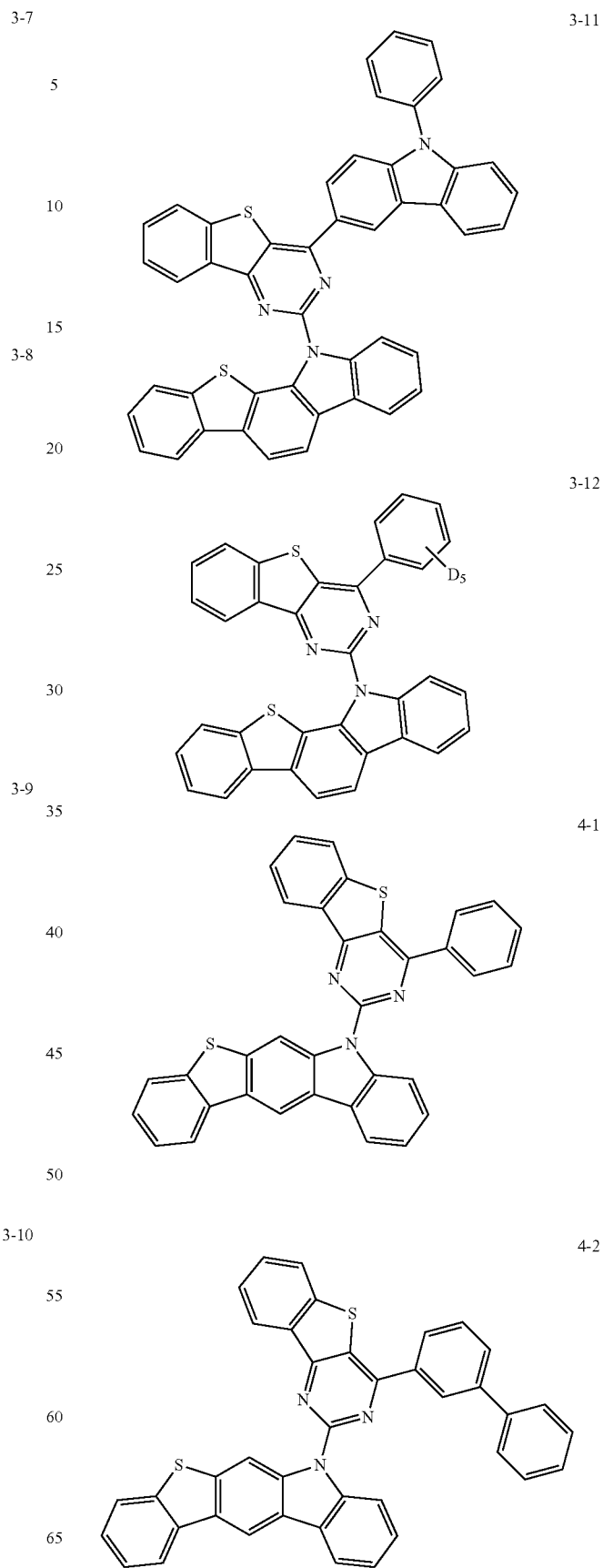

4-3
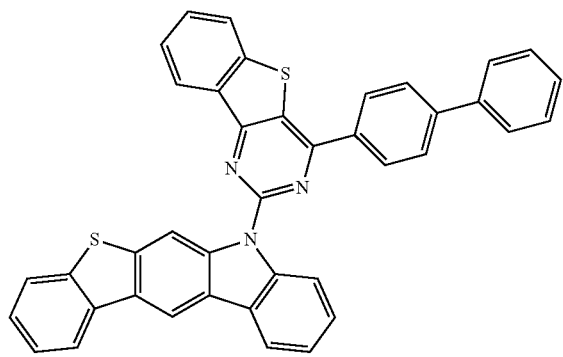
4-4
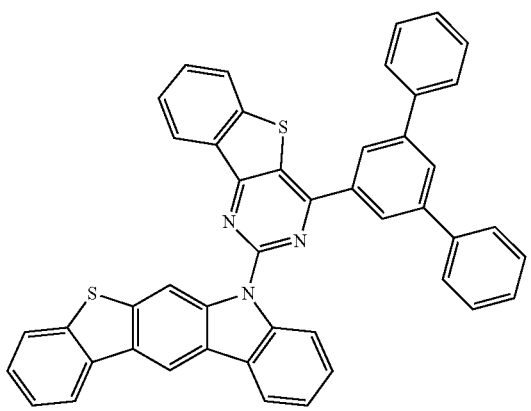
4-5
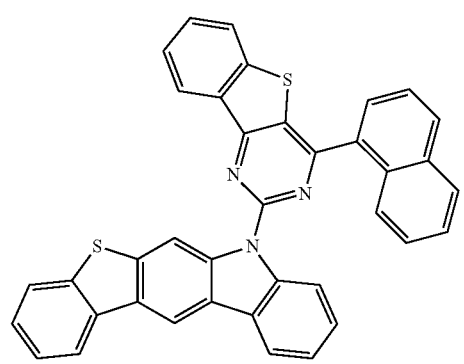
4-6
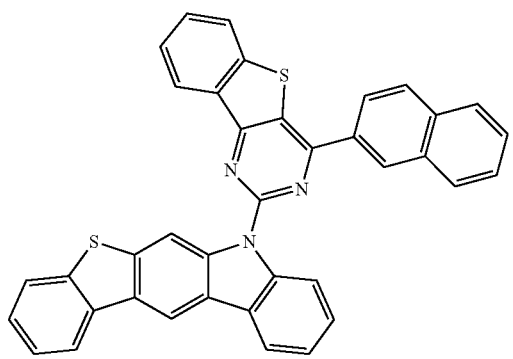
4-7
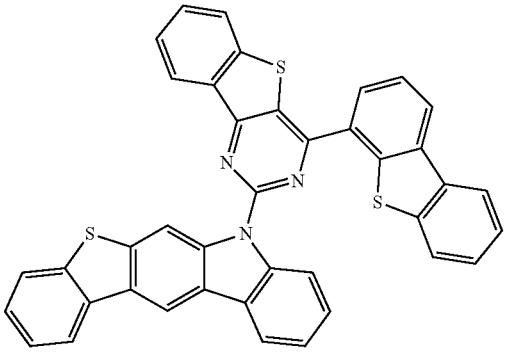
4-8
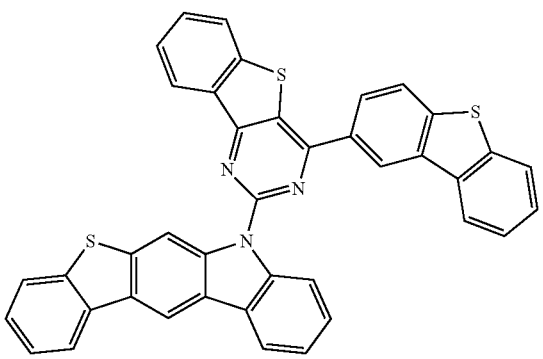
4-9
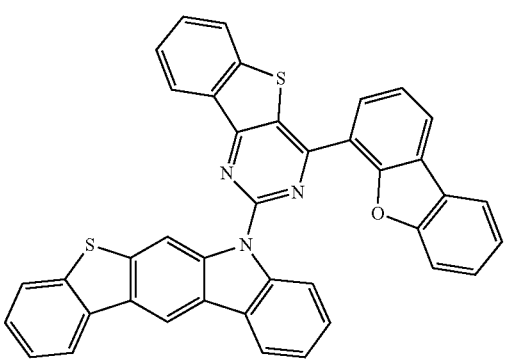
4-10
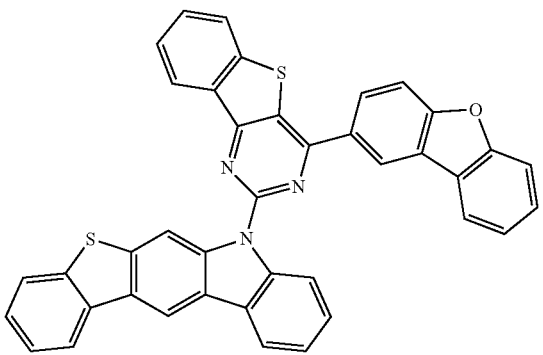

4-11
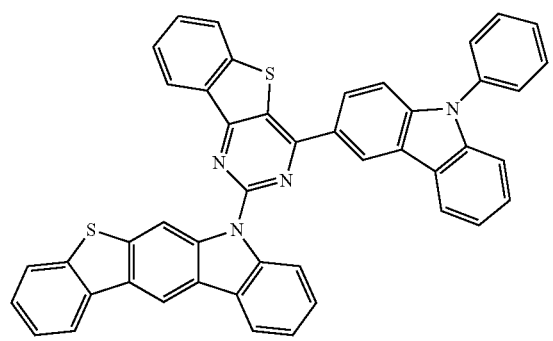
4-12
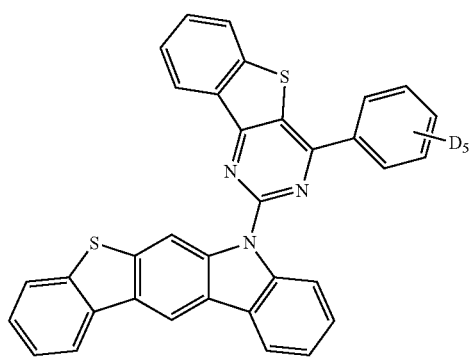
5-1
5-2
5-3
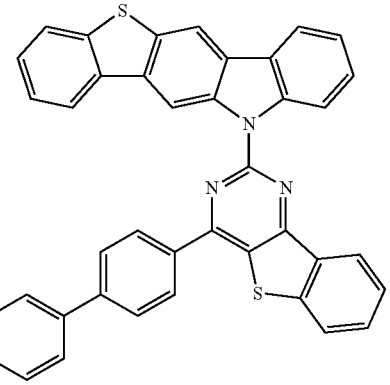
5-4
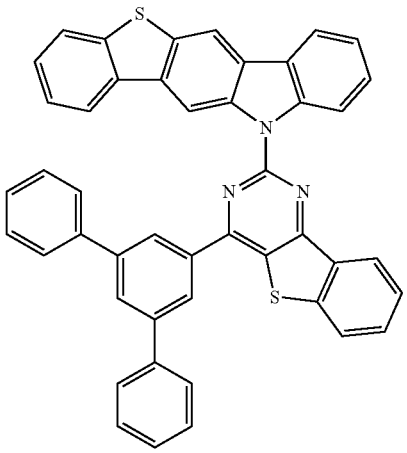
5-5
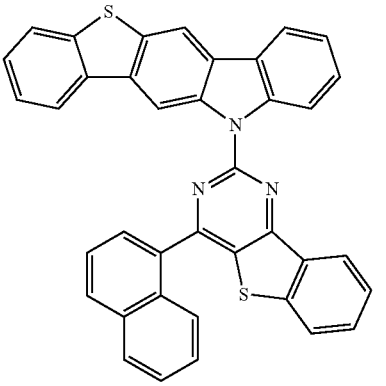
5-6
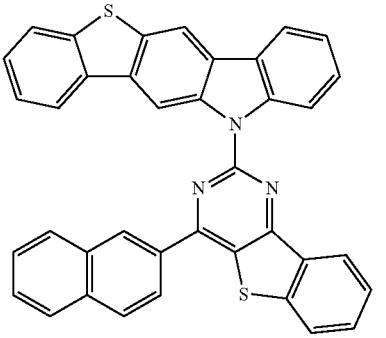

-continued
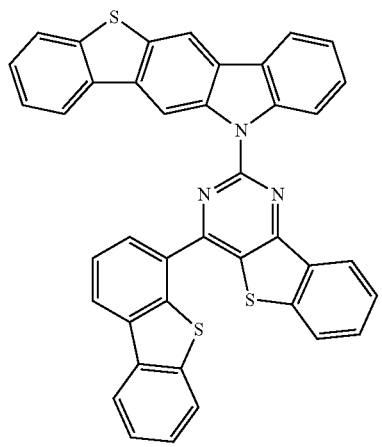
5-7
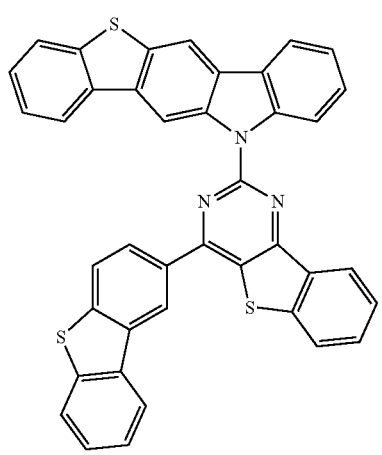
5-8
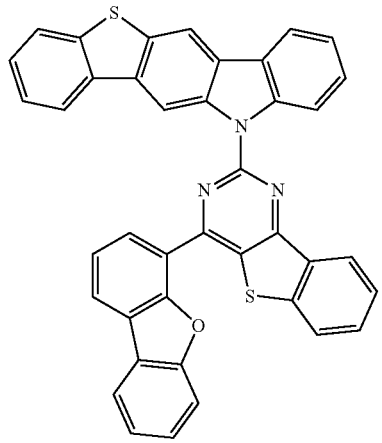
5-9
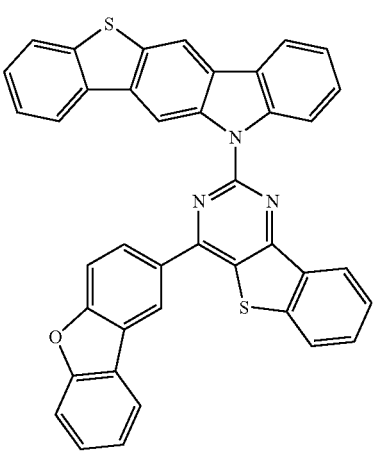
5-10
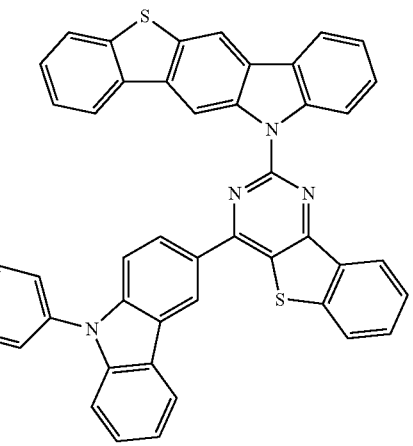
5-11
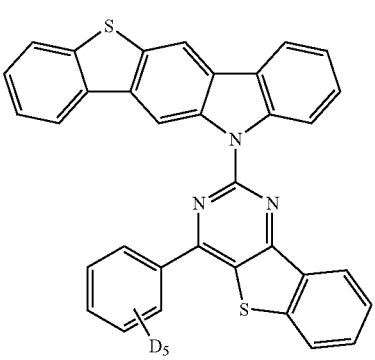
5-12
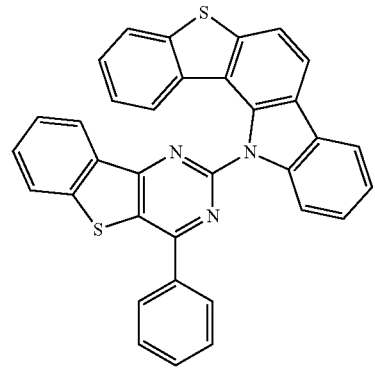
6-1

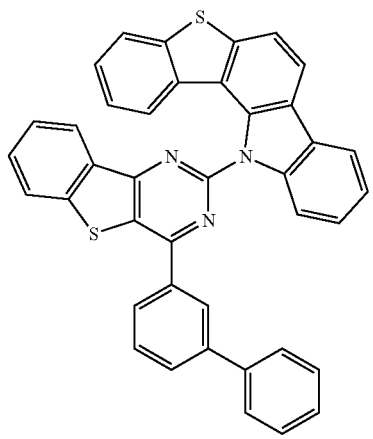
6-2
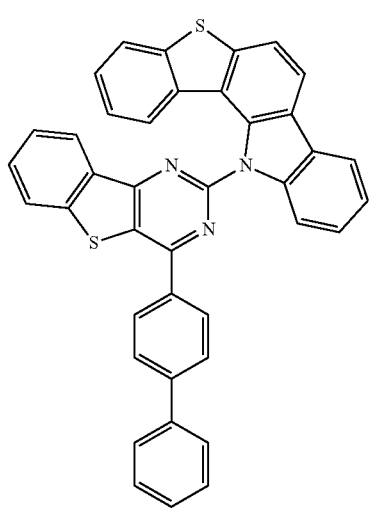
6-3
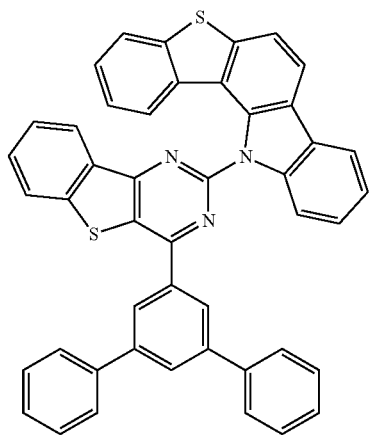
6-4
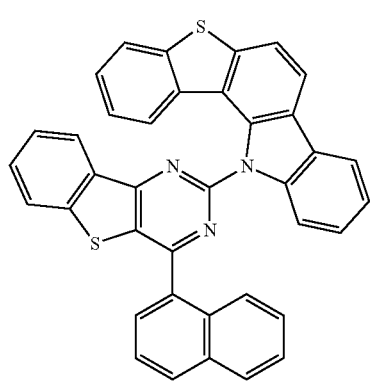
6-5
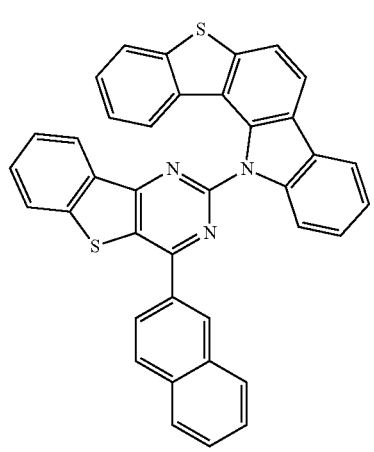
6-6
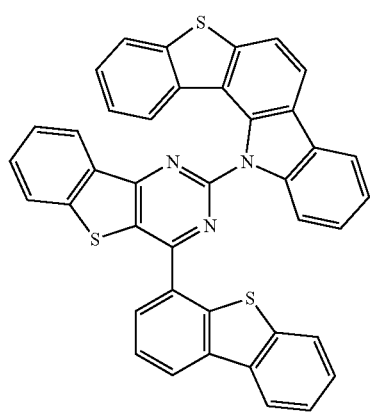
6-7

6-8
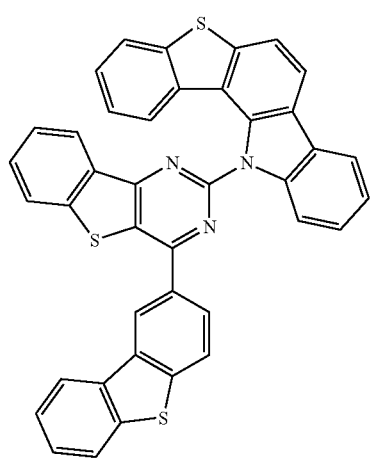
6-9
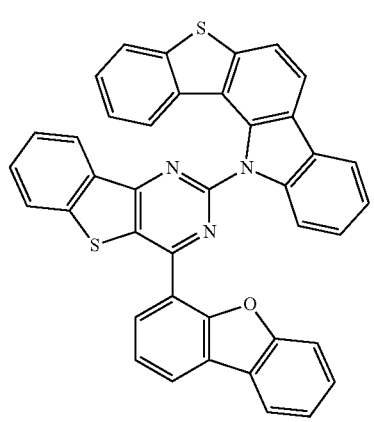
6-10
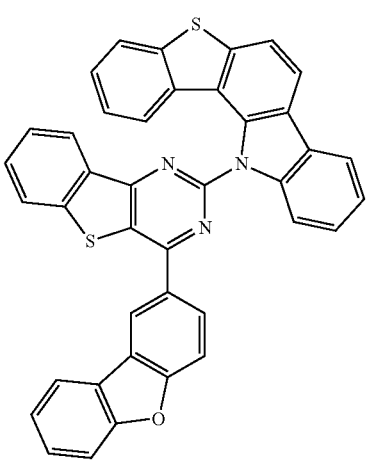
6-11
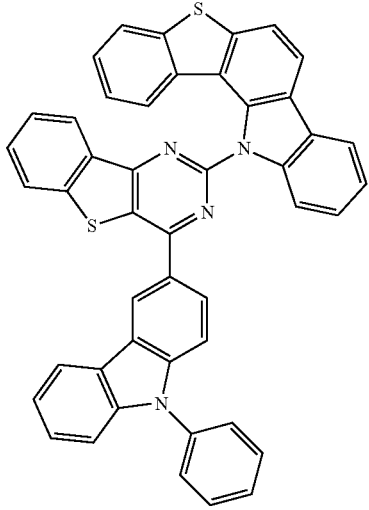
6-12
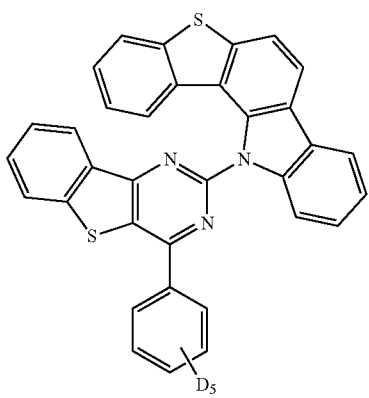
7-1
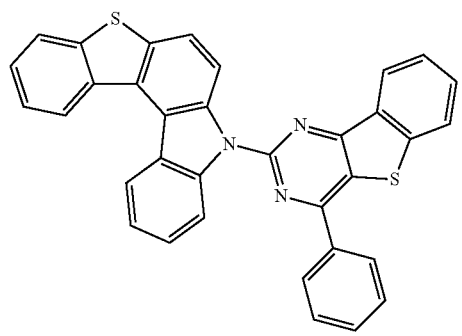
7-2
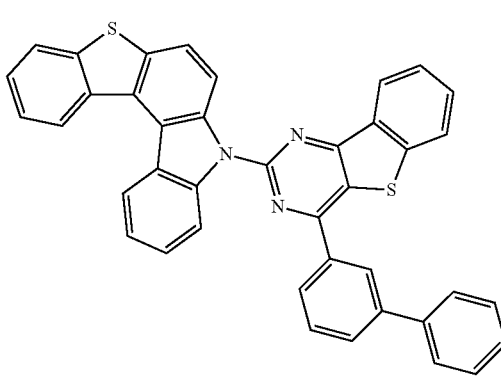

7-3
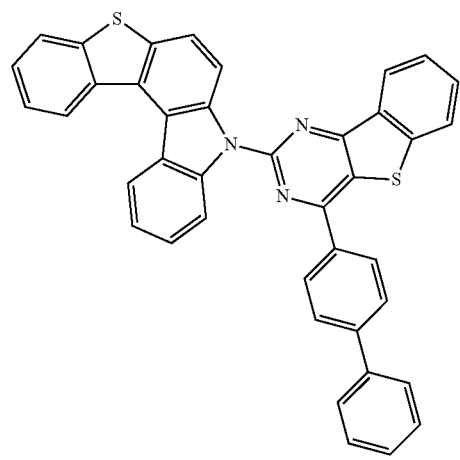
7-4
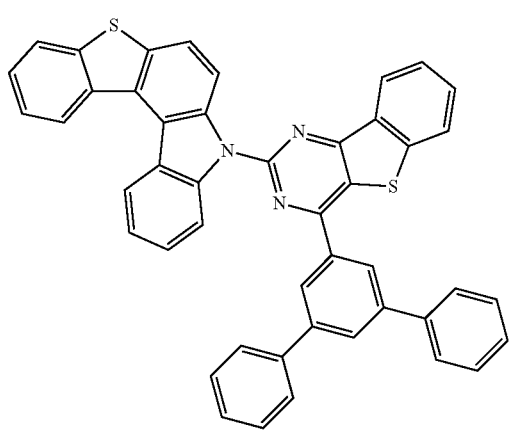
7-5
7-6
7-7
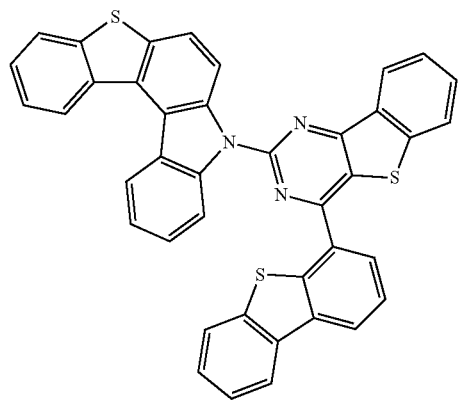
7-8
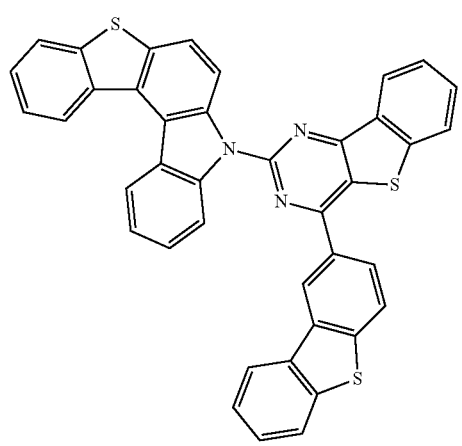
7-9
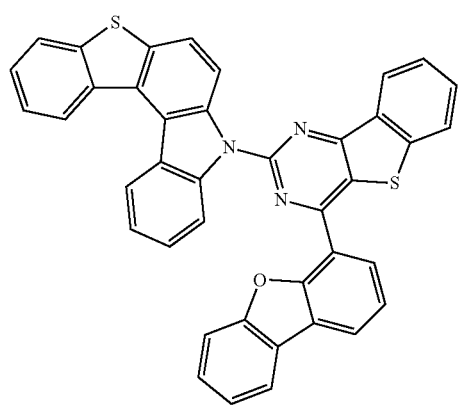

7-10
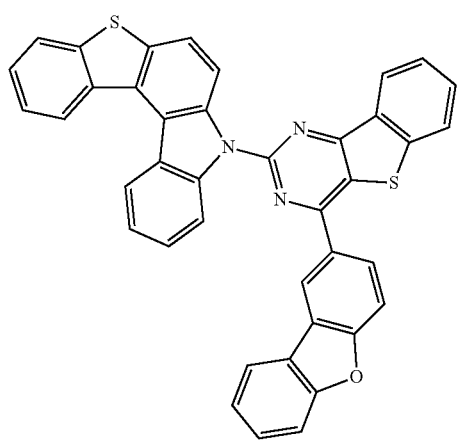
7-11
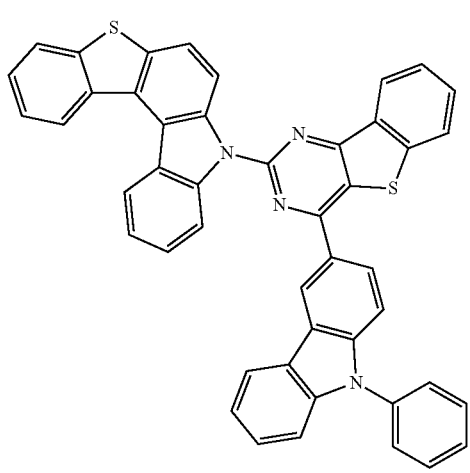
7-12
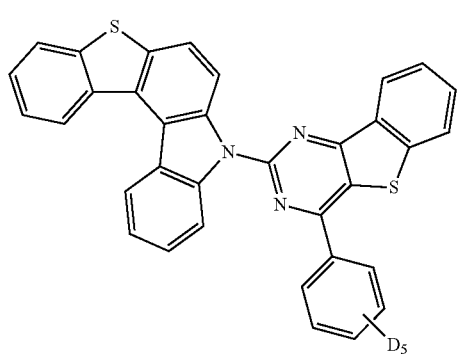
8-1
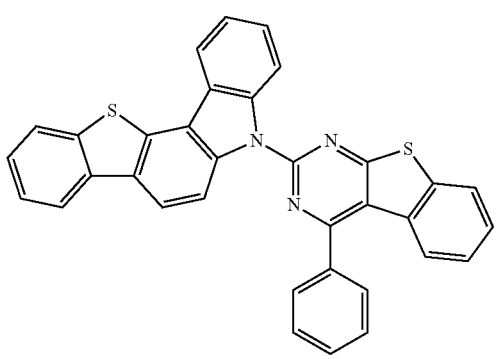
8-2
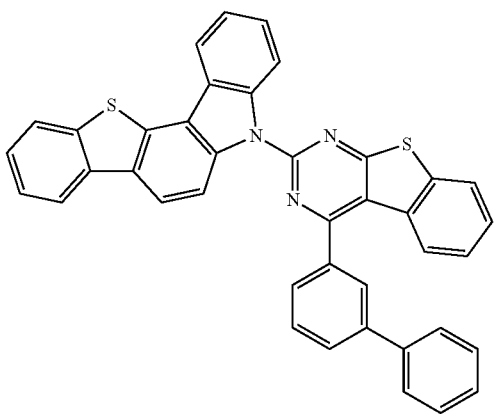
8-3
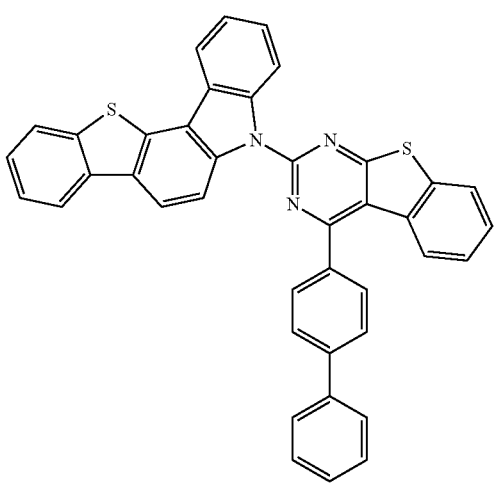
8-4
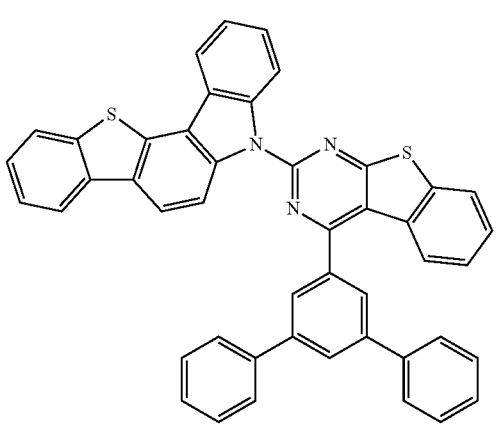

-continued
8-5
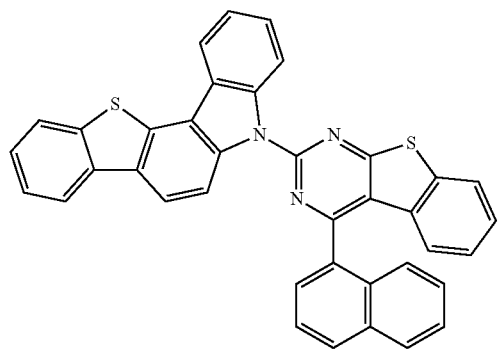
8-6
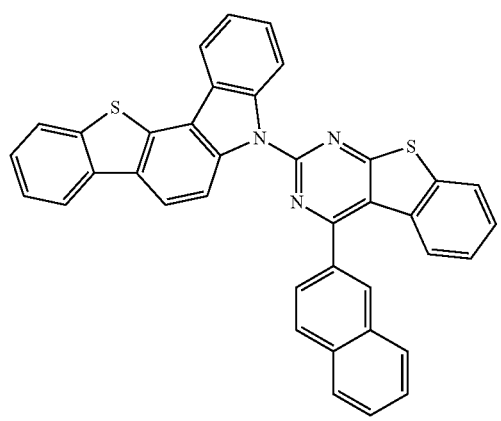
8-7
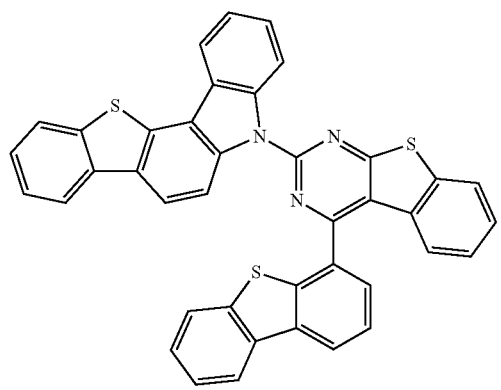
8-8
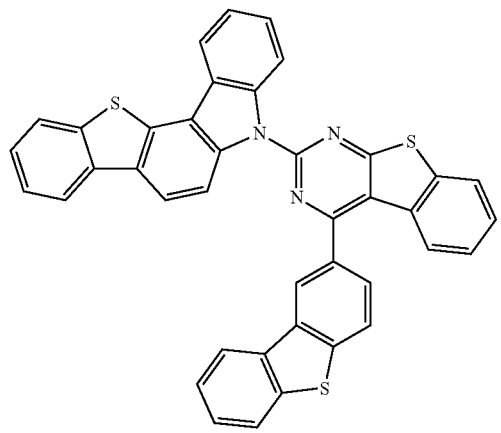
-continued
8-9
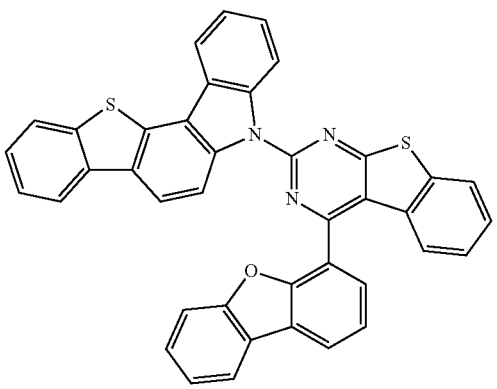
8-10
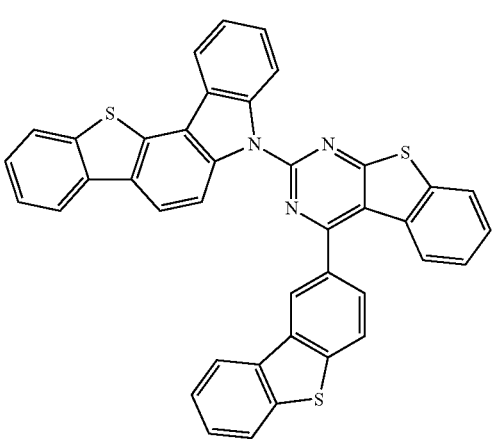
8-11
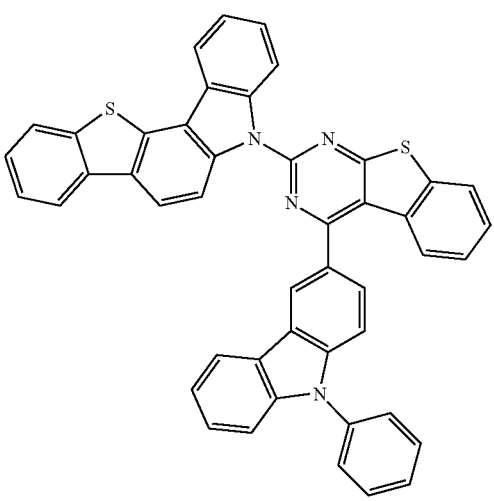

8-12
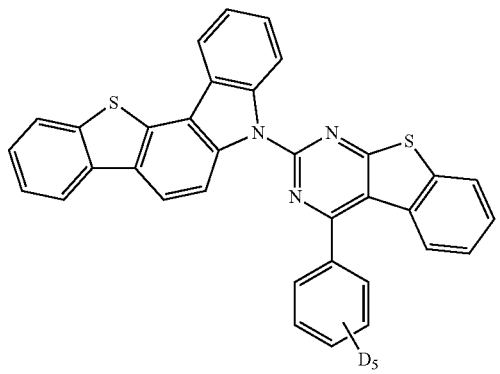
9-1
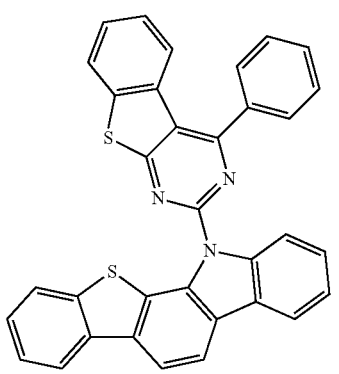
9-2
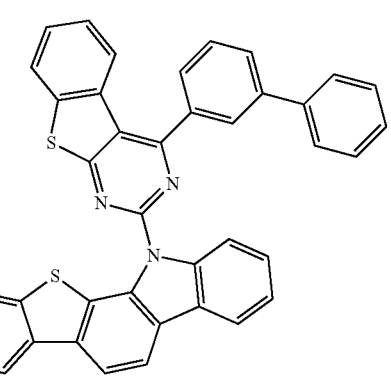
9-3
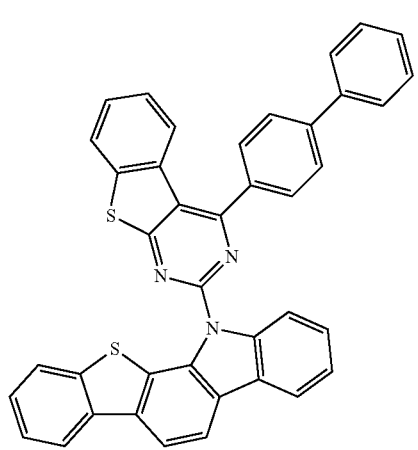
9-4
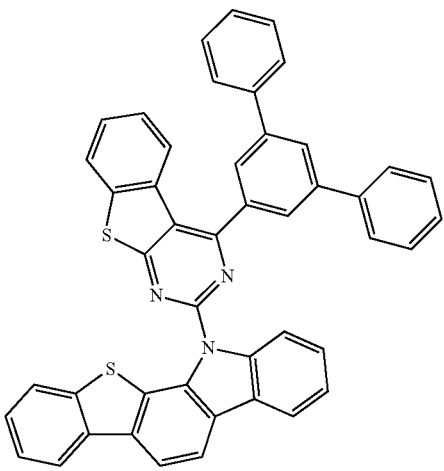
9-5
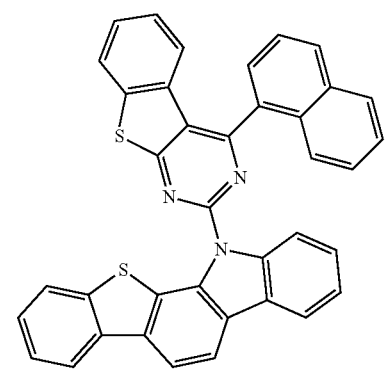
9-6
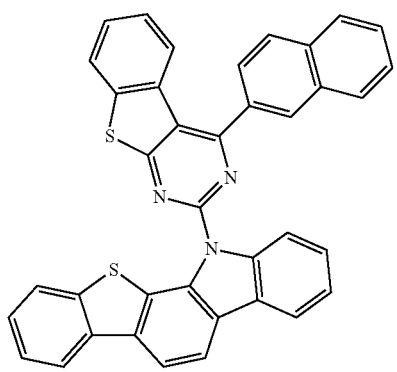
9-7
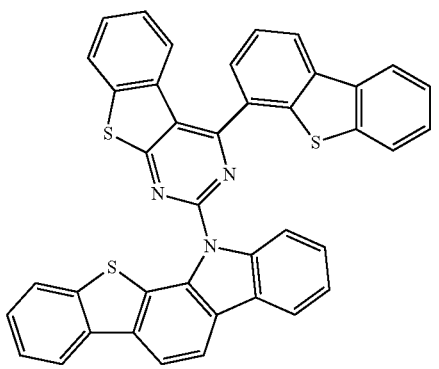

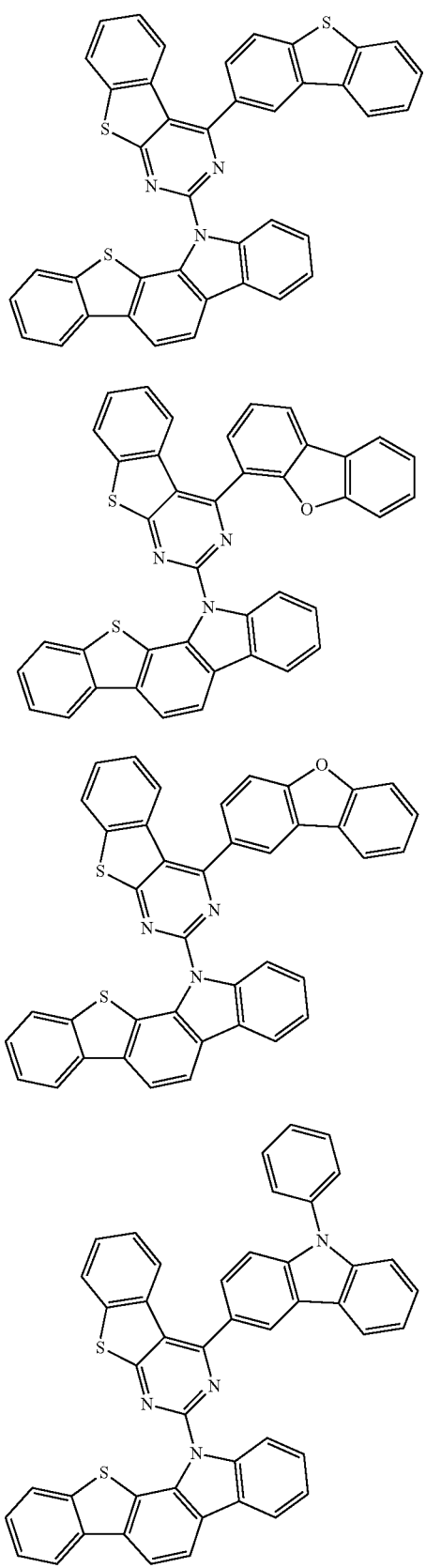
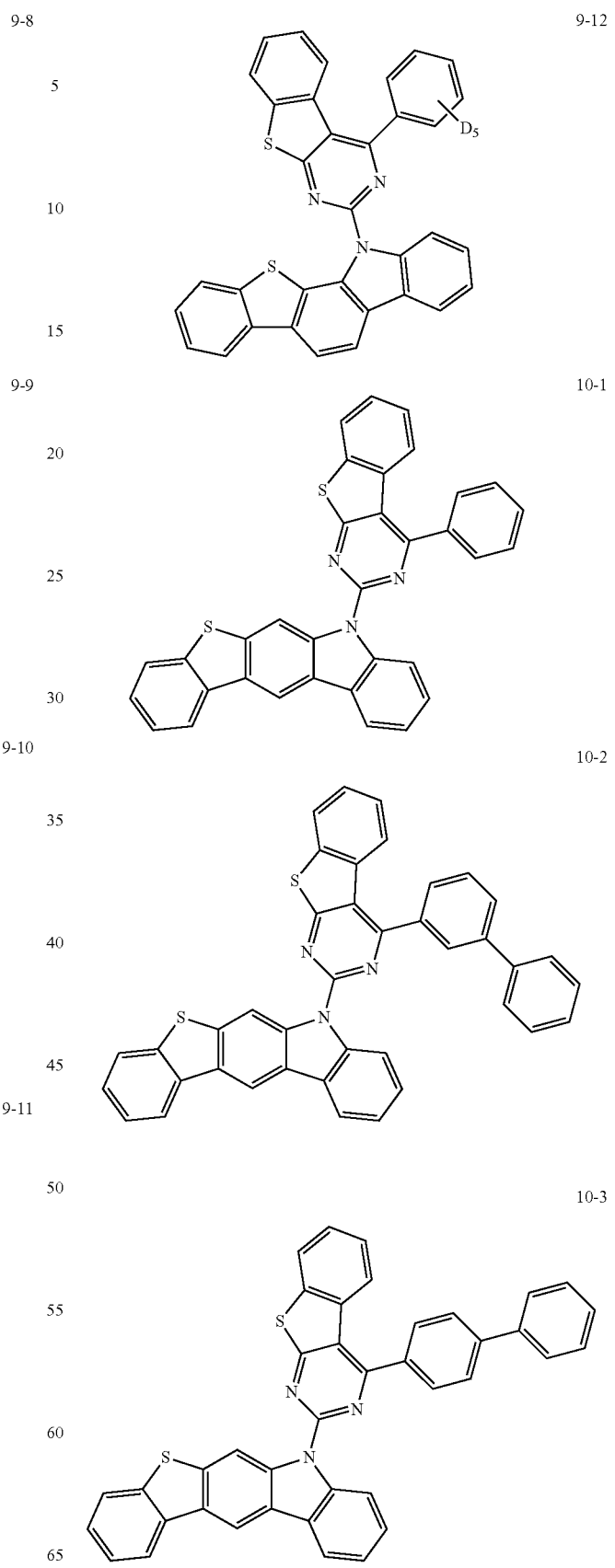

10-4
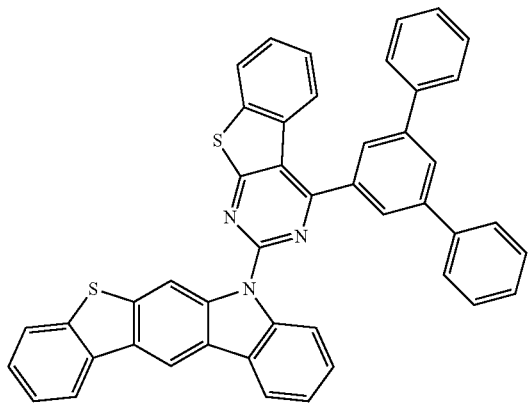
10-5
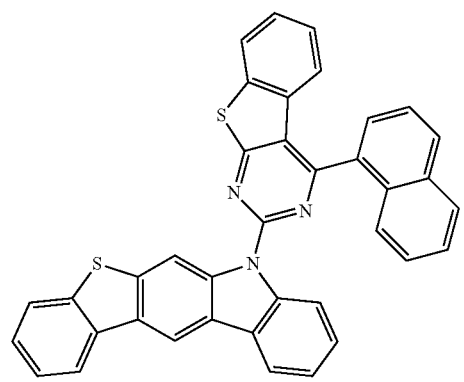
10-6
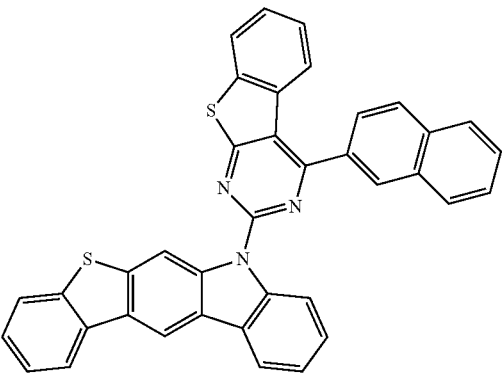
10-7
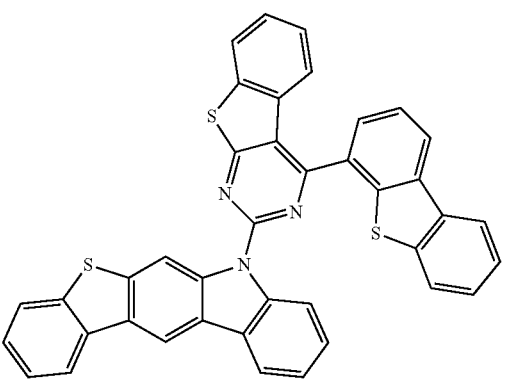
10-8
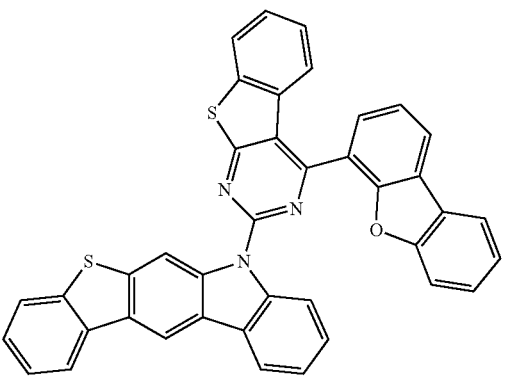
10-9
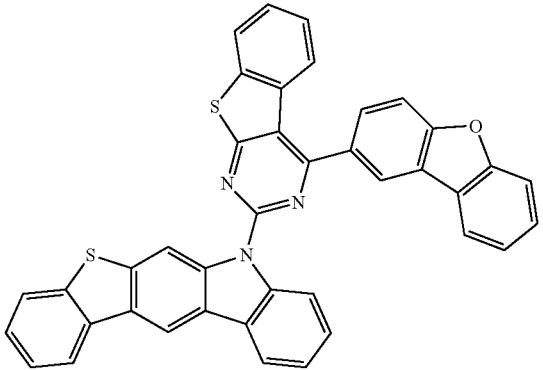
10-10
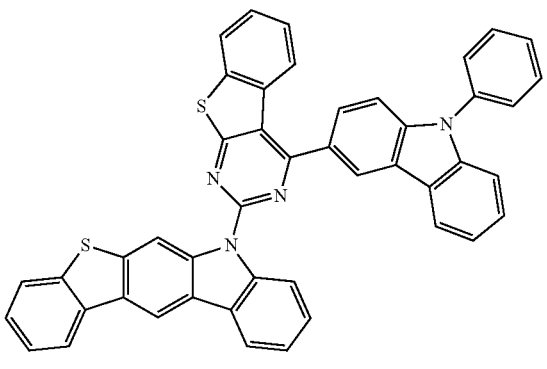
10-11

10-12
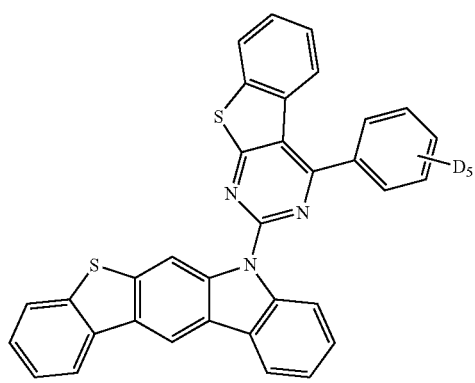
11-1
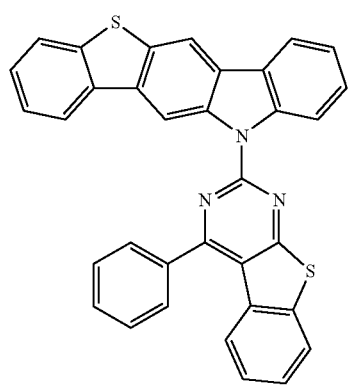
11-2
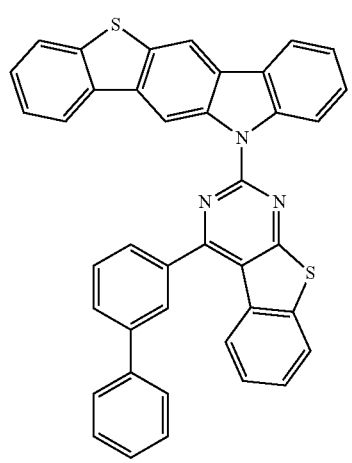
11-3
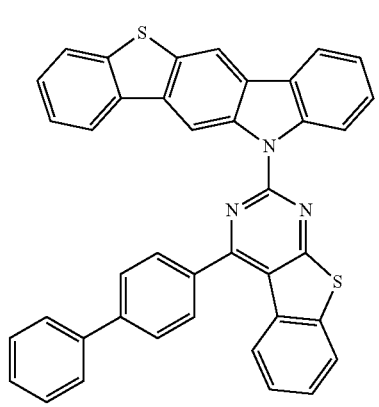
11-4
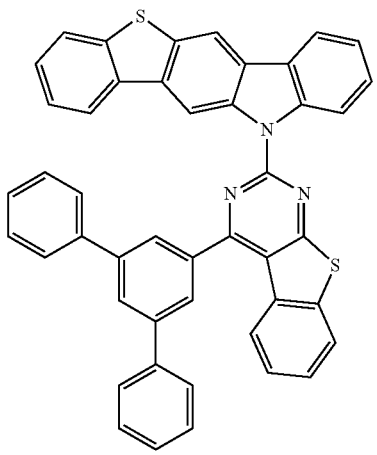
11-5
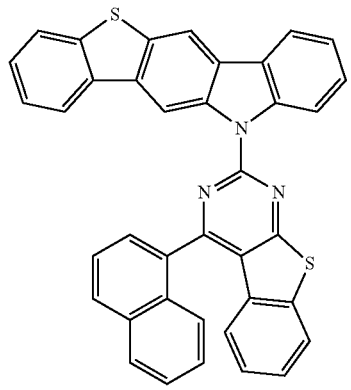
11-6
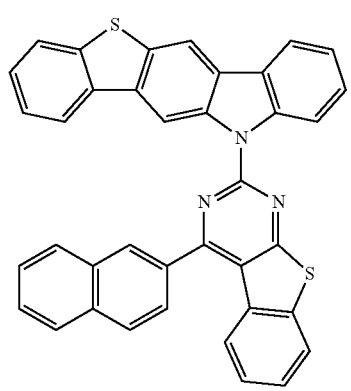

11-7
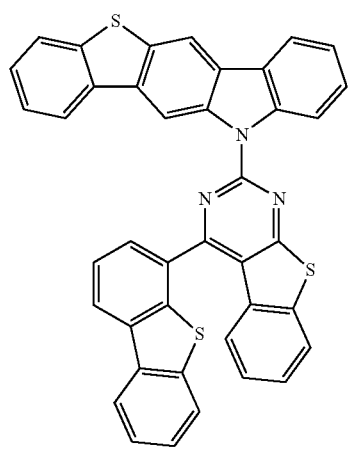
11-8
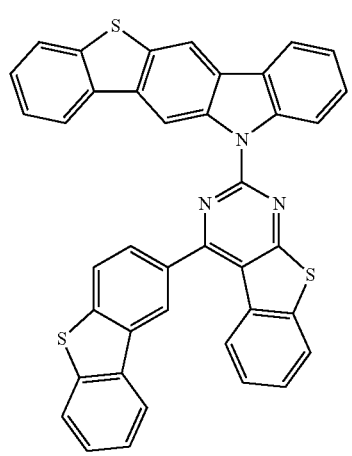
11-9
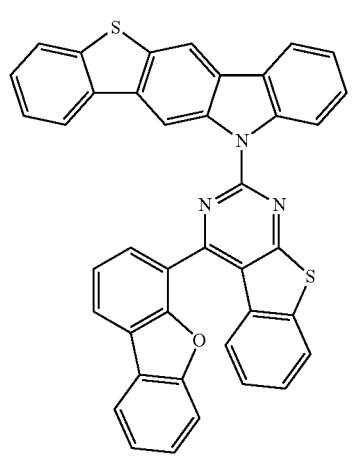
11-10
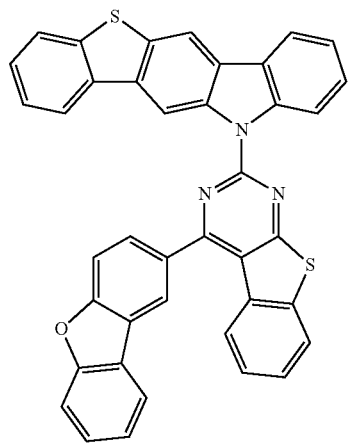
11-11
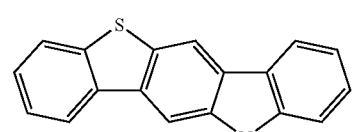
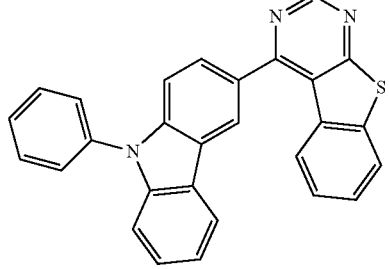
11-12
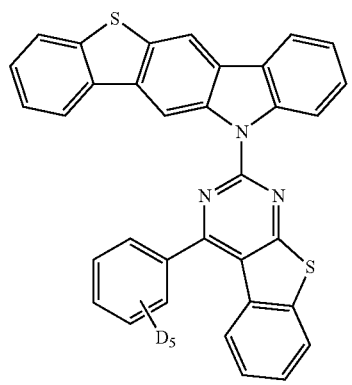
12-1
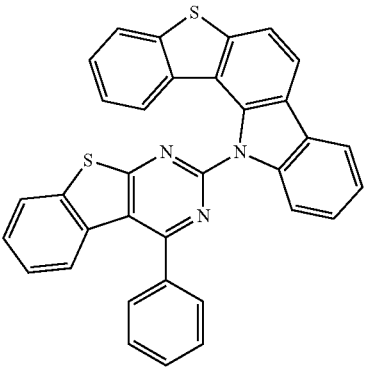

12-2
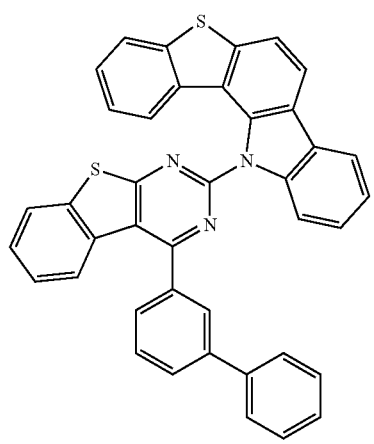
12-3
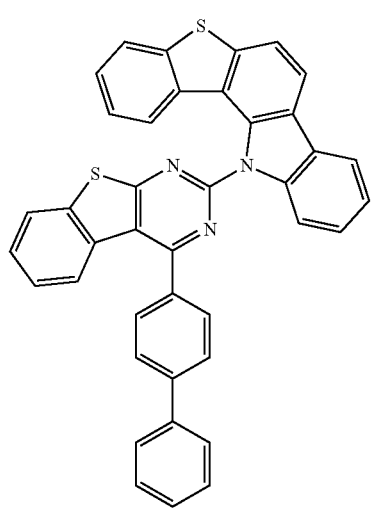
12-4
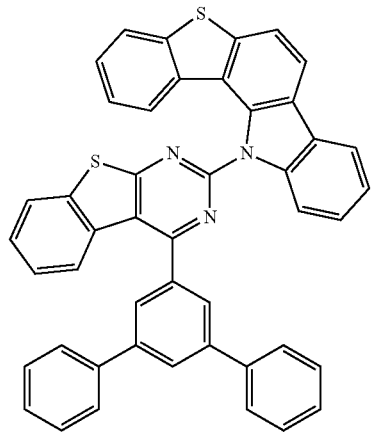
12-5
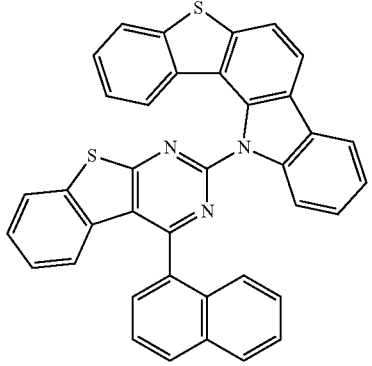
12-6
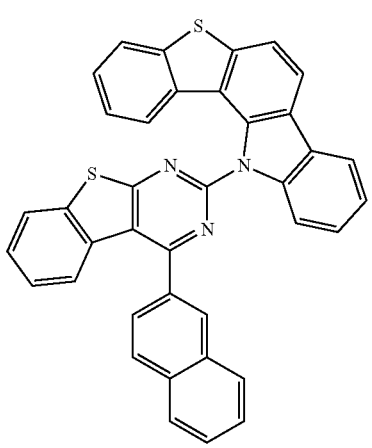
12-7
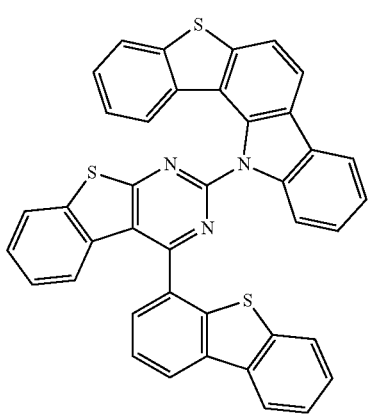

12-8
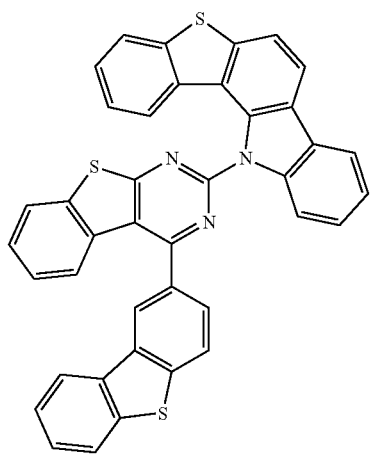
12-9
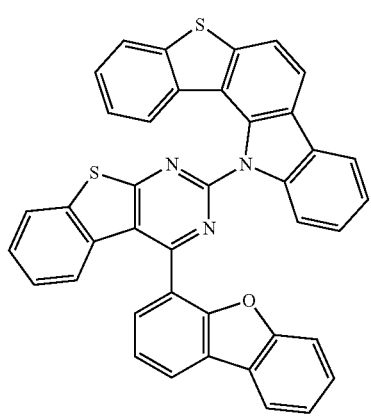
12-10
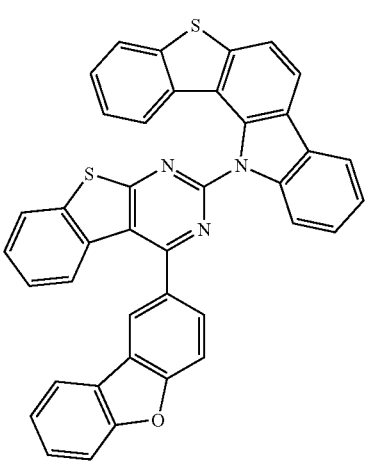
12-11
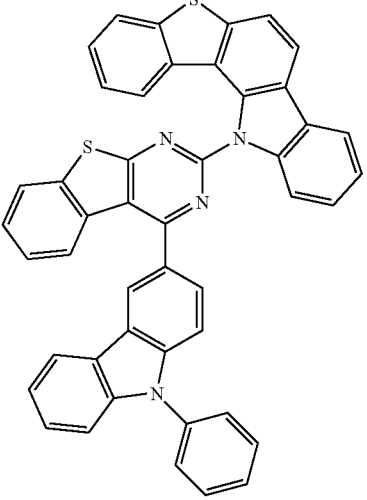
12-12
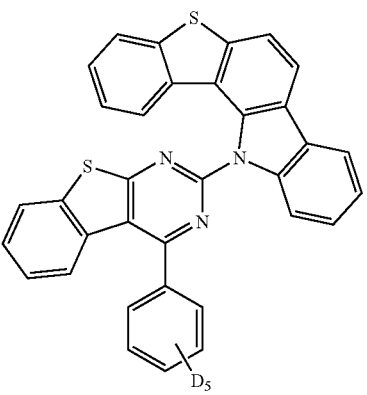
13-1
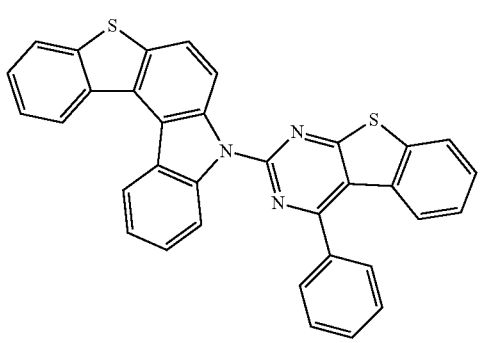
13-2
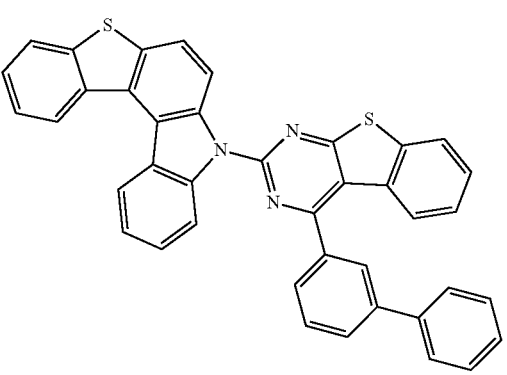

-continued
13-3
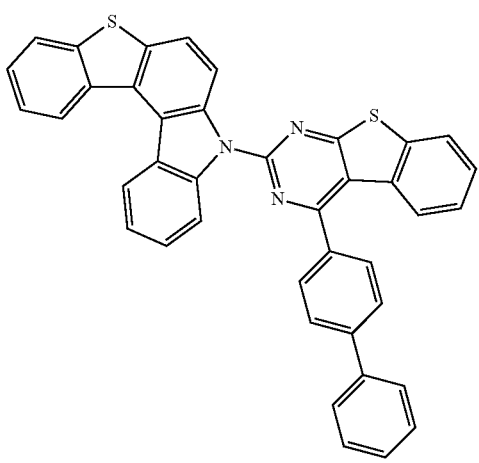
13-4
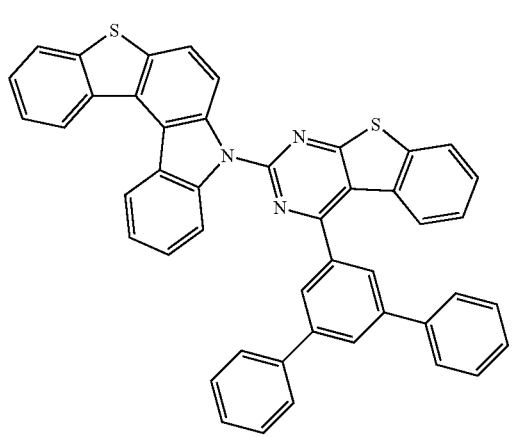
13-5
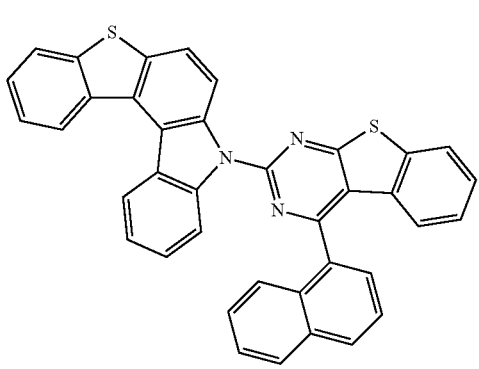
13-6
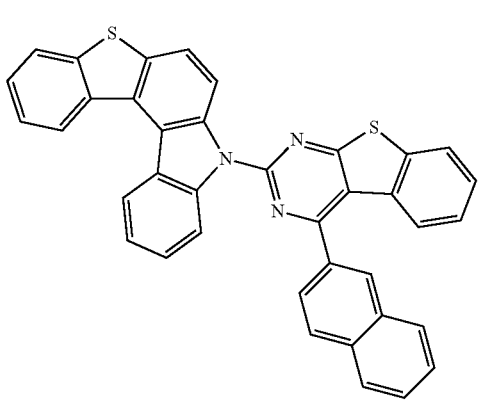
-continued
13-7
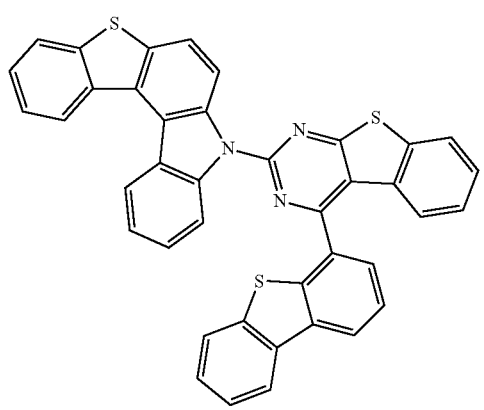
13-8
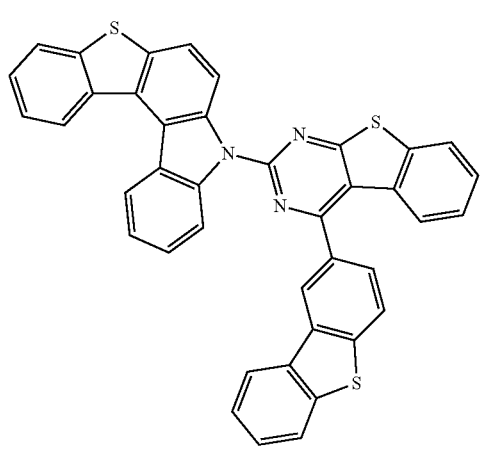
13-9
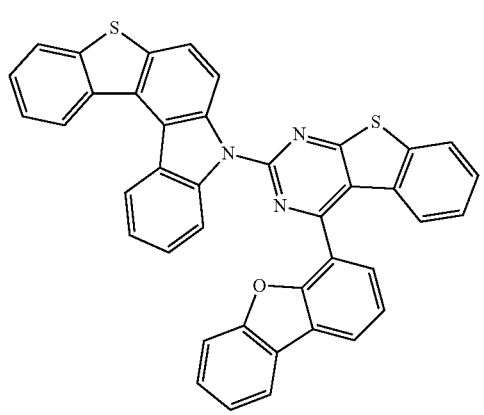

-continued
13-10
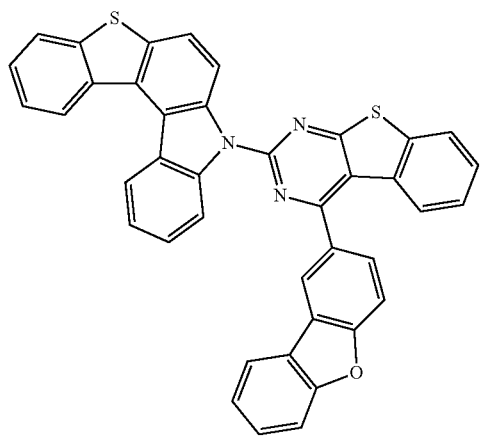
13-11
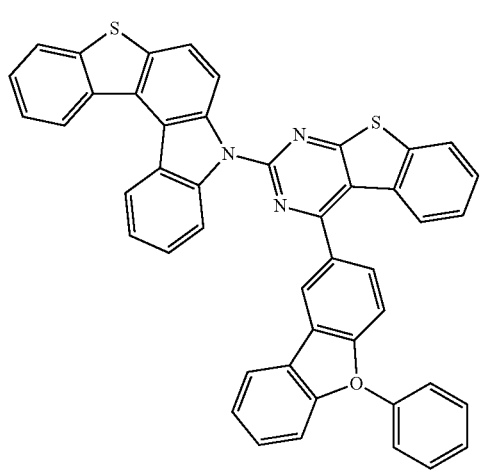
13-12
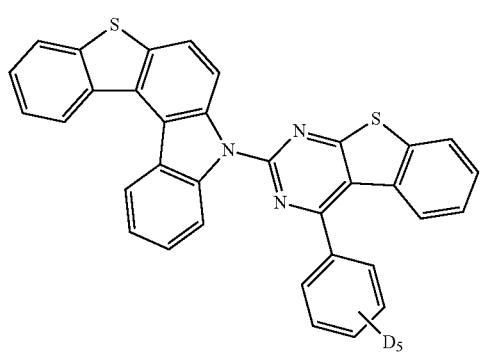
14-1
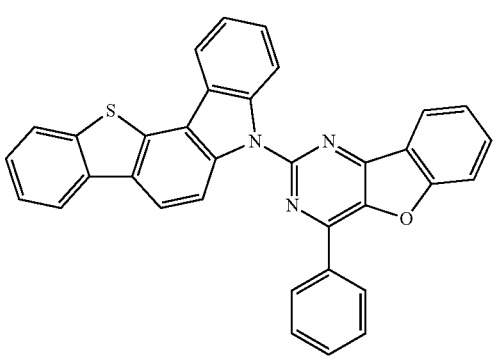
14-2
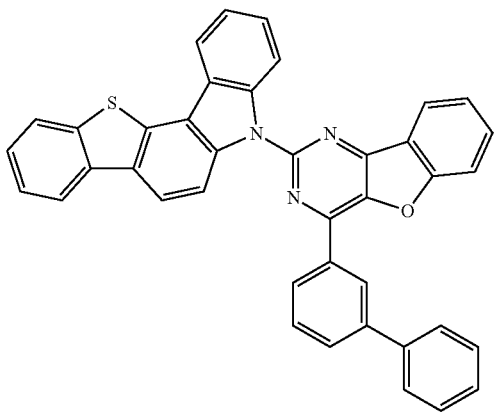
14-3
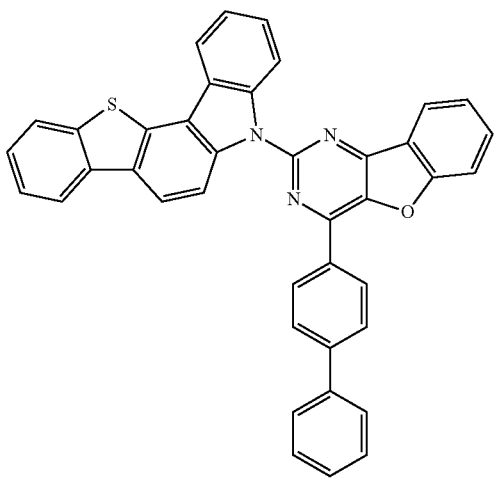
14-4
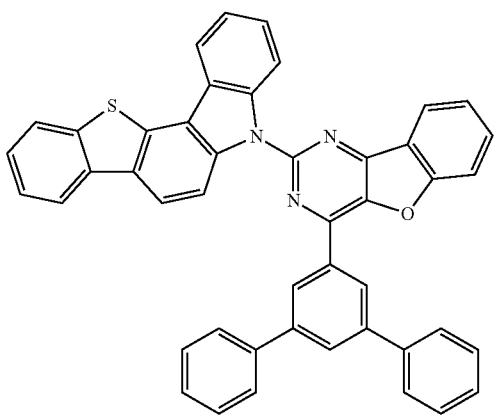
14-5
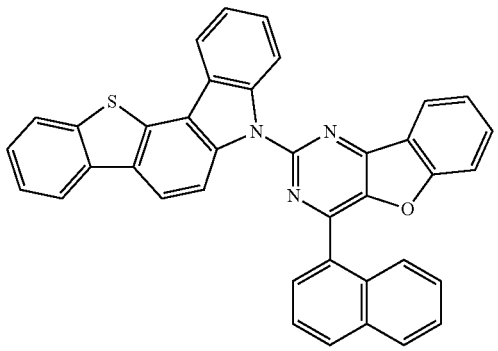

14-6 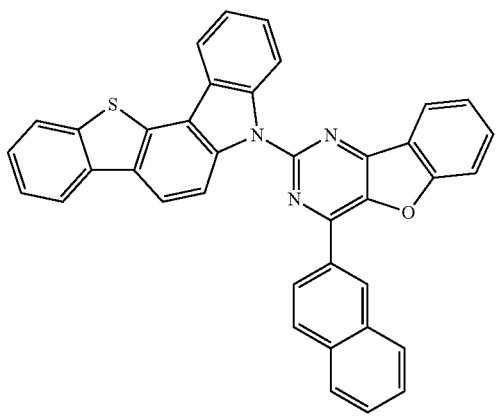
14-7 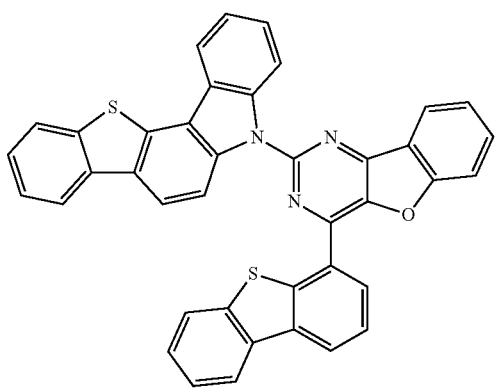
14-8 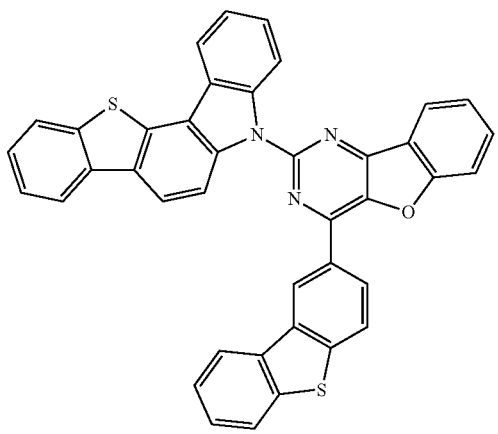
14-9 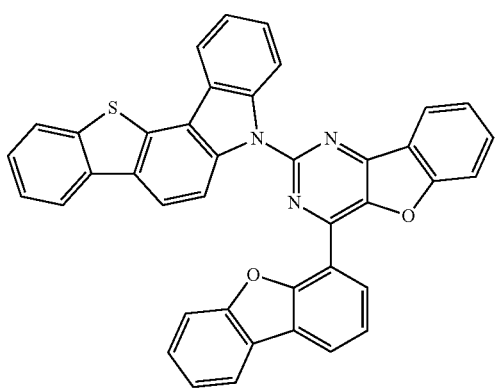
14-10 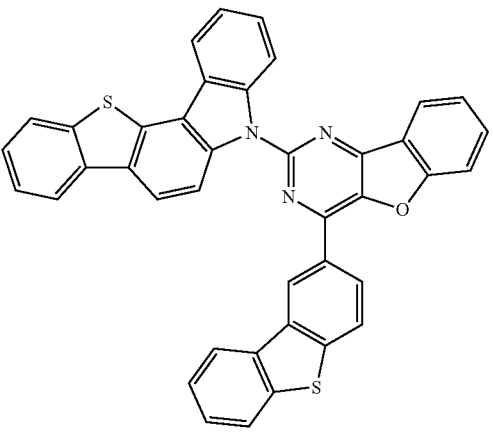
14-11 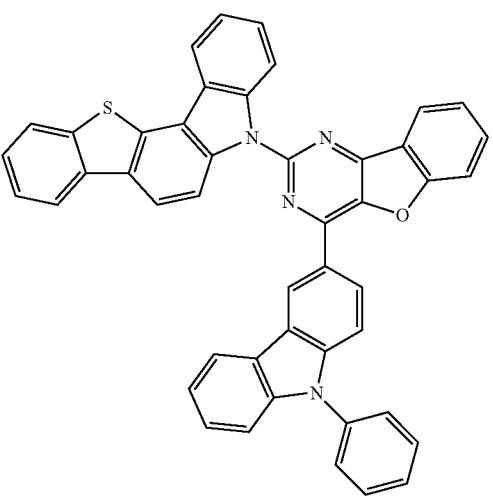
14-12 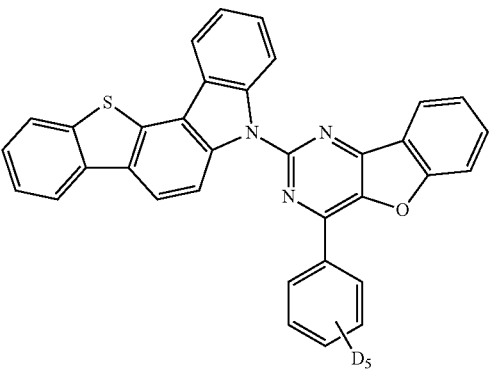
15-1 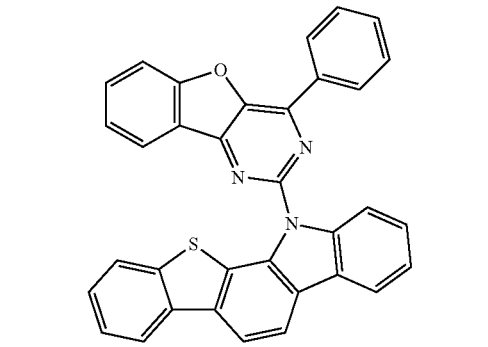

15-2
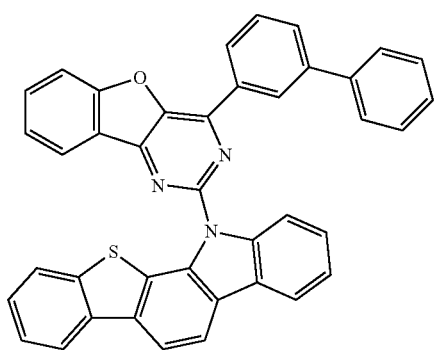
15-3
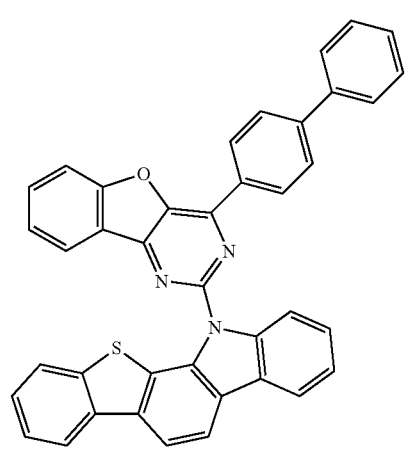
15-4
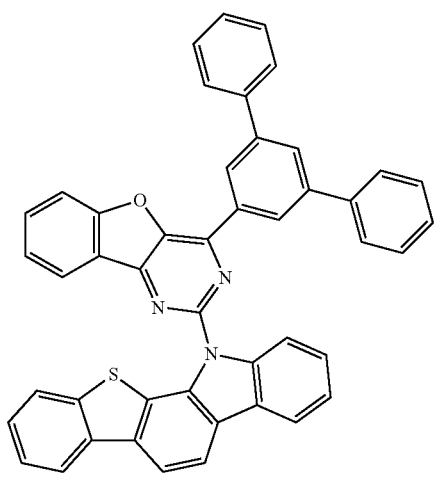
15-5
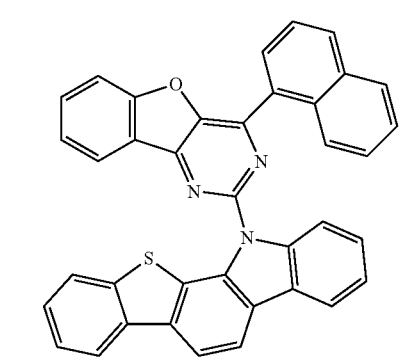
15-6
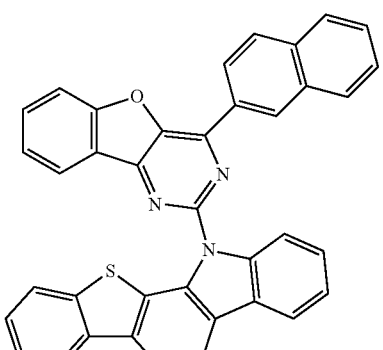
15-7
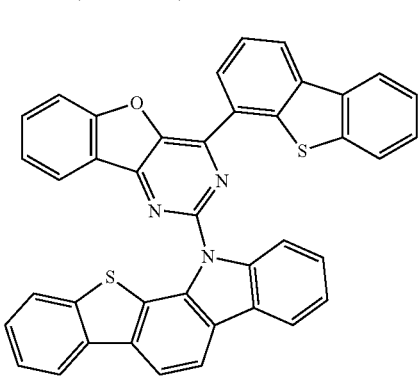
15-8
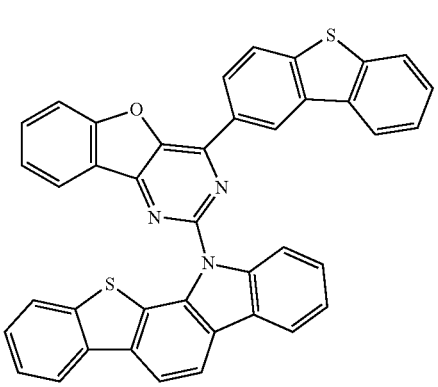
15-9
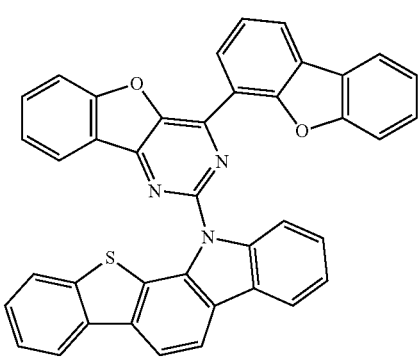

-continued
15-10
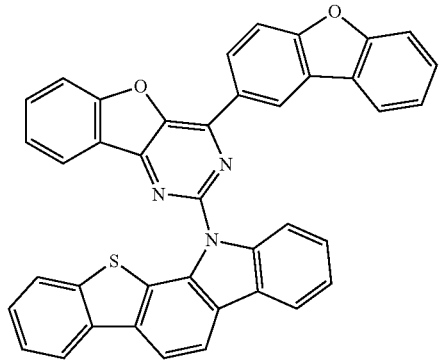
15-11
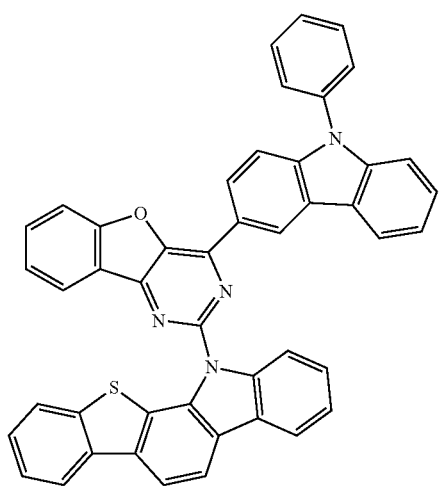
15-12
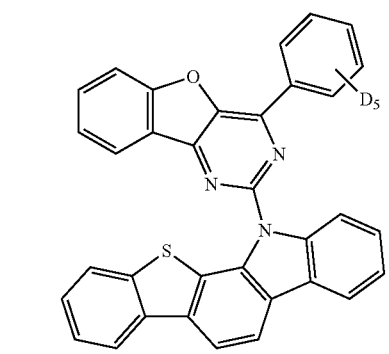
16-1
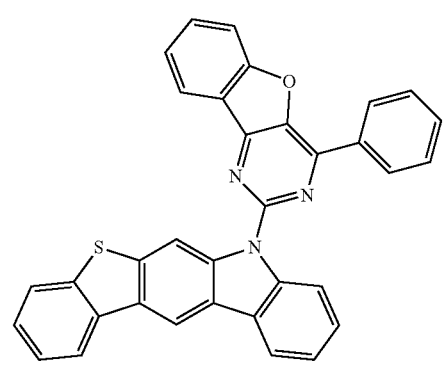
-continued
16-2
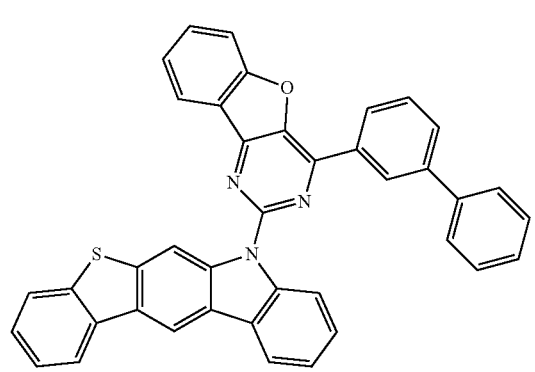
16-3
16-4
16-5
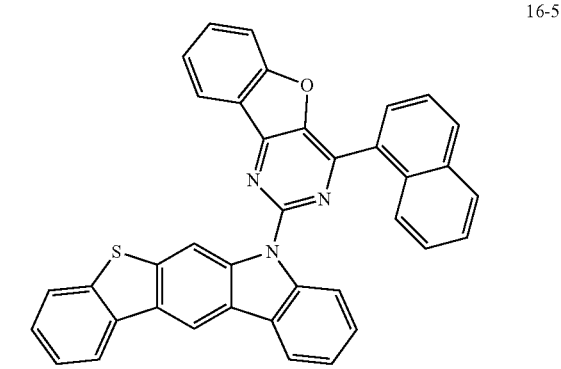

16-6
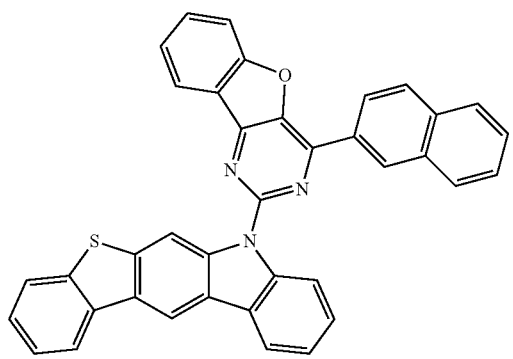
16-7
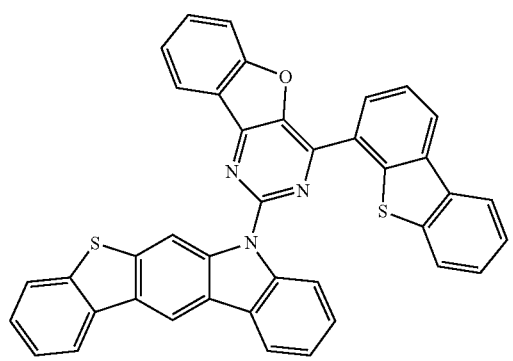
16-8
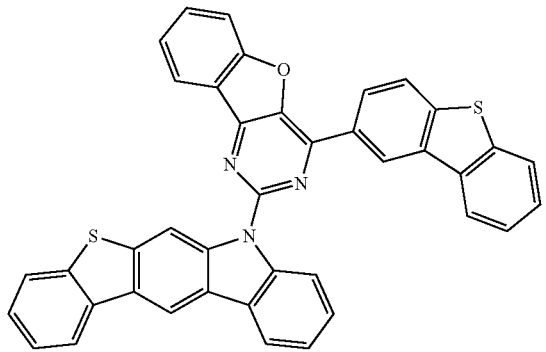
16-9
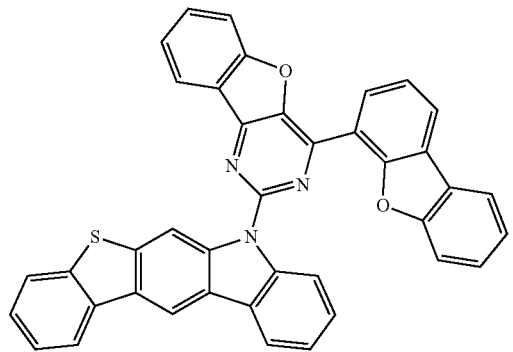
16-10
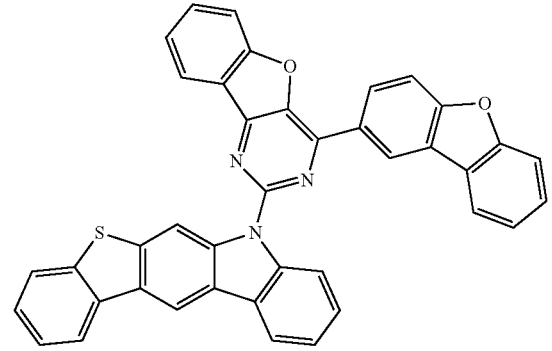
16-11
16-12
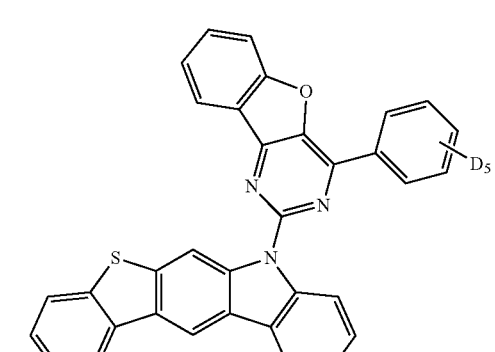
17-1
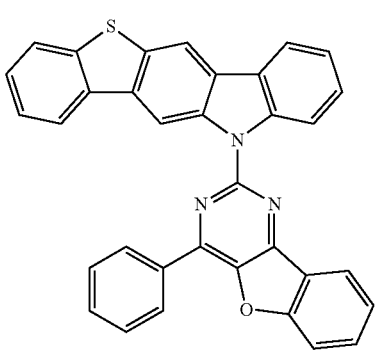

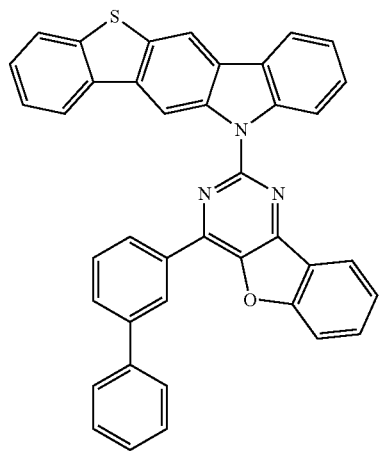
17-2
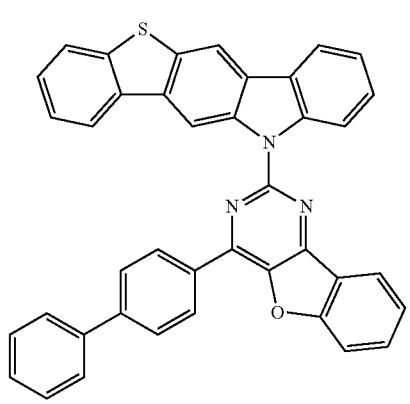
17-3
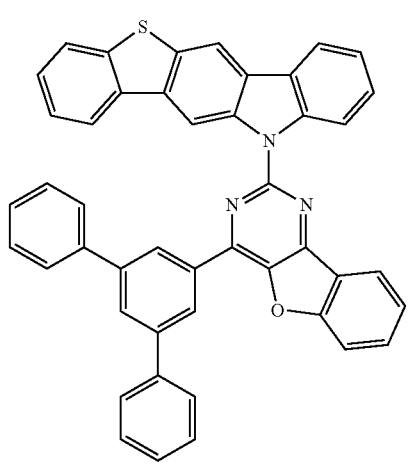
17-4
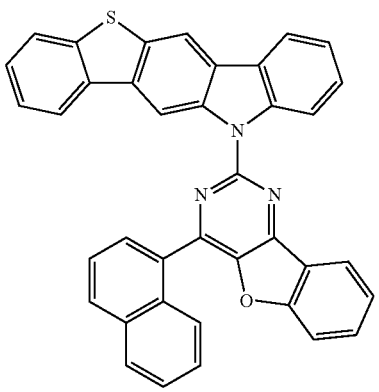
17-5
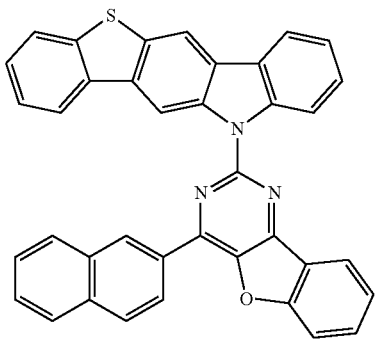
17-6
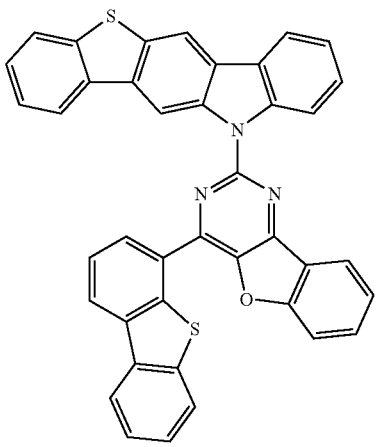
17-7
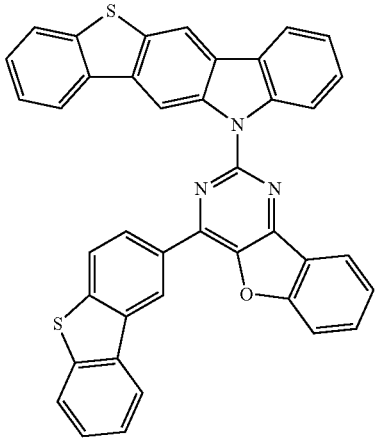
17-8

17-9
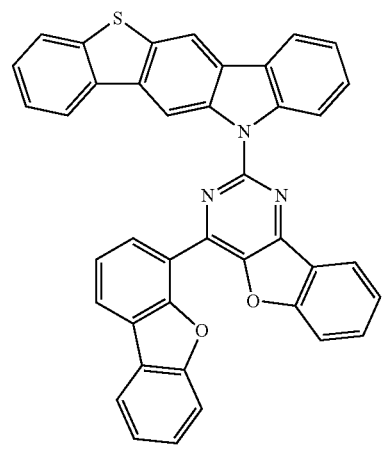
17-10
17-11
17-12
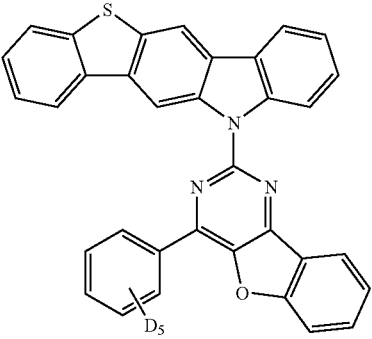
18-1
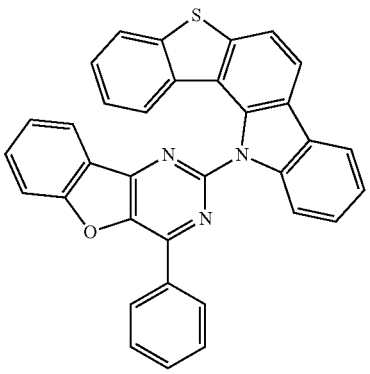
18-2
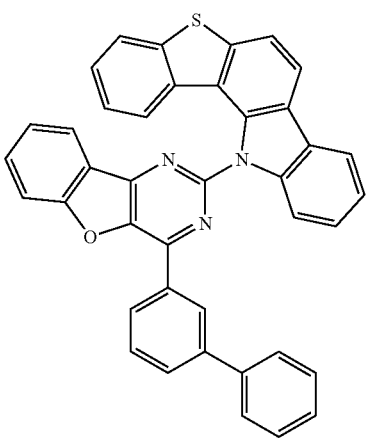
18-3
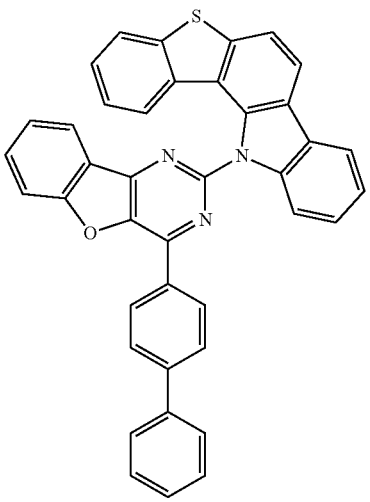

18-4
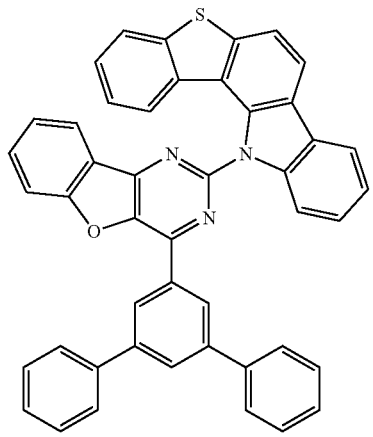
18-5
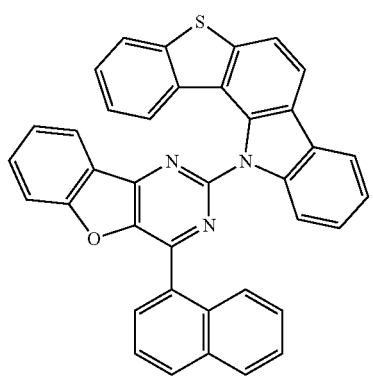
18-6
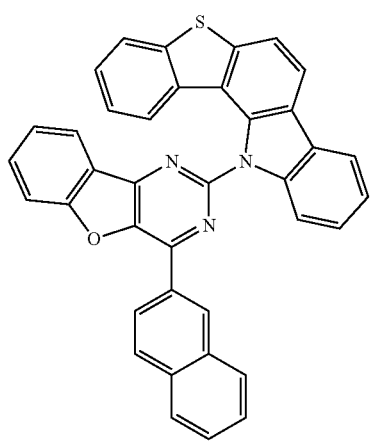
18-7
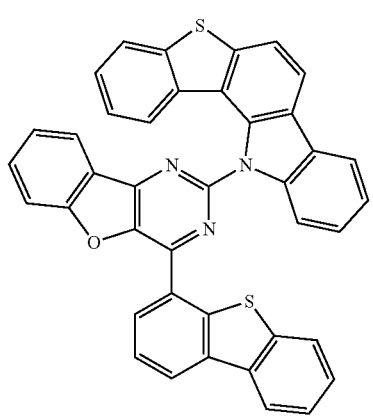
18-8
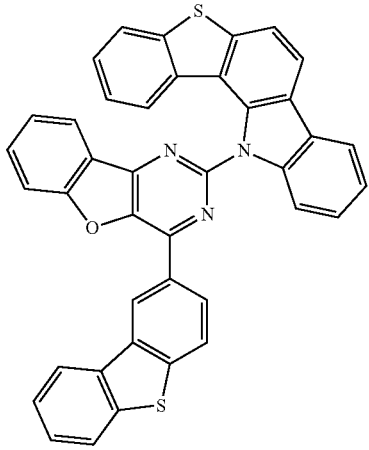
18-9
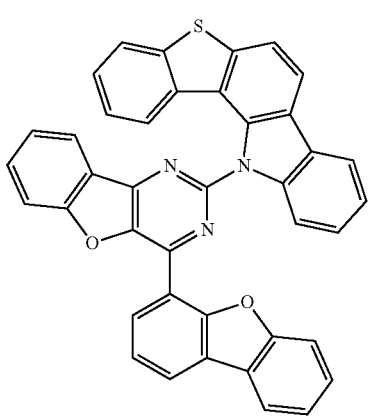
18-10
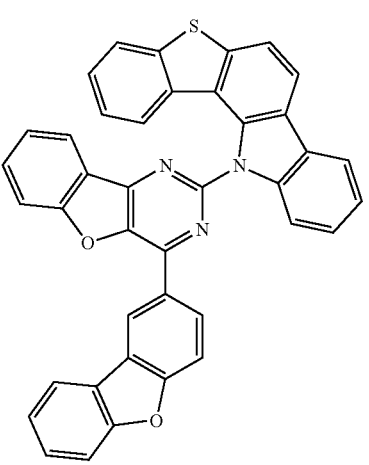

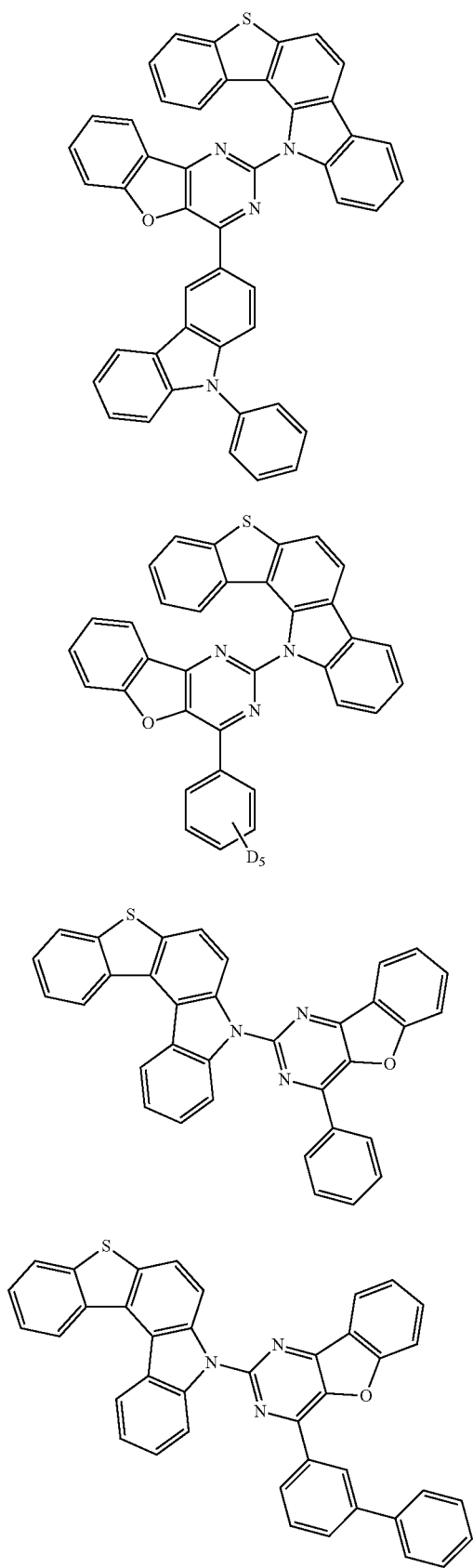
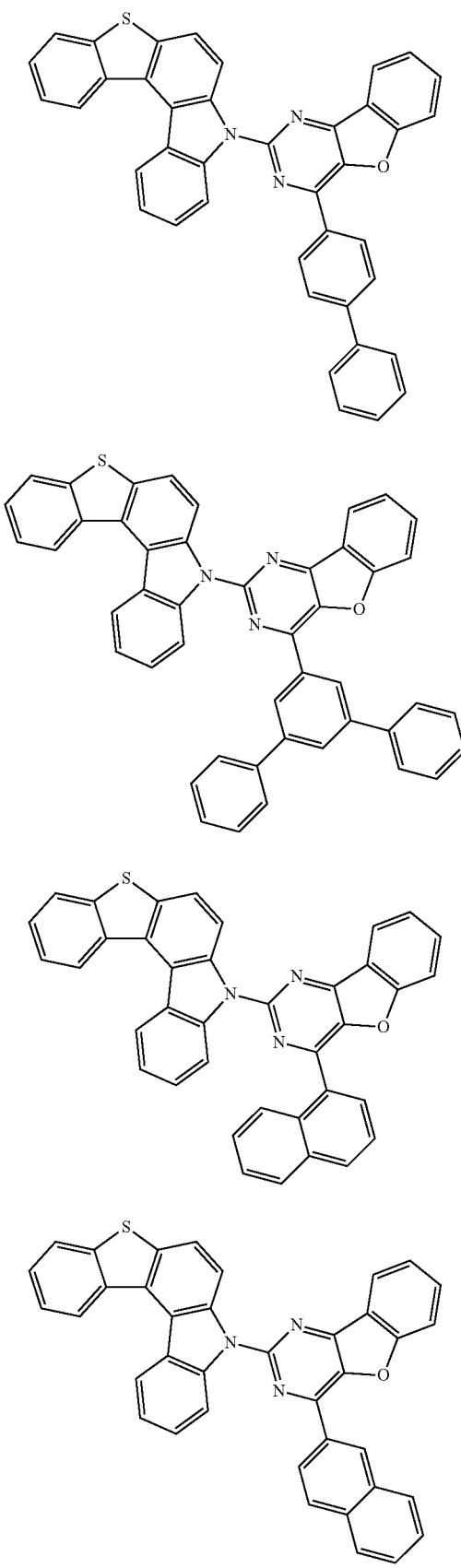

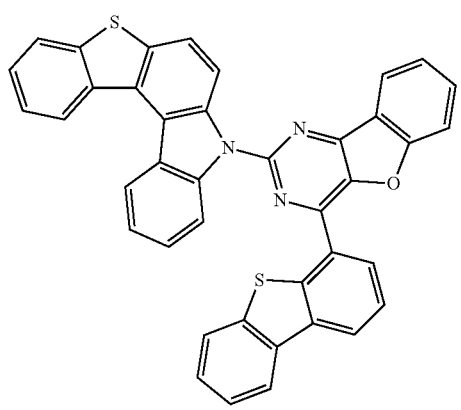
19-7
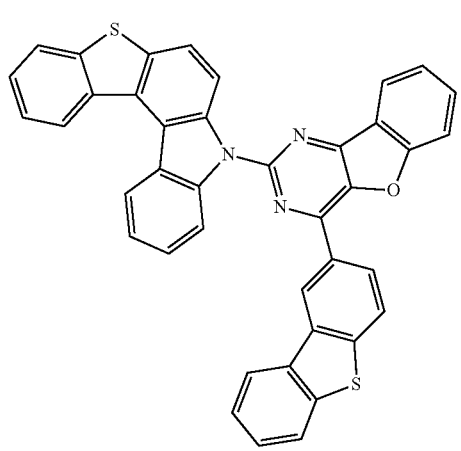
19-8
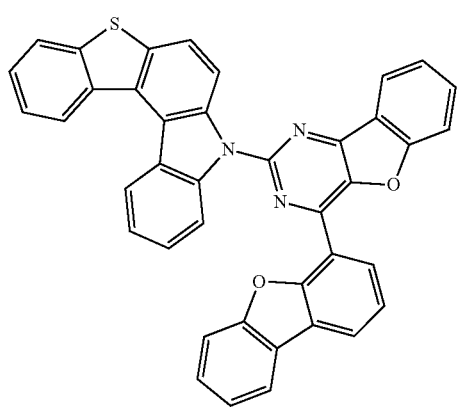
19-9
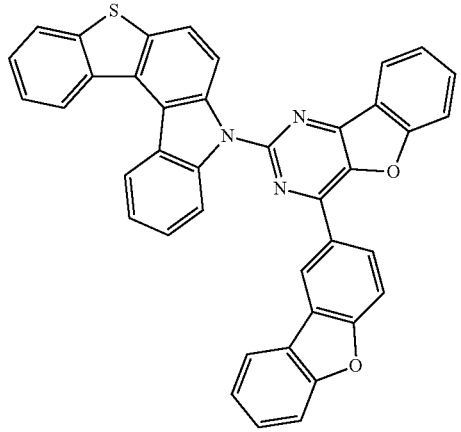
19-10
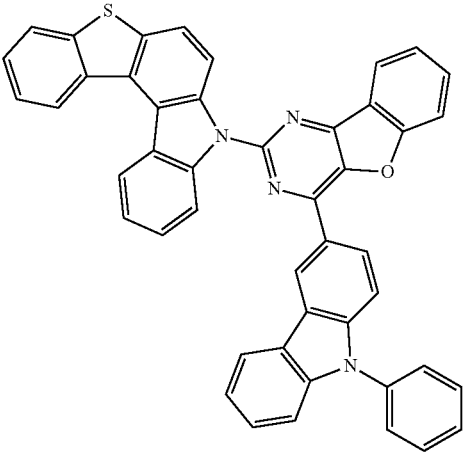
19-11
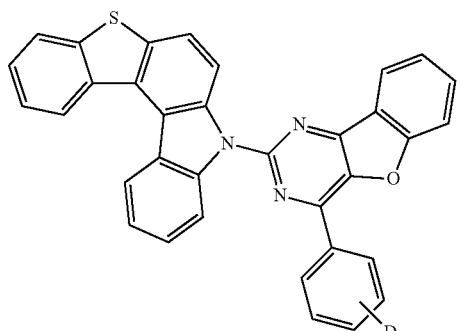
19-12
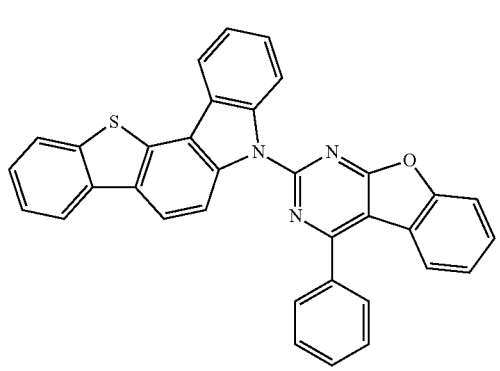
20-1

-continued
20-2
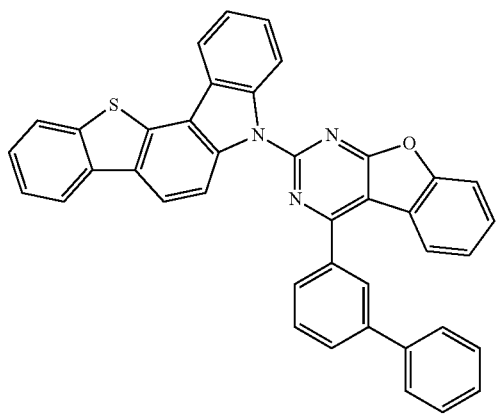
20-3
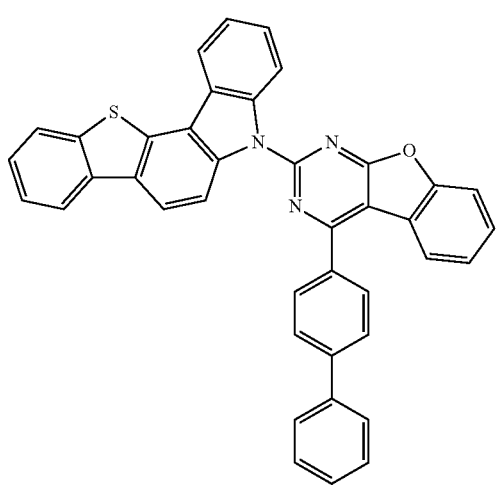
20-4
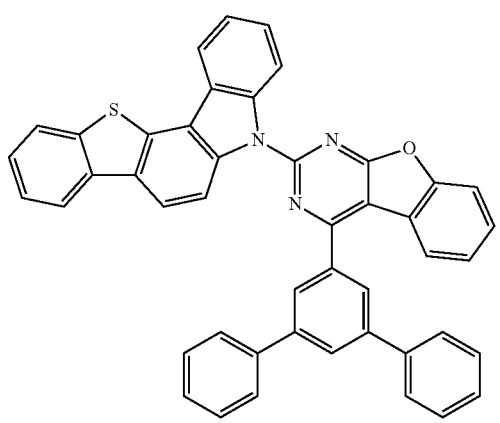
-continued
20-5
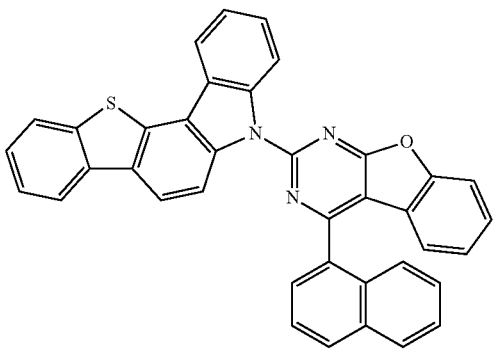
20-6
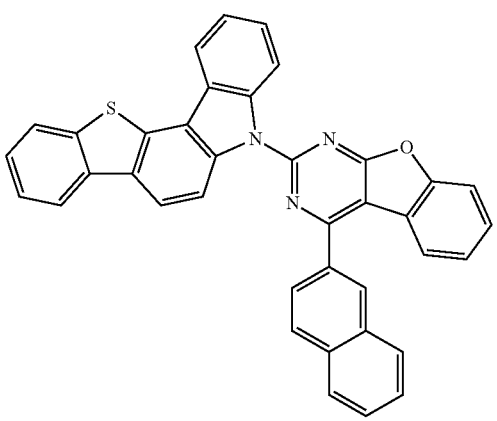
20-7
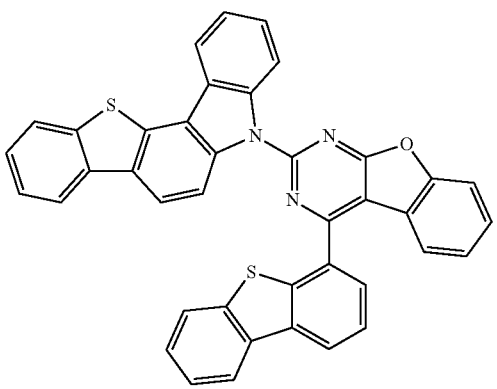
20-8
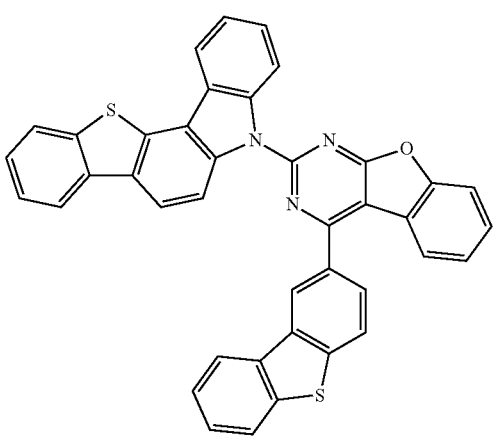

20-9
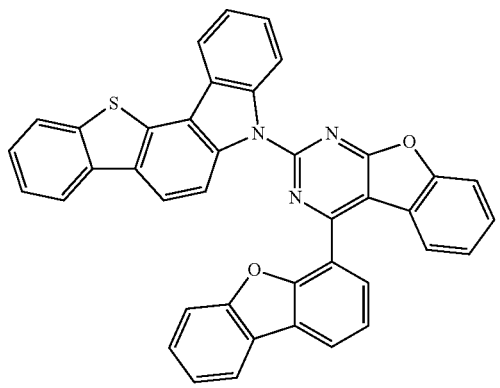
20-10
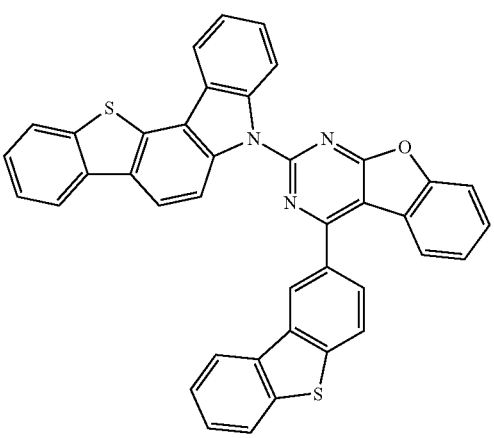
20-11
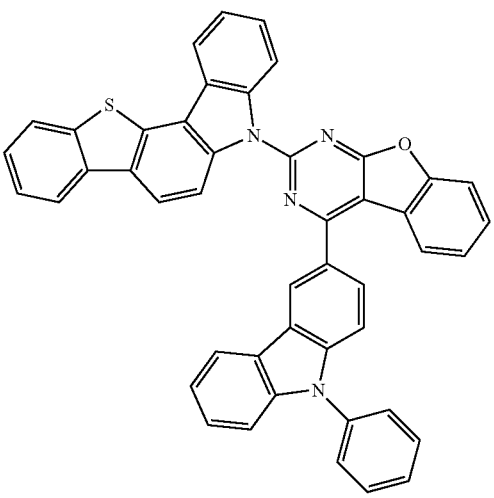
20-12
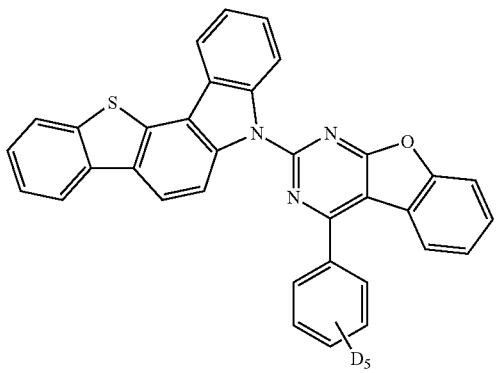
21-1
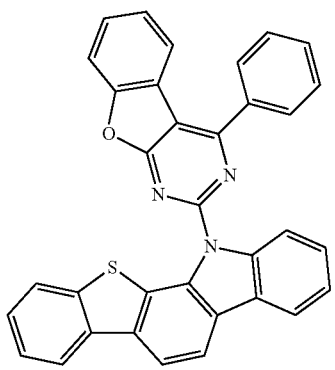
21-2
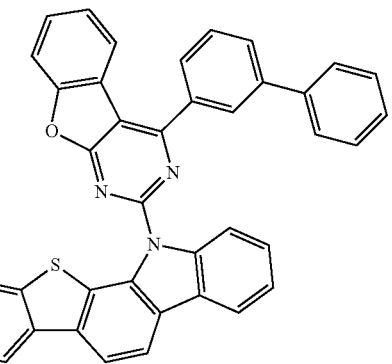
21-3
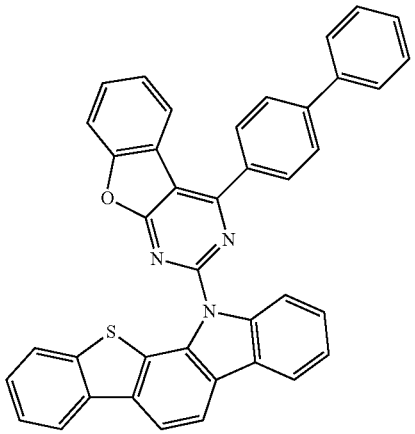

-continued
21-4
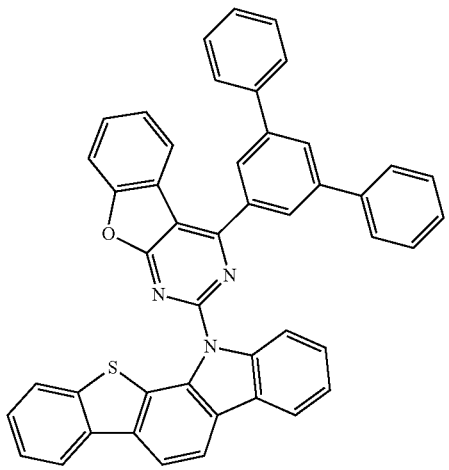
21-5
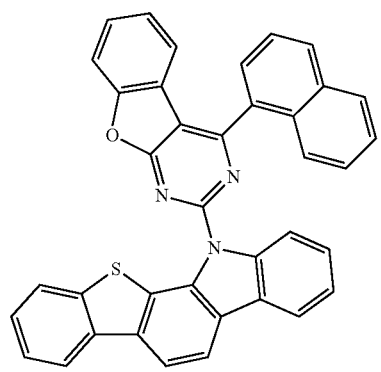
21-6
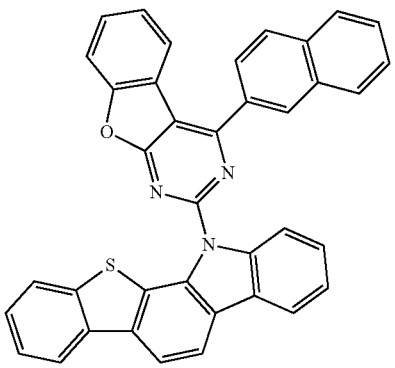
21-7
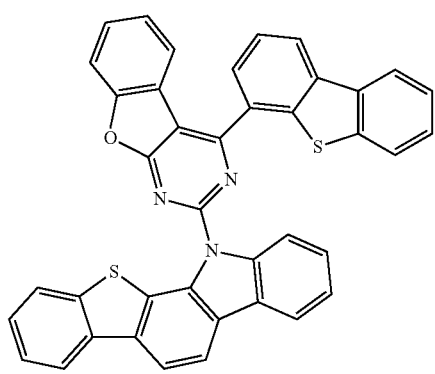
-continued
21-8
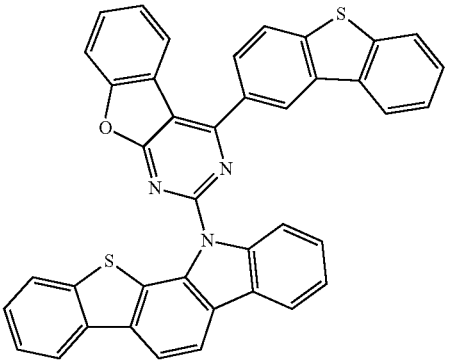
21-9
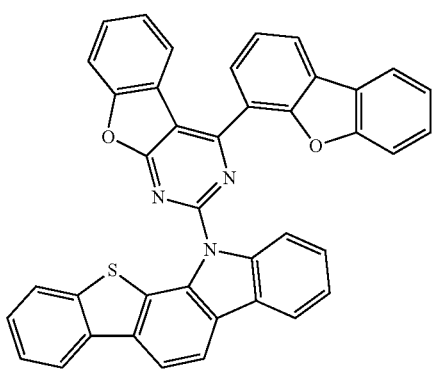
21-10
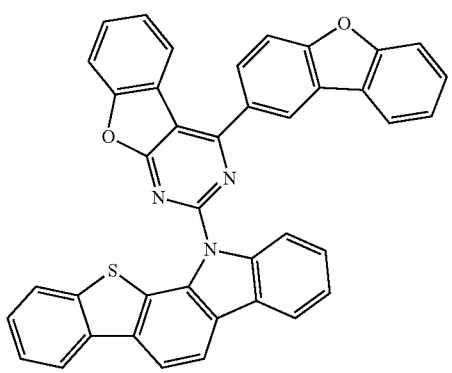
21-11
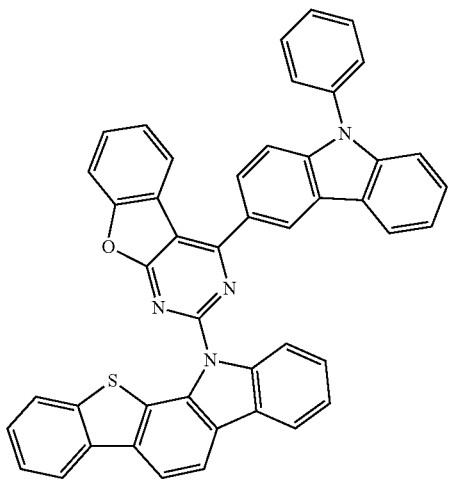

21-12
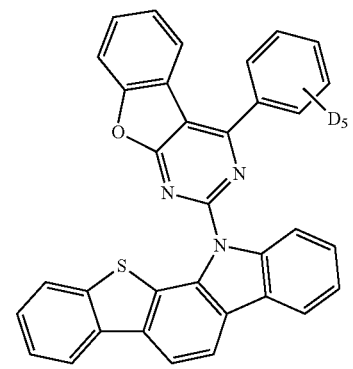
22-1
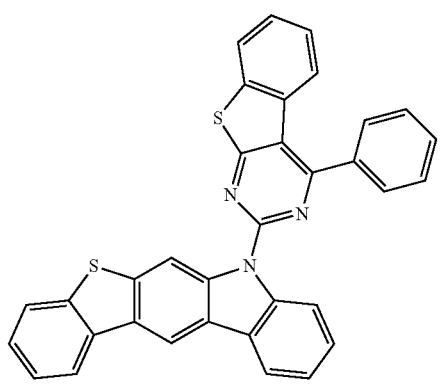
22-2
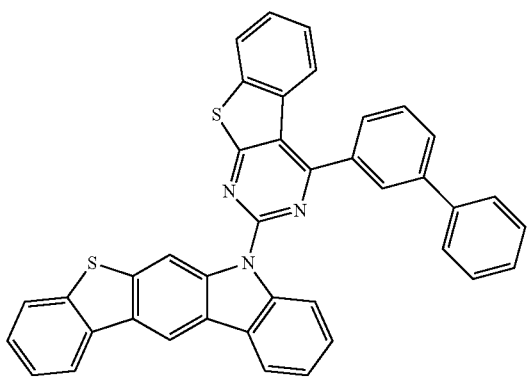
22-3
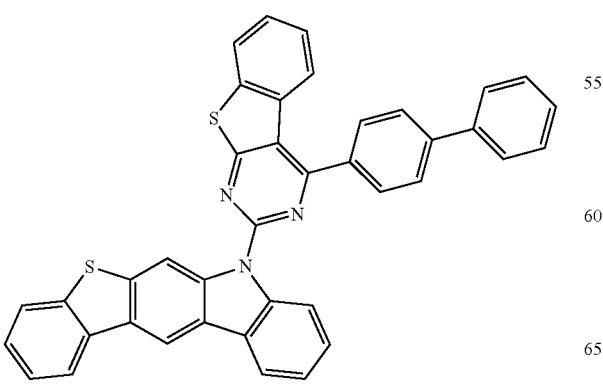
22-4
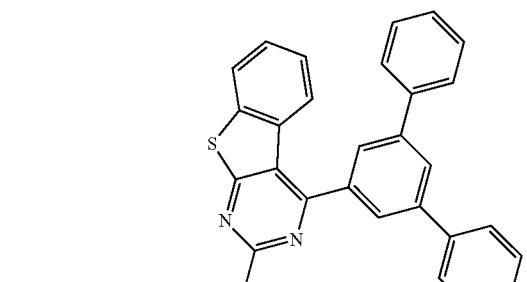
22-5
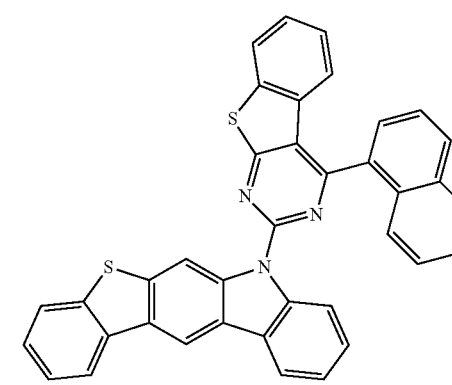
22-6
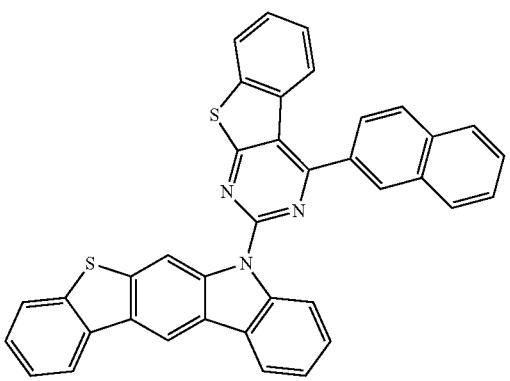
22-7
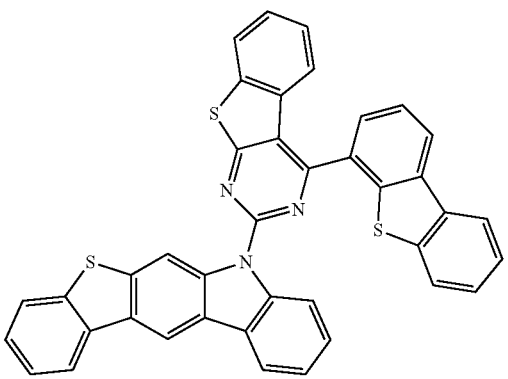

22-8
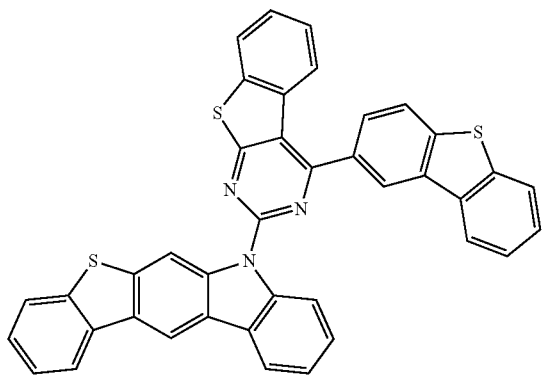
22-9
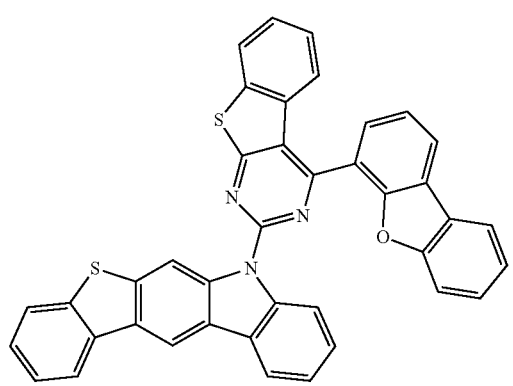
22-10
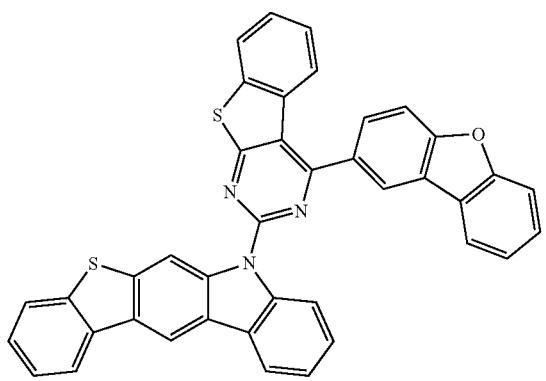
22-11
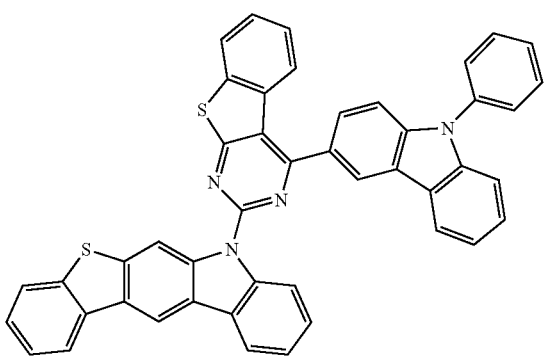
22-12
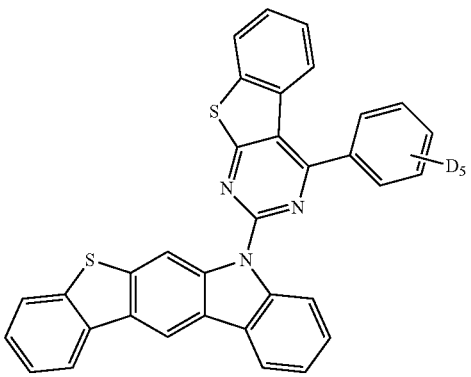
23-1
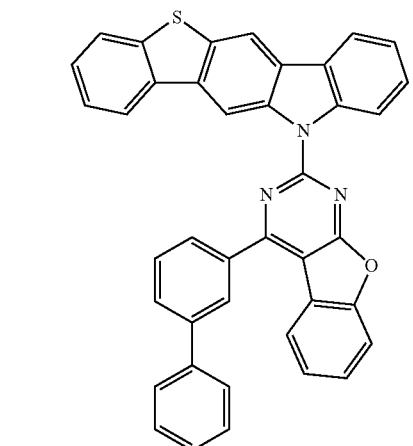
23-2
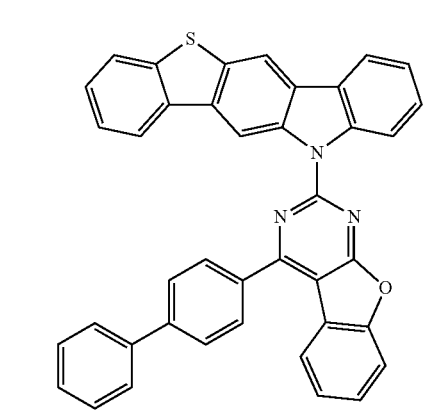
23-3
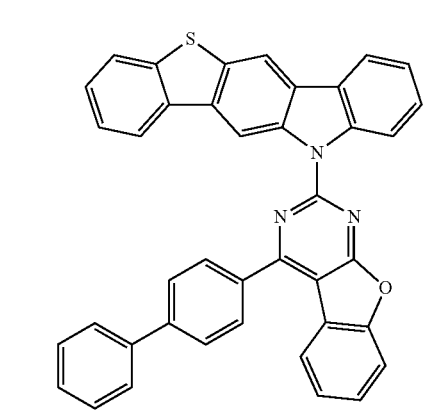

23-4
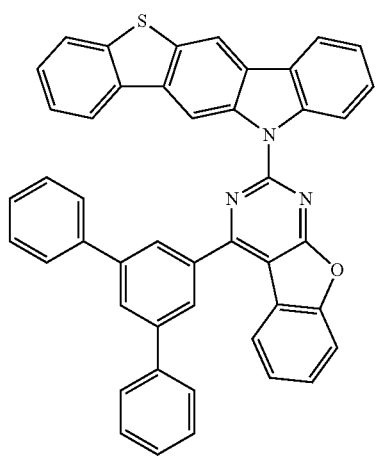
23-5
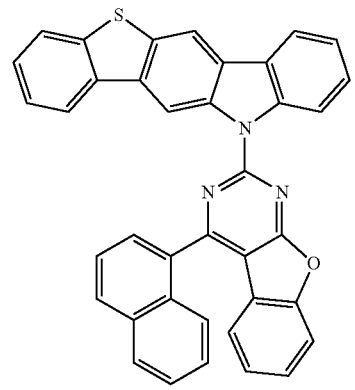
23-6
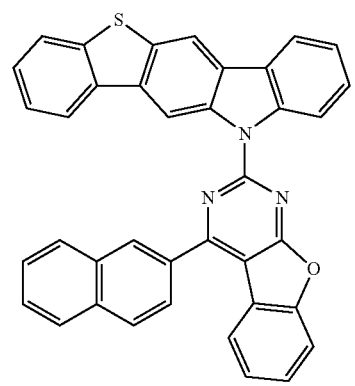
23-7
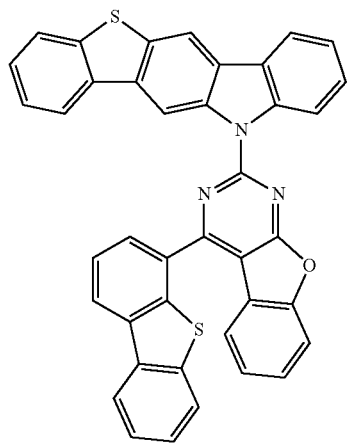
23-8
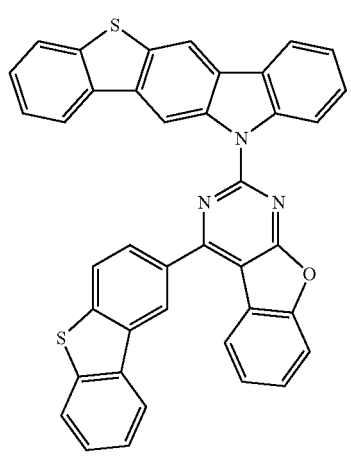
23-9
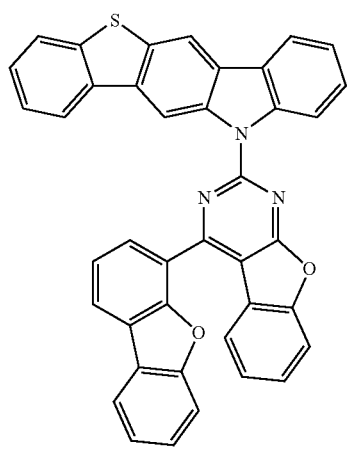

23-10
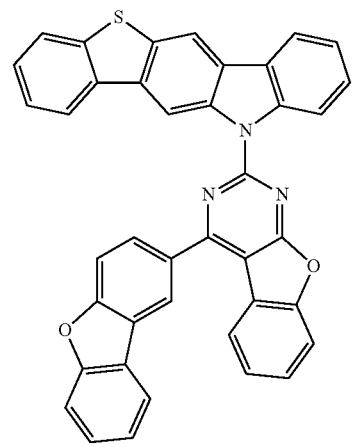
23-11
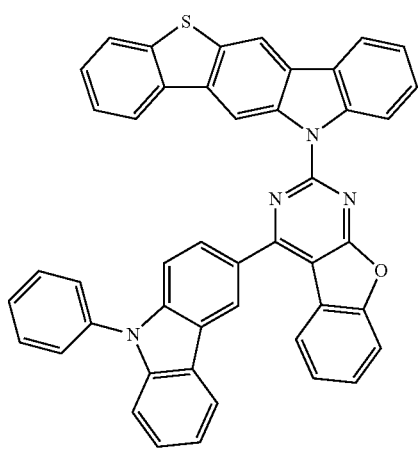
23-12
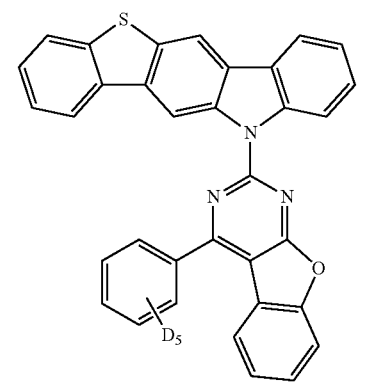
24-1
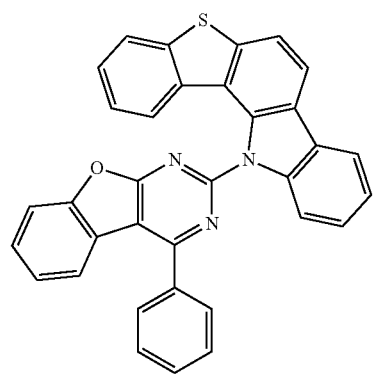
24-2
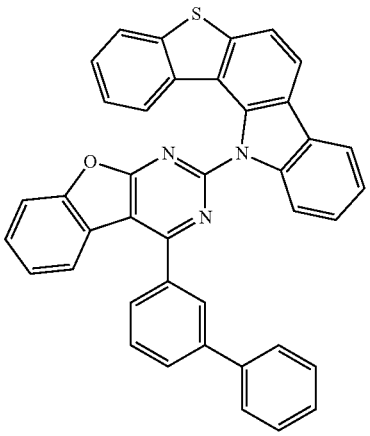
24-3
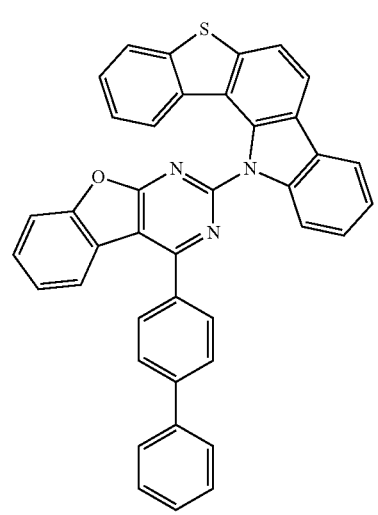
24-4
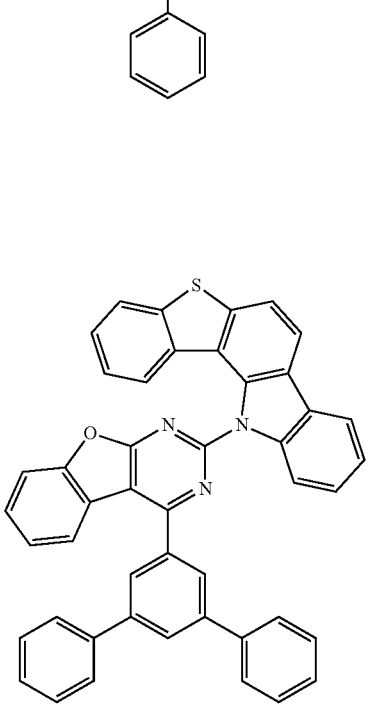

24-5
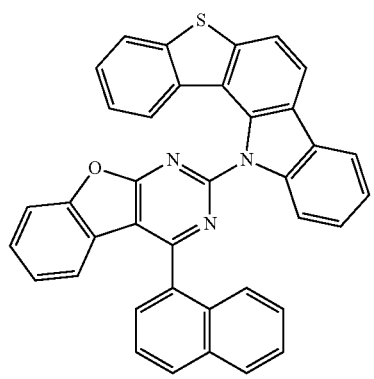
24-6
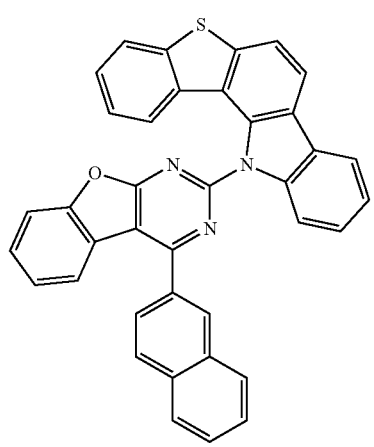
24-7
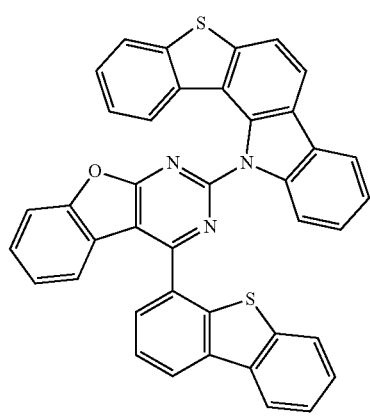
24-8
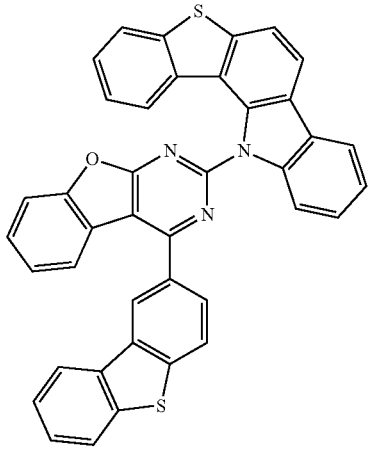
24-9
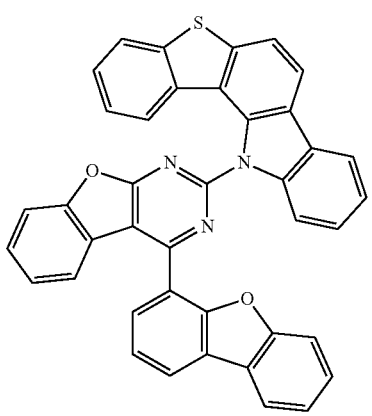
24-10
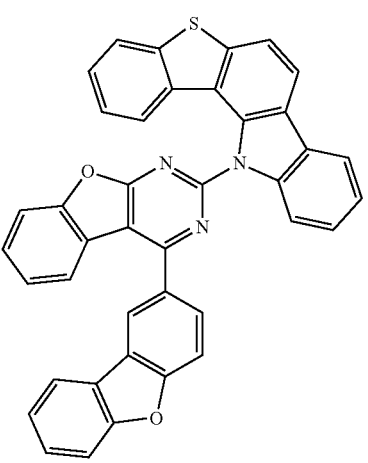

-continued
24-11
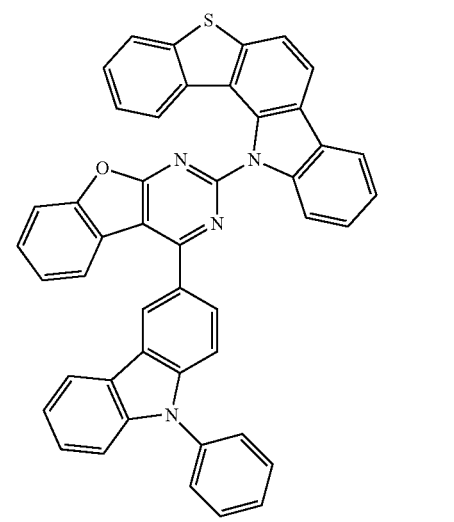
24-12
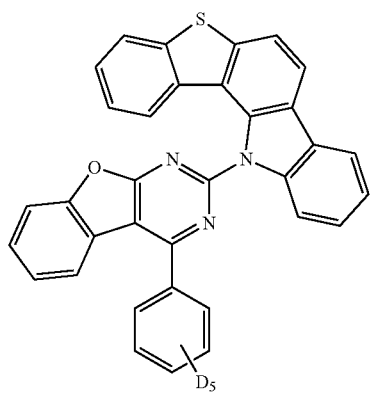
25-1
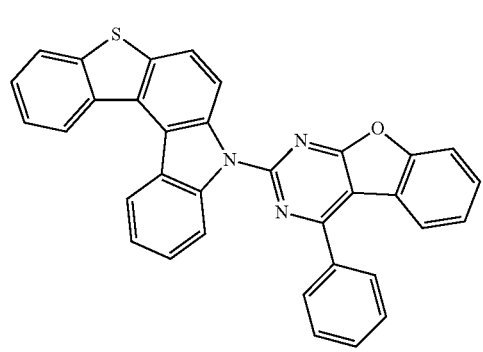
25-2
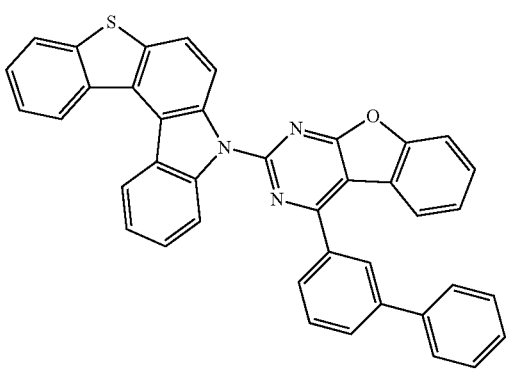
-continued
25-3
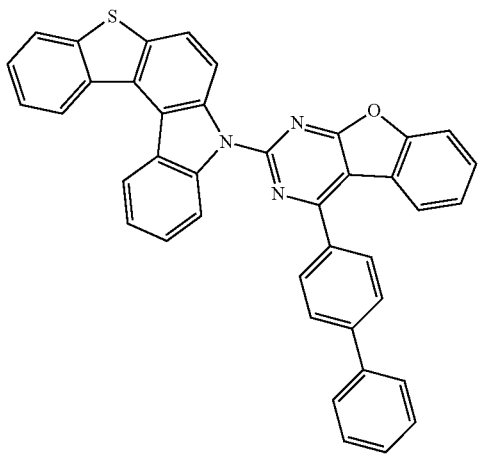
25-4
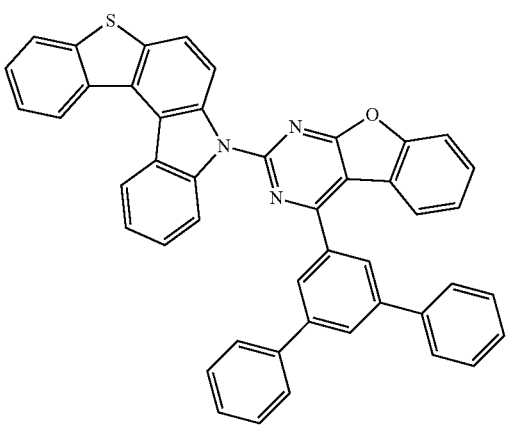
25-5
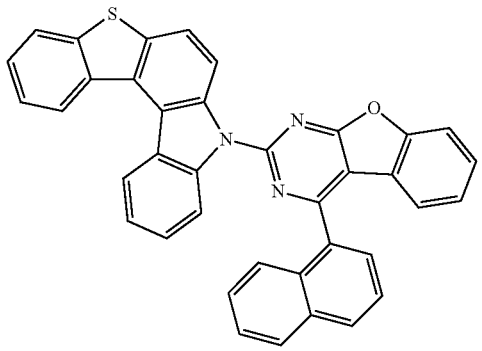

25-6
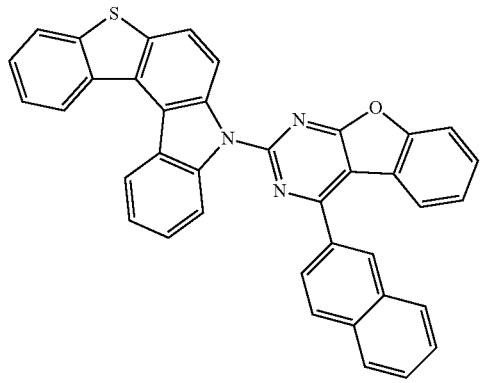
25-9
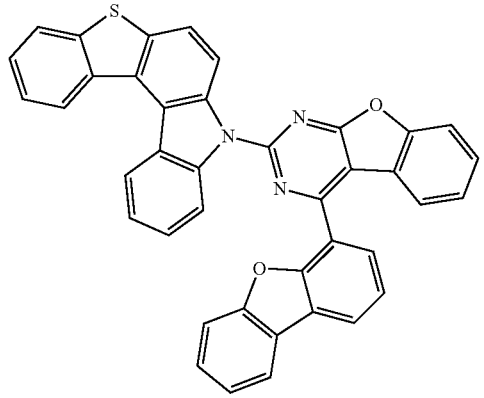
25-7
25-10
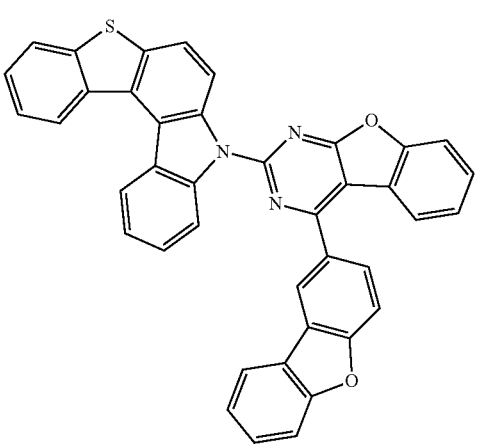
25-8
25-11
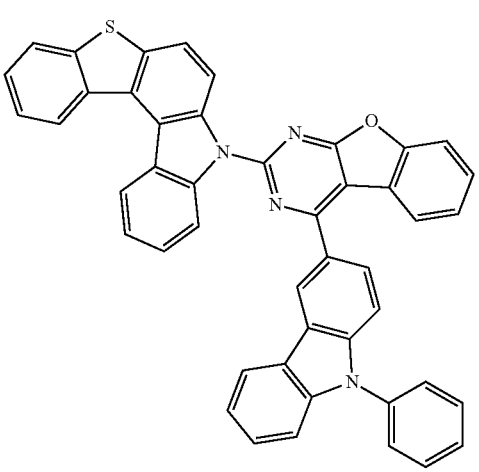

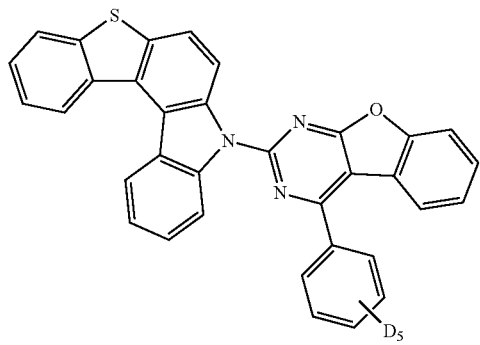

25-12

In another aspect of the present invention, there is provided a compound for an organic electric element represented by Formula 1 above.

In another aspect of the present invention, there is provided an organic electric element comprising the compound represented by Formula 1 above.

The organic electric element can comprise a first electrode, a second electrode, and an organic material layer disposed between the first electrode and the second electrode, wherein the organic material layer may comprise the compound represented by Formula 1. The compound by represented Formula 1 may be contained in at least one layer of a hole injection layer, a hole transport layer, an emission-auxiliary layer, and a light emitting layer of the organic material layer. In order words, the compound represented by Formula 1 may be used as materials of a hole injection layer, a hole transport layer, an emission-auxiliary layer, or a light emitting layer. Preferably, compound by represented Formula 1 may be used as phosphorescent host material of a light emitting layer.

Preferably, there is provided an organic electric element of which an organic material layer comprise a compound represented by Formulas 2 or 3.

Preferably, there is provided an organic electric element of which an organic material layer comprise a compound represented by Formulas 4 or 9.

Preferably, there is provided an organic electric element of which an organic material layer comprise at least one of compounds 2-1 to 2-12, 3-1 to 3-12, 4-1 to 4-12, 5-1 to 5-12, 6-1 to 6-12, 7-1 to 7-12, 8-1 to 8-12, 9-1 to 9-12, 10-1 to 10-12, 11-1 to 11-12, 12-1 to 12-12, 13-1 to 13-12, 14-1 to 14-12, 15-1 to 15-12, 16-1 to 16-12, 17-1 to 17-12, 18-1 to 18-12, 19-1 to 19-12, 20-1 to 20-12, 21-1 to 21-12, 22-1 to 22-12, 23-1 to 23-12, 24-1 to 24-12, and 25-1 to 25-12.

Preferably, compound included in the organic material layer may be a single compound or a mixture of two or more compounds represented by Formula 1. For example, compound 2-1 alone or a mixture of compounds 2-1 and 2-2 may be used as a host material of a light emitting layer.

A organic material layer may be formed by spin coating process, nozzle printing process, inkjet printing process, slot coating or dip coating process, or roll-to-roll process.

In another aspect of the present invention, the present invention provides an organic electric element further including a layer to improve luminescent efficiency which is formed on at least one of the sides the first or second electrodes, which is opposite to the organic material layer. Preferably, a layer to improve luminescent efficiency may comprise compound by represented Formula 1.

In another aspect of the present invention, the present invention provides an electronic device comprising a display device and a control unit for controlling the display device, wherein the display device comprises an organic electric element comprising an organic material layer and the organic material layer comprises a compound according to the present invention.

Here, the organic electric element may be any one of an organic light emitting diode, an organic solar cell, an organic photo conductor, an organic transistor, and an element for monochromatic or white illumination.

Hereinafter, Synthesis method of the inventive compound according to one embodiment of the present invention and Preparation method of an organic electric element will be described in detail by way of example. However, the following examples are only for illustrative purposes and are not intended to limit the scope of the present invention.

SYNTHESIS EXAMPLE

The compounds (final products) of the present invention represented by Formula 1 can be synthesized by reaction of Sub 1 and Sub 2 as illustrated in, but not limited to, the following Reaction Scheme 1.

<Reaction Scheme 1>

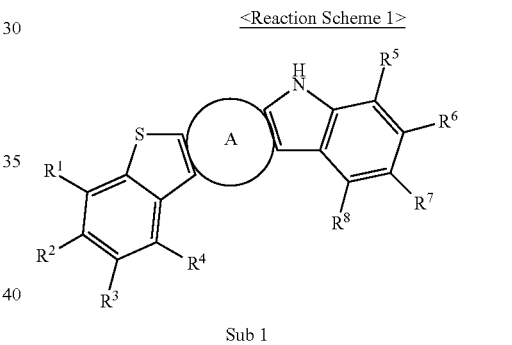

Sub 1

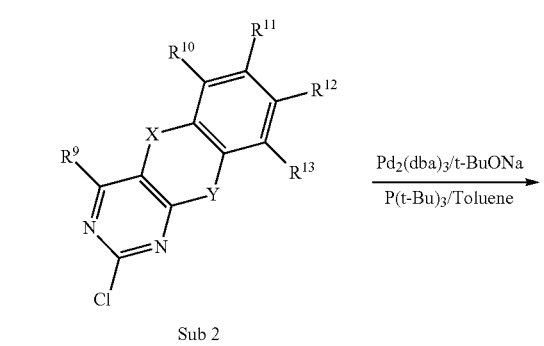

Sub 2

93
-continued

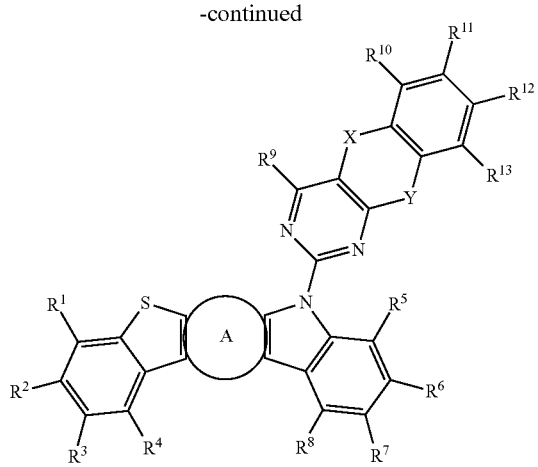

Final products

I. Synthesis Example of Sub 1

Compound Sub 1 of Reaction Scheme 1 can be synthesized, but not limited to, by the following Reaction Scheme 2.

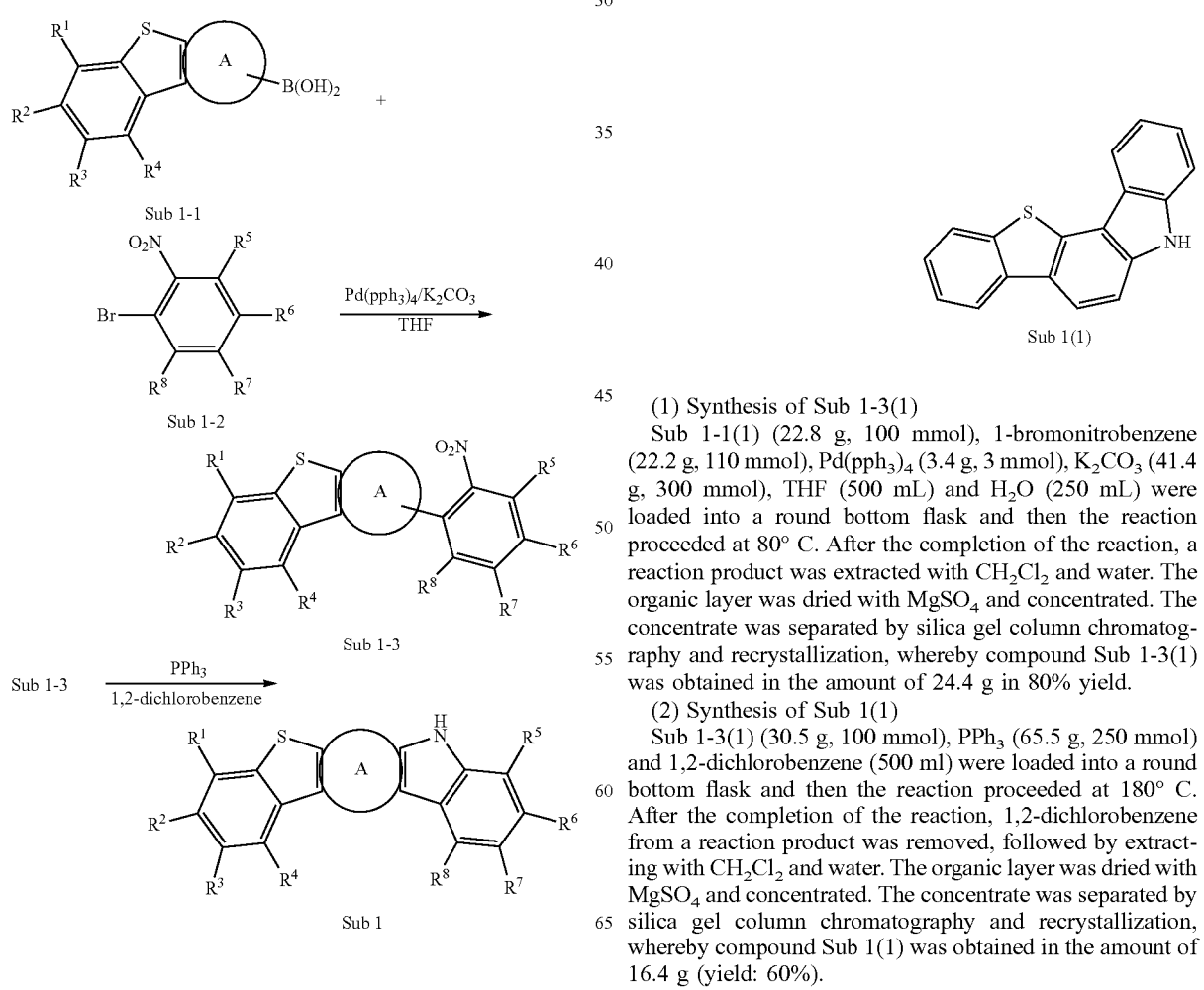

94

1. Synthesis of Sub 1(2)

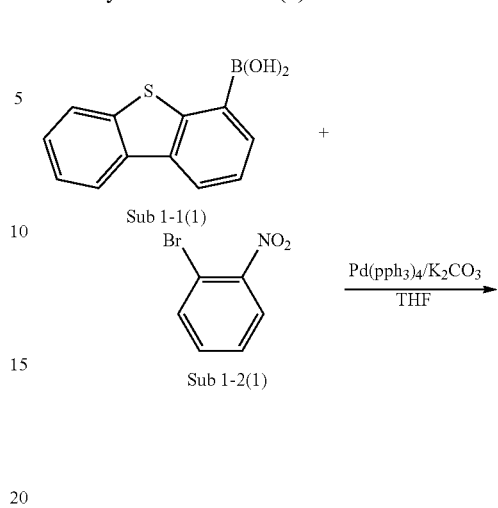

(1) Synthesis of Sub 1-3(1)

Sub 1-1(1) (22.8 g, 100 mmol), 1-bromonitrobenzene (22.2 g, 110 mmol), Pd(pph₃)₄ (3.4 g, 3 mmol), K₂CO₃ (41.4 g, 300 mmol), THF (500 mL) and H₂O (250 mL) were loaded into a round bottom flask and then the reaction proceeded at 80° C. After the completion of the reaction, a reaction product was extracted with CH₂Cl₂ and water. The organic layer was dried with MgSO₄ and concentrated. The concentrate was separated by silica gel column chromatography and recrystallization, whereby compound Sub 1-3(1) was obtained in the amount of 24.4 g in 80% yield.

(2) Synthesis of Sub 1(1)

Sub 1-3(1) (30.5 g, 100 mmol), PPh₃ (65.5 g, 250 mmol) and 1,2-dichlorobenzene (500 ml) were loaded into a round bottom flask and then the reaction proceeded at 180° C. After the completion of the reaction, 1,2-dichlorobenzene from a reaction product was removed, followed by extracting with CH₂Cl₂ and water. The organic layer was dried with MgSO₄ and concentrated. The concentrate was separated by silica gel column chromatography and recrystallization, whereby compound Sub 1(1) was obtained in the amount of 16.4 g (yield: 60%).

2. Synthesis of Sub 1(2) and Sub 1(3)

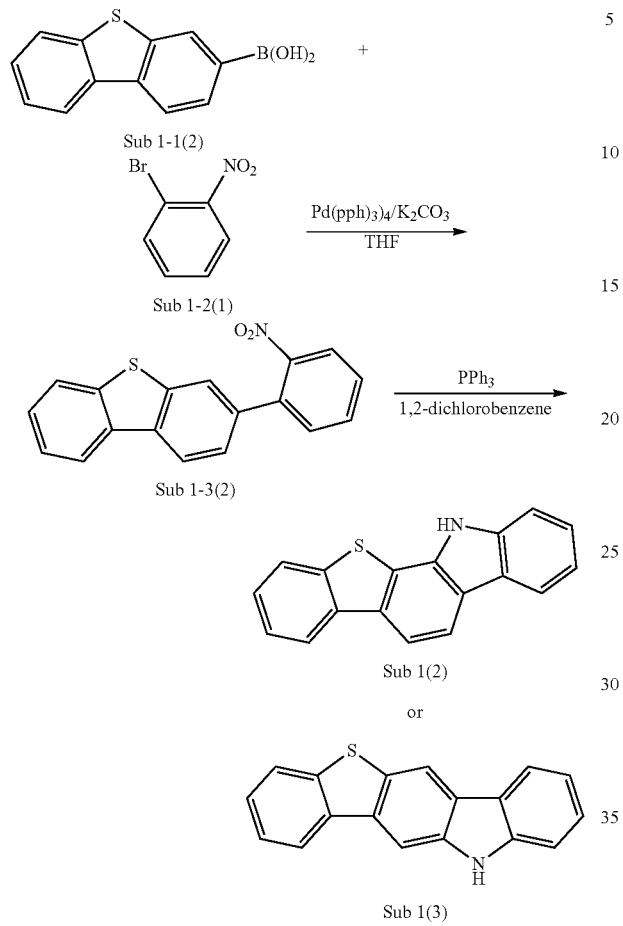

(1) Synthesis of Synthesis of Sub 1-3(2)

Compound Sub 1-3(2) was obtained in the amount of 24.4 g (yield: 80%) where Sub 1-1(2) (22.8 g, 100 mmol), 1-bromonitrobenzene (22.2 g, 110 mmol), Pd(pph$_3$)$_4$ (3.4 g, 3 mmol), K$_2$CO$_3$ (41.4 g, 300 mmol), THF (500 mL) and H$_2$O (250 mL) were used in the same manner as described above for the synthesis of compound Sub 1-3(1).

(2) Synthesis of Sub 1(2) and Sub 1(3)

Compounds Sub 1(2) and Sub 1(3) were each obtained in the amount of 5.7 g (yield: 21%) and 8.7 g (yield: 32%) where Sub 1-3(2) (30.5 g, 100 mmol), PPh$_3$ (65.5 g, 250 mmol) and 1,2-dichlorobenzene (500 ml) were used in the same manner as described above for the synthesis of compound Sub 1(1).

3. Synthesis of Synthesis of Sub 1(4) and Sub 1(5)

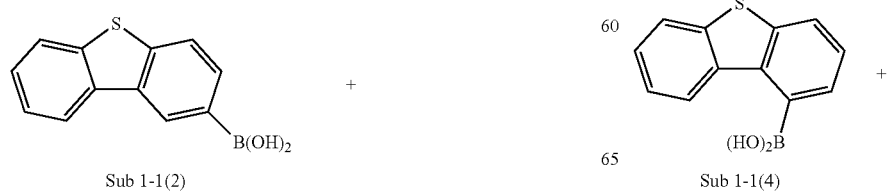

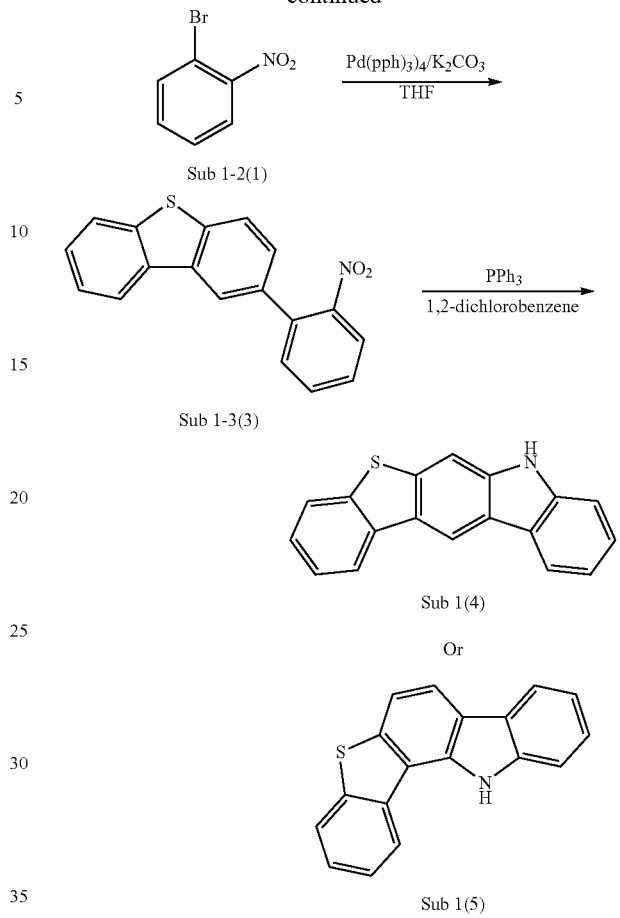

(1) Synthesis of Sub 1-3(3)

Compound Sub 1-3(3) was obtained in the amount of 25.0 g (yield: 82%) where Sub 1-1(3) (22.8 g, 100 mmol), 1-bromonitrobenzene (22.2 g, 110 mmol), Pd(pph$_3$)$_4$ (3.4 g, 3 mmol), K$_2$CO$_3$ (41.4 g, 300 mmol), THF (500 mL) and H$_2$O (250 mL) were used in the same manner as described above for the synthesis of compound Sub 1-3(1).

(2) Synthesis of Sub 1(4) and Sub 1(5)

Compounds Sub 1(4) and Sub 1(5) were each obtained in the amount of 6.8 g (yield: 25%) and 10.1 g (yield: 37%) where Sub 1-3(3) (30.5 g, 100 mmol), PPh$_3$ (65.5 g, 250 mmol) and 1,2-dichlorobenzene (500 ml) were used in the same manner as described above for the synthesis of compound Sub 1(1).

4. Synthesis of Sub 1(6)

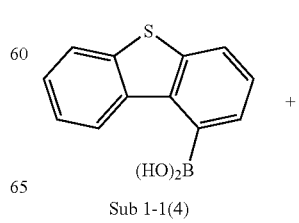

-continued

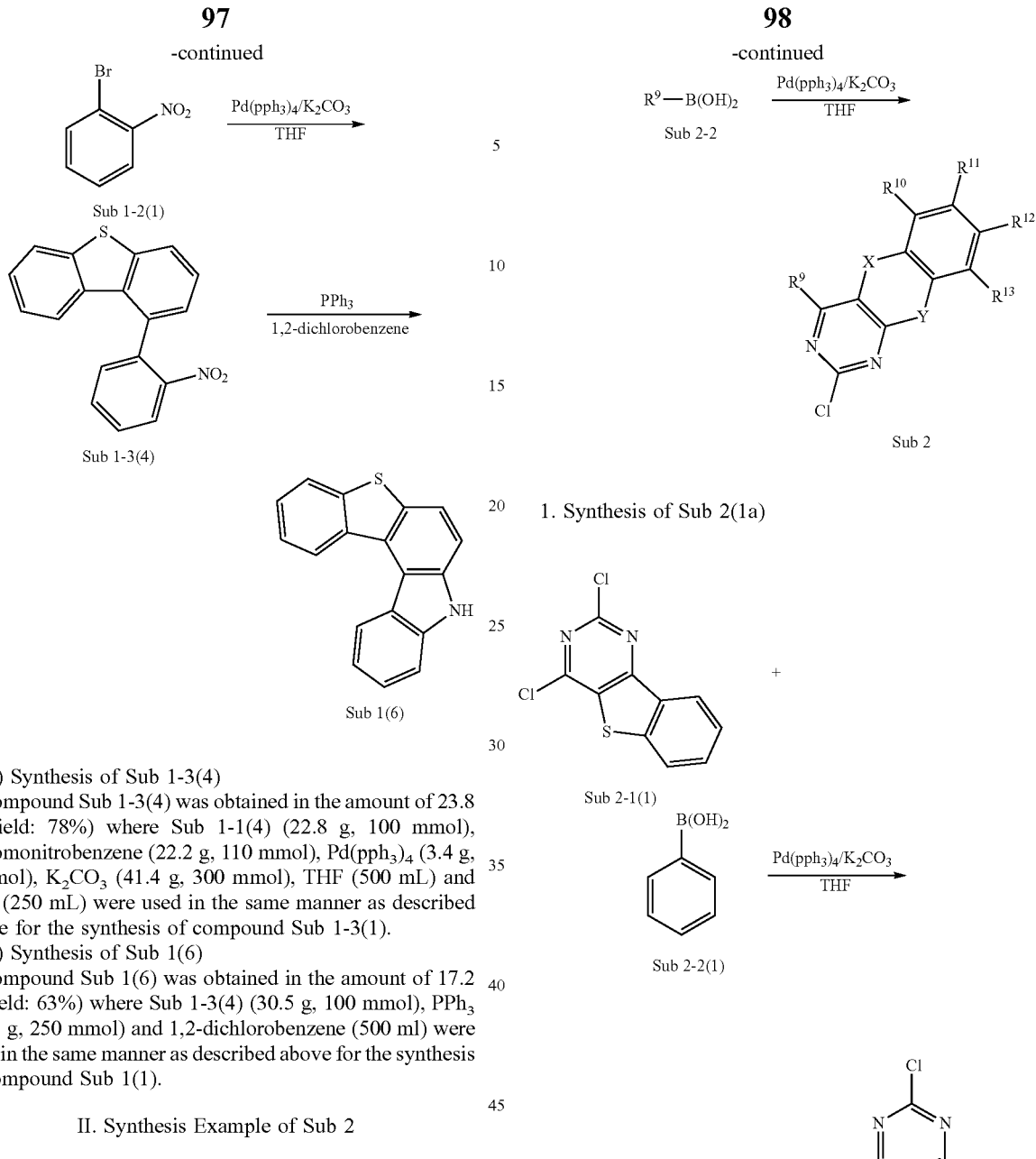

(1) Synthesis of Sub 1-3(4)

Compound Sub 1-3(4) was obtained in the amount of 23.8 g (yield: 78%) where Sub 1-1(4) (22.8 g, 100 mmol), 1-bromonitrobenzene (22.2 g, 110 mmol), Pd(pph$_3$)$_4$ (3.4 g, 3 mmol), K$_2$CO$_3$ (41.4 g, 300 mmol), THF (500 mL) and H$_2$O (250 mL) were used in the same manner as described above for the synthesis of compound Sub 1-3(1).

(2) Synthesis of Sub 1(6)

Compound Sub 1(6) was obtained in the amount of 17.2 g (yield: 63%) where Sub 1-3(4) (30.5 g, 100 mmol), PPh$_3$ (65.5 g, 250 mmol) and 1,2-dichlorobenzene (500 ml) were used in the same manner as described above for the synthesis of compound Sub 1(1).

II. Synthesis Example of Sub 2

Compound Sub 2 of the above Reaction Scheme 1 can be synthesized as illustrated in, but not limited to, the following Reaction Scheme 3.

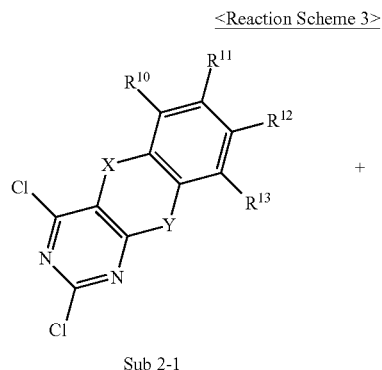

1. Synthesis of Sub 2(1a)

Sub 2-1(1) (5.1 g, 20 mmol) was loaded into a round bottom flask and then Sub 2-2(1) (2.9 g, 24 mmol), Pd(PPh$_3$)$_4$ (0.7 g, 0.6 mmol), NaOH (2.4 g, 60 mmol), THF (60 mL) and water (30 mL) were added. Then, the reactant was heated to reflux at 80~90° C. After the completion of the reaction, a reaction product was diluted with distilled water at room temperature and then extracted with CH$_2$Cl$_2$ and water. The organic layer was dried with MgSO$_4$ and concentrated. The concentrate was separated by silica gel column chromatography and recrystallization, whereby compound Sub 2(1a) was obtained in the amount of 4.8 g in 81% yield.

2. Synthesis of Sub 2(2a)

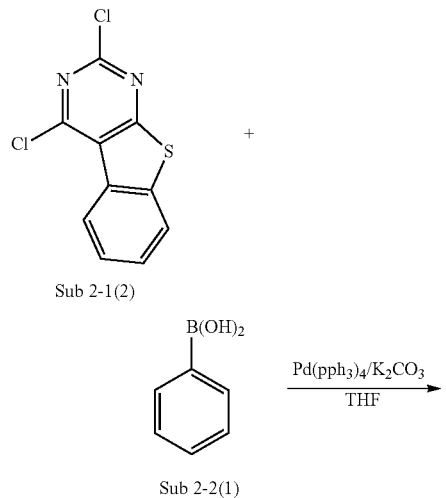

Sub 2-1(2) (5.1 g, 20 mmol) was loaded into a round bottom flask and then Sub 2-2(1) (2.9 g, 24 mmol), Pd(PPh$_3$)$_4$ (0.7 g, 0.6 mmol), NaOH (2.4 g, 60 mmol), THF (60 mL) and water (30 mL) were added. Then, compound Sub 2(2a) was obtained in the amount of 5.0 g (yield: 85%) by using the same manner as described above for the synthesis of compound Sub 2(1a).

3. Synthesis of Sub 2(3a)

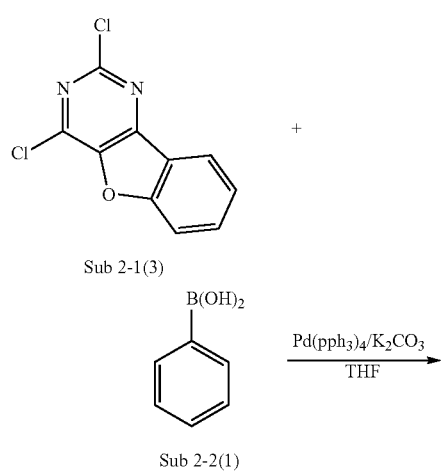

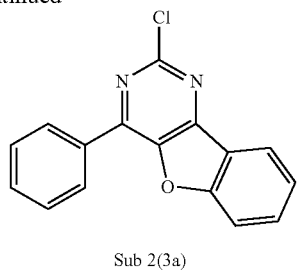

Sub 2-1(3) (4.8 g, 20 mmol) was loaded into a round bottom flask and then Sub 2-2(1) (2.9 g, 24 mmol), Pd(PPh$_3$)$_4$ (0.7 g, 0.6 mmol), NaOH (2.4 g, 60 mmol), THF (60 mL) and water (30 mL) were added. Then, compound Sub 2(3a) was obtained in the amount of 4.9 g (yield: 87%) by using the same manner as described above for the synthesis of compound Sub 2(1a).

4. Synthesis of Sub 2(4a)

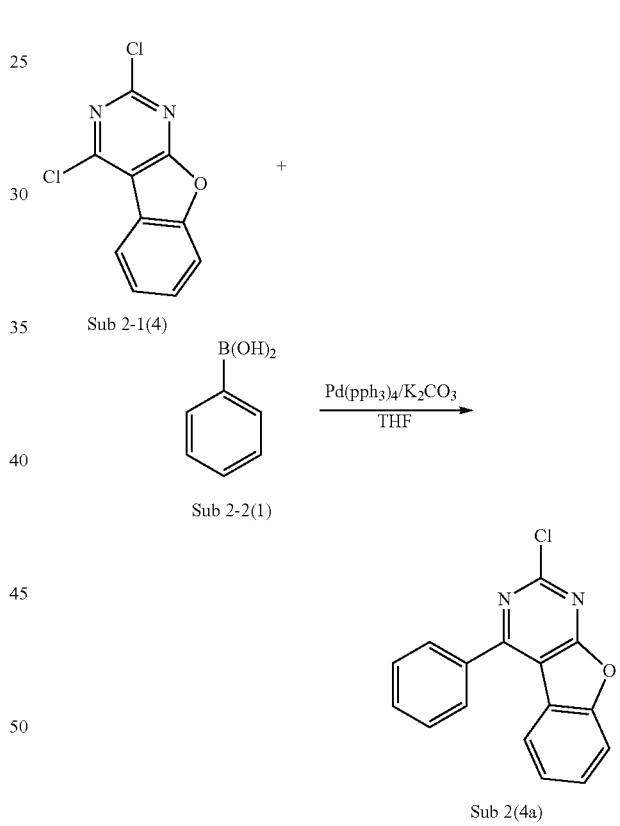

Sub 2-1(4) (4.8 g, 20 mmol) was loaded into a round bottom flask and then Sub 2-2(1) (2.9 g, 24 mmol), Pd(PPh$_3$)$_4$ (0.7 g, 0.6 mmol), NaOH (2.4 g, 60 mmol), THF (60 mL) and water (30 mL) were added. Then, compound Sub 2(4a) was obtained in the amount of 5.0 g (yield: 89%) by using the same manner as described above for the synthesis of compound Sub 2(1a).

Meanwhile, the compounds comprised in Sub 2 may be, but not limited to, the following compounds, and Table 1 below shows FD-MS (Field Desorption-Mass Spectrometry) data of the compounds.

-continued
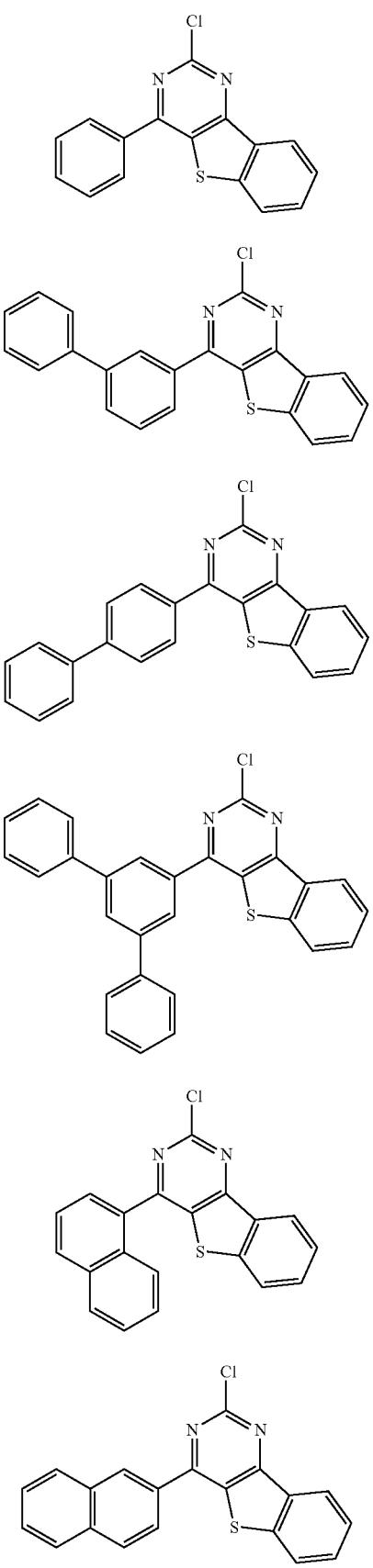
Sub 2(1a)
Sub 2(1b)
Sub 2(1c)
Sub 2(1d)
Sub 2(1e)
Sub 2(1f)
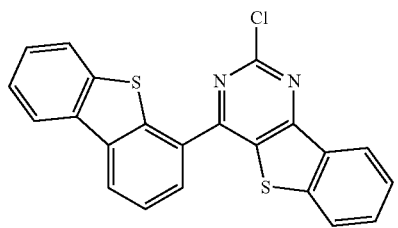
Sub 2(1g)
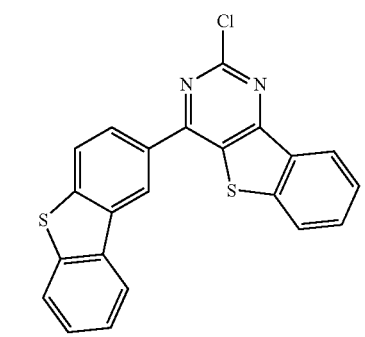
Sub 2(1h)
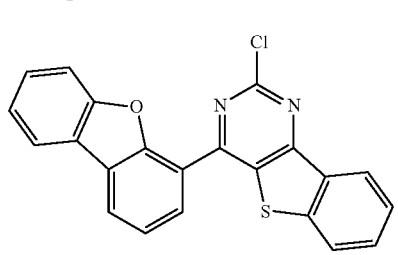
Sub (21i)
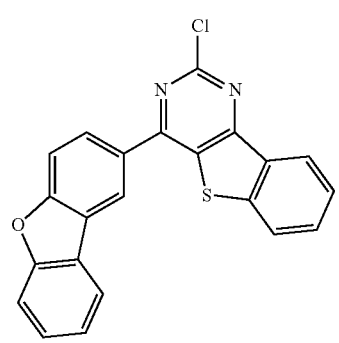
Sub 2(1j)
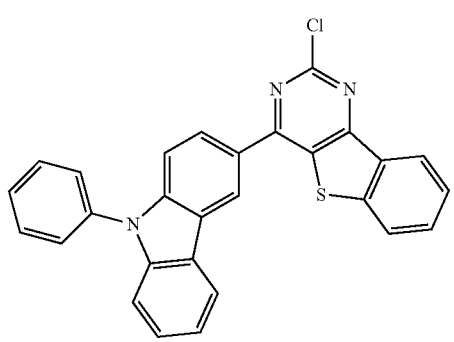
Sub 2(1k)

Sub 2(1l)
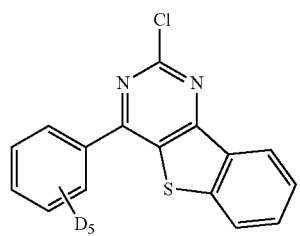
Sub 2(2a)
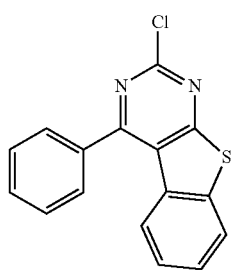
Sub 2(2b)
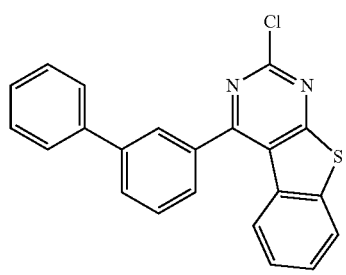
Sub 2(2c)
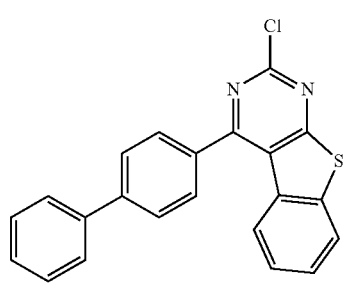
Sub 2(2d)
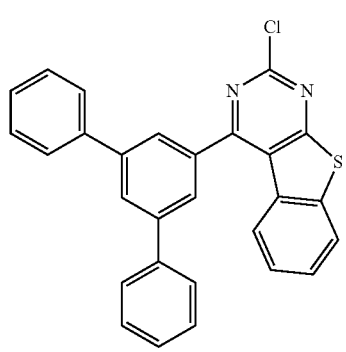
Sub 2(2e)
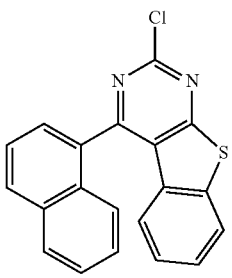
Sub 2(2f)
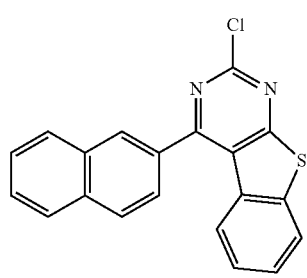
Sub 2(2g)
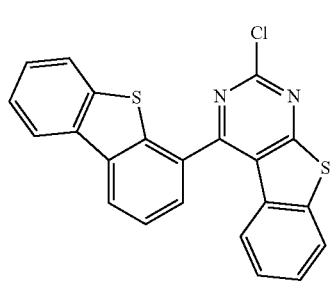
Sub 2(2h)
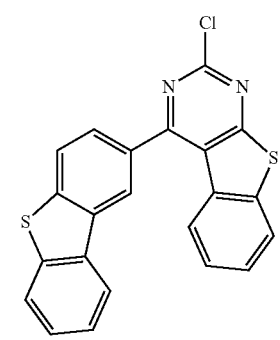
Sub 2(2i)
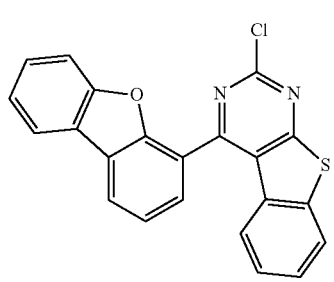

Sub 2(2j)
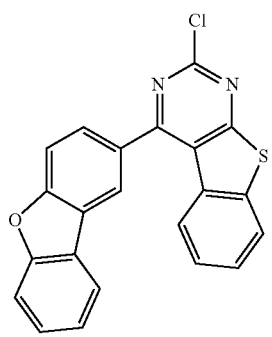
Sub 2(2k)
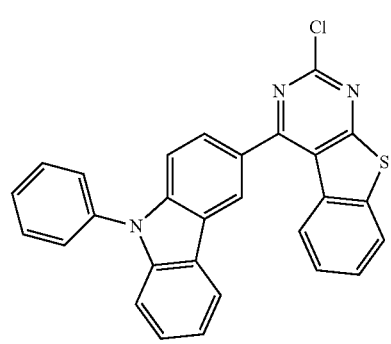
Sub 2(2l)
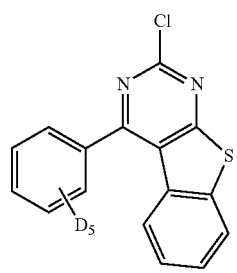
Sub 2(3a)
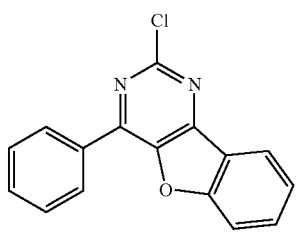
Sub 2(3b)
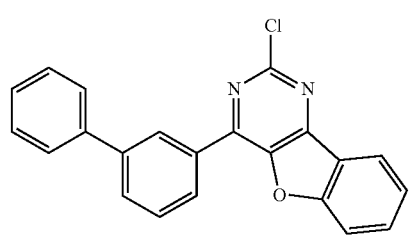
Sub 2(3c)
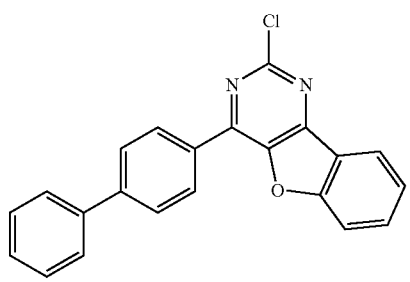
Sub 2(3d)
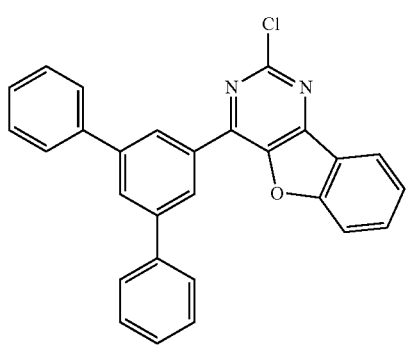
Sub 2(3e)
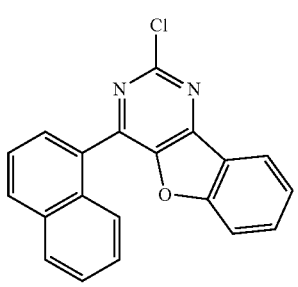
Sub 2(3f)
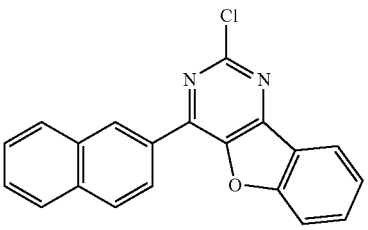
Sub 2(3g)
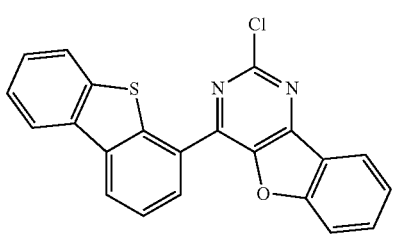

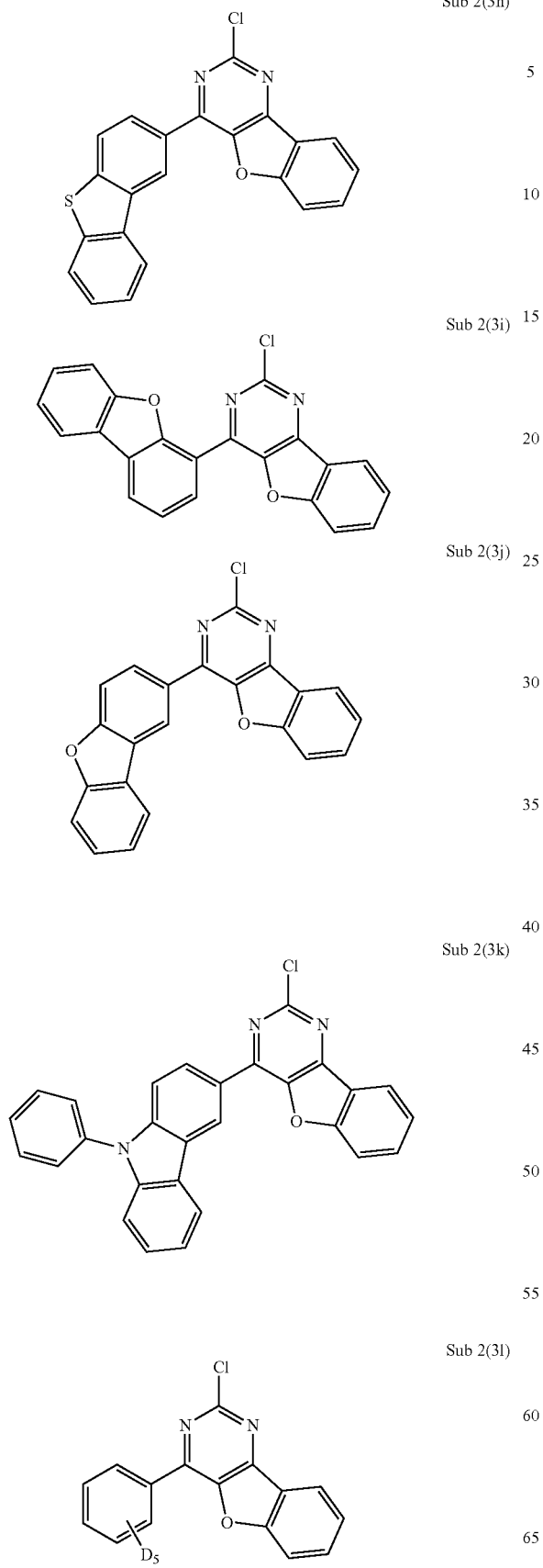
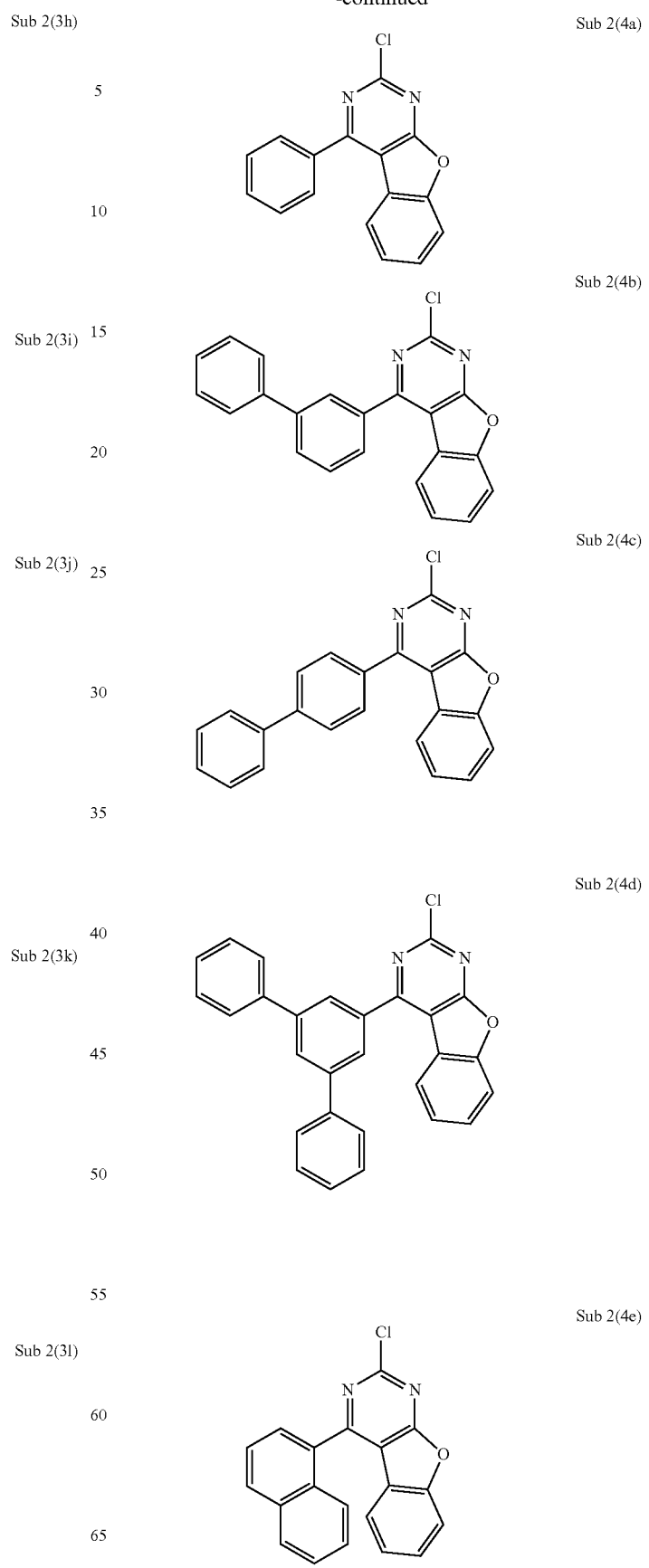

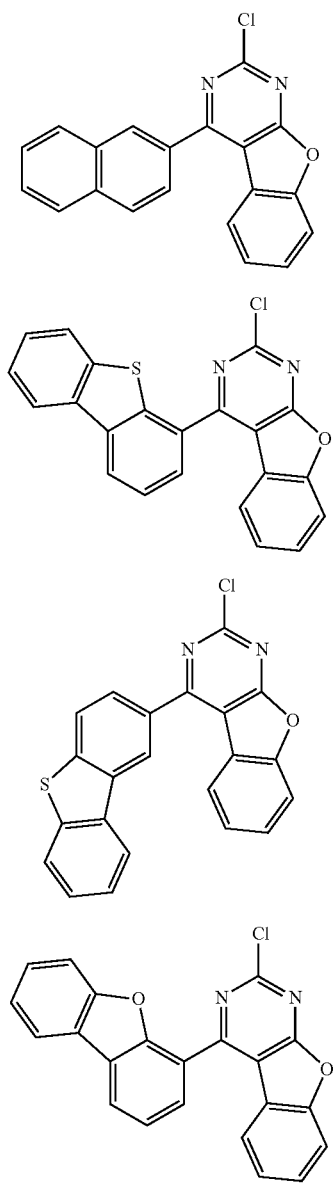

Sub 2(4f)

Sub 2(4g)

Sub 2(4h)

Sub 2(4i)

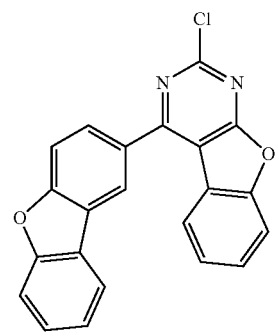

Sub 2(4j)

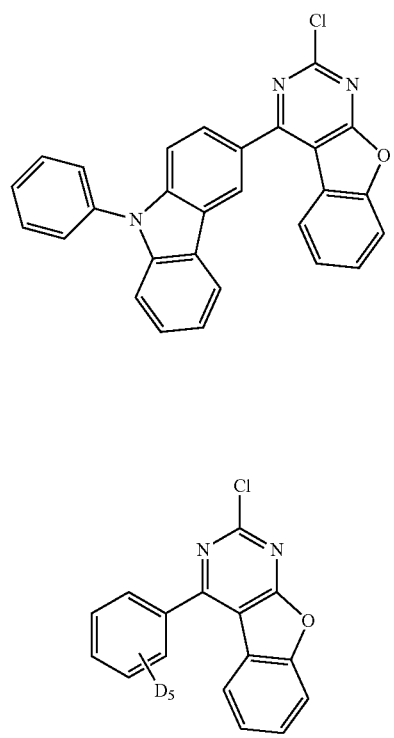

Sub 2(4k)

Sub 2(4l)

TABLE 1

| Compound | FD-MS | Compound | FD-MS |
| --- | --- | --- | --- |
| Sub 2(1a) | m/z = 296.77($C_{18}H_9ClN_2S$ = 296.02) | Sub 2(1b) | m/z = 372.87($C_{22}H_{13}ClN_2S$ = 372.05) |
| Sub 2(1c) | m/z = 372.87($C_{22}H_{13}ClN_2S$ = 372.05) | Sub 2(1d) | m/z = 448.97($C_{23}H_{17}ClN_2S$ = 448.08) |
| Sub 2(1e) | m/z = 346.83($C_{20}H_{11}ClN_2S$ = 346.03) | Sub 2(1f) | m/z = 346.83($C_{20}H_{11}ClN_2S$ = 346.03) |
| Sub 2(1g) | m/z = 402.92($C_{23}H_{11}ClN_2S_2$ = 402.01) | Sub 2(1h) | m/z = 402.92($C_{22}H_{11}ClN_2S_2$ = 296.02) |
| Sub 2(1i) | m/z = 386.85($C_{22}H_{11}ClN_2OS$ = 386.03) | Sub 2(1j) | m/z = 386.85($C_{22}H_{11}ClN_2OS$ = 386.03) |
| Sub 2(1k) | m/z = 461.96($C_{28}H_{16}ClN_2S$ = 461.08) | Sub 2(1l) | m/z = 321.88($C_{17}H_{12}D_5ClN_2S$ = 321.11) |
| Sub 2(2a) | m/z = 296.77($C_{16}H_9ClN_2S$ = 296.02) | Sub 2(2b) | m/z = 372.87($C_{22}H_{13}ClN_2S$ = 372.05) |
| Sub 2(2c) | m/z = 372.87($C_{22}H_{13}ClN_2S$ = 372.05) | Sub 2(2d) | m/z = 448.97($C_{23}H_{17}ClN_2S$ = 448.08) |
| Sub 2(2e) | m/z = 346.83($C_{20}H_{11}ClN_2S$ = 346.03) | Sub 2(2f) | m/z = 346.83($C_{20}H_{11}ClN_2S$ = 346.03) |
| Sub 2(2g) | m/z = 402.92($C_{22}H_{11}ClN_2S_2$ = 402.01) | Sub 2(2h) | m/z = 402.92($C_{22}H_{11}ClN_2S_2$ = 296.02) |
| Sub 2(2i) | m/z = 386.85($C_{22}H_{11}ClN_2OS$ = 386.03) | Sub 2(2j) | m/z = 386.85($C_{22}H_{11}ClN_2OS$ = 386.03) |
| Sub 2(2k) | m/z = 461.96($C_{23}H_{18}ClN_2S$ = 461.08) | Sub 2(2l) | m/z = 321.88($C_{17}H_{12}D_5ClN_2S$ = 321.11) |
| Sub 2(3a) | m/z = 280.71($C_{16}H_9ClN_2O$ = 280.04) | Sub 2(3b) | m/z = 356.88($C_{22}H_{13}ClN_2O$ = 356.07) |
| Sub 2(3c) | m/z = 356.88($C_{22}H_{13}ClN_2O$ = 356.07) | Sub 2(3d) | m/z = 432.90($C_{23}H_{17}ClN_2O$ = 432.10) |
| Sub 2(3e) | m/z = 330.77($C_{20}H_{11}ClN_2O$ = 330.06) | Sub 2(3f) | m/z = 330.77($C_{20}H_{11}ClN_2O$ = 330.06) |
| Sub 2(3g) | m/z = 386.85($C_{22}H_{11}ClN_2OS$ = 386.03) | Sub 2(3h) | m/z = 386.85($C_{22}H_{11}ClN_2OS$ = 386.03) |
| Sub 2(3i) | m/z = 370.79($C_{22}H_{11}ClN_2O_2$ = 370.05) | Sub 2(3j) | m/z = 370.79($C_{22}H_{11}ClN_2O_2$ = 370.05) |
| Sub 2(3k) | m/z = 445.90($C_{28}H_{18}ClN_2O$ = 445.10) | Sub 2(3l) | m/z = 305.81($C_{17}H_{12}D_5ClN_2O$ = 305.13) |

TABLE 1-continued

| Compound | FD-MS | Compound | FD-MS |
| --- | --- | --- | --- |
| Sub 2(4a) | m/z = 280.71($C_{16}H_9ClN_2O$ = 280.04) | Sub 2(4b) | m/z = 356.88($C_{22}H_{13}ClN_2O$ = 356.07) |
| Sub 2(4c) | m/z = 356.88($C_{22}H_{13}ClN_2O$ = 356.07) | Sub 2(4d) | m/z = 432.90($C_{23}H_{17}ClN_2O$ = 432.10) |
| Sub 2(4e) | m/z = 330.77($C_{20}H_{11}ClN_2O$ = 330.06) | Sub 2(4f) | m/z = 330.77($C_{20}H_{11}ClN_2O$ = 330.06) |
| Sub 2(4g) | m/z = 386.85($C_{22}H_{11}ClN_2OS$ = 386.03) | Sub 2(4h) | m/z = 386.85($C_{22}H_{11}ClN_2OS$ = 386.03) |
| Sub 2(4i) | m/z = 370.79($C_{22}H_{11}ClN_2O_2$ = 370.05) | Sub 2(4j) | m/z = 370.79($C_{22}H_{11}ClN_2O_2$ = 370.05) |
| Sub 2(4k) | m/z = 445.90($C_{28}H_{18}ClN_2O$ = 445.10) | Sub 2(4l) | m/z = 305.81($C_{17}H_{12}D_5ClN_2O$ = 305.13) |

III. Synthesis of Final Product

Sub 1 (1 eq.) was loaded into a round bottom flask and then dissolved in THF. After Sub 2 (1.2 eq.), $Pd_2(dba)_3$ (0.03 eq.), $P(t-Bu)_3$ (0.1 eq.) and t-BuONa (3 eq.) were added into the round bottom flask, a mixture was refluxed with stirring. After the completion of the reaction, a reaction product was extracted with $CH_2Cl_2$ and water. The organic layer was dried with $MgSO_4$ and concentrated. The concentrate was separated by silica gel column chromatography and recrystallization, whereby final product was obtained.

1. Synthesis Example of 2-1

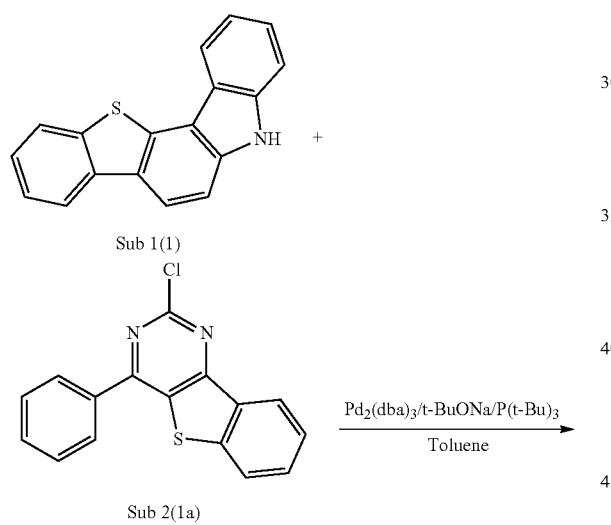

Sub 1(1) (5.4 g, 20 mmol), Sub 2(1a) (7.1 g, 24 mmol), $Pd_2(dba)_3$ (0.3 g, 0.6 mmol), $P(t-Bu)_3$ (0.2 g, 2 mmol), t-BuONa (5.8 g, 60 mmol) and toluene (300 mL) were loaded into a round bottom flask and then reaction proceeded at 100° C. After the completion of the reaction, a reaction product was extracted with $CH_2Cl_2$ and water. The organic layer was dried with $MgSO_4$ and concentrated. The concentrate was separated by silica gel column chromatography and recrystallization, whereby compound 2-1 was obtained in the amount of 8.3 g (yield: 78%).

2. Synthesis Example of 2-11

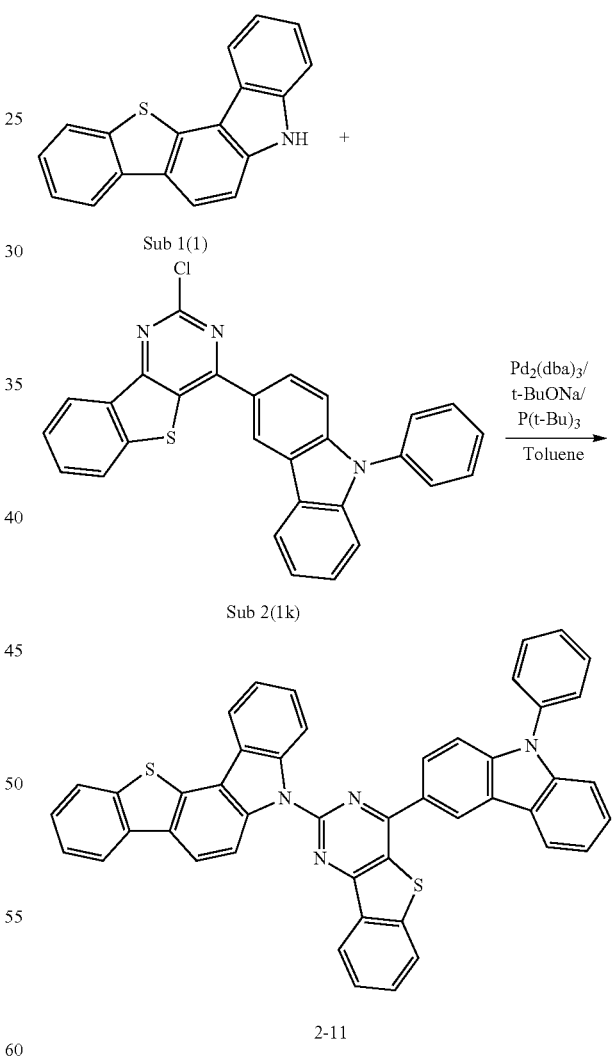

Compound 2-11 was obtained in the amount of 10.5 g (yield: 75%) where Sub 1(1) (5.4 g, 20 mmol), Sub 2(1 k) (11.0 g, 24 mmol), $Pd_2(dba)_3$ (0.3 g, 0.6 mmol), $P(t-Bu)_3$ (0.2 g, 2 mmol), t-BuONa (5.8 g, 60 mmol) and toluene (300 mL) were used in the same manner as described above for the synthesis of compound 2-1.

3. Synthesis Example of 2-12

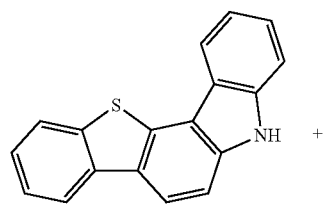

Sub 1(1)

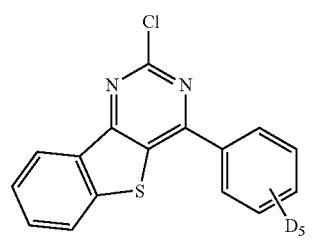

Sub 2(1)

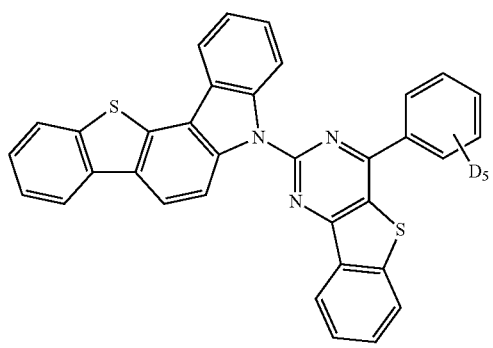

2-12

Compound 2-12 was obtained in the amount of 9.8 g (yield: 87%) where Sub 1(1) (5.4 g, 20 mmol), Sub 2(11) (7.7 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

4. Synthesis Example of 3-1

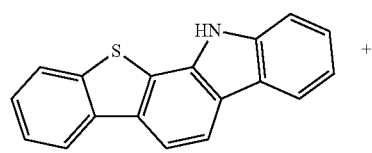

Sub 1(2)

-continued

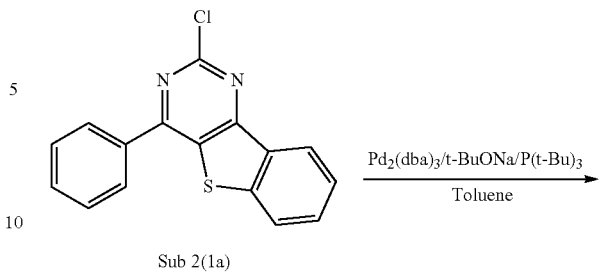

Sub 2(1a)

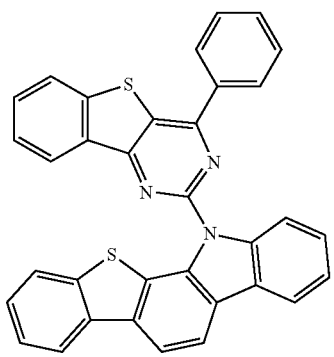

3-1

Compound 3-1 was obtained in the amount of 7.5 g (yield: 70%) where Sub 1(2) (5.4 g, 20 mmol), Sub 2(1a) (7.1 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

5. Synthesis Example of 3-7

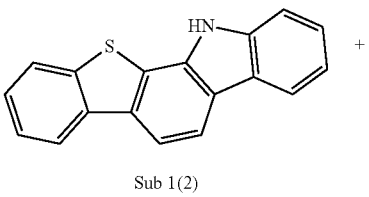

Sub 1(2)

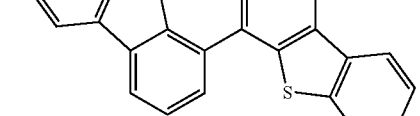

Sub 2(1g)

-continued

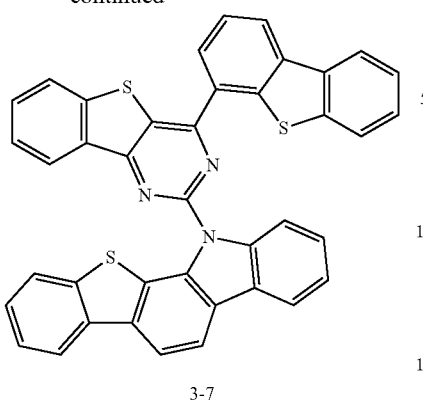

3-7

Compound 3-7 was obtained in the amount of 10.8 g (yield: 84%) where Sub 1(2) (5.4 g, 20 mmol), Sub 1(1 g) (9.6 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

6. Synthesis Example of 3-9

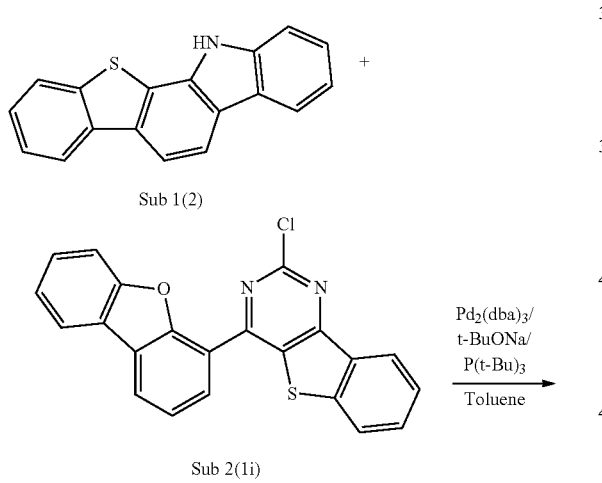

3-9

Compound 3-9 was obtained in the amount of 9.2 g (yield: 74%) where Sub 1(2) (5.4 g, 20 mmol), Sub 2(1i) (9.3 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

7. Synthesis Example of 4-1

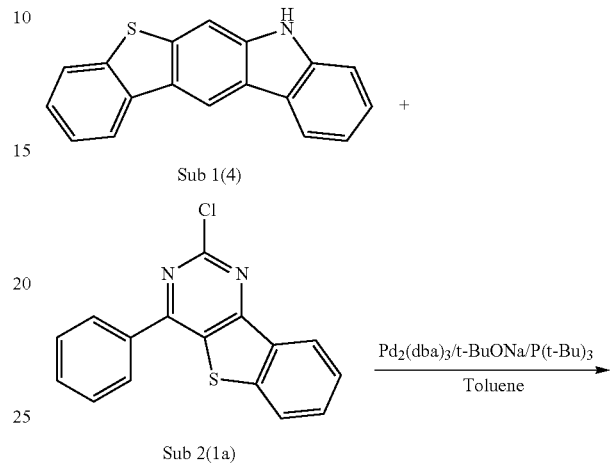

4-1

Compound 4-1 was obtained in the amount of 8.1 g (yield: 76%) where Sub 1(4) (5.4 g, 20 mmol), Sub 2(1a) (7.1 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

8. Synthesis Example of 4-2

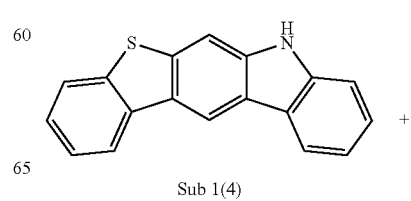

Sub 1(4)

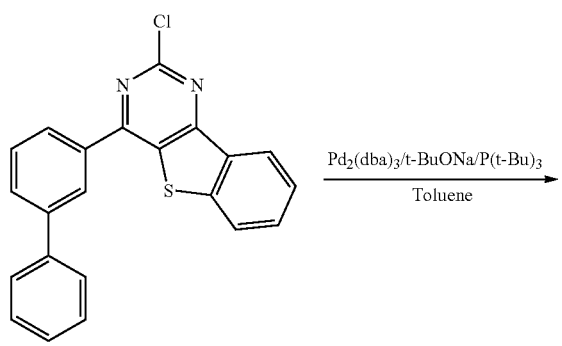

Sub 2(1b)

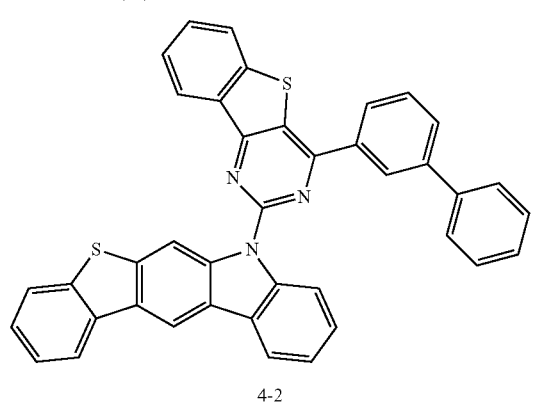

4-2

Compound 4-2 was obtained in the amount of 9.3 g (yield: 76%) where Sub 1(4) (5.4 g, 20 mmol), Sub 2(1b) (8.9 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

9. Synthesis Example of 5-4

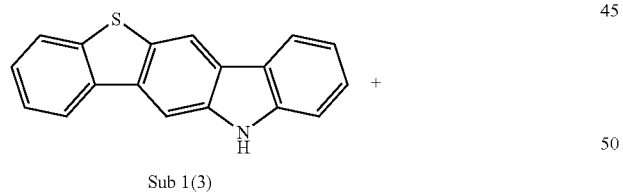

Sub 1(3)

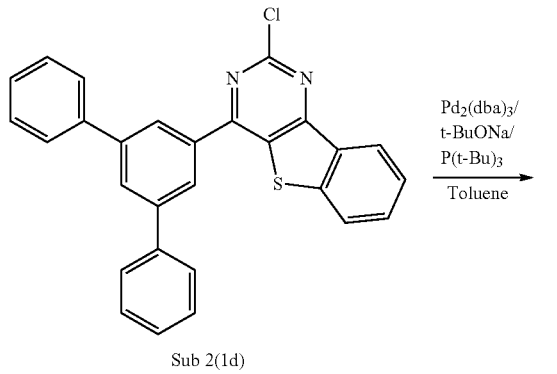

Sub 2(1d)

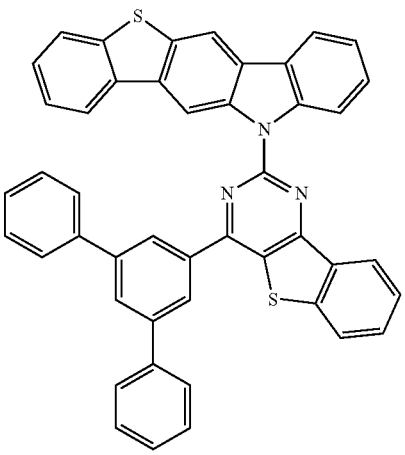

5-4

Compound 5-4 was obtained in the amount of 11.9 g (yield: 87%) where Sub 1(3) (5.4 g, 20 mmol), Sub 2(1d) (10.8 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

10. Synthesis Example of 6-5

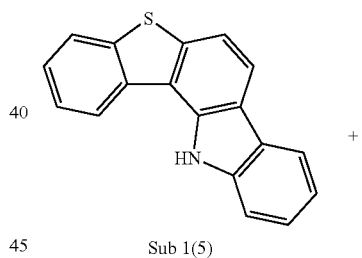

Sub 1(5)

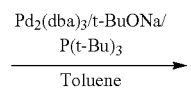

Sub 2(1e)

-continued

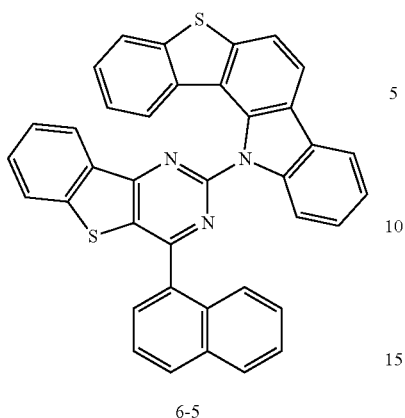

6-5

Compound 6-5 was obtained in the amount of 8.8 g (yield: 75%) where Sub 1(5) (5.4 g, 20 mmol), Sub 2(1e) (8.3 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

11. Synthesis Example of 7-8

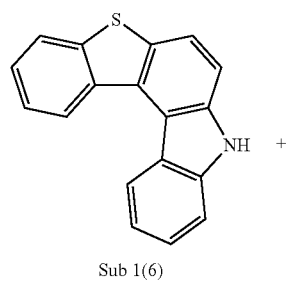

Sub 1(6)

+

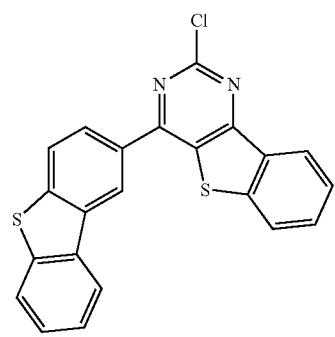

Sub 2(1h)

-continued

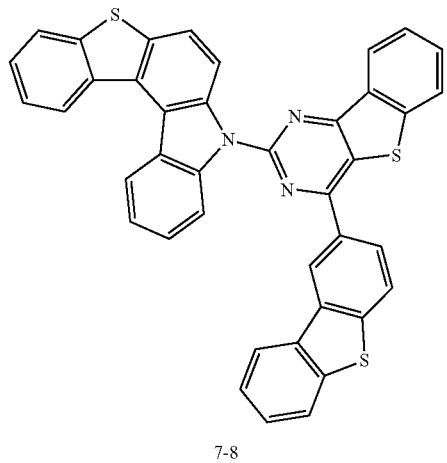

7-8

Compound 7-8 was obtained in the amount of 10.5 g (yield: 82%) where Sub 1(6) (5.4 g, 20 mmol), Sub 2(1h) (9.7 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

12. Synthesis Example of 8-1

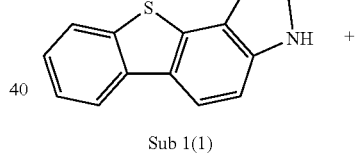

Sub 1(1)

+

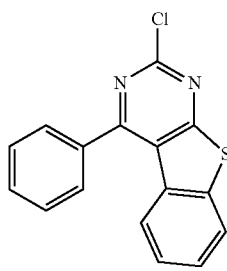

Sub 2(2a)

Pd$_2$(dba)$_3$/t-BuONa/P(t-Bu)$_3$
Toluene

-continued

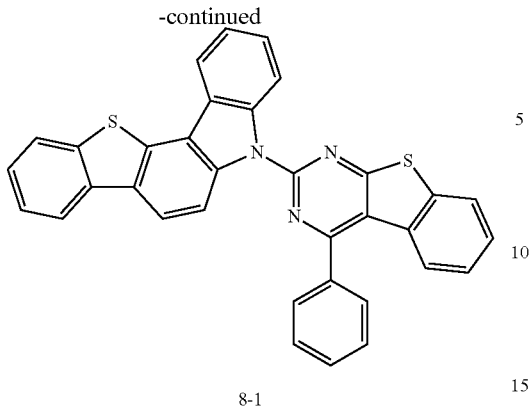

8-1

Compound 8-1 was obtained in the amount of 9.1 g (yield: 85%) where Sub 1(1) (5.4 g, 20 mmol), Sub 2(2a) (7.1 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

13. Synthesis Example of 9-1

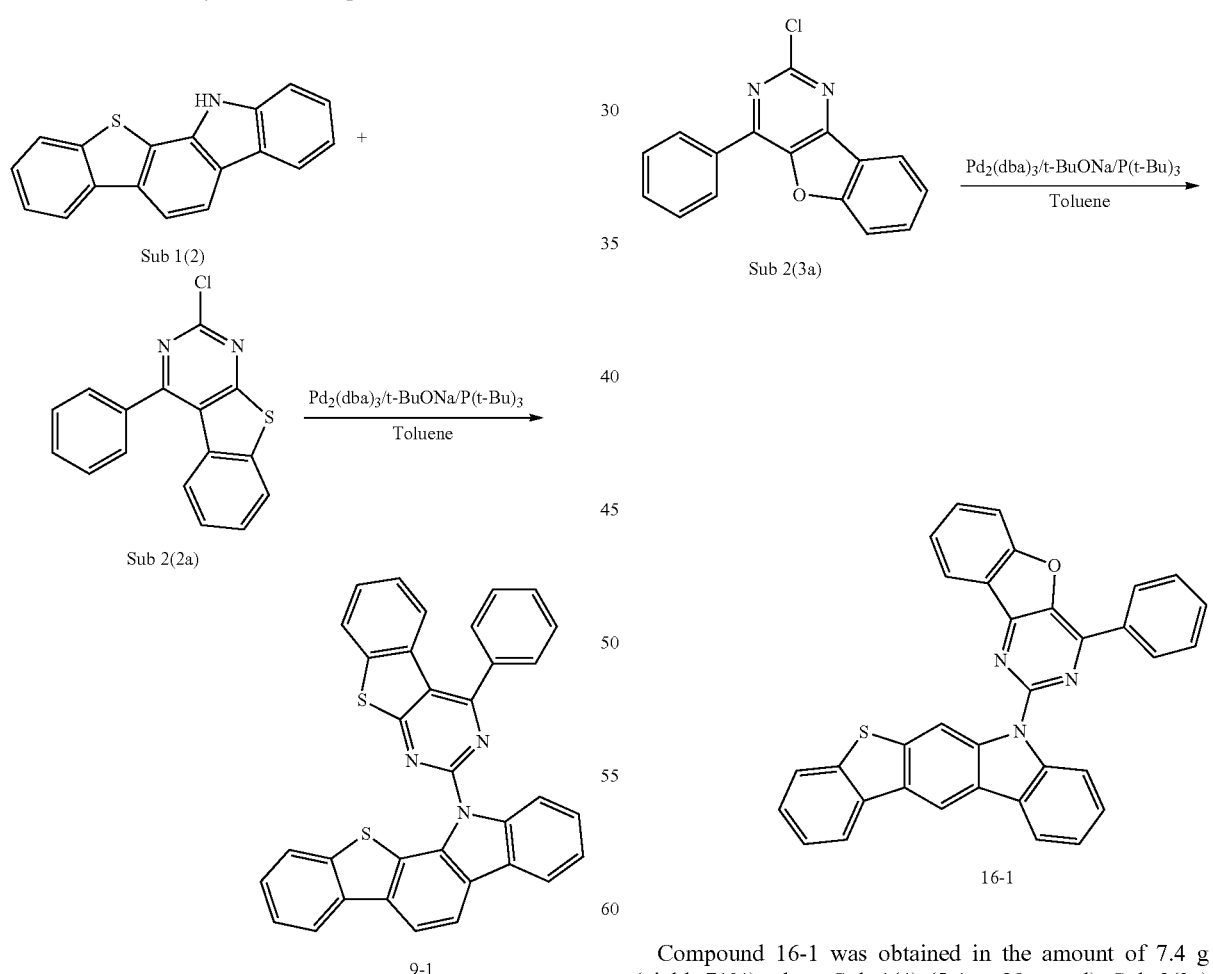

Sub 1(2)

Sub 2(2a)

9-1

Compound 9-1 was obtained in the amount of 8.9 g (yield: 83%) where Sub 1(2) (5.4 g, 20 mmol), Sub 2(2a) (7.1 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

14. Synthesis Example of 16-1

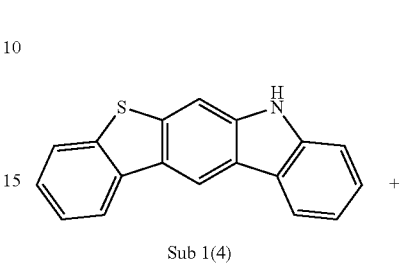

Sub 1(4)

Sub 2(3a)

16-1

Compound 16-1 was obtained in the amount of 7.4 g (yield: 71%) where Sub 1(4) (5.4 g, 20 mmol), Sub 2(3a) (6.7 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

15. Synthesis Example of 24-1

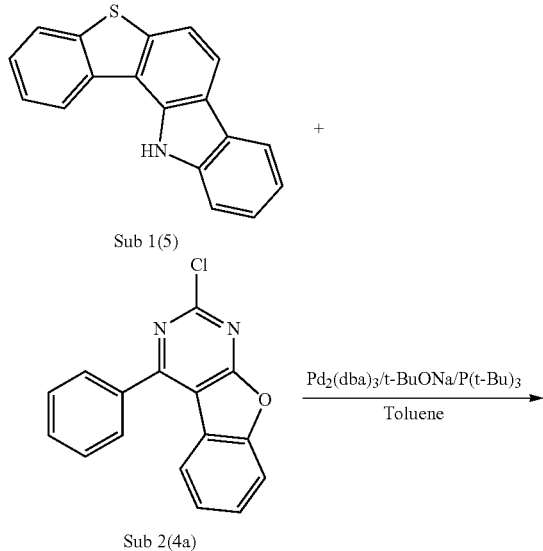

Sub 1(5)

Sub 2(4a)

Pd$_2$(dba)$_3$/t-BuONa/P(t-Bu)$_3$
Toluene

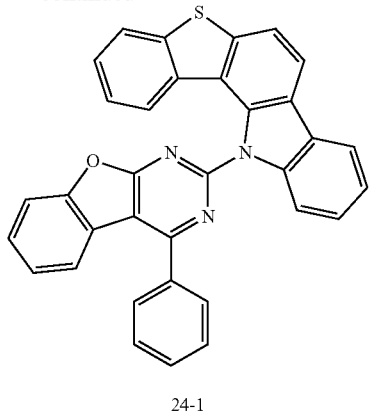

24-1

Compound 24-1 was obtained in the amount of 7.7 g (yield: 74%) where Sub 1(5) (5.4 g, 20 mmol), Sub 2(4a) (6.7 g, 24 mmol), Pd$_2$(dba)$_3$ (0.3 g, 0.6 mmol), P(t-Bu)$_3$ (0.2 g, 2 mmol), t-BuONa (5.8 g, 60 mmol) and toluene (300 mL) were used in the same manner as described above for the synthesis of compound 2-1.

TABLE 2

| Compound | FD-MS | Compound | FD-MS |
|---|---|---|---|
| 2-1 | m/z = 533.66($C_{34}H_{19}N_3S_2$ = 533.10) | 2-2 | m/z = 609.76($C_{40}H_{23}N_3S_2$ = 609.13) |
| 2-3 | m/z = 609.76($C_{40}H_{23}N_3S_2$ = 609.73) | 2-4 | m/z = 685.16($C_{46}H_{27}N_3S_2$ = 685.16) |
| 2-5 | m/z = 583.72($C_{38}H_{21}N_3S_2$ = 583.12) | 2-6 | m/z = 583.72($C_{38}H_{21}N_3S_2$ = 583.12) |
| 2-7 | m/z = 639.81($C_{40}H_{21}N_3S_3$ = 639.09) | 2-8 | m/z = 639.81($C_{40}H_{21}N_3S_3$ = 639.09) |
| 2-9 | m/z = 623.74($C_{40}H_{21}N_3OS_2$ = 623.11) | 2-10 | m/z = 623.74($C_{40}H_{21}N_3OS_2$ = 623.11) |
| 2-11 | m/z = 698.86($C_{46}H_{26}N_4S_2$ = 698.16) | 2-12 | m/z = 558.77($C_{35}H_{22}D_5N_3S_2$ = 558.20) |
| 3-1 | m/z = 533.66($C_{34}H_{19}N_3S_2$ = 533.10) | 3-2 | m/z = 609.76($C_{40}H_{23}N_3S_2$ = 609.13) |
| 3-3 | m/z = 609.76($C_{40}H_{23}N_3S_2$ = 609.73) | 3-4 | m/z = 685.16($C_{46}H_{27}N_3S_2$ = 685.16) |
| 3-5 | m/z = 583.72($C_{38}H_{21}N_3S_2$ = 583.12) | 3-6 | m/z = 583.72($C_{38}H_{21}N_3S_2$ = 583.12) |
| 3-7 | m/z = 639.81($C_{40}H_{21}N_3S_3$ = 639.09) | 3-8 | m/z = 639.81($C_{40}H_{21}N_3S_3$ = 639.09) |
| 3-9 | m/z = 623.74($C_{40}H_{21}N_3OS_2$ = 623.11) | 3-10 | m/z = 623.74($C_{40}H_{21}N_3OS_2$ = 623.11) |
| 3-11 | m/z = 698.86($C_{46}H_{26}N_4S_2$ = 698.16) | 3-12 | m/z = 558.77($C_{35}H_{22}D_5N_3S_2$ = 558.20) |
| 4-1 | m/z = 533.66($C_{34}H_{19}N_3S_2$ = 533.10) | 4-2 | m/z = 609.76($C_{40}H_{23}N_3S_2$ = 609.13) |
| 4-3 | m/z = 609.76($C_{40}H_{23}N_3S_2$ = 609.73) | 4-4 | m/z = 685.16($C_{46}H_{27}N_3S_2$ = 685.16) |
| 4-5 | m/z = 583.72($C_{38}H_{21}N_3S_2$ = 583.12) | 4-6 | m/z = 583.72($C_{38}H_{21}N_3S_2$ = 583.12) |
| 4-7 | m/z = 639.81($C_{40}H_{21}N_3S_3$ = 639.09) | 4-8 | m/z = 639.81($C_{40}H_{21}N_3S_3$ = 639.09) |
| 4-9 | m/z = 623.74($C_{40}H_{21}N_3OS_2$ = 623.11) | 4-10 | m/z = 623.74($C_{40}H_{21}N_3OS_2$ = 623.11) |
| 4-11 | m/z = 698.86($C_{46}H_{26}N_4S_2$ = 698.16) | 4-12 | m/z = 558.77($C_{35}H_{22}D_5N_3S_2$ = 558.20) |
| 5-1 | m/z = 533.66($C_{34}H_{19}N_3S_2$ = 533.10) | 5-2 | m/z = 609.76($C_{40}H_{23}N_3S_2$ = 609.13) |
| 5-3 | m/z = 609.76($C_{40}H_{23}N_3S_2$ = 609.73) | 5-4 | m/z = 685.16($C_{46}H_{27}N_3S_2$ = 685.16) |
| 5-5 | m/z = 583.72($C_{38}H_{21}N_3S_2$ = 583.12) | 5-6 | m/z = 583.72($C_{38}H_{21}N_3S_2$ = 583.12) |
| 5-7 | m/z = 639.81($C_{40}H_{21}N_3S_3$ = 639.09) | 5-8 | m/z = 639.81($C_{40}H_{21}N_3S_3$ = 639.09) |
| 5-9 | m/z = 623.74($C_{40}H_{21}N_3OS_2$ = 623.11) | 5-10 | m/z = 623.74($C_{40}H_{21}N_3OS_2$ = 623.11) |
| 5-11 | m/z = 698.86($C_{46}H_{26}N_4S_2$ = 698.16) | 5-12 | m/z = 558.77($C_{35}H_{22}D_5N_3S_2$ = 558.20) |
| 6-1 | m/z = 533.66($C_{34}H_{19}N_3S_2$ = 533.10) | 6-2 | m/z = 609.76($C_{40}H_{23}N_3S_2$ = 609.13) |
| 6-3 | m/z = 609.76($C_{40}H_{23}N_3S_2$ = 609.73) | 6-4 | m/z = 685.16($C_{46}H_{27}N_3S_2$ = 685.16) |
| 6-5 | m/z = 583.72($C_{38}H_{21}N_3S_2$ = 583.12) | 6-6 | m/z = 583.72($C_{38}H_{21}N_3S_2$ = 583.12) |
| 6-7 | m/z = 639.81($C_{40}H_{21}N_3S_3$ = 639.09) | 6-8 | m/z = 639.81($C_{40}H_{21}N_3S_3$ = 639.09) |
| 6-9 | m/z = 623.74($C_{40}H_{21}N_3OS_2$ = 623.11) | 6-10 | m/z = 623.74($C_{40}H_{21}N_3OS_2$ = 623.11) |
| 6-11 | m/z = 698.86($C_{46}H_{26}N_4S_2$ = 698.16) | 6-12 | m/z = 558.77($C_{35}H_{22}D_5N_3S_2$ = 558.20) |
| 7-1 | m/z = 533.66($C_{34}H_{19}N_3S_2$ = 533.10) | 7-2 | m/z = 609.76($C_{40}H_{23}N_3S_2$ = 609.13) |
| 7-3 | m/z = 609.76($C_{40}H_{23}N_3S_2$ = 609.73) | 7-4 | m/z = 685.16($C_{46}H_{27}N_3S_2$ = 685.16) |
| 7-5 | m/z = 583.72($C_{38}H_{21}N_3S_2$ = 583.12) | 7-6 | m/z = 583.72($C_{38}H_{21}N_3S_2$ = 583.12) |
| 7-7 | m/z = 639.81($C_{40}H_{21}N_3S_3$ = 639.09) | 7-8 | m/z = 639.81($C_{40}H_{21}N_3S_3$ = 639.09) |
| 7-9 | m/z = 623.74($C_{40}H_{21}N_3OS_2$ = 623.11) | 7-10 | m/z = 623.74($C_{40}H_{21}N_3OS_2$ = 623.11) |
| 7-11 | m/z = 698.86($C_{46}H_{26}N_4S_2$ = 698.16) | 7-12 | m/z = 558.77($C_{35}H_{22}D_5N_3S_2$ = 558.20) |
| 8-1 | m/z = 533.66($C_{34}H_{19}N_3S_2$ = 533.10) | 8-2 | m/z = 609.76($C_{40}H_{23}N_3S_2$ = 609.13) |
| 8-3 | m/z = 609.76($C_{40}H_{23}N_3S_2$ = 609.73) | 8-4 | m/z = 685.16($C_{46}H_{27}N_3S_2$ = 685.16) |
| 8-5 | m/z = 583.72($C_{38}H_{21}N_3S_2$ = 583.12) | 8-6 | m/z = 583.72($C_{38}H_{21}N_3S_2$ = 583.12) |
| 8-7 | m/z = 639.81($C_{40}H_{21}N_3S_3$ = 639.09) | 8-8 | m/z = 639.81($C_{40}H_{21}N_3S_3$ = 639.09) |
| 8-9 | m/z = 623.74($C_{40}H_{21}N_3OS_2$ = 623.11) | 8-10 | m/z = 623.74($C_{40}H_{21}N_3OS_2$ = 623.11) |
| 8-11 | m/z = 698.86($C_{46}H_{26}N_4S_2$ = 698.16) | 8-12 | m/z = 558.77($C_{35}H_{22}D_5N_3S_2$ = 558.20) |
| 9-1 | m/z = 533.66($C_{34}H_{19}N_3S_2$ = 533.10) | 9-2 | m/z = 609.76($C_{40}H_{23}N_3S_2$ = 609.13) |
| 9-3 | m/z = 609.76($C_{40}H_{23}N_3S_2$ = 609.73) | 9-4 | m/z = 685.16($C_{46}H_{27}N_3S_2$ = 685.16) |
| 9-5 | m/z = 583.72($C_{38}H_{21}N_3S_2$ = 583.12) | 9-6 | m/z = 583.72($C_{38}H_{21}N_3S_2$ = 583.12) |

TABLE 2-continued

| Compound | FD-MS | Compound | FD-MS |
|---|---|---|---|
| 9-7 | m/z = 639.81($C_{40}H_{21}N_3S_3$ = 639.09) | 9-8 | m/z = 639.81($C_{40}H_{21}N_3S_3$ = 639.09) |
| 9-9 | m/z = 623.74($C_{40}H_{21}N_3OS_2$ = 623.11) | 9-10 | m/z = 623.74($C_{40}H_{21}N_3OS_2$ = 623.11) |
| 9-11 | m/z = 698.86($C_{46}H_{26}N_4S_2$ = 698.16) | 9-12 | m/z = 558.77($C_{35}H_{22}D_5N_3S_2$ = 558.20) |
| 10-1 | m/z = 533.66($C_{34}H_{19}N_3S_2$ = 533.10) | 10-2 | m/z = 609.76($C_{40}H_{23}N_3S_2$ = 609.13) |
| 10-3 | m/z = 609.76($C_{40}H_{23}N_3S_2$ = 609.73) | 10-4 | m/z = 685.16($C_{46}H_{27}N_3S_2$ = 685.16) |
| 10-5 | m/z = 583.72($C_{38}H_{21}N_3S_2$ = 583.12) | 10-6 | m/z = 583.72($C_{38}H_{21}N_3S_2$ = 583.12) |
| 10-7 | m/z = 639.81($C_{40}H_{21}N_3S_3$ = 639.09) | 10-8 | m/z = 639.81($C_{40}H_{21}N_3S_3$ = 639.09) |
| 10-9 | m/z = 623.74($C_{40}H_{21}N_3OS_2$ = 623.11) | 10-10 | m/z = 623.74($C_{40}H_{21}N_3OS_2$ = 623.11) |
| 10-11 | m/z = 698.86($C_{46}H_{26}N_4S_2$ = 698.16) | 10-12 | m/z = 558.77($C_{35}H_{22}D_5N_3S_2$ = 558.20) |
| 11-1 | m/z = 533.66($C_{34}H_{19}N_3S_2$ = 533.10) | 11-2 | m/z = 609.76($C_{40}H_{23}N_3S_2$ = 609.13) |
| 11-3 | m/z = 609.76($C_{40}H_{23}N_3S_2$ = 609.73) | 11-4 | m/z = 685.16($C_{46}H_{27}N_3S_2$ = 685.16) |
| 11-5 | m/z = 583.72($C_{38}H_{21}N_3S_2$ = 583.12) | 11-6 | m/z = 583.72($C_{38}H_{21}N_3S_2$ = 583.12) |
| 11-7 | m/z = 639.81($C_{40}H_{21}N_3S_3$ = 639.09) | 11-8 | m/z = 639.81($C_{40}H_{21}N_3S_3$ = 639.09) |
| 11-9 | m/z = 623.74($C_{40}H_{21}N_3OS_2$ = 623.11) | 11-10 | m/z = 623.74($C_{40}H_{21}N_3OS_2$ = 623.11) |
| 11-11 | m/z = 698.86($C_{46}H_{26}N_4S_2$ = 698.16) | 11-12 | m/z = 558.77($C_{35}H_{22}D_5N_3S_2$ = 558.20) |
| 12-1 | m/z = 533.66($C_{34}H_{19}N_3S_2$ = 533.10) | 12-2 | m/z = 609.76($C_{40}H_{23}N_3S_2$ = 609.13) |
| 12-3 | m/z = 609.76($C_{40}H_{23}N_3S_2$ = 609.73) | 12-4 | m/z = 685.16($C_{46}H_{27}N_3S_2$ = 685.16) |
| 12-5 | m/z = 583.72($C_{38}H_{21}N_3S_2$ = 583.12) | 12-6 | m/z = 583.72($C_{38}H_{21}N_3S_2$ = 583.12) |
| 12-7 | m/z = 639.81($C_{40}H_{21}N_3S_3$ = 639.09) | 12-8 | m/z = 639.81($C_{40}H_{21}N_3S_3$ = 639.09) |
| 12-9 | m/z = 623.74($C_{40}H_{21}N_3OS_2$ = 623.11) | 12-10 | m/z = 623.74($C_{40}H_{21}N_3OS_2$ = 623.11) |
| 12-11 | m/z = 698.86($C_{46}H_{26}N_4S_2$ = 698.16) | 12-12 | m/z = 558.77($C_{35}H_{22}D_5N_3S_2$ = 558.20) |
| 13-1 | m/z = 533.66($C_{34}H_{19}N_3S_2$ = 533.10) | 13-2 | m/z = 609.76($C_{40}H_{23}N_3S_2$ = 609.13) |
| 13-3 | m/z = 609.76($C_{40}H_{23}N_3S_2$ = 609.73) | 13-4 | m/z = 685.16($C_{46}H_{27}N_3S_2$ = 685.16) |
| 13-5 | m/z = 583.72($C_{38}H_{21}N_3S_2$ = 583.12) | 13-6 | m/z = 583.72($C_{38}H_{21}N_3S_2$ = 583.12) |
| 13-7 | m/z = 639.81($C_{40}H_{21}N_3S_3$ = 639.09) | 13-8 | m/z = 639.81($C_{40}H_{21}N_3S_3$ = 639.09) |
| 13-9 | m/z = 623.74($C_{40}H_{21}N_3OS_2$ = 623.11) | 13-10 | m/z = 623.74($C_{40}H_{21}N_3OS_2$ = 623.11) |
| 13-11 | m/z = 698.86($C_{46}H_{26}N_4S_2$ = 698.16) | 13-12 | m/z = 558.77($C_{35}H_{22}D_5N_3S_2$ = 558.20) |
| 14-1 | m/z = 517.60($C_{34}H_{19}N_3OS_2$ = 517.12) | 14-2 | m/z = 593.70($C_{40}H_{23}N_3OS_2$ = 593.16) |
| 14-3 | m/z = 593.70($C_{40}H_{23}N_3OS_2$ = 593.16) | 14-4 | m/z = 669.79($C_{46}H_{27}N_3OS_2$ = 669.19) |
| 14-5 | m/z = 657.66($C_{38}H_{21}N_3OS_2$ = 657.14) | 14-6 | m/z = 657.66($C_{38}H_{21}N_3OS_2$ = 657.14) |
| 14-7 | m/z = 623.74($C_{40}H_{21}N_3OS_2$ = 623.11) | 14-8 | m/z = 623.74($C_{40}H_{21}N_3OS_2$ = 623.11) |
| 14-9 | m/z = 607.68($C_{40}H_{21}N_3O_2S$ = 607.14) | 14-10 | m/z = 607.68($C_{40}H_{21}N_3O_2S$ = 607.14) |
| 14-11 | m/z = 682.18($C_{46}H_{26}N_4OS$ = 742.24) | 14-12 | m/z = 542.70($C_{35}H_{22}D_5N_3OS$ = 542.22) |
| 15-1 | m/z = 517.60($C_{34}H_{19}N_3OS_2$ = 517.12) | 15-2 | m/z = 593.70($C_{40}H_{23}N_3OS_2$ = 593.16) |
| 15-3 | m/z = 593.70($C_{40}H_{23}N_3OS_2$ = 593.16) | 15-4 | m/z = 669.79($C_{46}H_{27}N_3OS_2$ = 669.19) |
| 15-5 | m/z = 657.66($C_{38}H_{21}N_3OS_2$ = 657.14) | 15-6 | m/z = 657.66($C_{38}H_{21}N_3OS_2$ = 657.14) |
| 15-7 | m/z = 623.74($C_{40}H_{21}N_3OS_2$ = 623.11) | 15-8 | m/z = 623.74($C_{40}H_{21}N_3OS_2$ = 623.11) |
| 15-9 | m/z = 607.68($C_{40}H_{21}N_3O_2S$ = 607.14) | 15-10 | m/z = 607.68($C_{40}H_{21}N_3O_2S$ = 607.14) |
| 15-11 | m/z = 682.18($C_{46}H_{26}N_4OS$ = 742.24) | 15-12 | m/z = 542.70($C_{35}H_{22}D_5N_3OS$ = 542.22) |
| 16-1 | m/z = 517.60($C_{34}H_{19}N_3OS_2$ = 517.12) | 16-2 | m/z = 593.70($C_{40}H_{23}N_3OS_2$ = 593.16) |
| 16-3 | m/z = 593.70($C_{40}H_{23}N_3OS_2$ = 593.16) | 16-4 | m/z = 669.79($C_{46}H_{27}N_3OS_2$ = 669.19) |
| 16-5 | m/z = 657.66($C_{38}H_{21}N_3OS_2$ = 657.14) | 16-6 | m/z = 657.66($C_{38}H_{21}N_3OS_2$ = 657.14) |
| 16-7 | m/z = 623.74($C_{40}H_{21}N_3OS_2$ = 623.11) | 16-8 | m/z = 623.74($C_{40}H_{21}N_3OS_2$ = 623.11) |
| 16-9 | m/z = 607.68($C_{40}H_{21}N_3O_2S$ = 607.14) | 16-10 | m/z = 607.68($C_{40}H_{21}N_3O_2S$ = 607.14) |
| 16-11 | m/z = 682.18($C_{46}H_{26}N_4OS$ = 742.24) | 16-12 | m/z = 542.70($C_{35}H_{22}D_5N_3OS$ = 542.22) |
| 17-1 | m/z = 517.60($C_{34}H_{19}N_3OS_2$ = 517.12) | 17-2 | m/z = 593.70($C_{40}H_{23}N_3OS_2$ = 593.16) |
| 17-3 | m/z = 593.70($C_{40}H_{23}N_3OS_2$ = 593.16) | 17-4 | m/z = 669.79($C_{46}H_{27}N_3OS_2$ = 669.19) |
| 17-5 | m/z = 657.66($C_{38}H_{21}N_3OS_2$ = 657.14) | 17-6 | m/z = 657.66($C_{38}H_{21}N_3OS_2$ = 657.14) |
| 17-7 | m/z = 623.74($C_{40}H_{21}N_3OS_2$ = 623.11) | 17-8 | m/z = 623.74($C_{40}H_{21}N_3OS_2$ = 623.11) |
| 17-9 | m/z = 607.68($C_{40}H_{21}N_3O_2S$ = 607.14) | 17-10 | m/z = 607.68($C_{40}H_{21}N_3O_2S$ = 607.14) |
| 17-11 | m/z = 682.18($C_{46}H_{26}N_4OS$ = 742.24) | 17-12 | m/z = 542.70($C_{35}H_{22}D_5N_3OS$ = 542.22) |
| 18-1 | m/z = 517.60($C_{34}H_{19}N_3OS_2$ = 517.12) | 18-2 | m/z = 593.70($C_{40}H_{23}N_3OS_2$ = 593.16) |
| 18-3 | m/z = 593.70($C_{40}H_{23}N_3OS_2$ = 593.16) | 18-4 | m/z = 669.79($C_{46}H_{27}N_3OS_2$ = 669.19) |
| 18-5 | m/z = 657.66($C_{38}H_{21}N_3OS_2$ = 657.14) | 18-6 | m/z = 657.66($C_{38}H_{21}N_3OS_2$ = 657.14) |
| 18-7 | m/z = 623.74($C_{40}H_{21}N_3OS_2$ = 623.11) | 18-8 | m/z = 623.74($C_{40}H_{21}N_3OS_2$ = 623.11) |
| 18-9 | m/z = 607.68($C_{40}H_{21}N_3O_2S$ = 607.14) | 18-10 | m/z = 607.68($C_{40}H_{21}N_3O_2S$ = 607.14) |
| 18-11 | m/z = 682.18($C_{46}H_{26}N_4OS$ = 742.24) | 18-12 | m/z = 542.70($C_{35}H_{22}D_5N_3OS$ = 542.22) |
| 19-1 | m/z = 517.60($C_{34}H_{19}N_3OS_2$ = 517.12) | 19-2 | m/z = 593.70($C_{40}H_{23}N_3OS_2$ = 593.16) |
| 19-3 | m/z = 593.70($C_{40}H_{23}N_3OS_2$ = 593.16) | 19-4 | m/z = 669.79($C_{46}H_{27}N_3OS_2$ = 669.19) |
| 19-5 | m/z = 657.66($C_{38}H_{21}N_3OS_2$ = 657.14) | 19-6 | m/z = 657.66($C_{38}H_{21}N_3OS_2$ = 657.14) |
| 19-7 | m/z = 623.74($C_{40}H_{21}N_3OS_2$ = 623.11) | 19-8 | m/z = 623.74($C_{40}H_{21}N_3OS_2$ = 623.11) |
| 19-9 | m/z = 607.68($C_{40}H_{21}N_3O_2S$ = 607.14) | 19-10 | m/z = 607.68($C_{40}H_{21}N_3O_2S$ = 607.14) |
| 19-11 | m/z = 682.18($C_{46}H_{26}N_4OS$ = 742.24) | 19-12 | m/z = 542.70($C_{35}H_{22}D_5N_3OS$ = 542.22) |
| 20-1 | m/z = 517.60($C_{34}H_{19}N_3OS_2$ = 517.12) | 20-2 | m/z = 593.70($C_{40}H_{23}N_3OS_2$ = 593.16) |
| 20-3 | m/z = 593.70($C_{40}H_{23}N_3OS_2$ = 593.16) | 20-4 | m/z = 669.79($C_{46}H_{27}N_3OS_2$ = 669.19) |
| 20-5 | m/z = 657.66($C_{38}H_{21}N_3OS_2$ = 657.14) | 20-6 | m/z = 657.66($C_{38}H_{21}N_3OS_2$ = 657.14) |
| 20-7 | m/z = 623.74($C_{40}H_{21}N_3OS_2$ = 623.11) | 20-8 | m/z = 623.74($C_{40}H_{21}N_3OS_2$ = 623.11) |
| 20-9 | m/z = 607.68($C_{40}H_{21}N_3O_2S$ = 607.14) | 20-10 | m/z = 607.68($C_{40}H_{21}N_3O_2S$ = 607.14) |
| 20-11 | m/z = 682.18($C_{46}H_{26}N_4OS$ = 742.24) | 20-12 | m/z = 542.70($C_{35}H_{22}D_5N_3OS$ = 542.22) |
| 21-1 | m/z = 517.60($C_{34}H_{19}N_3OS_2$ = 517.12) | 21-2 | m/z = 593.70($C_{40}H_{23}N_3OS_2$ = 593.16) |
| 21-3 | m/z = 593.70($C_{40}H_{23}N_3OS_2$ = 593.16) | 21-4 | m/z = 669.79($C_{46}H_{27}N_3OS_2$ = 669.19) |
| 21-5 | m/z = 657.66($C_{38}H_{21}N_3OS_2$ = 657.14) | 21-6 | m/z = 657.66($C_{38}H_{21}N_3OS_2$ = 657.14) |
| 21-7 | m/z = 623.74($C_{40}H_{21}N_3OS_2$ = 623.11) | 21-8 | m/z = 623.74($C_{40}H_{21}N_3OS_2$ = 623.11) |
| 21-9 | m/z = 607.68($C_{40}H_{21}N_3O_2S$ = 607.14) | 21-10 | m/z = 607.68($C_{40}H_{21}N_3O_2S$ = 607.14) |
| 21-11 | m/z = 682.18($C_{46}H_{26}N_4OS$ = 742.24) | 21-12 | m/z = 542.70($C_{35}H_{22}D_5N_3OS$ = 542.22) |
| 22-1 | m/z = 517.60($C_{34}H_{19}N_3OS_2$ = 517.12) | 22-2 | m/z = 593.70($C_{40}H_{23}N_3OS_2$ = 593.16) |
| 22-3 | m/z = 593.70($C_{40}H_{23}N_3OS_2$ = 593.16) | 22-4 | m/z = 669.79($C_{46}H_{27}N_3OS_2$ = 669.19) |
| 22-5 | m/z = 657.66($C_{38}H_{21}N_3OS_2$ = 657.14) | 22-6 | m/z = 657.66($C_{38}H_{21}N_3OS_2$ = 657.14) |

TABLE 2-continued

| Compound | FD-MS | Compound | FD-MS |
|---|---|---|---|
| 22-7 | m/z = 623.74($C_{40}H_{21}N_3OS_2$ = 623.11) | 22-8 | m/z = 623.74($C_{40}H_{21}N_3OS_2$ = 623.11) |
| 22-9 | m/z = 607.68($C_{40}H_{21}N_3O_2S$ = 607.14) | 22-10 | m/z = 607.68($C_{40}H_{21}N_3O_2S$ = 607.14) |
| 22-11 | m/z = 682.18($C_{46}H_{26}N_4OS$ = 742.24) | 22-12 | m/z = 542.70($C_{35}H_{22}D_5N_3OS$ = 542.22) |
| 23-1 | m/z = 517.60($C_{34}H_{19}N_3OS_2$ = 517.12) | 23-2 | m/z = 593.70($C_{40}H_{23}N_3OS_2$ = 593.16) |
| 23-3 | m/z = 593.70($C_{40}H_{23}N_3OS_2$ = 593.16) | 23-4 | m/z = 669.79($C_{46}H_{27}N_3OS_2$ = 669.19) |
| 23-5 | m/z = 657.66($C_{38}H_{21}N_3OS_2$ = 657.14) | 23-6 | m/z = 657.66($C_{38}H_{21}N_3OS_2$ = 657.14) |
| 23-7 | m/z = 623.74($C_{40}H_{21}N_3OS_2$ = 623.11) | 23-8 | m/z = 623.74($C_{40}H_{21}N_3OS_2$ = 623.11) |
| 23-9 | m/z = 607.68($C_{40}H_{21}N_3O_2S$ = 607.14) | 23-10 | m/z = 607.68($C_{40}H_{21}N_3O_2S$ = 607.14) |
| 23-11 | m/z = 682.18($C_{46}H_{26}N_4OS$ = 742.24) | 23-12 | m/z = 542.70($C_{35}H_{22}D_5N_3OS$ = 542.22) |
| 24-1 | m/z = 517.60($C_{34}H_{19}N_3OS_2$ = 517.12) | 24-2 | m/z = 593.70($C_{40}H_{23}N_3OS_2$ = 593.16) |
| 24-3 | m/z = 593.70($C_{40}H_{23}N_3OS_2$ = 593.16) | 24-4 | m/z = 669.79($C_{46}H_{27}N_3OS_2$ = 669.19) |
| 24-5 | m/z = 657.66($C_{38}H_{21}N_3OS_2$ = 657.14) | 24-6 | m/z = 657.66($C_{38}H_{21}N_3OS_2$ = 657.14) |
| 24-7 | m/z = 623.74($C_{40}H_{21}N_3OS_2$ = 623.11) | 24-8 | m/z = 623.74($C_{40}H_{21}N_3OS_2$ = 623.11) |
| 24-9 | m/z = 607.68($C_{40}H_{21}N_3O_2S$ = 607.14) | 24-10 | m/z = 607.68($C_{40}H_{21}N_3O_2S$ = 607.14) |
| 24-11 | m/z = 682.18($C_{46}H_{26}N_4OS$ = 742.24) | 24-12 | m/z = 542.70($C_{35}H_{22}D_5N_3OS$ = 542.22) |
| 25-1 | m/z = 517.60($C_{34}H_{19}N_3OS_2$ = 517.12) | 25-2 | m/z = 593.70($C_{40}H_{23}N_3OS_2$ = 593.16) |
| 25-3 | m/z = 593.70($C_{40}H_{23}N_3OS_2$ = 593.16) | 25-4 | m/z = 669.79($C_{46}H_{27}N_3OS_2$ = 669.19) |
| 25-5 | m/z = 657.66($C_{38}H_{21}N_3OS_2$ = 657.14) | 25-6 | m/z = 657.66($C_{38}H_{21}N_3OS_2$ = 657.14) |
| 25-7 | m/z = 623.74($C_{40}H_{21}N_3OS_2$ = 623.11) | 25-8 | m/z = 623.74($C_{40}H_{21}N_3OS_2$ = 623.11) |
| 25-9 | m/z = 607.68($C_{40}H_{21}N_3O_2S$ = 607.14) | 25-10 | m/z = 607.68($C_{40}H_{21}N_3O_2S$ = 607.14) |
| 25-11 | m/z = 682.18($C_{46}H_{26}N_4OS$ = 742.24) | 25-12 | m/z = 542.70($C_{35}H_{22}D_5N_3OS$ = 542.22) |

Fabrication and Evaluation of Organic Electronic Element

[Example 1] Red OLED (a Phosphorescent Host)

Organic light emitting diodes (OLEDs) were fabricated according to a conventional method by using a compound of the present invention as a phosphorescent host material.

First, an ITO layer (anode) was formed on a glass substrate, and a film of $N^1$-(naphthalen-2-yl)-$N^4$,$N^4$-bis(4-(naphthalen-2-yl(phenyl)amino)phenyl)-$N^1$-phenylbenzene-1,4diamine (hereinafter abbreviated as "2-TNATA") was vacuum-deposited on the ITO layer to form a hole injection layer with a thickness of 60 nm.

Subsequently, 4,4-bis[N-(1-naphthyl)-N-phenylamino]biphenyl (hereinafter abbreviated as "NPD") was vacuum-deposited with a thickness of 60 nm on the hole injection layer to form a hole transport layer.

Subsequently, a light emitting layer with a thickness of 30 nm was deposited on the hole transport layer by doping the hole transport layer with the compound 2-1 of the present invention as a host material and bis-(1-phenylisoquinolyl)iridium(III)acetylacetonate (hereinafter abbreviated as "(piq)$_2$Ir(acac)") as a dopant material in a weight ratio of 95:5.

Next, a film of ((1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "Alq$_3$") was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] To [Test Example 288] Red OLED (a Phosphorescent Host)

The OLED was manufactured in the same manner as described in Example 1, except that any one of the compounds 2-2 to 2-12, 3-1 to 3-12, 4-1 to 4-12, 5-1 to 5-12, 6-1 to 6-12, 7-1 to 7-12, 8-1 to 8-12, 9-1 to 9-12, 10-1 to 10-12, 11-1 to 11-12, 12-1 to 12-12, 13-1 to 13-12, 14-1 to 14-12, 15-1 to 15-12, 16-1 to 16-12, 17-1 to 17-12, 18-1 to 18-12, 19-1 to 19-12, 20-1 to 20-12, 21-1 to 21-12, 22-1 to 22-12, 23-1 to 23-12, 24-1 to 24-12 and 25-1 to 25-12 of the present invention in the Table 3 below was used as the host material of the light emitting layer, instead of the inventive compound 2-1.

[Comparative Example 1] to [Comparative Example 8]

An OLED was manufactured in the same manner as described in Test Example 1, except that any one of the Comparative Compounds A to H below was used as the host material of the light emitting layer, instead of the inventive compound 2-1.

<Comp.Com A> <Comp.Com B> <Comp.Com C> <Comp.Com D>
<Comp.Com E> <Comp.Com F> <Comp.Com G> <Comp.Com H>

A forward bias DC voltage was applied to each of the OLEDs manufactured through Examples 1 to 288 and Comparative Example 1 to 8, and electro-luminescence (EL) characteristics of the OLED were measured by PR-650 (Photoresearch). Also, T95 life span was measured by life span measuring equipment (Mcscience) at a reference brightness of 2500 cd/m$^2$. Table below shows evaluation results of OLEDs manufactured Test Examples and Comparative Examples.

TABLE 3

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| comp. Ex(1) | Comp. Com A | 6.3 | 35.2 | 2500.0 | 7.1 | 74.4 | (0.66, 0.32) |
| comp. Ex(2) | Comp. Com B | 6.0 | 32.1 | 2500.0 | 7.8 | 80.3 | (0.67, 0.32) |
| comp. Ex(3) | Comp. Com C | 5.3 | 25.8 | 2500.0 | 9.7 | 96.3 | (0.66, 0.32) |

TABLE 3-continued

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| comp. Ex(4) | Comp. Com D | 5.2 | 25.5 | 2500.0 | 9.8 | 105.3 | (0.66, 0.33) |
| comp. Ex(5) | Comp. Com E | 5.7 | 27.2 | 2500.0 | 9.2 | 99.8 | (0.65, 0.32) |
| comp. Ex(6) | Comp. Com F | 5.6 | 26.9 | 2500.0 | 9.3 | 98.2 | (0.65, 0.32) |
| comp. Ex(7) | Comp. Com G | 5.5 | 26.3 | 2500.0 | 9.5 | 94.5 | (0.65, 0.32) |
| comp. Ex(8) | Comp. Com H | 5.8 | 27.8 | 2500.0 | 9.0 | 92.1 | (0.65, 0.32) |
| Ex. (1) | Com. (2-1) | 4.4 | 14.8 | 2500.0 | 16.8 | 114.8 | (0.65, 0.35) |
| Ex. (2) | Com. (2-2) | 4.3 | 14.9 | 2500.0 | 16.8 | 102.5 | (0.65, 0.35) |
| Ex. (3) | Com. (2-3) | 4.4 | 15.1 | 2500.0 | 16.5 | 114.1 | (0.66, 0.35) |
| Ex. (4) | Com. (2-4) | 4.4 | 15.1 | 2500.0 | 16.5 | 112.3 | (0.66, 0.35) |
| Ex. (5) | Com. (2-5) | 4.4 | 14.8 | 2500.0 | 16.9 | 117.3 | (0.66, 0.35) |
| Ex. (6) | Com. (2-6) | 4.3 | 14.8 | 2500.0 | 16.9 | 102.1 | (0.66, 0.35) |
| Ex. (7) | Com. (2-7) | 4.3 | 14.9 | 2500.0 | 16.7 | 100.5 | (0.66, 0.35) |
| Ex. (8) | Com. (2-8) | 4.4 | 14.7 | 2500.0 | 17.0 | 119.7 | (0.66, 0.35) |
| Ex. (9) | Com. (2-9) | 4.3 | 14.9 | 2500.0 | 16.8 | 107.5 | (0.66, 0.35) |
| Ex. (10) | Com. (2-10) | 4.3 | 15.1 | 2500.0 | 16.6 | 110.0 | (0.66, 0.35) |
| Ex. (11) | Com. (2-11) | 4.4 | 14.9 | 2500.0 | 16.8 | 106.3 | (0.66, 0.35) |
| Ex. (12) | Com. (2-12) | 4.4 | 15.3 | 2500.0 | 16.3 | 108.2 | (0.66, 0.35) |
| Ex. (13) | Com. (3-1) | 4.6 | 16.3 | 2500.0 | 15.3 | 105.4 | (0.66, 0.35) |
| Ex. (14) | Com. (3-2) | 4.6 | 16.4 | 2500.0 | 15.2 | 106.7 | (0.66, 0.35) |
| Ex. (15) | Com. (3-3) | 4.4 | 16.1 | 2500.0 | 15.5 | 102.7 | (0.66, 0.35) |
| Ex. (16) | Com. (3-4) | 4.5 | 16.6 | 2500.0 | 15.1 | 105.5 | (0.66, 0.35) |
| Ex. (17) | Com. (3-5) | 4.5 | 16.3 | 2500.0 | 15.3 | 102.5 | (0.66, 0.35) |
| Ex. (18) | Com. (3-6) | 4.6 | 16.6 | 2500.0 | 15.0 | 108.1 | (0.66, 0.35) |
| Ex. (19) | Com. (3-7) | 4.4 | 16.0 | 2500.0 | 15.7 | 111.0 | (0.66, 0.35) |
| Ex. (20) | Com. (3-8) | 4.5 | 16.3 | 2500.0 | 15.3 | 101.7 | (0.66, 0.35) |
| Ex. (21) | Com. (3-9) | 4.5 | 16.1 | 2500.0 | 15.5 | 103.7 | (0.66, 0.35) |
| Ex. (22) | Com. (3-10) | 4.5 | 15.9 | 2500.0 | 15.8 | 109.2 | (0.66, 0.35) |
| Ex. (23) | Com. (3-11) | 4.5 | 15.7 | 2500.0 | 15.9 | 101.8 | (0.66, 0.35) |
| Ex. (24) | Com. (3-12) | 4.4 | 15.8 | 2500.0 | 15.8 | 102.2 | (0.66, 0.35) |
| Ex. (25) | Com. (4-1) | 4.9 | 19.4 | 2500.0 | 12.9 | 108.1 | (0.66, 0.35) |
| Ex. (26) | Com. (4-2) | 4.8 | 20.2 | 2500.0 | 12.4 | 115.7 | (0.66, 0.35) |
| Ex. (27) | Com. (4-3) | 4.7 | 20.4 | 2500.0 | 12.3 | 112.3 | (0.66, 0.35) |
| Ex. (28) | Com. (4-4) | 4.9 | 20.5 | 2500.0 | 12.2 | 103.4 | (0.66, 0.35) |
| Ex. (29) | Com. (4-5) | 4.9 | 19.4 | 2500.0 | 12.9 | 119.5 | (0.66, 0.35) |
| Ex. (30) | Com. (4-6) | 4.8 | 20.3 | 2500.0 | 12.3 | 111.6 | (0.66, 0.35) |
| Ex. (31) | Com. (4-7) | 4.8 | 20.2 | 2500.0 | 12.4 | 118.2 | (0.66, 0.35) |
| Ex. (32) | Com. (4-8) | 4.8 | 20.7 | 2500.0 | 12.1 | 109.4 | (0.66, 0.35) |
| Ex. (33) | Com. (4-9) | 4.8 | 19.5 | 2500.0 | 12.8 | 117.4 | (0.66, 0.35) |
| Ex. (34) | Com. (4-10) | 4.8 | 19.7 | 2500.0 | 12.7 | 112.5 | (0.66, 0.35) |
| Ex. (35) | Com. (4-11) | 4.7 | 20.7 | 2500.0 | 12.1 | 101.4 | (0.66, 0.35) |
| Ex. (36) | Com. (4-12) | 4.8 | 20.0 | 2500.0 | 12.5 | 100.8 | (0.66, 0.35) |
| Ex. (37) | Com. (5-1) | 4.7 | 19.1 | 2500.0 | 13.1 | 119.0 | (0.66, 0.35) |
| Ex. (38) | Com. (5-2) | 4.8 | 18.1 | 2500.0 | 13.8 | 110.6 | (0.66, 0.35) |
| Ex. (39) | Com. (5-3) | 4.6 | 18.8 | 2500.0 | 13.3 | 116.9 | (0.66, 0.35) |
| Ex. (40) | Com. (5-4) | 4.7 | 18.3 | 2500.0 | 13.7 | 116.0 | (0.66, 0.35) |
| Ex. (41) | Com. (5-5) | 4.7 | 18.2 | 2500.0 | 13.7 | 116.8 | (0.66, 0.35) |
| Ex. (42) | Com. (5-6) | 4.6 | 18.1 | 2500.0 | 13.8 | 112.6 | (0.66, 0.35) |
| Ex. (43) | Com. (5-7) | 4.8 | 19.0 | 2500.0 | 13.2 | 102.7 | (0.66, 0.35) |
| Ex. (44) | Com. (5-8) | 4.6 | 18.5 | 2500.0 | 13.5 | 119.9 | (0.66, 0.35) |
| Ex. (45) | Com. (5-9) | 4.8 | 18.5 | 2500.0 | 13.5 | 110.1 | (0.66, 0.35) |
| Ex. (46) | Com. (5-10) | 4.6 | 17.9 | 2500.0 | 13.9 | 106.2 | (0.66, 0.35) |
| Ex. (47) | Com. (5-11) | 4.6 | 18.3 | 2500.0 | 13.7 | 117.0 | (0.66, 0.35) |
| Ex. (48) | Com. (5-12) | 4.6 | 18.6 | 2500.0 | 13.5 | 119.0 | (0.66, 0.35) |
| Ex. (49) | Com. (6-1) | 5.0 | 21.1 | 2500.0 | 11.8 | 118.3 | (0.66, 0.35) |
| Ex. (50) | Com. (6-2) | 5.0 | 21.9 | 2500.0 | 11.4 | 119.6 | (0.66, 0.35) |
| Ex. (51) | Com. (6-3) | 4.9 | 21.4 | 2500.0 | 11.7 | 112.1 | (0.66, 0.35) |
| Ex. (52) | Com. (6-4) | 4.9 | 21.1 | 2500.0 | 11.8 | 115.4 | (0.66, 0.35) |
| Ex. (53) | Com. (6-5) | 4.8 | 22.1 | 2500.0 | 11.3 | 113.9 | (0.66, 0.35) |
| Ex. (54) | Com. (6-6) | 5.0 | 22.2 | 2500.0 | 11.3 | 110.4 | (0.66, 0.35) |
| Ex. (55) | Com. (6-7) | 4.9 | 21.7 | 2500.0 | 11.5 | 101.5 | (0.66, 0.35) |
| Ex. (56) | Com. (6-8) | 4.8 | 21.3 | 2500.0 | 11.8 | 114.7 | (0.66, 0.35) |
| Ex. (57) | Com. (6-9) | 4.8 | 21.3 | 2500.0 | 11.7 | 100.9 | (0.66, 0.35) |
| Ex. (58) | Com. (6-10) | 4.9 | 21.6 | 2500.0 | 11.6 | 103.7 | (0.66, 0.35) |
| Ex. (59) | Com. (6-11) | 5.0 | 21.0 | 2500.0 | 11.9 | 106.6 | (0.66, 0.35) |
| Ex. (60) | Com. (6-12) | 4.9 | 21.8 | 2500.0 | 11.5 | 106.8 | (0.66, 0.35) |
| Ex. (61) | Com. (7-1) | 4.7 | 16.7 | 2500.0 | 15.0 | 113.5 | (0.66, 0.35) |
| Ex. (62) | Com. (7-2) | 4.7 | 17.3 | 2500.0 | 14.4 | 105.6 | (0.66, 0.35) |
| Ex. (63) | Com. (7-3) | 4.6 | 17.0 | 2500.0 | 14.7 | 116.6 | (0.66, 0.35) |
| Ex. (64) | Com. (7-4) | 4.5 | 17.8 | 2500.0 | 14.1 | 100.3 | (0.66, 0.35) |
| Ex. (65) | Com. (7-5) | 4.7 | 16.9 | 2500.0 | 14.8 | 116.9 | (0.66, 0.35) |
| Ex. (66) | Com. (7-6) | 4.6 | 16.8 | 2500.0 | 14.8 | 105.7 | (0.66, 0.35) |
| Ex. (67) | Com. (7-7) | 4.5 | 17.2 | 2500.0 | 14.6 | 119.3 | (0.66, 0.35) |
| Ex. (68) | Com. (7-8) | 4.7 | 17.0 | 2500.0 | 14.7 | 109.2 | (0.66, 0.35) |
| Ex. (69) | Com. (7-9) | 4.6 | 17.9 | 2500.0 | 14.0 | 104.5 | (0.66, 0.35) |
| Ex. (70) | Com. (7-10) | 4.6 | 17.3 | 2500.0 | 14.4 | 109.9 | (0.66, 0.35) |
| Ex. (71) | Com. (7-11) | 4.5 | 17.0 | 2500.0 | 14.7 | 100.5 | (0.66, 0.35) |

TABLE 3-continued

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (72) | Com. (7-12) | 4.6 | 16.9 | 2500.0 | 14.8 | 113.5 | (0.66, 0.35) |
| Ex. (73) | Com. (8-1) | 4.3 | 15.4 | 2500.0 | 16.2 | 101.9 | (0.66, 0.35) |
| Ex. (74) | Com. (8-2) | 4.3 | 15.4 | 2500.0 | 16.2 | 119.5 | (0.66, 0.35) |
| Ex. (75) | Com. (8-3) | 4.5 | 14.9 | 2500.0 | 16.8 | 114.3 | (0.66, 0.35) |
| Ex. (76) | Com. (8-4) | 4.3 | 15.1 | 2500.0 | 16.6 | 111.9 | (0.66, 0.35) |
| Ex. (77) | Com. (8-5) | 4.4 | 15.6 | 2500.0 | 16.1 | 102.6 | (0.66, 0.35) |
| Ex. (78) | Com. (8-6) | 4.4 | 15.0 | 2500.0 | 16.6 | 110.9 | (0.66, 0.35) |
| Ex. (79) | Com. (8-7) | 4.3 | 15.5 | 2500.0 | 16.1 | 101.6 | (0.66, 0.35) |
| Ex. (80) | Com. (8-8) | 4.4 | 15.1 | 2500.0 | 16.6 | 109.4 | (0.66, 0.35) |
| Ex. (81) | Com. (8-9) | 4.3 | 15.1 | 2500.0 | 16.6 | 101.4 | (0.66, 0.35) |
| Ex. (82) | Com. (8-10) | 4.5 | 15.0 | 2500.0 | 16.7 | 116.8 | (0.66, 0.35) |
| Ex. (83) | Com. (8-11) | 4.5 | 14.8 | 2500.0 | 16.9 | 111.7 | (0.66, 0.35) |
| Ex. (84) | Com. (8-12) | 4.6 | 15.4 | 2500.0 | 16.2 | 116.1 | (0.66, 0.35) |
| Ex. (85) | Com. (9-1) | 4.5 | 16.4 | 2500.0 | 15.3 | 104.7 | (0.66, 0.35) |
| Ex. (86) | Com. (9-2) | 4.6 | 15.9 | 2500.0 | 15.7 | 100.2 | (0.66, 0.35) |
| Ex. (87) | Com. (9-3) | 4.4 | 15.6 | 2500.0 | 16.0 | 108.7 | (0.66, 0.35) |
| Ex. (88) | Com. (9-4) | 4.4 | 15.8 | 2500.0 | 15.8 | 100.3 | (0.66, 0.35) |
| Ex. (89) | Com. (9-5) | 4.5 | 15.8 | 2500.0 | 15.9 | 116.5 | (0.66, 0.35) |
| Ex. (90) | Com. (9-6) | 4.5 | 16.0 | 2500.0 | 15.6 | 103.7 | (0.66, 0.35) |
| Ex. (91) | Com. (9-7) | 4.4 | 15.9 | 2500.0 | 15.7 | 115.0 | (0.66, 0.35) |
| Ex. (92) | Com. (9-8) | 4.6 | 15.7 | 2500.0 | 15.9 | 114.2 | (0.66, 0.35) |
| Ex. (93) | Com. (9-9) | 4.4 | 15.7 | 2500.0 | 15.9 | 100.5 | (0.66, 0.35) |
| Ex. (94) | Com. (9-10) | 4.5 | 16.5 | 2500.0 | 15.2 | 111.0 | (0.66, 0.35) |
| Ex. (95) | Com. (9-11) | 4.4 | 16.5 | 2500.0 | 15.2 | 104.7 | (0.66, 0.35) |
| Ex. (96) | Com. (9-12) | 4.5 | 16.1 | 2500.0 | 15.5 | 112.5 | (0.66, 0.35) |
| Ex. (97) | Com. (10-1) | 4.8 | 20.7 | 2500.0 | 12.1 | 105.1 | (0.65, 0.35) |
| Ex. (98) | Com. (10-2) | 4.8 | 20.2 | 2500.0 | 12.4 | 105.8 | (0.65, 0.35) |
| Ex. (99) | Com. (10-3) | 4.7 | 19.9 | 2500.0 | 12.6 | 116.6 | (0.66, 0.35) |
| Ex. (100) | Com. (10-4) | 4.8 | 19.6 | 2500.0 | 12.8 | 107.3 | (0.66, 0.35) |
| Ex. (101) | Com. (10-5) | 4.7 | 20.0 | 2500.0 | 12.5 | 100.2 | (0.66, 0.35) |
| Ex. (102) | Com. (10-6) | 4.8 | 20.6 | 2500.0 | 12.2 | 106.4 | (0.66, 0.35) |
| Ex. (103) | Com. (10-7) | 4.7 | 20.4 | 2500.0 | 12.3 | 112.2 | (0.66, 0.35) |
| Ex. (104) | Com. (10-8) | 4.8 | 20.3 | 2500.0 | 12.3 | 101.1 | (0.66, 0.35) |
| Ex. (105) | Com. (10-9) | 4.9 | 19.3 | 2500.0 | 13.0 | 105.2 | (0.66, 0.35) |
| Ex. (106) | Com. (10-10) | 4.8 | 20.1 | 2500.0 | 12.4 | 102.9 | (0.66, 0.35) |
| Ex. (107) | Com. (10-11) | 4.7 | 19.7 | 2500.0 | 12.7 | 119.0 | (0.66, 0.35) |
| Ex. (108) | Com. (10-12) | 4.8 | 20.1 | 2500.0 | 12.5 | 101.7 | (0.66, 0.35) |
| Ex. (109) | Com. (11-1) | 4.7 | 18.4 | 2500.0 | 13.6 | 101.9 | (0.66, 0.35) |
| Ex. (110) | Com. (11-2) | 4.7 | 18.6 | 2500.0 | 13.4 | 108.6 | (0.66, 0.35) |
| Ex. (111) | Com. (11-3) | 4.7 | 18.0 | 2500.0 | 13.9 | 110.5 | (0.66, 0.35) |
| Ex. (112) | Com. (11-4) | 4.7 | 18.3 | 2500.0 | 13.7 | 110.8 | (0.66, 0.35) |
| Ex. (113) | Com. (11-5) | 4.7 | 17.9 | 2500.0 | 14.0 | 102.9 | (0.66, 0.35) |
| Ex. (114) | Com. (11-6) | 4.8 | 18.6 | 2500.0 | 13.4 | 115.5 | (0.66, 0.35) |
| Ex. (115) | Com. (11-7) | 4.6 | 17.9 | 2500.0 | 13.9 | 112.8 | (0.66, 0.35) |
| Ex. (116) | Com. (11-8) | 4.7 | 18.2 | 2500.0 | 13.8 | 106.5 | (0.66, 0.35) |
| Ex. (117) | Com. (11-9) | 4.6 | 18.8 | 2500.0 | 13.3 | 105.5 | (0.66, 0.35) |
| Ex. (118) | Com. (11-10) | 4.8 | 18.4 | 2500.0 | 13.6 | 113.6 | (0.66, 0.35) |
| Ex. (119) | Com. (11-11) | 4.8 | 19.2 | 2500.0 | 13.0 | 103.0 | (0.66, 0.35) |
| Ex. (120) | Com. (11-12) | 4.7 | 19.2 | 2500.0 | 13.0 | 109.6 | (0.66, 0.35) |
| Ex. (121) | Com. (12-1) | 4.9 | 20.9 | 2500.0 | 12.0 | 119.4 | (0.66, 0.35) |
| Ex. (122) | Com. (12-2) | 4.9 | 20.9 | 2500.0 | 11.9 | 107.1 | (0.66, 0.35) |
| Ex. (123) | Com. (12-3) | 4.8 | 22.6 | 2500.0 | 11.1 | 113.0 | (0.66, 0.35) |
| Ex. (124) | Com. (12-4) | 4.9 | 21.9 | 2500.0 | 11.4 | 100.9 | (0.66, 0.35) |
| Ex. (125) | Com. (12-5) | 4.9 | 21.3 | 2500.0 | 11.7 | 115.6 | (0.66, 0.35) |
| Ex. (126) | Com. (12-6) | 4.8 | 22.0 | 2500.0 | 11.4 | 115.0 | (0.66, 0.35) |
| Ex. (127) | Com. (12-7) | 4.9 | 21.1 | 2500.0 | 11.8 | 111.0 | (0.66, 0.35) |
| Ex. (128) | Com. (12-8) | 5.0 | 22.1 | 2500.0 | 11.3 | 103.1 | (0.66, 0.35) |
| Ex. (129) | Com. (12-9) | 4.8 | 21.8 | 2500.0 | 11.5 | 116.2 | (0.66, 0.35) |
| Ex. (130) | Com. (12-10) | 4.8 | 22.2 | 2500.0 | 11.3 | 102.3 | (0.66, 0.35) |
| Ex. (131) | Com. (12-11) | 5.0 | 21.6 | 2500.0 | 11.6 | 101.7 | (0.66, 0.35) |
| Ex. (132) | Com. (12-12) | 4.9 | 21.4 | 2500.0 | 11.7 | 107.1 | (0.66, 0.35) |
| Ex. (133) | Com. (13-1) | 4.5 | 16.9 | 2500.0 | 14.8 | 110.6 | (0.66, 0.35) |
| Ex. (134) | Com. (13-2) | 4.6 | 17.4 | 2500.0 | 14.3 | 104.9 | (0.66, 0.35) |
| Ex. (135) | Com. (13-3) | 4.7 | 17.3 | 2500.0 | 14.5 | 119.3 | (0.66, 0.35) |
| Ex. (136) | Com. (13-4) | 4.7 | 17.4 | 2500.0 | 14.4 | 116.4 | (0.66, 0.35) |
| Ex. (137) | Com. (13-5) | 4.7 | 17.1 | 2500.0 | 14.6 | 118.4 | (0.66, 0.35) |
| Ex. (138) | Com. (13-6) | 4.6 | 17.2 | 2500.0 | 14.5 | 108.0 | (0.66, 0.35) |
| Ex. (139) | Com. (13-7) | 4.6 | 16.7 | 2500.0 | 15.0 | 105.8 | (0.66, 0.35) |
| Ex. (140) | Com. (13-8) | 4.6 | 17.6 | 2500.0 | 14.2 | 118.5 | (0.66, 0.35) |
| Ex. (141) | Com. (13-9) | 4.6 | 17.8 | 2500.0 | 14.0 | 119.5 | (0.66, 0.35) |
| Ex. (142) | Com. (13-10) | 4.6 | 17.0 | 2500.0 | 14.7 | 112.1 | (0.66, 0.35) |
| Ex. (143) | Com. (13-11) | 4.6 | 17.1 | 2500.0 | 14.6 | 106.7 | (0.66, 0.35) |
| Ex. (144) | Com. (13-12) | 4.5 | 16.9 | 2500.0 | 14.8 | 110.0 | (0.66, 0.35) |
| Ex. (145) | Com. (14-1) | 4.4 | 16.2 | 2500.0 | 15.4 | 111.9 | (0.66, 0.35) |
| Ex. (146) | Com. (14-2) | 4.5 | 16.1 | 2500.0 | 15.5 | 115.4 | (0.66, 0.35) |
| Ex. (147) | Com. (14-3) | 4.4 | 15.7 | 2500.0 | 15.9 | 120.0 | (0.66, 0.35) |

TABLE 3-continued

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (148) | Com. (14-4) | 4.5 | 16.7 | 2500.0 | 15.0 | 105.8 | (0.66, 0.35) |
| Ex. (149) | Com. (14-5) | 4.5 | 16.6 | 2500.0 | 15.1 | 101.4 | (0.66, 0.35) |
| Ex. (150) | Com. (14-6) | 4.4 | 16.0 | 2500.0 | 15.7 | 118.7 | (0.66, 0.35) |
| Ex. (151) | Com. (14-7) | 4.5 | 16.0 | 2500.0 | 15.7 | 105.3 | (0.66, 0.35) |
| Ex. (152) | Com. (14-8) | 4.4 | 15.9 | 2500.0 | 15.8 | 109.9 | (0.66, 0.35) |
| Ex. (153) | Com. (14-9) | 4.5 | 15.8 | 2500.0 | 15.9 | 108.8 | (0.66, 0.35) |
| Ex. (154) | Com. (14-10) | 4.5 | 16.0 | 2500.0 | 15.6 | 109.7 | (0.66, 0.35) |
| Ex. (155) | Com. (14-11) | 4.6 | 15.8 | 2500.0 | 15.9 | 107.4 | (0.66, 0.35) |
| Ex. (156) | Com. (14-12) | 4.4 | 16.4 | 2500.0 | 15.2 | 103.2 | (0.66, 0.35) |
| Ex. (157) | Com. (15-1) | 4.6 | 17.8 | 2500.0 | 14.0 | 101.4 | (0.66, 0.35) |
| Ex. (158) | Com. (15-2) | 4.6 | 16.9 | 2500.0 | 14.8 | 106.0 | (0.66, 0.35) |
| Ex. (159) | Com. (15-3) | 4.7 | 17.1 | 2500.0 | 14.6 | 117.4 | (0.66, 0.35) |
| Ex. (160) | Com. (15-4) | 4.6 | 16.8 | 2500.0 | 14.9 | 115.7 | (0.66, 0.35) |
| Ex. (161) | Com. (15-5) | 4.6 | 16.7 | 2500.0 | 15.0 | 115.2 | (0.66, 0.35) |
| Ex. (162) | Com. (15-6) | 4.7 | 16.7 | 2500.0 | 15.0 | 114.6 | (0.66, 0.35) |
| Ex. (163) | Com. (15-7) | 4.6 | 16.8 | 2500.0 | 14.9 | 112.1 | (0.66, 0.35) |
| Ex. (164) | Com. (15-8) | 4.6 | 17.3 | 2500.0 | 14.4 | 103.1 | (0.66, 0.35) |
| Ex. (165) | Com. (15-9) | 4.7 | 17.3 | 2500.0 | 14.4 | 105.2 | (0.66, 0.35) |
| Ex. (166) | Com. (15-10) | 4.6 | 17.7 | 2500.0 | 14.2 | 104.5 | (0.66, 0.35) |
| Ex. (167) | Com. (15-11) | 4.6 | 16.7 | 2500.0 | 14.9 | 116.8 | (0.66, 0.35) |
| Ex. (168) | Com. (15-12) | 4.7 | 16.9 | 2500.0 | 14.8 | 103.0 | (0.66, 0.35) |
| Ex. (169) | Com. (16-1) | 4.8 | 21.9 | 2500.0 | 11.4 | 101.1 | (0.66, 0.35) |
| Ex. (170) | Com. (16-2) | 5.0 | 21.1 | 2500.0 | 11.8 | 107.4 | (0.66, 0.35) |
| Ex. (171) | Com. (16-3) | 4.8 | 21.6 | 2500.0 | 11.6 | 100.3 | (0.66, 0.35) |
| Ex. (172) | Com. (16-4) | 4.9 | 22.0 | 2500.0 | 11.4 | 111.1 | (0.66, 0.35) |
| Ex. (173) | Com. (16-5) | 5.0 | 22.4 | 2500.0 | 11.2 | 114.6 | (0.66, 0.35) |
| Ex. (174) | Com. (16-6) | 4.9 | 21.4 | 2500.0 | 11.7 | 100.4 | (0.66, 0.35) |
| Ex. (175) | Com. (16-7) | 4.9 | 22.5 | 2500.0 | 11.1 | 116.9 | (0.66, 0.35) |
| Ex. (176) | Com. (16-8) | 4.8 | 20.9 | 2500.0 | 12.0 | 111.8 | (0.66, 0.35) |
| Ex. (177) | Com. (16-9) | 5.0 | 21.7 | 2500.0 | 11.5 | 107.7 | (0.66, 0.35) |
| Ex. (178) | Com. (16-10) | 4.9 | 21.5 | 2500.0 | 11.6 | 102.1 | (0.66, 0.35) |
| Ex. (179) | Com. (16-11) | 4.9 | 21.7 | 2500.0 | 11.5 | 108.2 | (0.66, 0.35) |
| Ex. (180) | Com. (16-12) | 5.0 | 20.9 | 2500.0 | 12.0 | 115.8 | (0.66, 0.35) |
| Ex. (181) | Com. (17-1) | 4.9 | 19.9 | 2500.0 | 12.6 | 100.2 | (0.66, 0.35) |
| Ex. (182) | Com. (17-2) | 4.9 | 19.2 | 2500.0 | 13.0 | 103.0 | (0.66, 0.35) |
| Ex. (183) | Com. (17-3) | 4.8 | 19.5 | 2500.0 | 12.8 | 114.3 | (0.66, 0.35) |
| Ex. (184) | Com. (17-4) | 4.9 | 20.0 | 2500.0 | 12.5 | 118.1 | (0.66, 0.35) |
| Ex. (185) | Com. (17-5) | 4.8 | 20.0 | 2500.0 | 12.5 | 103.9 | (0.66, 0.35) |
| Ex. (186) | Com. (17-6) | 4.7 | 20.7 | 2500.0 | 12.1 | 102.0 | (0.66, 0.35) |
| Ex. (187) | Com. (17-7) | 4.8 | 20.6 | 2500.0 | 12.2 | 102.7 | (0.66, 0.35) |
| Ex. (188) | Com. (17-8) | 4.8 | 20.2 | 2500.0 | 12.4 | 101.0 | (0.66, 0.35) |
| Ex. (189) | Com. (17-9) | 4.7 | 19.6 | 2500.0 | 12.8 | 108.7 | (0.66, 0.35) |
| Ex. (190) | Com. (17-10) | 4.8 | 19.8 | 2500.0 | 12.6 | 111.5 | (0.66, 0.35) |
| Ex. (191) | Com. (17-11) | 4.8 | 19.4 | 2500.0 | 12.9 | 106.3 | (0.66, 0.35) |
| Ex. (192) | Com. (17-12) | 4.9 | 19.6 | 2500.0 | 12.7 | 110.1 | (0.66, 0.35) |
| Ex. (193) | Com. (18-1) | 5.0 | 24.0 | 2500.0 | 10.4 | 103.9 | (0.66, 0.35) |
| Ex. (194) | Com. (18-2) | 4.9 | 23.2 | 2500.0 | 10.8 | 101.3 | (0.66, 0.35) |
| Ex. (195) | Com. (18-3) | 5.1 | 23.5 | 2500.0 | 10.6 | 114.4 | (0.66, 0.35) |
| Ex. (196) | Com. (18-4) | 5.0 | 22.9 | 2500.0 | 10.9 | 120.0 | (0.66, 0.35) |
| Ex. (197) | Com. (18-5) | 5.0 | 23.6 | 2500.0 | 10.6 | 118.5 | (0.66, 0.35) |
| Ex. (198) | Com. (18-6) | 5.0 | 23.2 | 2500.0 | 10.8 | 105.0 | (0.66, 0.35) |
| Ex. (199) | Com. (18-7) | 5.1 | 24.7 | 2500.0 | 10.1 | 115.1 | (0.66, 0.35) |
| Ex. (200) | Com. (18-8) | 5.0 | 24.7 | 2500.0 | 10.1 | 101.8 | (0.66, 0.35) |
| Ex. (201) | Com. (18-9) | 4.9 | 23.7 | 2500.0 | 10.6 | 104.3 | (0.66, 0.35) |
| Ex. (202) | Com. (18-10) | 4.9 | 24.8 | 2500.0 | 10.1 | 102.8 | (0.66, 0.35) |
| Ex. (203) | Com. (18-11) | 5.0 | 24.6 | 2500.0 | 10.2 | 113.5 | (0.66, 0.35) |
| Ex. (204) | Com. (18-12) | 5.0 | 23.4 | 2500.0 | 10.7 | 102.1 | (0.66, 0.35) |
| Ex. (205) | Com. (19-1) | 4.8 | 18.4 | 2500.0 | 13.6 | 109.3 | (0.66, 0.35) |
| Ex. (206) | Com. (19-2) | 4.6 | 18.8 | 2500.0 | 13.3 | 114.3 | (0.66, 0.35) |
| Ex. (207) | Com. (19-3) | 4.7 | 18.2 | 2500.0 | 13.7 | 119.1 | (0.66, 0.35) |
| Ex. (208) | Com. (19-4) | 4.7 | 17.9 | 2500.0 | 14.0 | 100.3 | (0.66, 0.35) |
| Ex. (209) | Com. (19-5) | 4.7 | 18.5 | 2500.0 | 13.5 | 106.5 | (0.66, 0.35) |
| Ex. (210) | Com. (19-6) | 4.6 | 18.7 | 2500.0 | 13.4 | 103.9 | (0.66, 0.35) |
| Ex. (211) | Com. (19-7) | 4.8 | 18.9 | 2500.0 | 13.2 | 115.5 | (0.66, 0.35) |
| Ex. (212) | Com. (19-8) | 4.7 | 18.8 | 2500.0 | 13.3 | 103.9 | (0.66, 0.35) |
| Ex. (213) | Com. (19-9) | 4.6 | 18.2 | 2500.0 | 13.8 | 108.9 | (0.66, 0.35) |
| Ex. (214) | Com. (19-10) | 4.6 | 18.9 | 2500.0 | 13.2 | 102.0 | (0.66, 0.35) |
| Ex. (215) | Com. (19-11) | 4.7 | 18.7 | 2500.0 | 13.4 | 102.1 | (0.66, 0.35) |
| Ex. (216) | Com. (19-12) | 4.7 | 18.3 | 2500.0 | 13.6 | 109.5 | (0.66, 0.35) |
| Ex. (217) | Com. (20-1) | 4.4 | 16.2 | 2500.0 | 15.4 | 115.6 | (0.66, 0.35) |
| Ex. (218) | Com. (20-2) | 4.4 | 16.3 | 2500.0 | 15.3 | 101.4 | (0.66, 0.35) |
| Ex. (219) | Com. (20-3) | 4.5 | 16.4 | 2500.0 | 15.3 | 112.6 | (0.66, 0.35) |
| Ex. (220) | Com. (20-4) | 4.5 | 16.3 | 2500.0 | 15.4 | 119.6 | (0.66, 0.35) |
| Ex. (221) | Com. (20-5) | 4.4 | 16.6 | 2500.0 | 15.1 | 115.8 | (0.66, 0.35) |
| Ex. (222) | Com. (20-6) | 4.5 | 16.6 | 2500.0 | 15.1 | 113.4 | (0.66, 0.35) |
| Ex. (223) | Com. (20-7) | 4.4 | 15.7 | 2500.0 | 15.9 | 118.3 | (0.66, 0.35) |

TABLE 3-continued

| | Compound | Voltage (V) | Current Density (mA/cm$^2$) | Brightness (cd/m$^2$) | Efficiency (cd/A) | Lifetime T(95) | CIE (x, y) |
|---|---|---|---|---|---|---|---|
| Ex. (224) | Com. (20-8) | 4.5 | 15.7 | 2500.0 | 16.0 | 108.5 | (0.66, 0.35) |
| Ex. (225) | Com. (20-9) | 4.6 | 16.3 | 2500.0 | 15.3 | 105.2 | (0.66, 0.35) |
| Ex. (226) | Com. (20-10) | 4.5 | 16.4 | 2500.0 | 15.2 | 104.5 | (0.66, 0.35) |
| Ex. (227) | Com. (20-11) | 4.5 | 16.1 | 2500.0 | 15.6 | 104.2 | (0.66, 0.35) |
| Ex. (228) | Com. (20-12) | 4.5 | 16.6 | 2500.0 | 15.0 | 115.5 | (0.66, 0.35) |
| Ex. (229) | Com. (21-1) | 4.7 | 16.8 | 2500.0 | 14.9 | 111.2 | (0.66, 0.35) |
| Ex. (230) | Com. (21-2) | 4.6 | 17.7 | 2500.0 | 14.1 | 102.1 | (0.66, 0.35) |
| Ex. (231) | Com. (21-3) | 4.6 | 17.5 | 2500.0 | 14.3 | 105.7 | (0.66, 0.35) |
| Ex. (232) | Com. (21-4) | 4.7 | 17.3 | 2500.0 | 14.5 | 109.8 | (0.66, 0.35) |
| Ex. (233) | Com. (21-5) | 4.7 | 17.1 | 2500.0 | 14.6 | 107.2 | (0.66, 0.35) |
| Ex. (234) | Com. (21-6) | 4.6 | 17.3 | 2500.0 | 14.4 | 106.5 | (0.66, 0.35) |
| Ex. (235) | Com. (21-7) | 4.7 | 16.8 | 2500.0 | 14.9 | 100.6 | (0.66, 0.35) |
| Ex. (236) | Com. (21-8) | 4.6 | 17.2 | 2500.0 | 14.6 | 104.8 | (0.66, 0.35) |
| Ex. (237) | Com. (21-9) | 4.6 | 17.5 | 2500.0 | 14.3 | 102.8 | (0.66, 0.35) |
| Ex. (238) | Com. (21-10) | 4.6 | 17.5 | 2500.0 | 14.2 | 119.2 | (0.66, 0.35) |
| Ex. (239) | Com. (21-11) | 4.5 | 16.8 | 2500.0 | 14.9 | 114.0 | (0.66, 0.35) |
| Ex. (240) | Com. (21-12) | 4.7 | 16.8 | 2500.0 | 14.9 | 115.1 | (0.66, 0.35) |
| Ex. (241) | Com. (22-1) | 4.6 | 21.1 | 2500.0 | 11.8 | 114.9 | (0.66, 0.35) |
| Ex. (242) | Com. (22-2) | 4.9 | 21.5 | 2500.0 | 11.6 | 104.2 | (0.66, 0.35) |
| Ex. (243) | Com. (22-3) | 4.9 | 22.4 | 2500.0 | 11.1 | 109.4 | (0.66, 0.35) |
| Ex. (244) | Com. (22-4) | 4.9 | 22.1 | 2500.0 | 11.3 | 107.2 | (0.66, 0.35) |
| Ex. (245) | Com. (22-5) | 4.9 | 22.7 | 2500.0 | 11.0 | 119.8 | (0.66, 0.35) |
| Ex. (246) | Com. (22-6) | 4.9 | 21.3 | 2500.0 | 11.7 | 114.4 | (0.66, 0.35) |
| Ex. (247) | Com. (22-7) | 5.0 | 22.4 | 2500.0 | 11.2 | 111.7 | (0.66, 0.35) |
| Ex. (248) | Com. (22-8) | 4.8 | 21.1 | 2500.0 | 11.8 | 105.2 | (0.66, 0.35) |
| Ex. (249) | Com. (22-9) | 4.9 | 21.5 | 2500.0 | 11.6 | 107.8 | (0.66, 0.35) |
| Ex. (250) | Com. (22-10) | 4.8 | 21.8 | 2500.0 | 11.5 | 110.6 | (0.66, 0.35) |
| Ex. (251) | Com. (22-11) | 4.8 | 21.2 | 2500.0 | 11.8 | 108.7 | (0.66, 0.35) |
| Ex. (252) | Com. (22-12) | 4.8 | 21.3 | 2500.0 | 11.7 | 104.7 | (0.66, 0.35) |
| Ex. (253) | Com. (23-1) | 4.8 | 19.3 | 2500.0 | 13.0 | 113.0 | (0.66, 0.35) |
| Ex. (254) | Com. (23-2) | 4.8 | 19.3 | 2500.0 | 13.0 | 104.8 | (0.66, 0.35) |
| Ex. (255) | Com. (23-3) | 4.8 | 19.3 | 2500.0 | 13.0 | 118.0 | (0.66, 0.35) |
| Ex. (256) | Com. (23-4) | 4.8 | 20.3 | 2500.0 | 12.3 | 113.2 | (0.66, 0.35) |
| Ex. (257) | Com. (23-5) | 4.9 | 20.2 | 2500.0 | 12.4 | 114.8 | (0.66, 0.35) |
| Ex. (258) | Com. (23-6) | 4.7 | 19.5 | 2500.0 | 12.8 | 101.2 | (0.66, 0.35) |
| Ex. (259) | Com. (23-7) | 4.7 | 19.5 | 2500.0 | 12.8 | 106.4 | (0.66, 0.35) |
| Ex. (260) | Com. (23-8) | 4.9 | 20.0 | 2500.0 | 12.5 | 108.8 | (0.66, 0.35) |
| Ex. (261) | Com. (23-9) | 4.8 | 20.8 | 2500.0 | 12.0 | 113.1 | (0.66, 0.35) |
| Ex. (262) | Com. (23-10) | 4.9 | 19.5 | 2500.0 | 12.9 | 108.8 | (0.66, 0.35) |
| Ex. (263) | Com. (23-11) | 4.9 | 19.9 | 2500.0 | 12.6 | 111.7 | (0.66, 0.35) |
| Ex. (264) | Com. (23-12) | 4.8 | 20.1 | 2500.0 | 12.5 | 103.9 | (0.66, 0.35) |
| Ex. (265) | Com. (24-1) | 5.0 | 23.5 | 2500.0 | 10.6 | 107.8 | (0.66, 0.35) |
| Ex. (266) | Com. (24-2) | 5.1 | 23.6 | 2500.0 | 10.6 | 116.2 | (0.66, 0.35) |
| Ex. (267) | Com. (24-3) | 4.9 | 23.4 | 2500.0 | 10.7 | 110.4 | (0.66, 0.35) |
| Ex. (268) | Com. (24-4) | 5.1 | 24.8 | 2500.0 | 10.1 | 110.7 | (0.66, 0.35) |
| Ex. (269) | Com. (24-5) | 5.0 | 22.9 | 2500.0 | 10.9 | 101.3 | (0.66, 0.35) |
| Ex. (270) | Com. (24-6) | 5.0 | 23.4 | 2500.0 | 10.7 | 104.3 | (0.66, 0.35) |
| Ex. (271) | Com. (24-7) | 5.0 | 23.2 | 2500.0 | 10.8 | 109.4 | (0.66, 0.35) |
| Ex. (272) | Com. (24-8) | 4.9 | 24.7 | 2500.0 | 10.1 | 113.4 | (0.66, 0.35) |
| Ex. (273) | Com. (24-9) | 5.1 | 23.1 | 2500.0 | 10.8 | 109.2 | (0.66, 0.35) |
| Ex. (274) | Com. (24-10) | 5.1 | 23.2 | 2500.0 | 10.8 | 114.3 | (0.66, 0.35) |
| Ex. (275) | Com. (24-11) | 4.9 | 23.5 | 2500.0 | 10.6 | 100.5 | (0.66, 0.35) |
| Ex. (276) | Com. (24-12) | 5.1 | 24.4 | 2500.0 | 10.2 | 114.3 | (0.66, 0.35) |
| Ex. (277) | Com. (25-1) | 4.8 | 18.4 | 2500.0 | 13.6 | 109.1 | (0.66, 0.35) |
| Ex. (278) | Com. (25-2) | 4.6 | 18.7 | 2500.0 | 13.3 | 115.8 | (0.66, 0.35) |
| Ex. (279) | Com. (25-3) | 4.7 | 18.9 | 2500.0 | 13.2 | 104.0 | (0.66, 0.35) |
| Ex. (280) | Com. (25-4) | 4.8 | 19.1 | 2500.0 | 13.1 | 118.5 | (0.66, 0.35) |
| Ex. (281) | Com. (25-5) | 4.7 | 18.4 | 2500.0 | 13.6 | 109.0 | (0.66, 0.35) |
| Ex. (282) | Com. (25-6) | 4.8 | 19.0 | 2500.0 | 13.2 | 103.7 | (0.66, 0.35) |
| Ex. (283) | Com. (25-7) | 4.7 | 18.1 | 2500.0 | 13.8 | 108.6 | (0.66, 0.35) |
| Ex. (284) | Com. (25-8) | 4.6 | 18.2 | 2500.0 | 13.7 | 118.6 | (0.66, 0.35) |
| Ex. (285) | Com. (25-9) | 4.6 | 18.5 | 2500.0 | 13.5 | 111.1 | (0.66, 0.35) |
| Ex. (286) | Com. (25-10) | 4.7 | 18.5 | 2500.0 | 13.5 | 100.6 | (0.66, 0.35) |
| Ex. (287) | Com. (25-11) | 4.8 | 18.2 | 2500.0 | 13.7 | 114.4 | (0.66, 0.35) |
| Ex. (288) | Com. (25-12) | 4.7 | 18.2 | 2500.0 | 13.7 | 104.8 | (0.66, 0.35) |

It can be seen from the results in Table 3 above, that the OLEDs employing the inventive compounds as phosphorescent host material showed predominantly improved luminescent efficiency and driving voltage.

Specifically, the OLEDs employing comparative compounds C, D, E, F, G or H as a phosphorescent host material showed decreased driving voltage, higher luminescent efficiency and life span, compared to the OLEDs employing comparative compounds A (CBP) or B (Bebq$_2$), wherein comparative compound A is used generally as a phosphorescent host material, and each of comparative compounds C, D, E, F, G or H has a heterocyclic ring comprising N and S and having a fused five rings as a core. Further, the OLEDs employing the inventive compounds as a phosphorescent host material showed improved results compared to the OLEDs employing comparative compounds, wherein the inventive compounds has the same core as comparative compounds C to H, but has a specific substituents such as benzothienopyrimidine or benzofuropyrimidine.

This is believed because the Comparative compounds A and B are excellent only in stability against electrons, while compound of which core is a heterocyclic ring comprising N and S and having a fused five rings is excellent in stability against holes as well as electrons, resulting in improving stability by decreasing the deterioration of the OLEDs.

It can be explained that the compound of the present invention, wherein the inventive compound is a heterocyclic ring comprising N and S and having a fused five rings as a core and is substituted with a specific substituent group such as benzothienopyrimidine or benzofuropyrimidine, has a higher T1 value than that of comparative compounds C to H, resulting in a decreased probability of a triplet-triplet annihilation and a improved energy balance in light emitting layer by high LUMO values, thereby further improving the luminous efficiency.

In addition, it can be explained that the substituent of benzothienopyrimidine or benzofuropyrimidine lowered the driving voltage of the OLEDs since the substituent has the improved a hole injection property due to the higher hole properties and has the improved packing density by forming a more planar structure compared to the substituents of Comparative Compounds A and B. This suggests that the characteristics of the compound and the device may be significantly dependent on the introduced substituents, even though the compound has the same core.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 1:

[Formula 1]

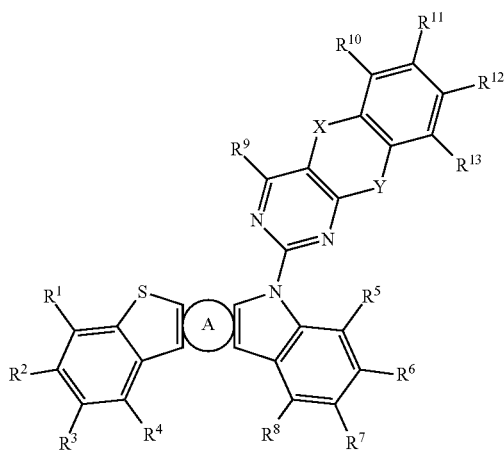

wherein,

A is a benzene ring,

X or Y is a single bond, and the other X or Y is O or S, $R^1$ to $R^8$ and $R^{10}$ to $R^{13}$ are each hydrogen, $R^9$ is a substituted or unsubstituted $C_6$-$C_{60}$ aryl group or $C_2$-$C_{60}$ heteroaryl group, wherein the aryl group or heteroaryl group may be each substituted with one or more substituents selected from the group consisting of deuterium; halogen; a silane group; a siloxane group; a boron group; a germanium group; a cyano group; a nitro group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group containing at least one heteroatom selected from the group consisting of O, N, S, Si and P; a $C_3$-$C_{20}$ cycloalkyl group; a $C_7$-$C_{20}$ arylalkyl group; and a $C_8$-$C_{20}$ arylalkenyl group.

2. The compound of claim 1, wherein Formula 1 is represented by one of Formulas below:

<Formula 2>

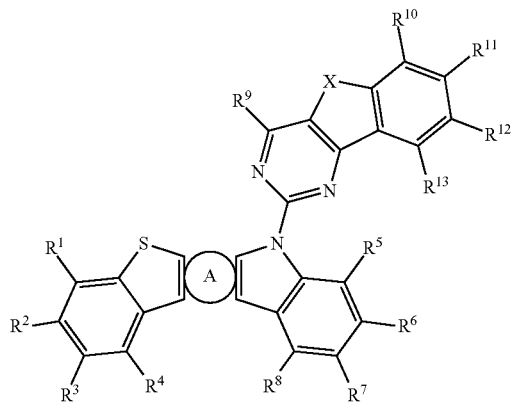

<Formula 3>

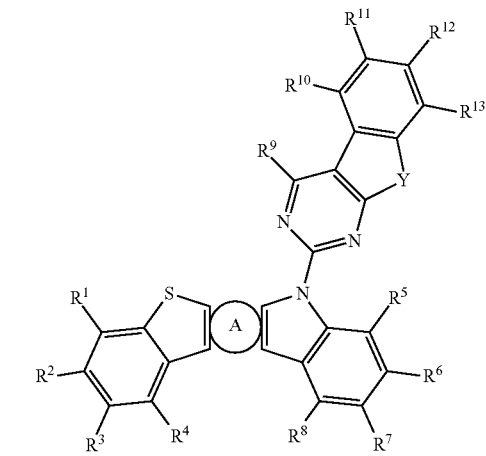

wherein, A, X, Y, and $R^1$ to $R^{13}$ are each defined as same in claim 1.

3. The compound of claim 1, wherein Formula 1 is any one of the compounds below:

<Formula 4>
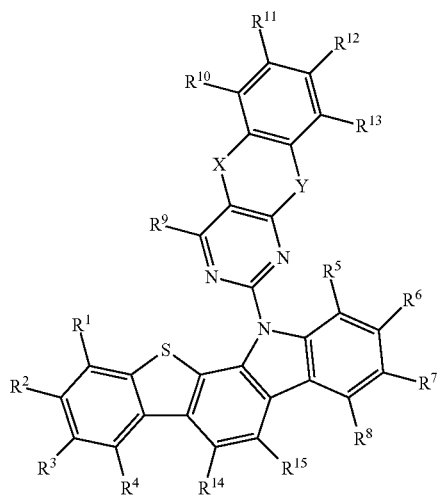
<Formula 5>
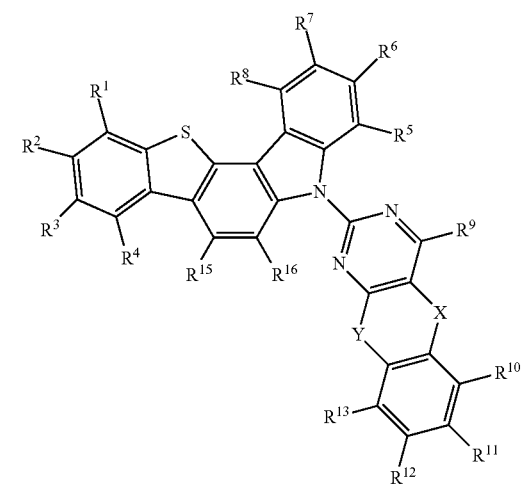
<Formula 6>
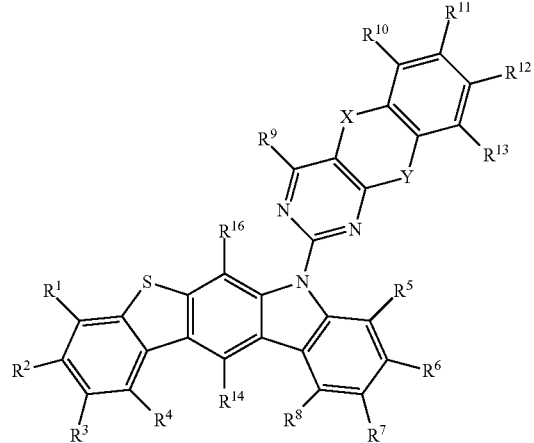
<Formula 7>
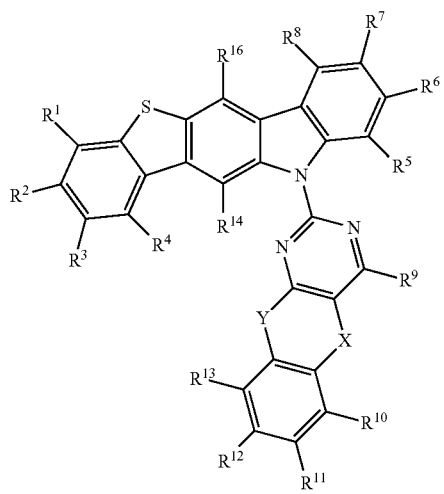
<Formula 8>
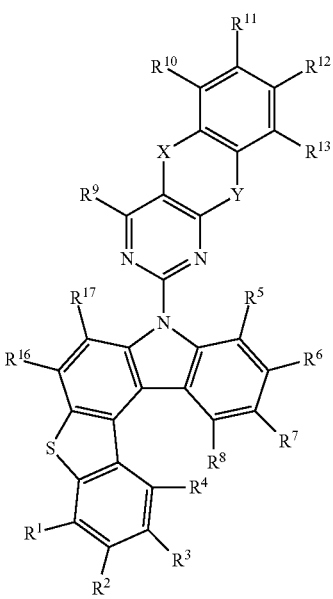
<Formula 9>
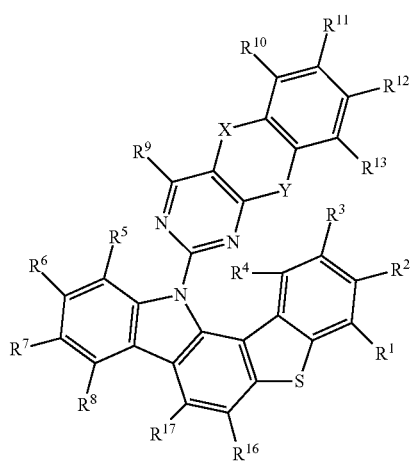
wherein X, Y, and $R^1$ to $R^{13}$ are each defined as same in claim 1, and $R^{14}$ to $R^{17}$ are each hydrogen.
4. The compound of claim 1, wherein Formula 1 is any one of the compounds below:

-continued
2-1
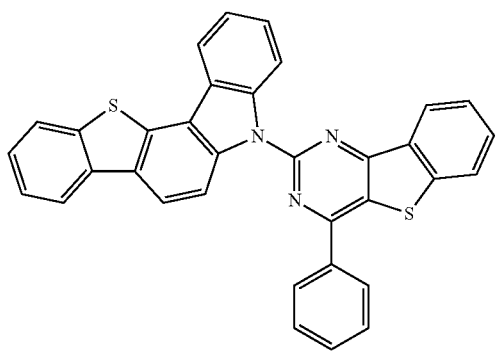
2-5
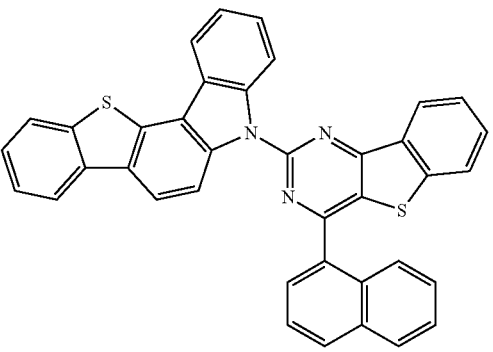
2-2
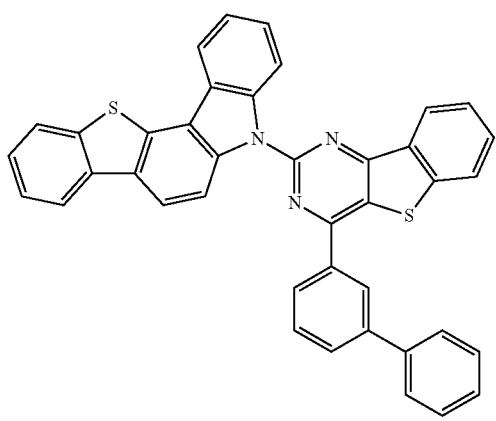
2-6
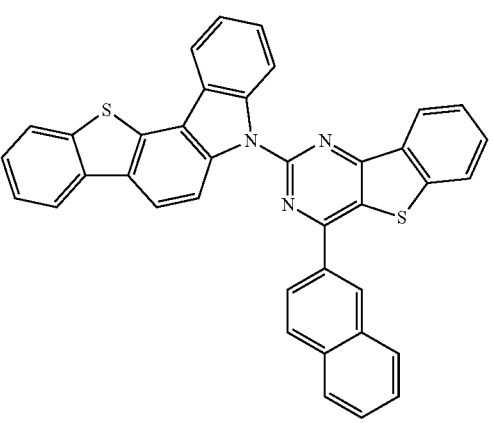
2-3
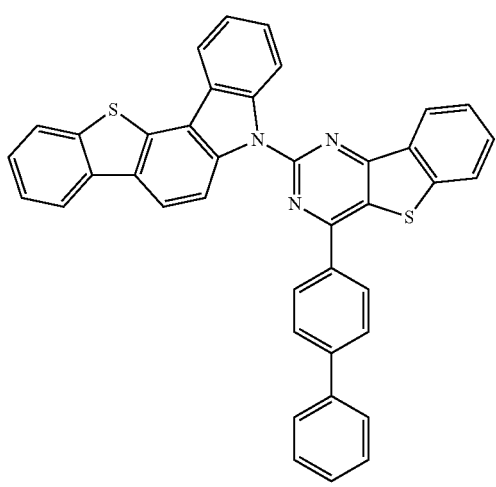
2-7
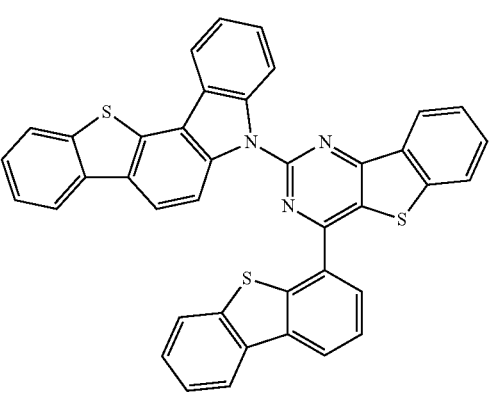
2-4
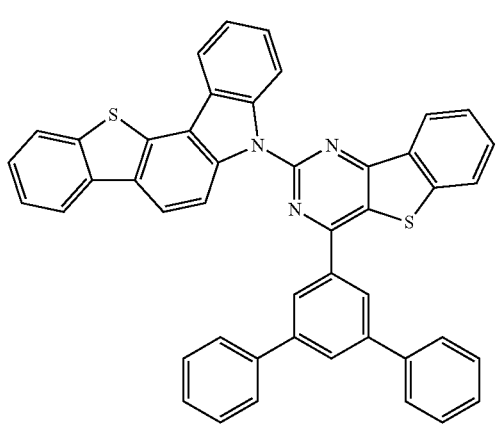
2-8
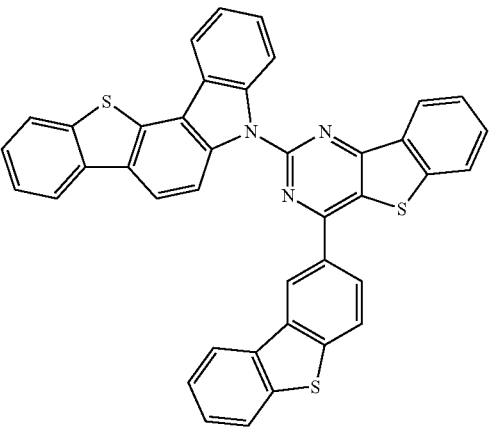

2-9
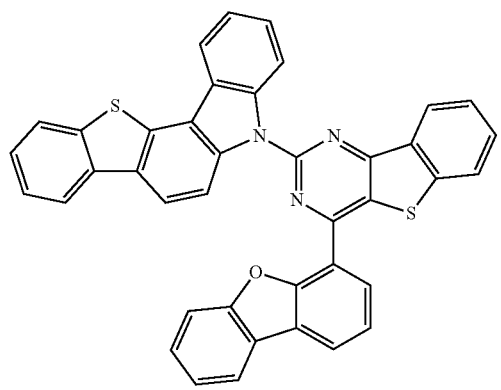
2-10
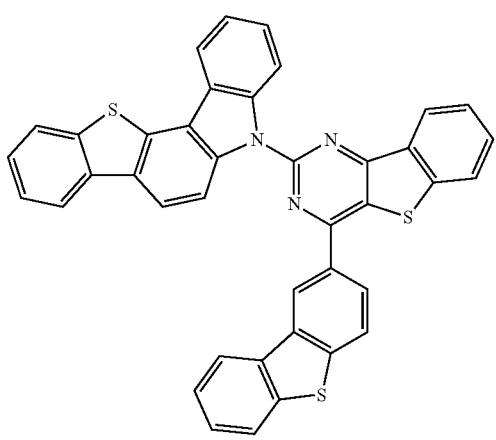
2-11
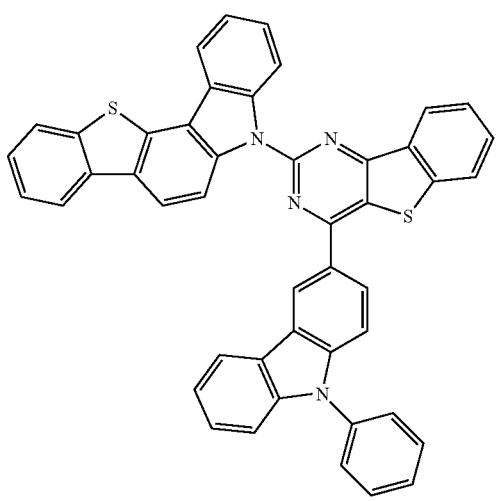
2-12
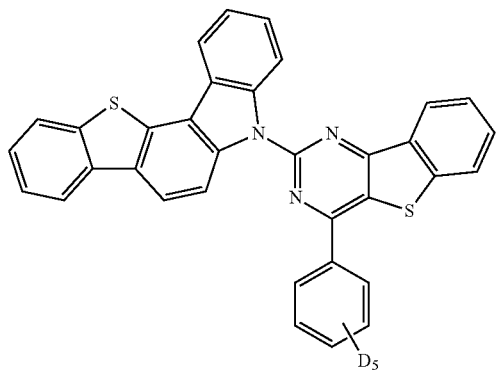
3-1
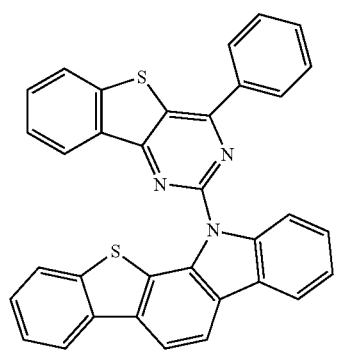
3-2
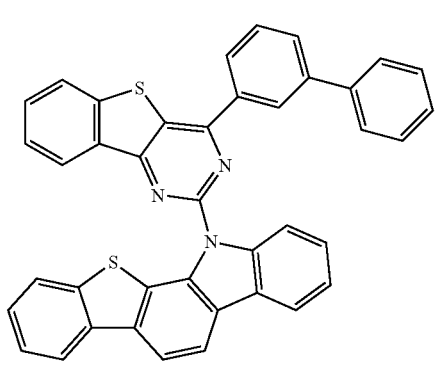
3-3
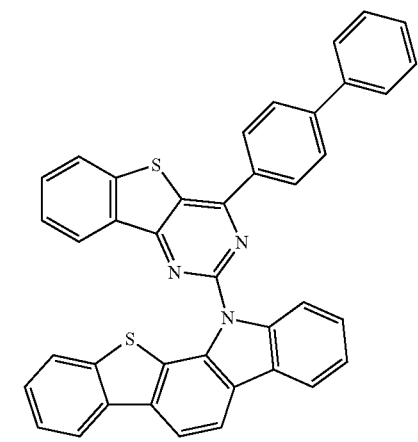

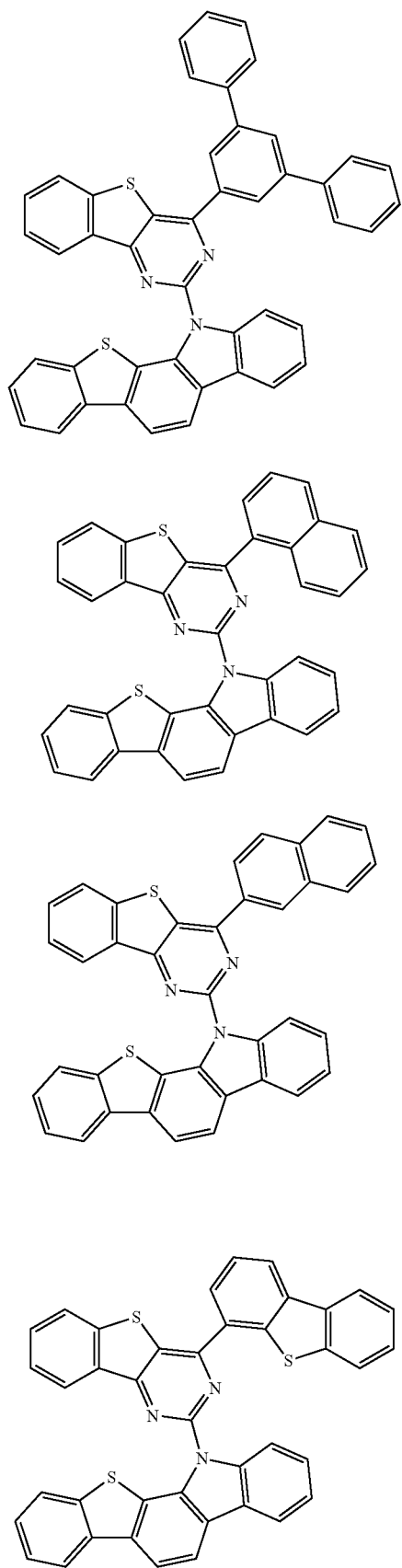
3-4
3-5
3-6
3-7
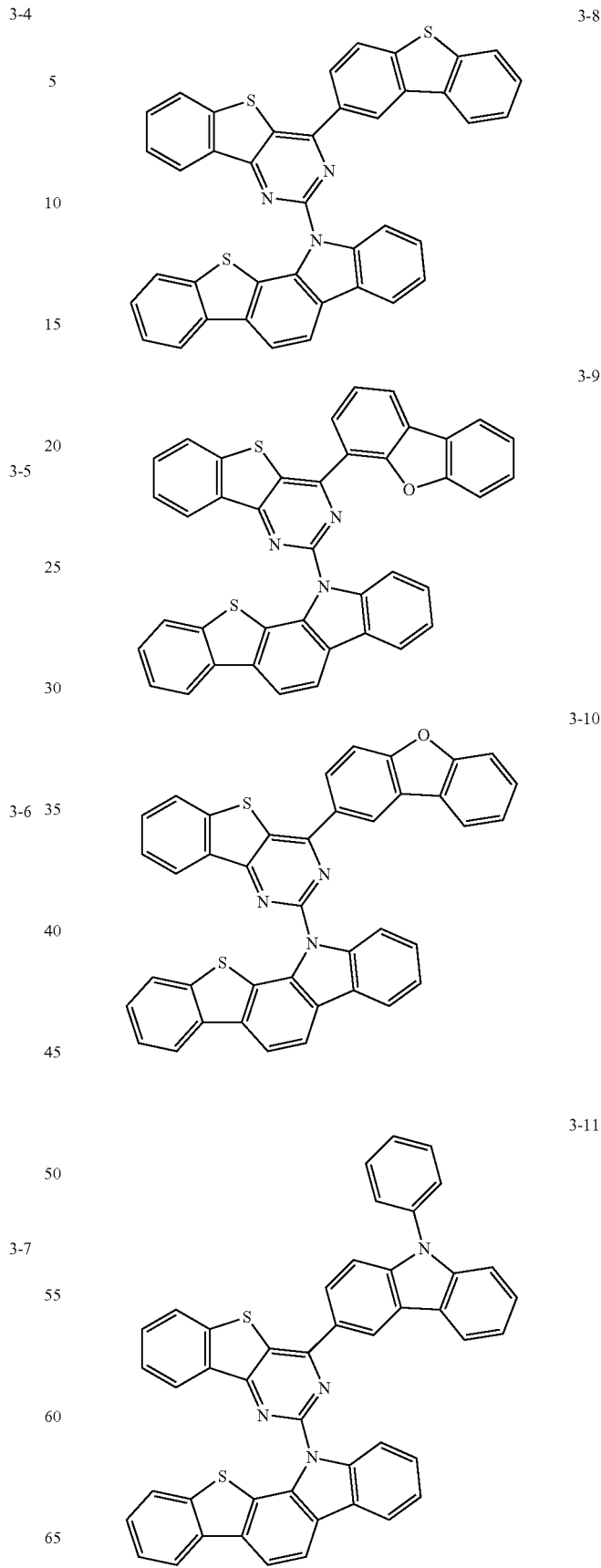
3-8
3-9
3-10
3-11

3-12
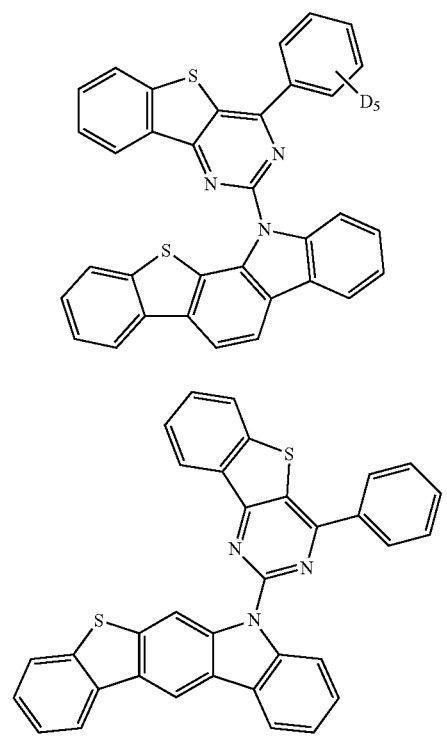
4-1
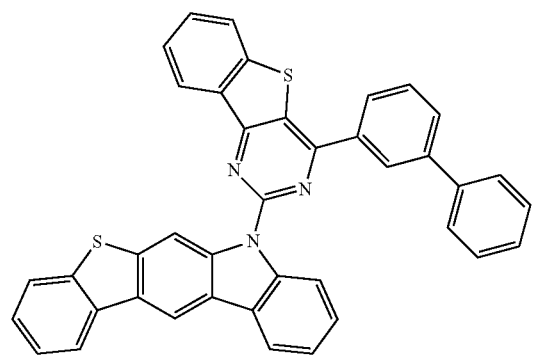
4-2
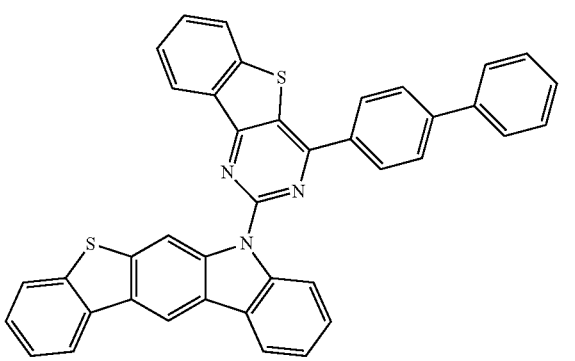
4-4
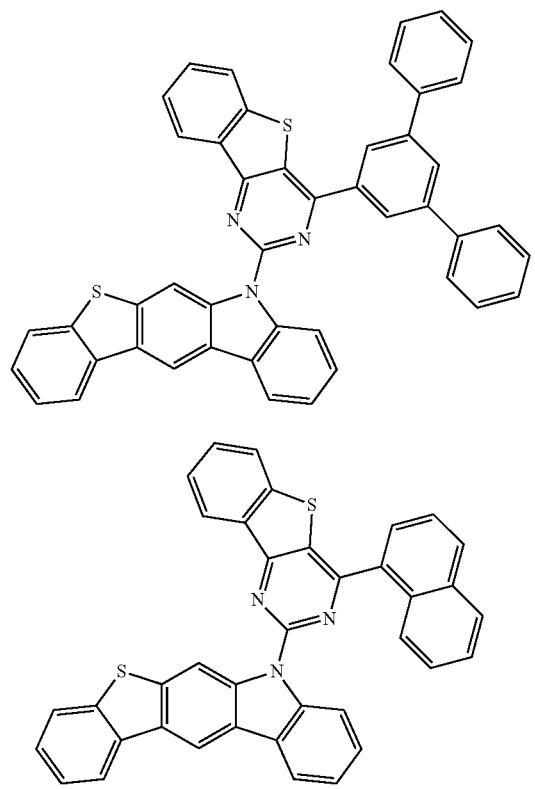
4-5
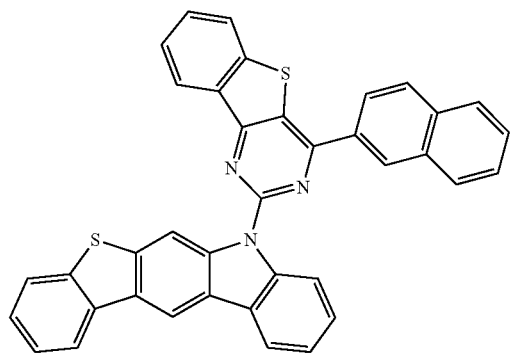
4-6
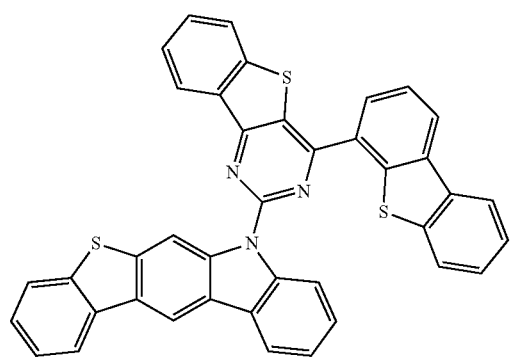

-continued
4-8
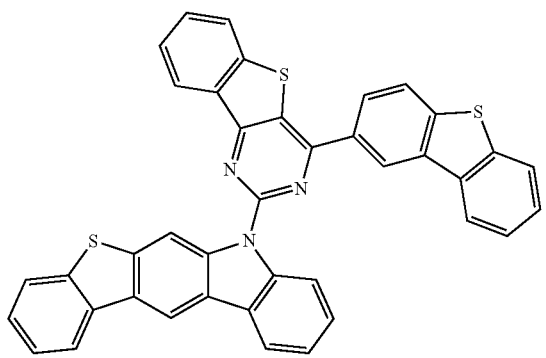
4-9
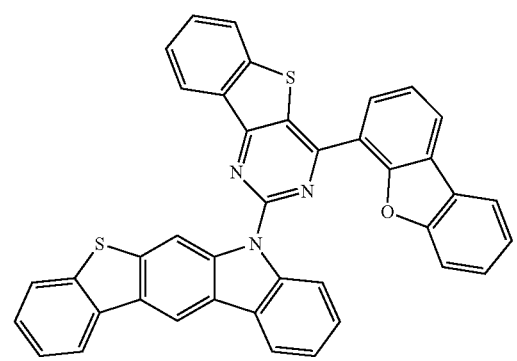
4-10
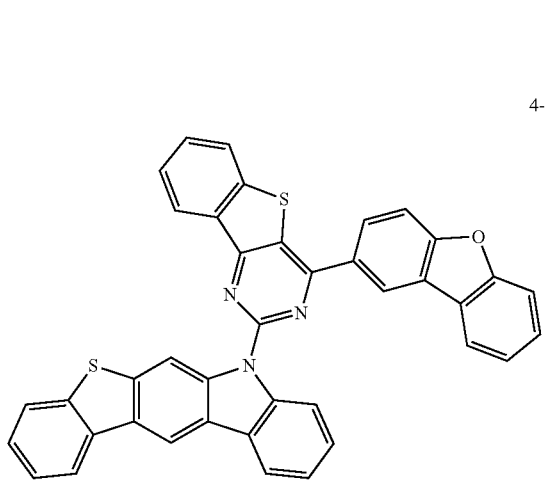
4-11
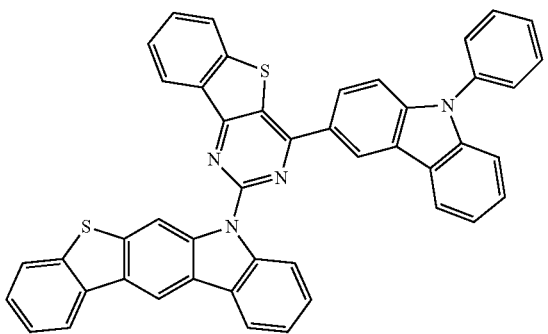
-continued
4-12
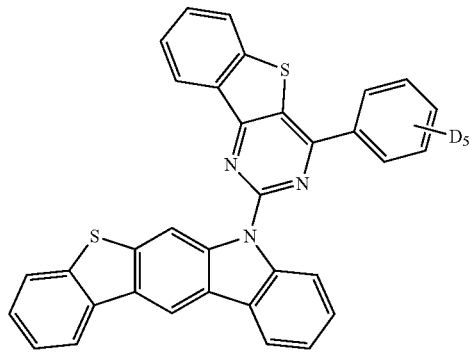
5-1
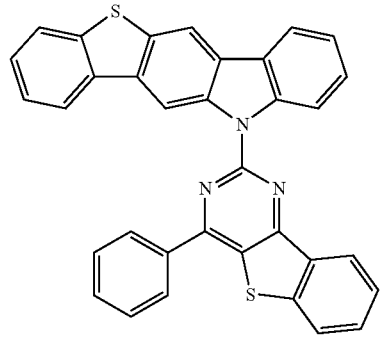
5-2
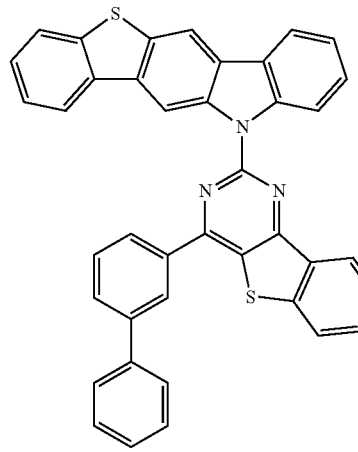
5-3
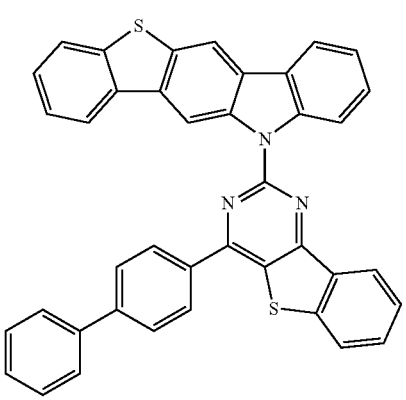

-continued
5-4
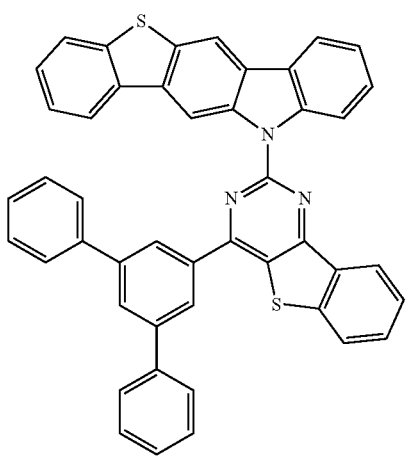
5-5
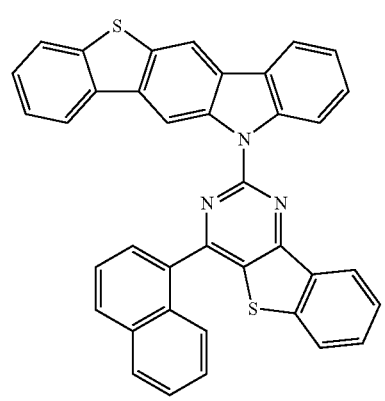
5-6
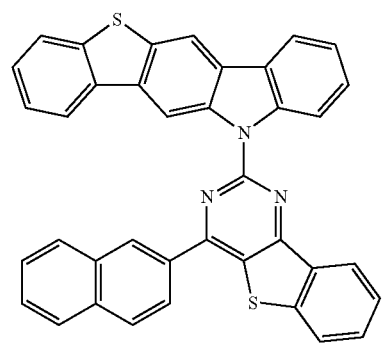
5-7
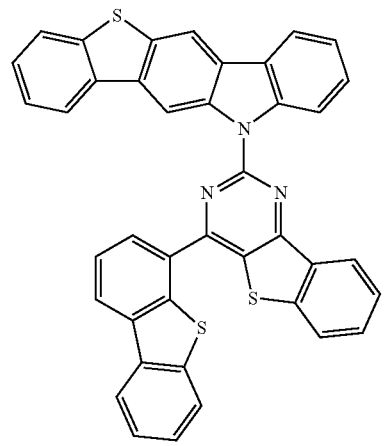
-continued
5-8
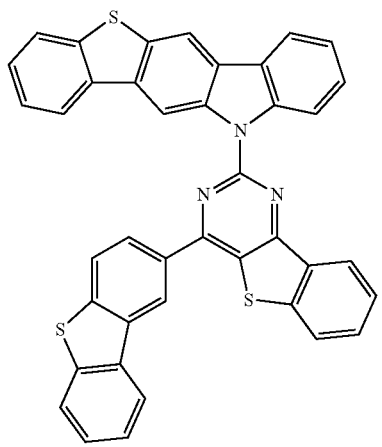
5-9
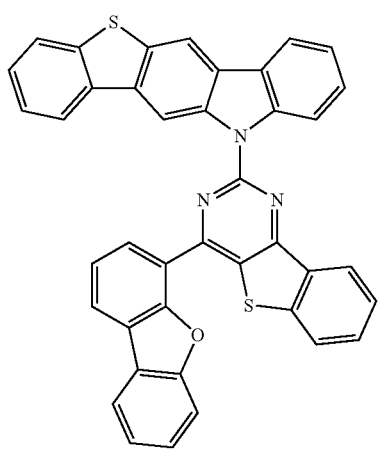
5-10
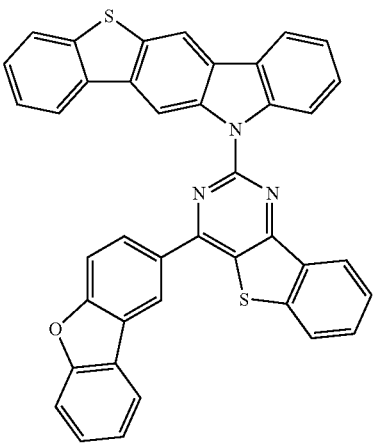

153
-continued
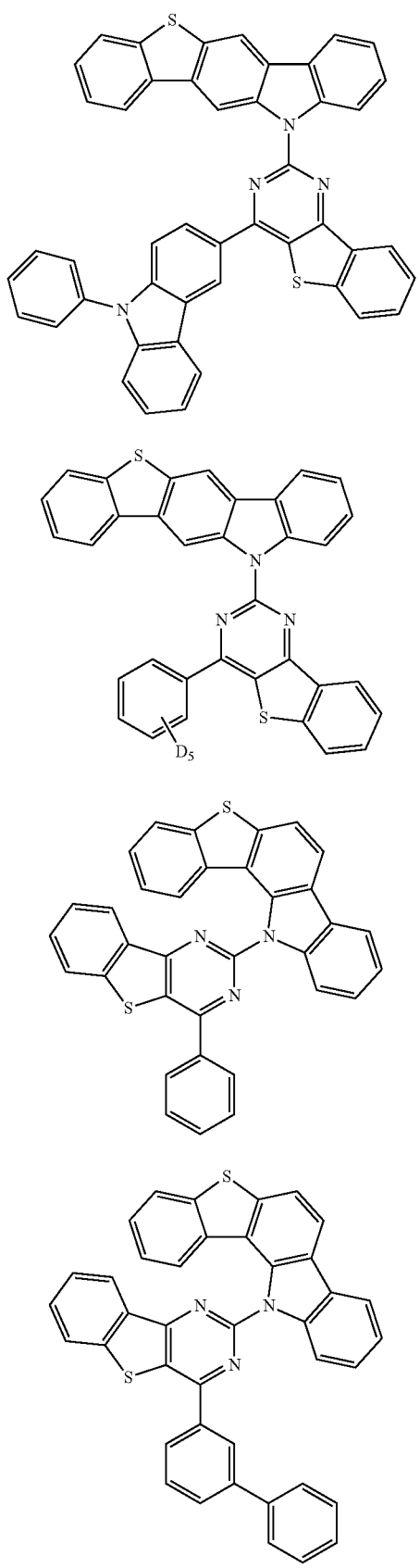
154
-continued
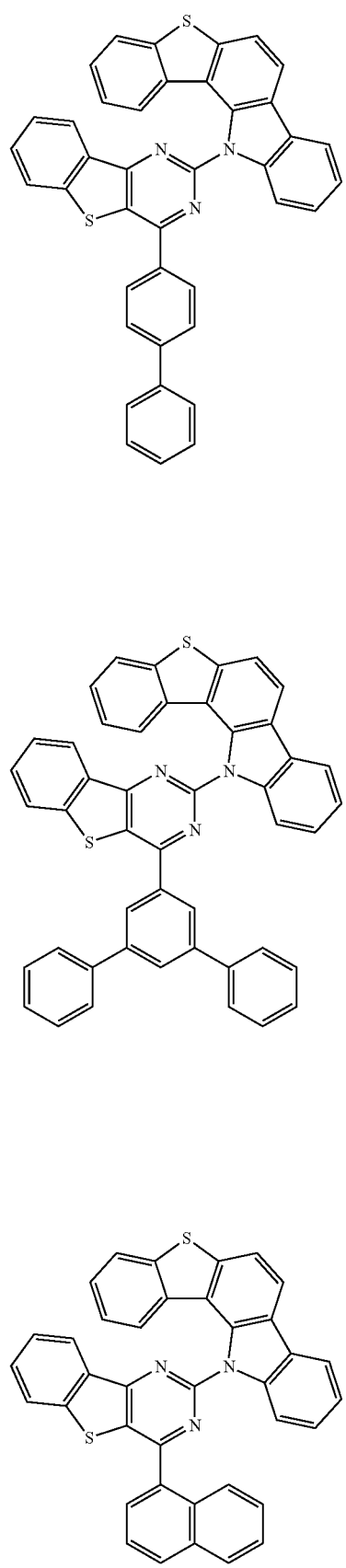

-continued
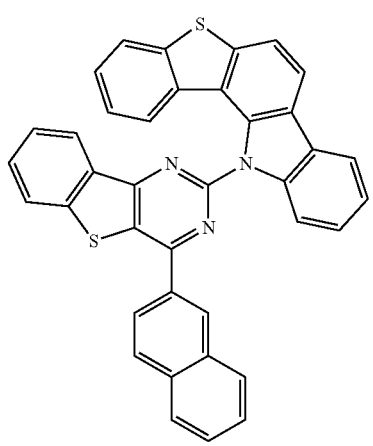
6-6
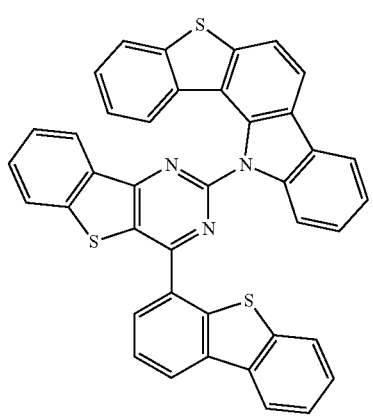
6-7
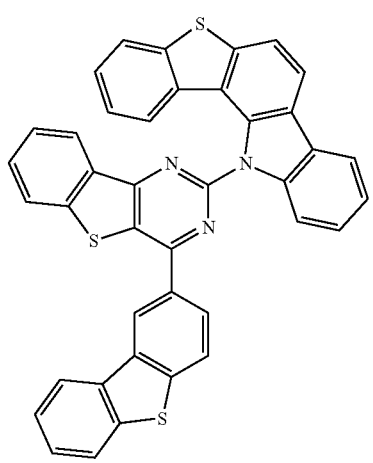
6-8
-continued
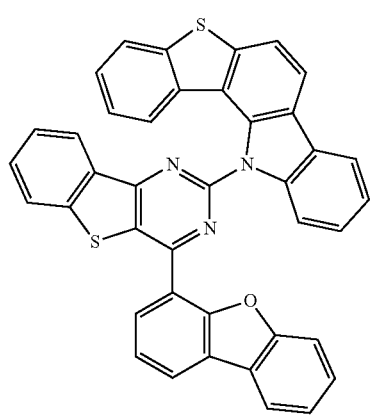
6-9
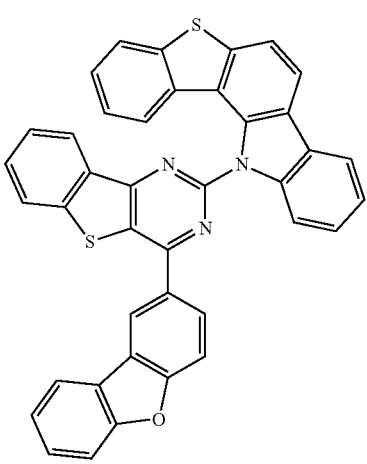
6-10
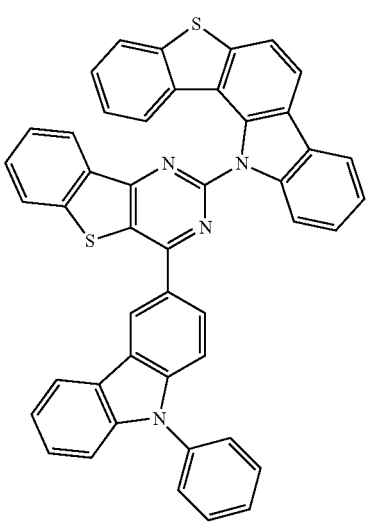
6-11

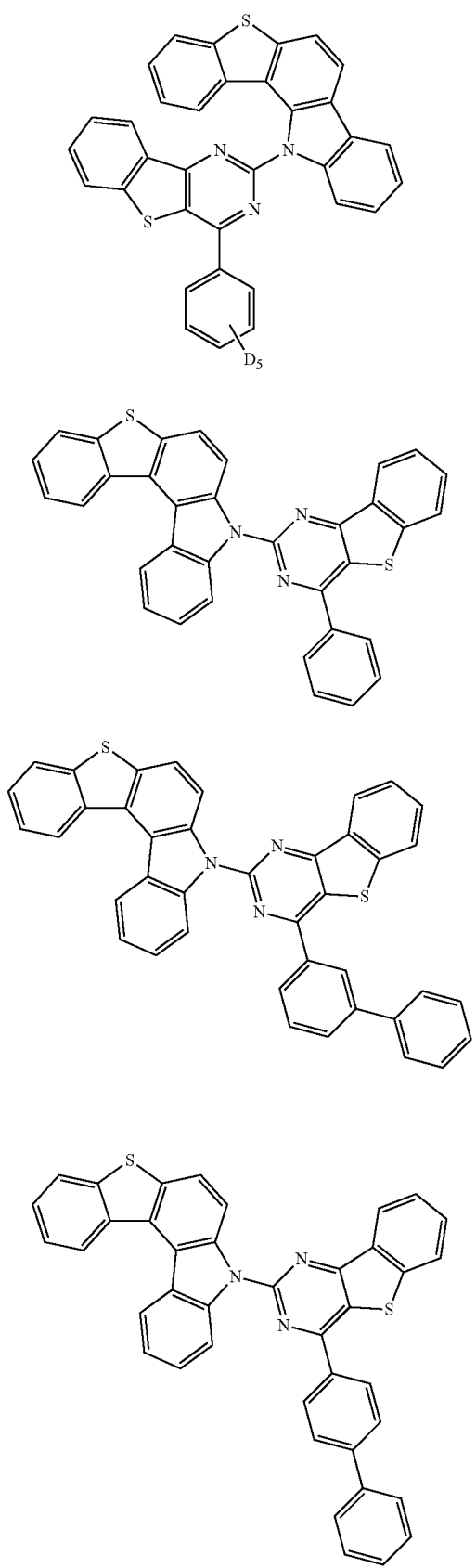
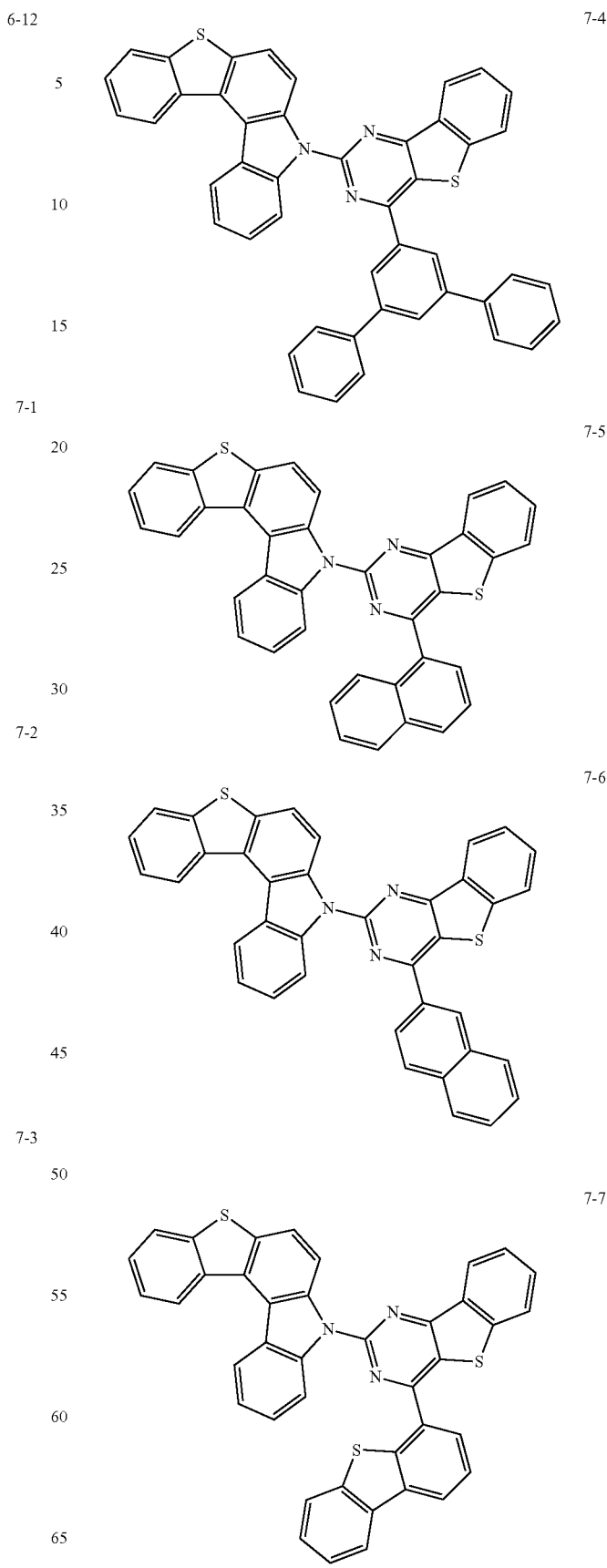

-continued
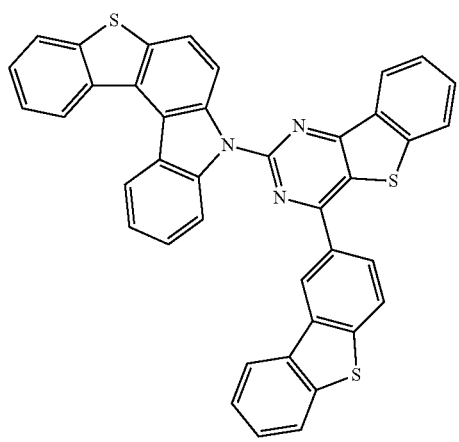
7-8
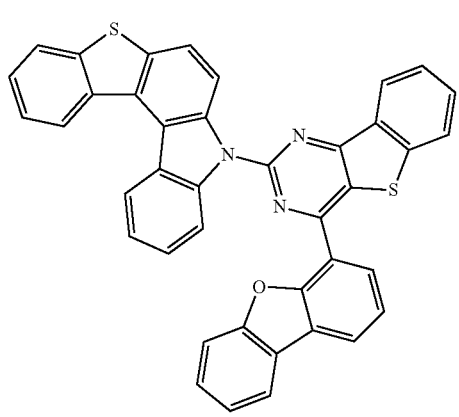
7-9
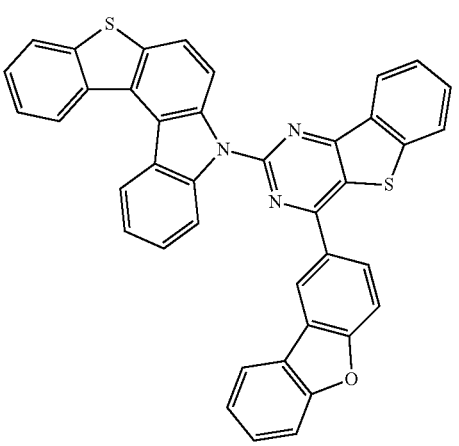
7-10
-continued
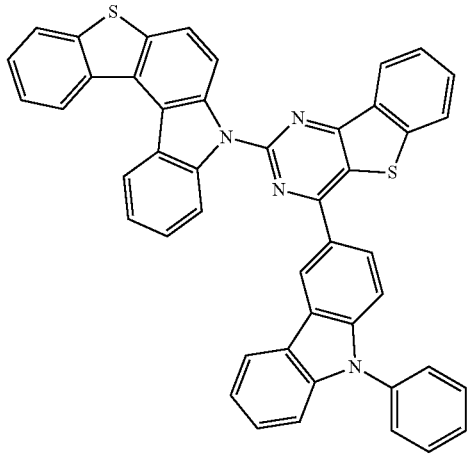
7-11
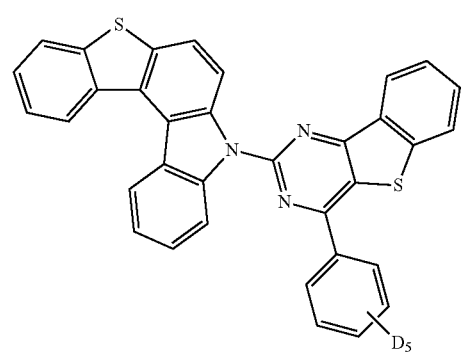
7-12
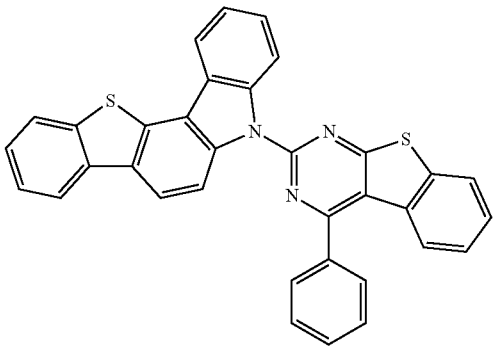
8-1
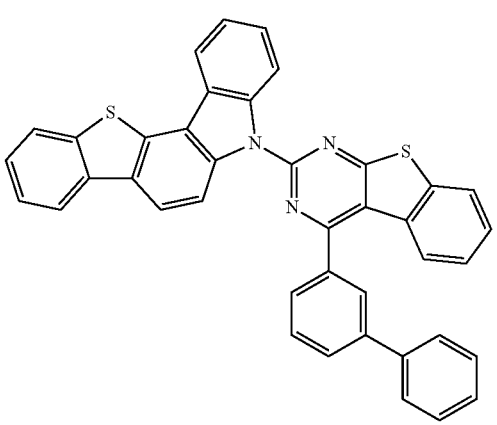
8-2

-continued
8-3
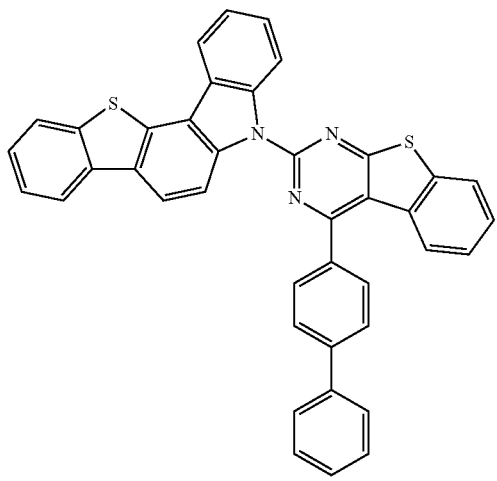
8-4
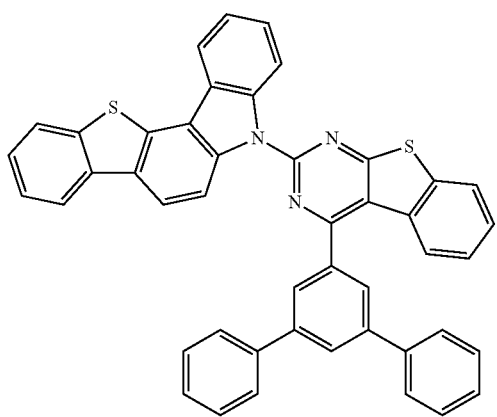
8-5
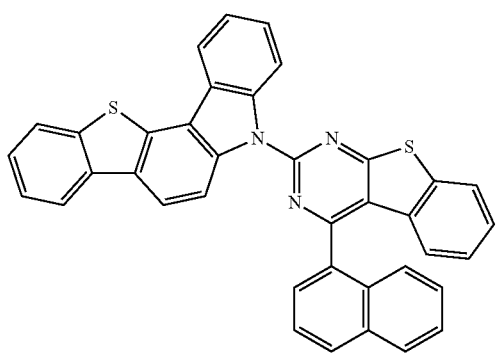
8-6
-continued
8-7
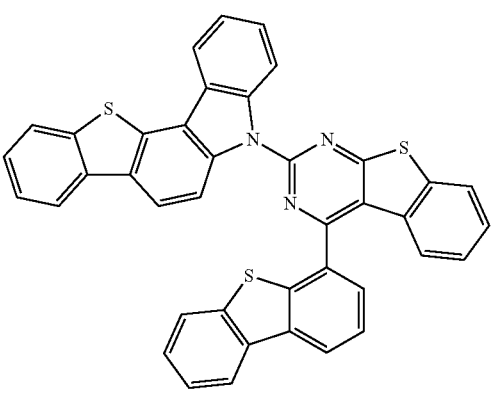
8-8
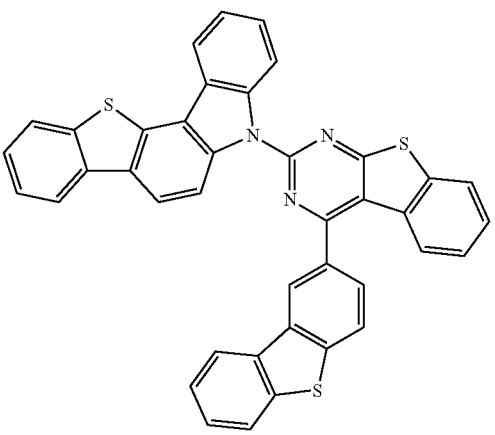
8-9
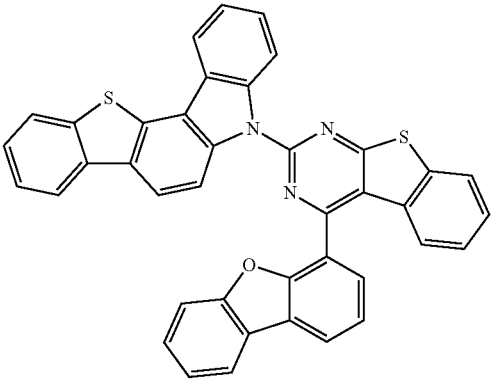
8-10
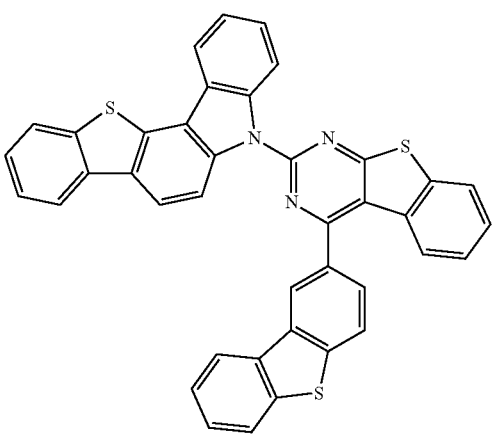

163
-continued
8-11
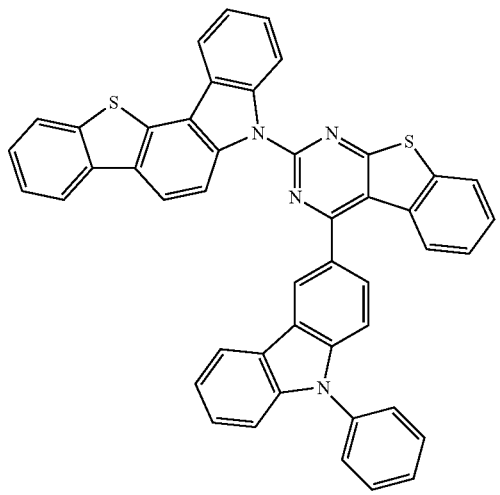
8-12
9-1
9-2
164
-continued
9-3
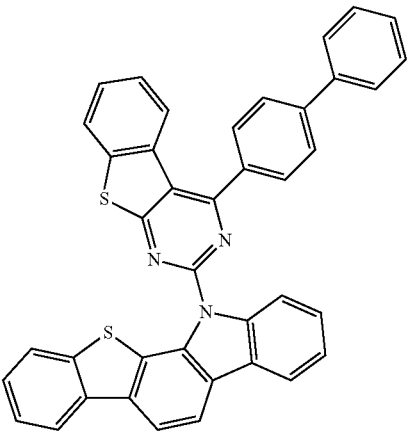
9-4
9-5
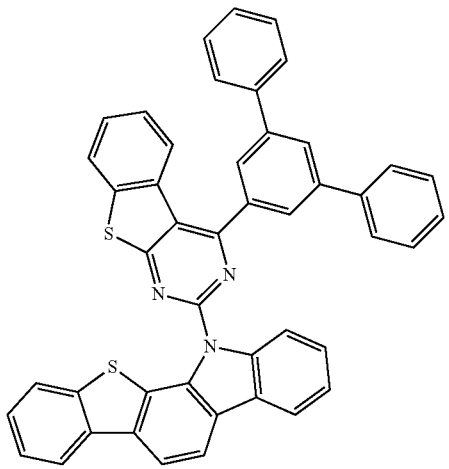
9-6
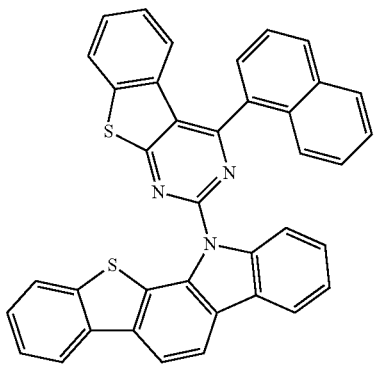
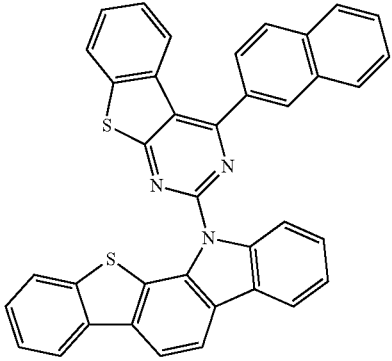

165
-continued
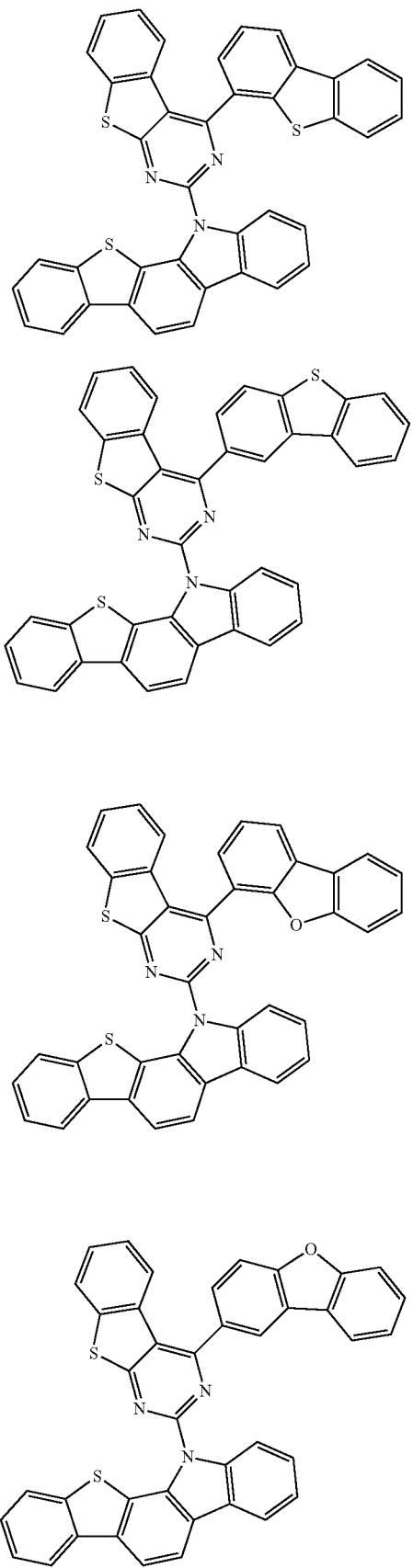
9-7
9-8
9-9
9-10
166
-continued
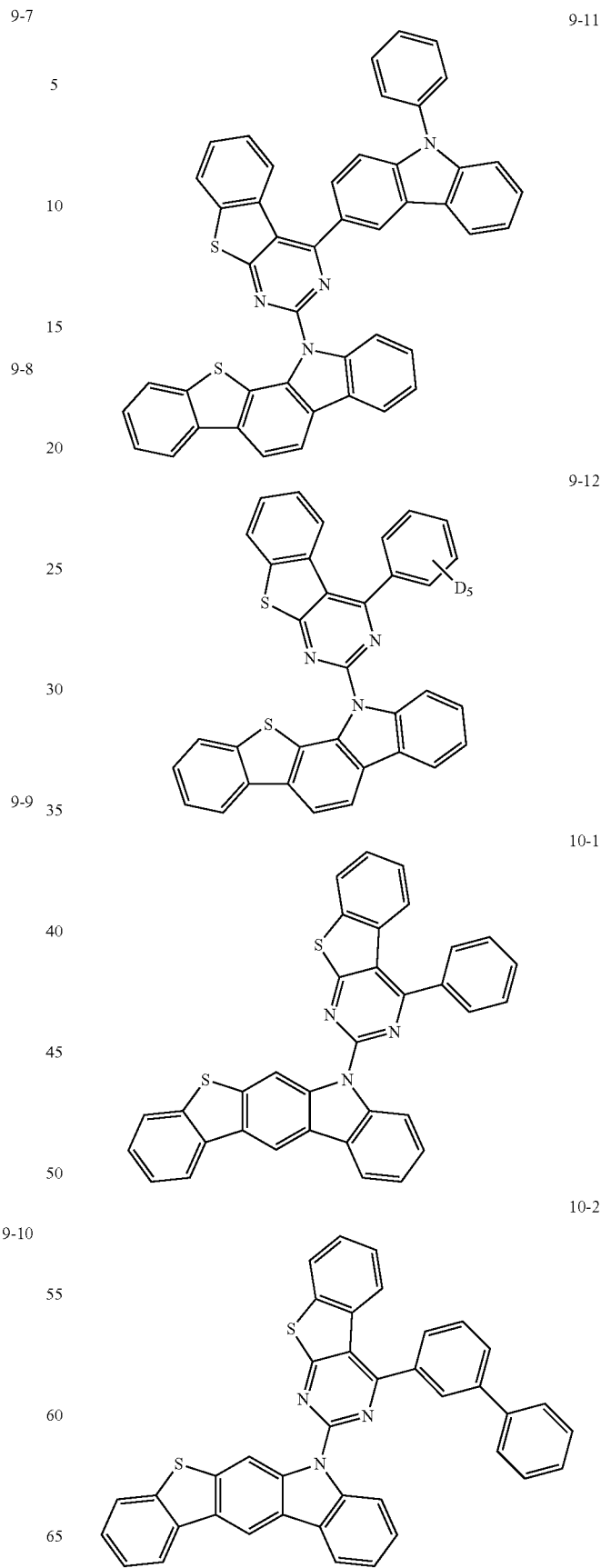
9-11
9-12
10-1
10-2

10-3
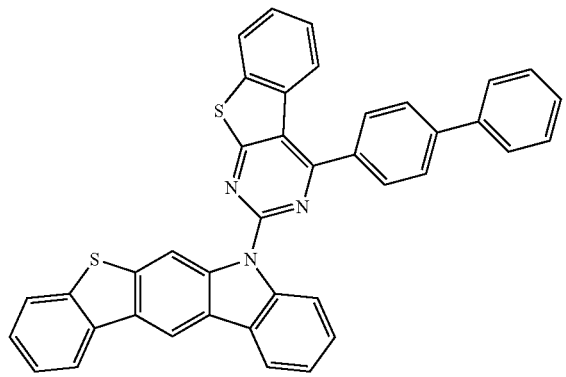
10-4
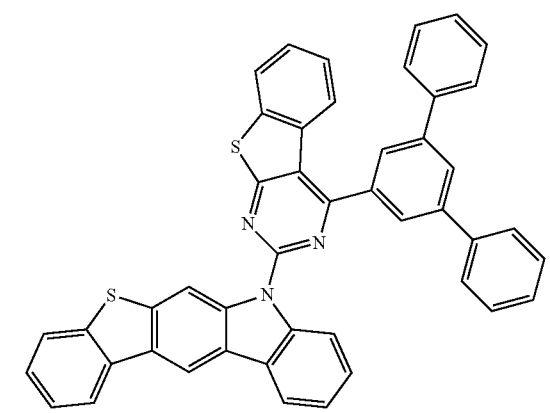
10-5
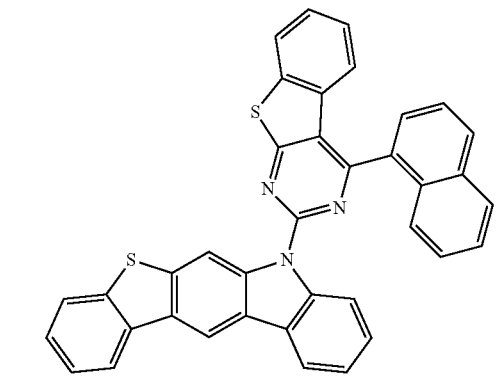
10-6
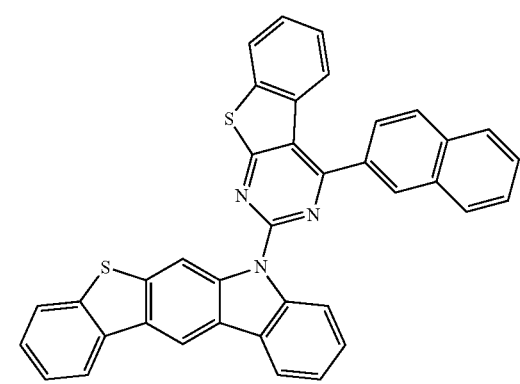
10-7
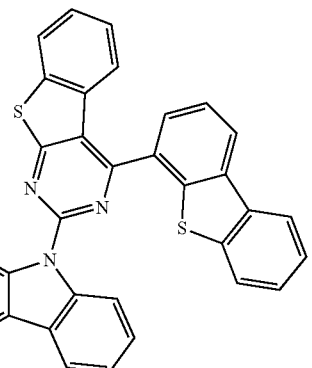
10-8
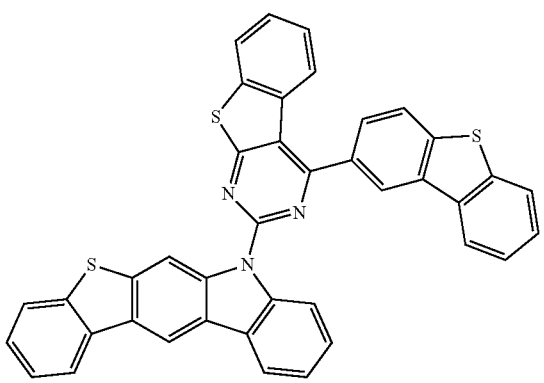
10-9
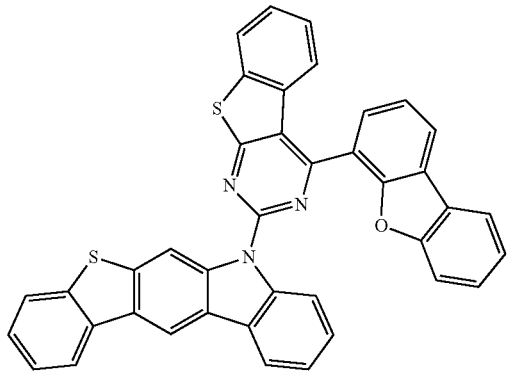
10-10
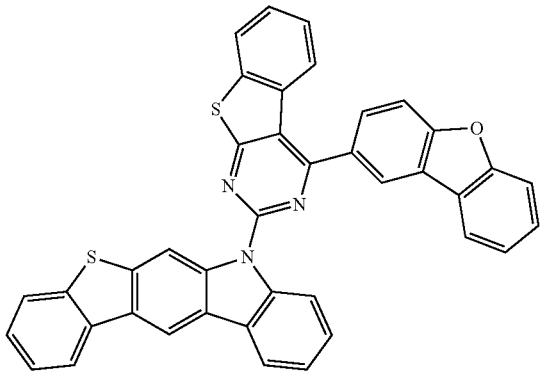

10-11
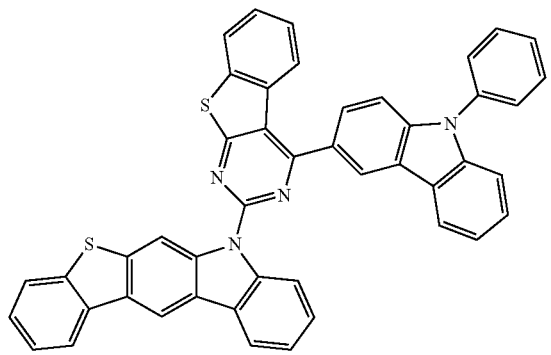
10-12
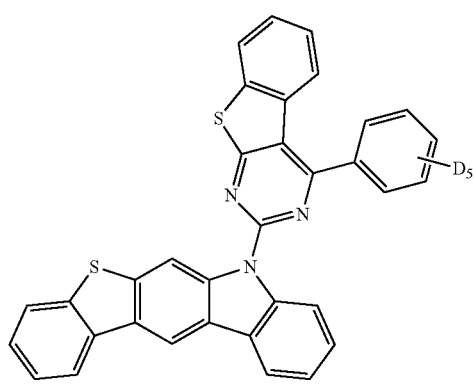
11-1
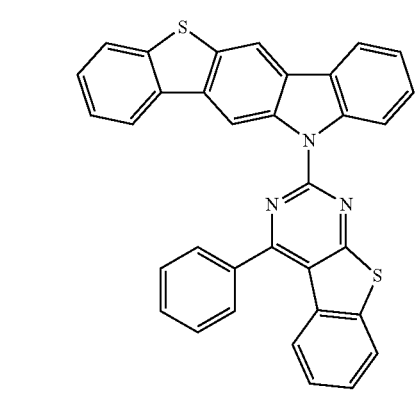
11-2
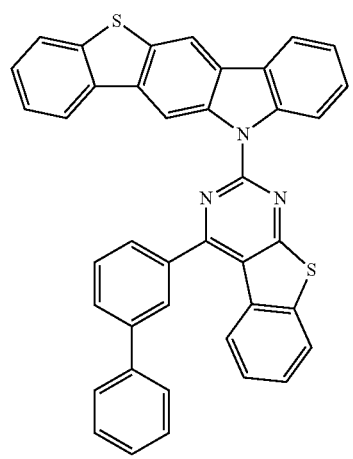
11-3
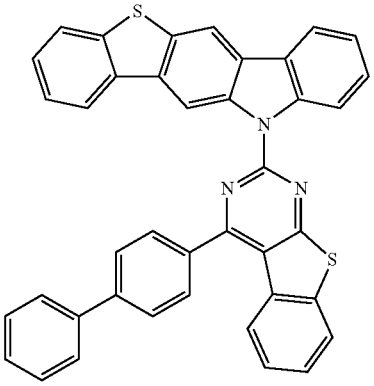
11-4
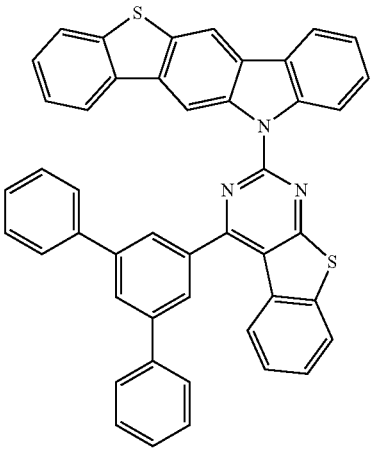
11-5
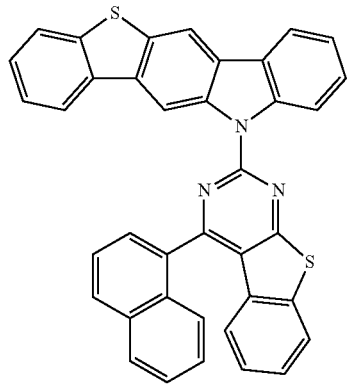
11-6
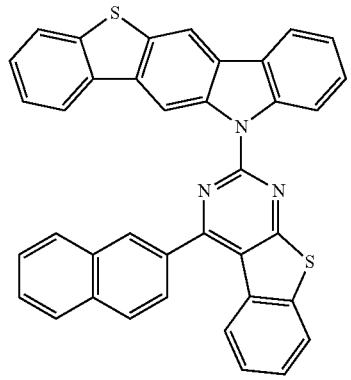

11-7
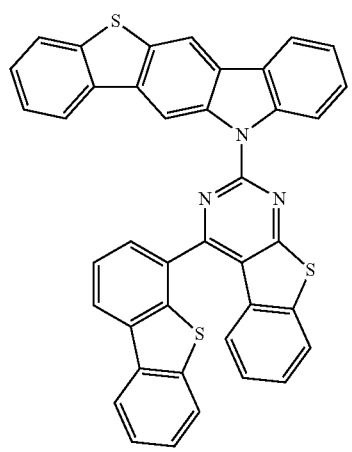
11-8
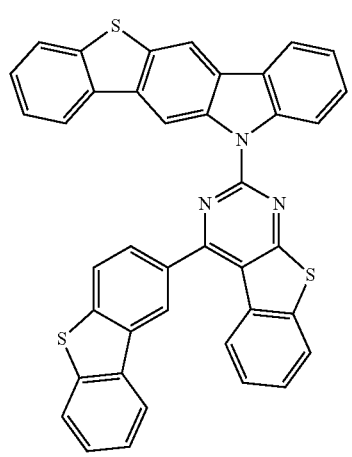
11-9
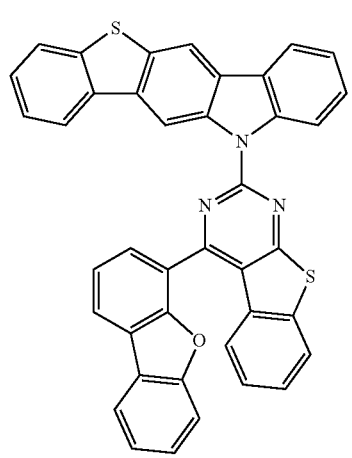
11-10
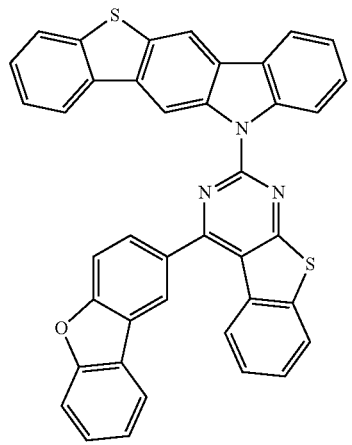
11-11
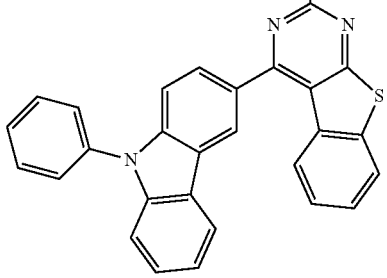
11-12
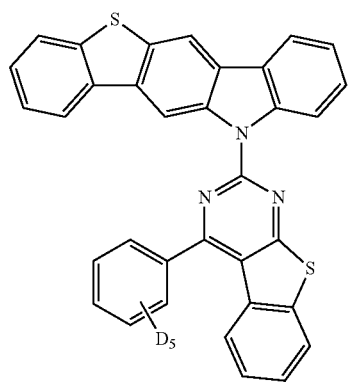
12-1
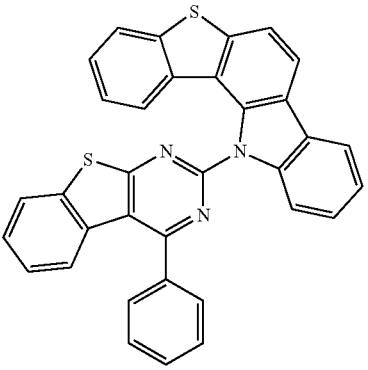

12-2 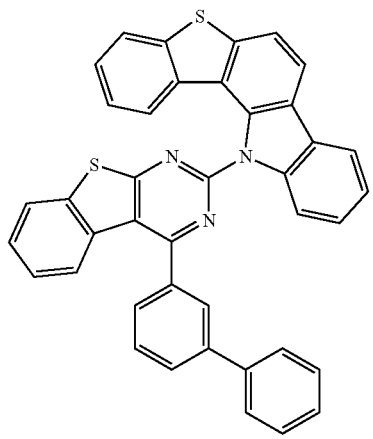
12-3 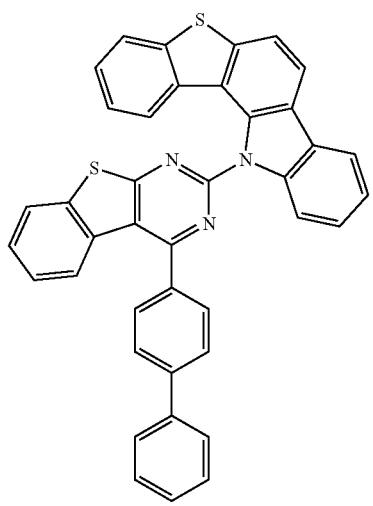
12-4 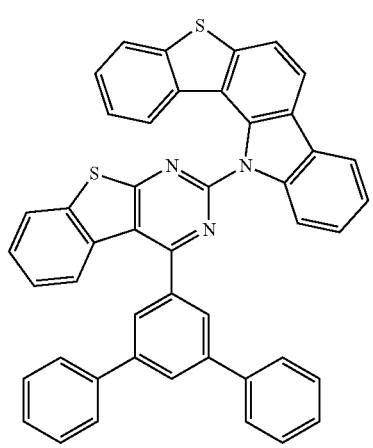
12-5 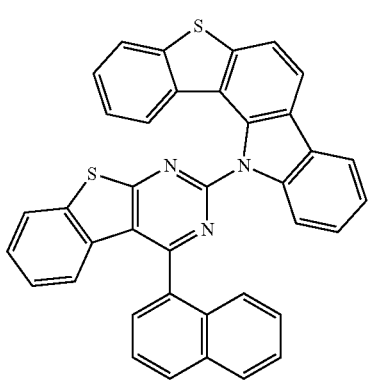
12-6 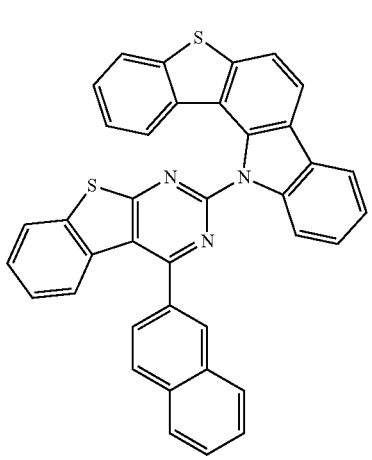
12-7 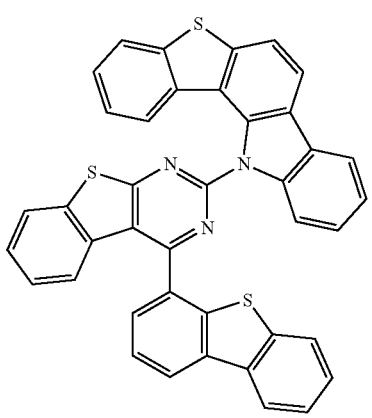

12-8
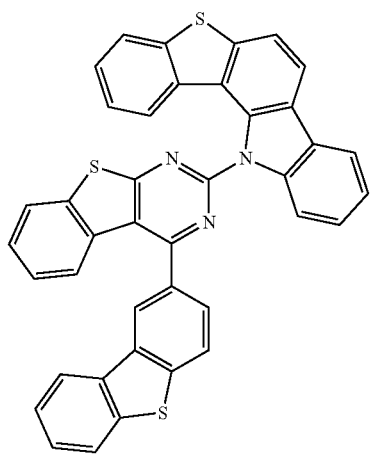
12-9
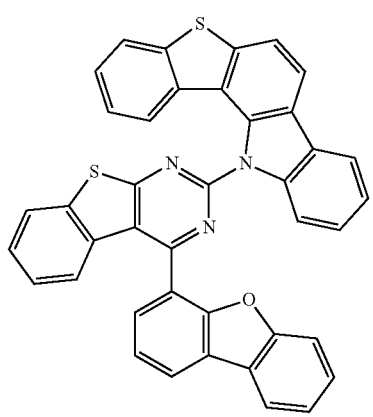
12-10
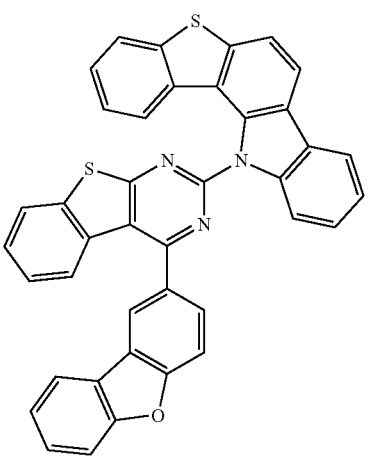
12-11
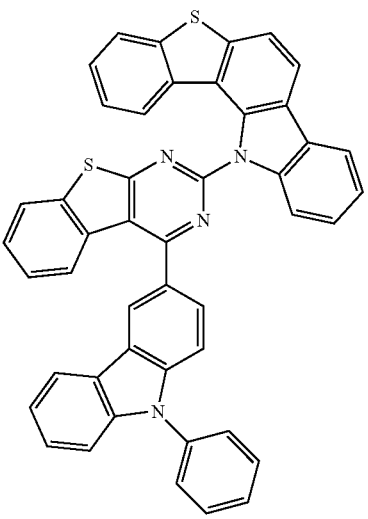
12-12
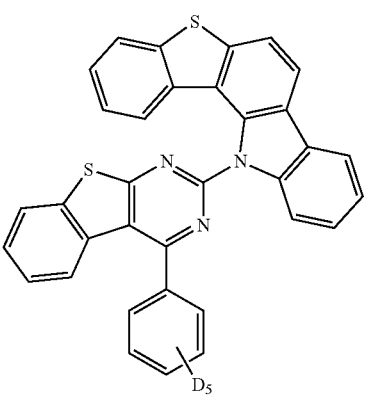
13-1
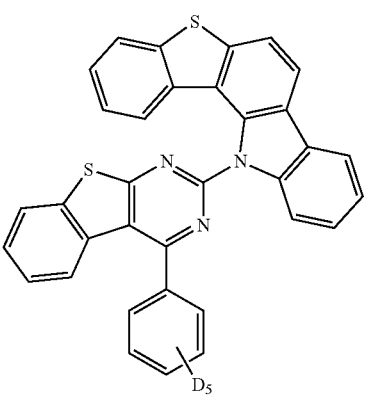
13-2
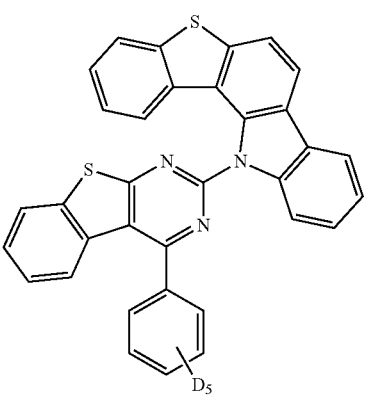

-continued
13-3
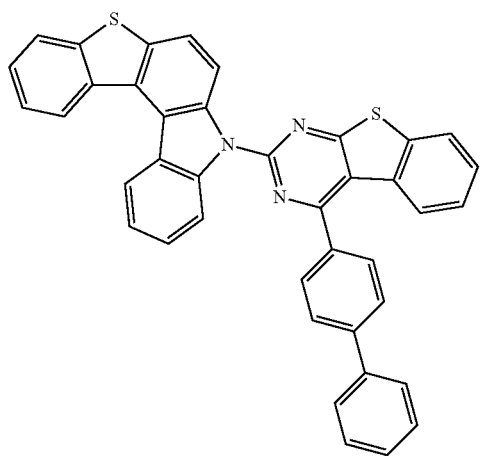
13-4
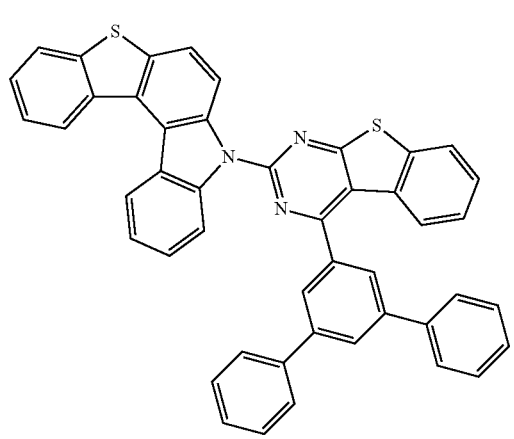
13-5
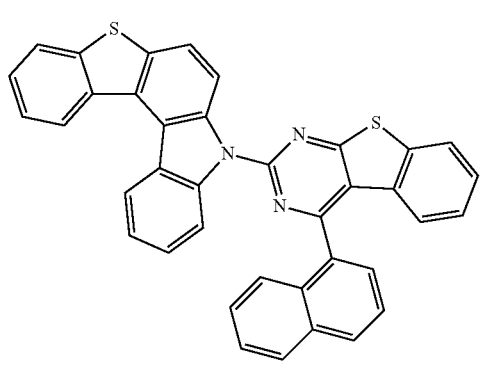
13-6
-continued
13-7
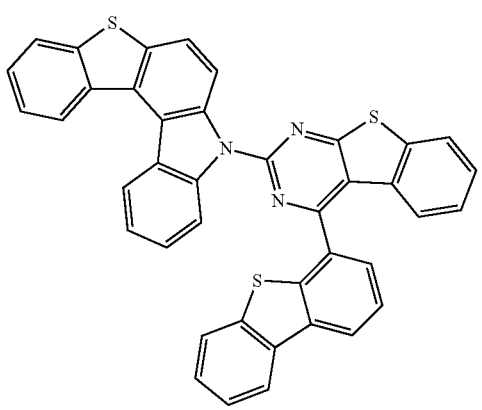
13-8
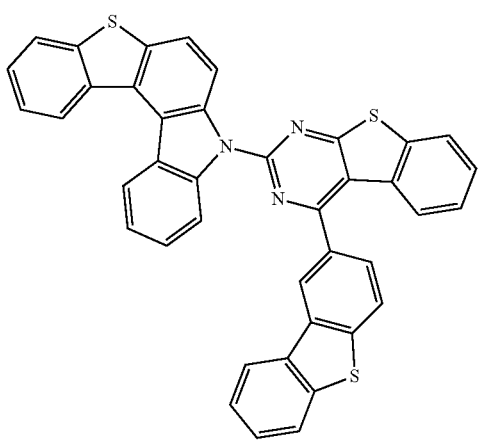
13-9
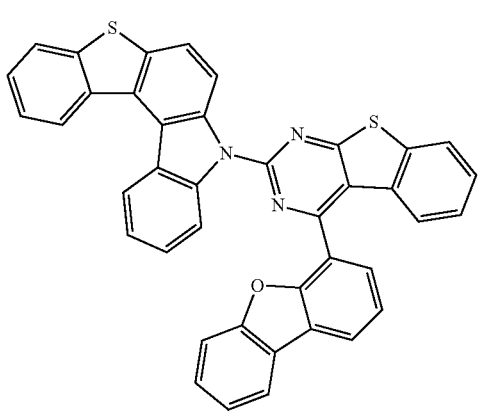

13-10
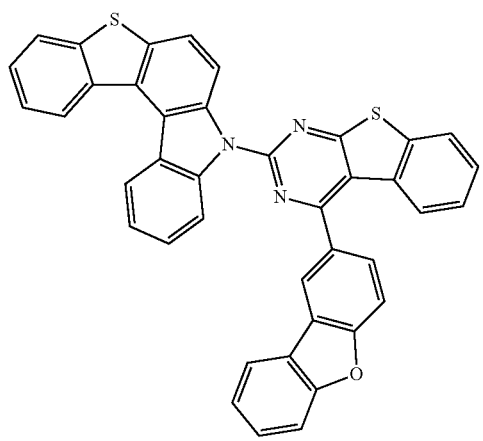
13-11
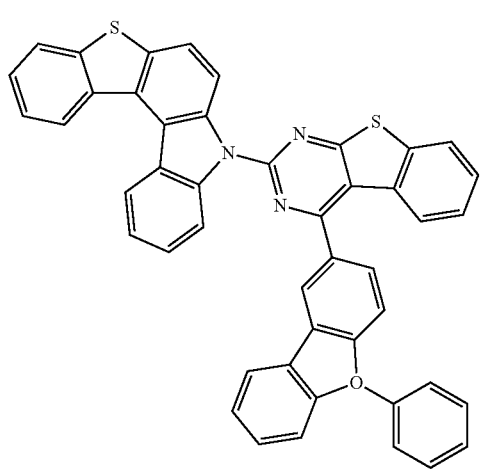
13-12
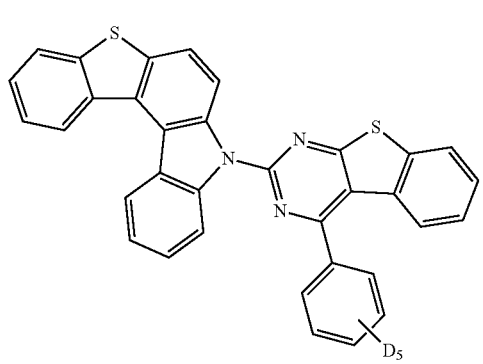
14-1
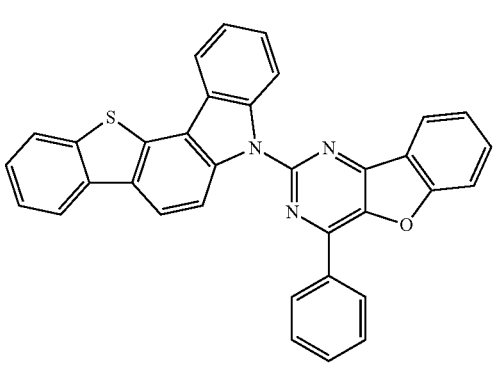
14-2
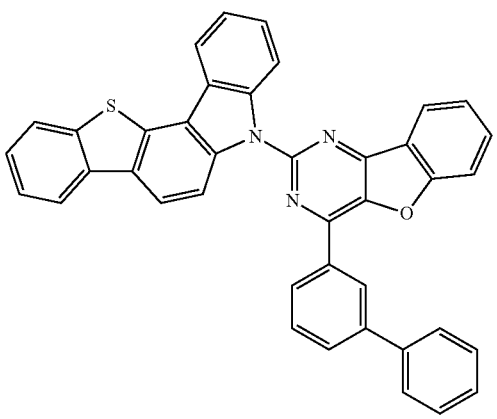
14-3
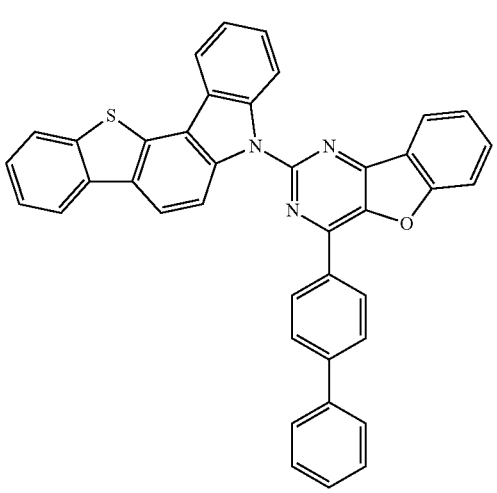
14-4
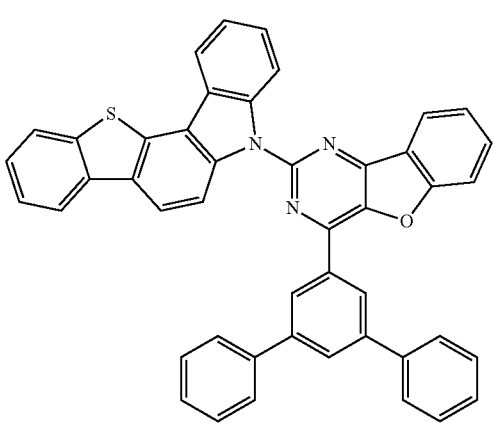

14-5
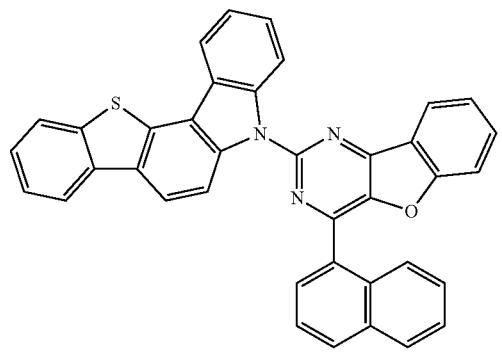
14-6
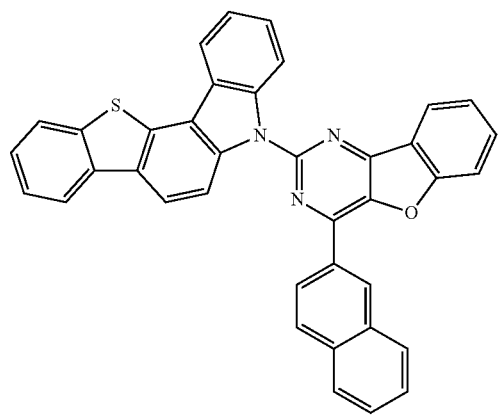
14-7
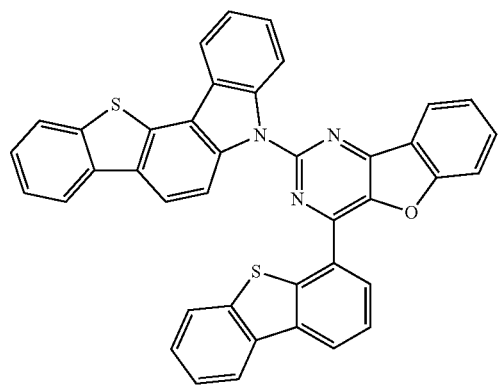
14-8
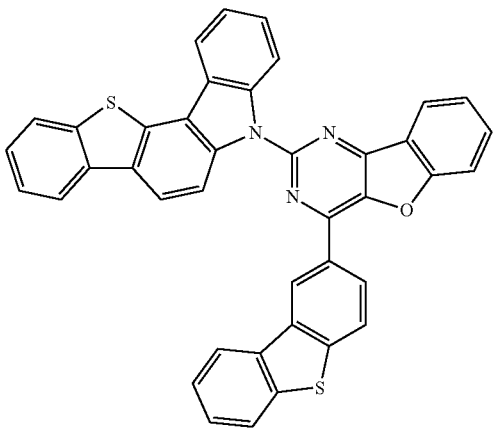
14-9
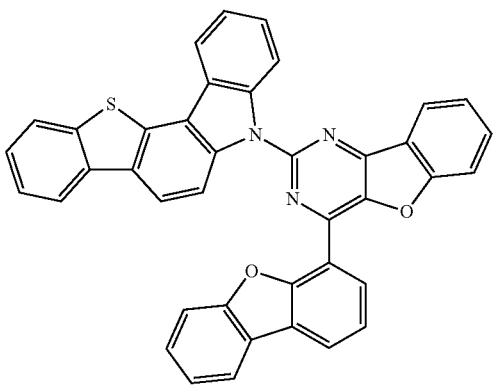
14-10

14-11
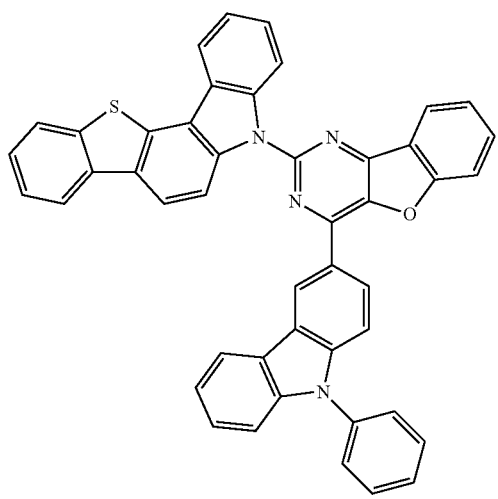
14-12
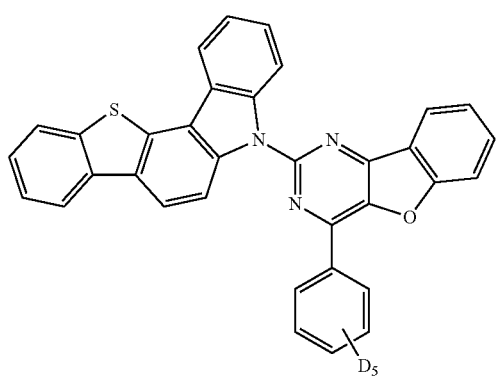
15-1
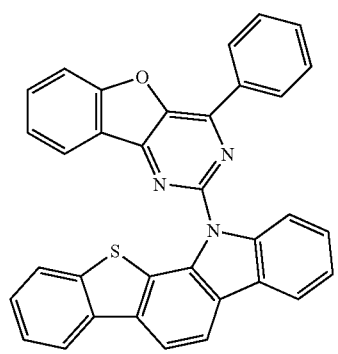
15-2
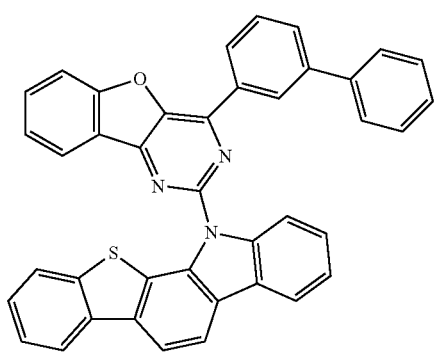
15-3
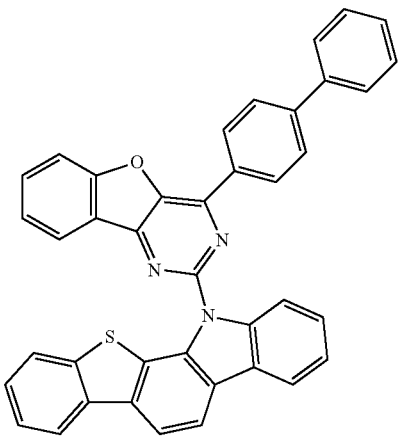
15-4
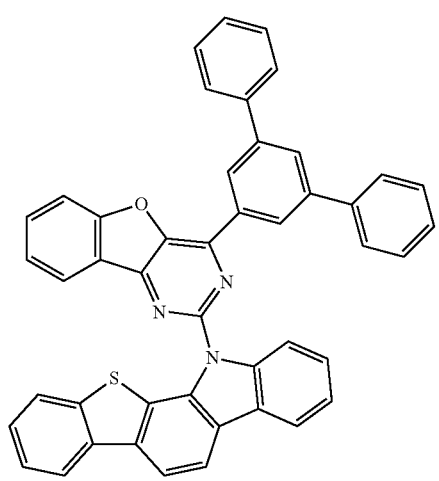
15-5
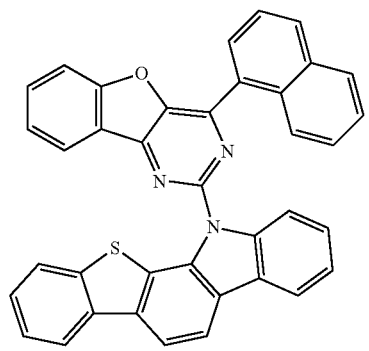
15-6
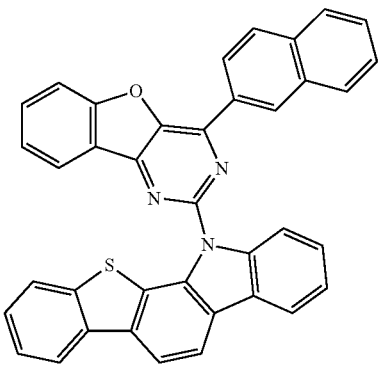

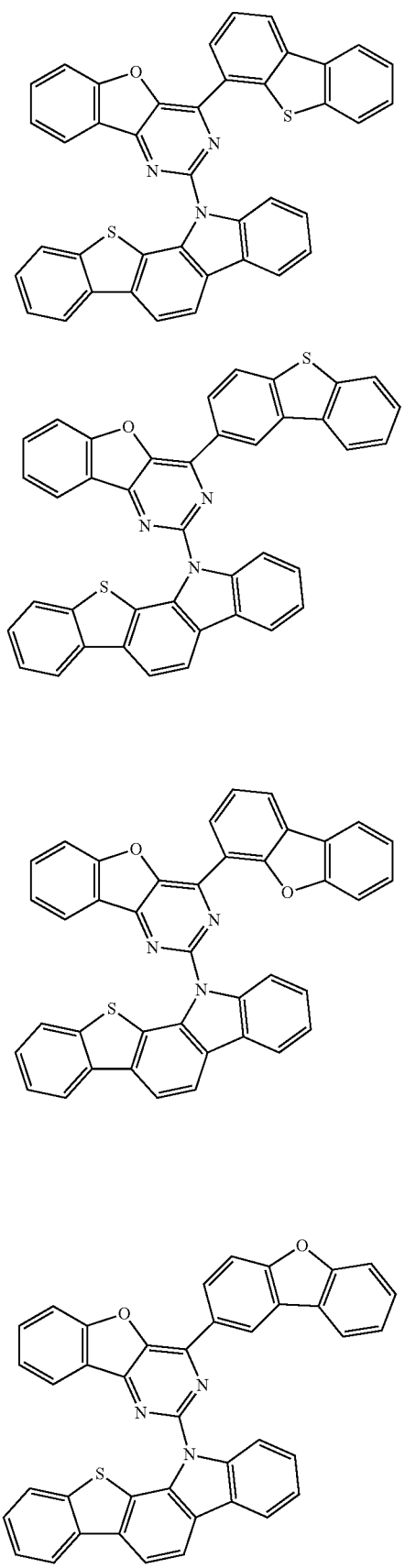
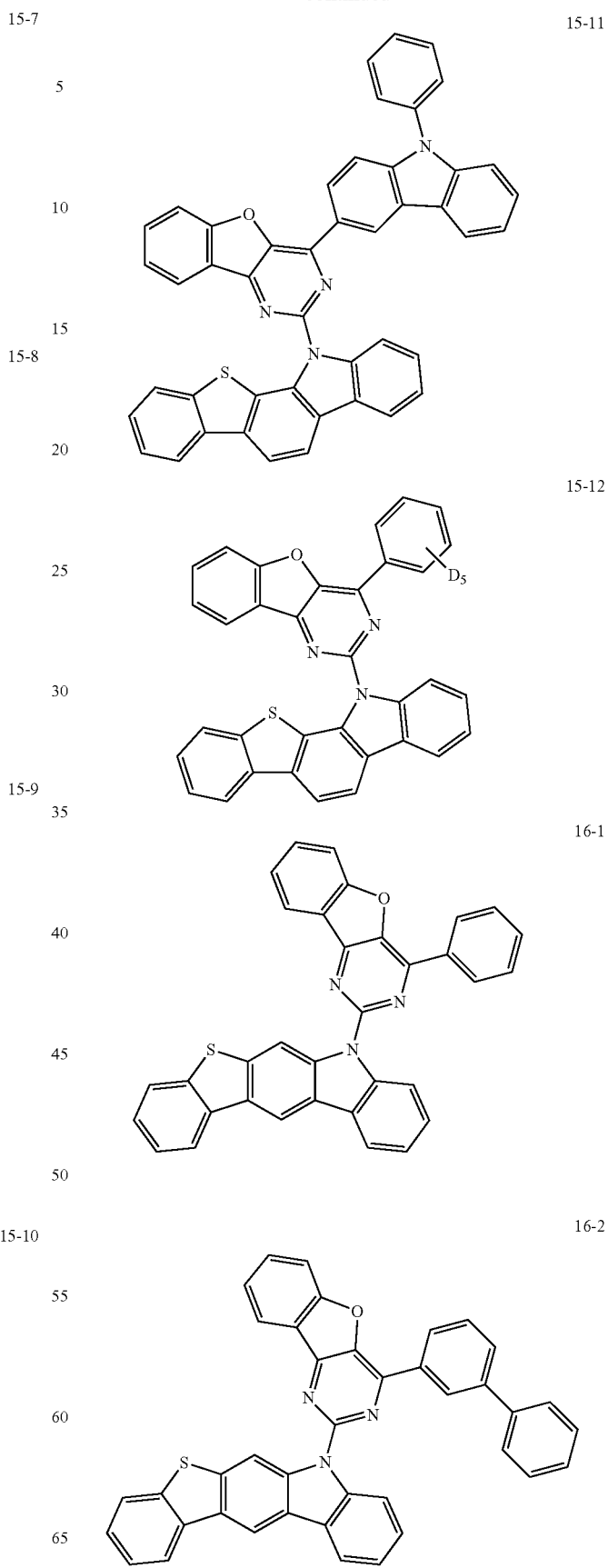

16-3
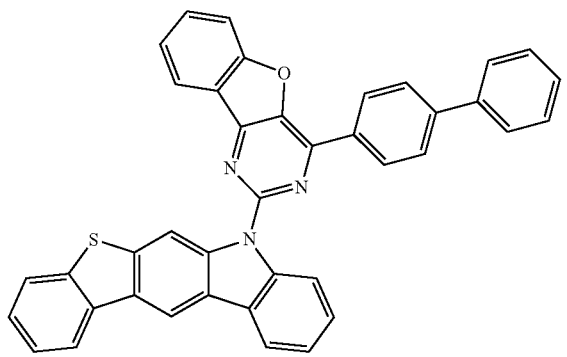
16-7
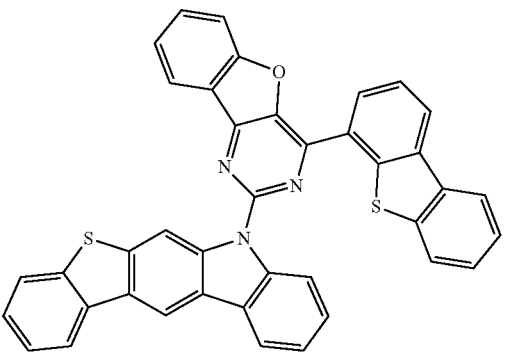
16-4
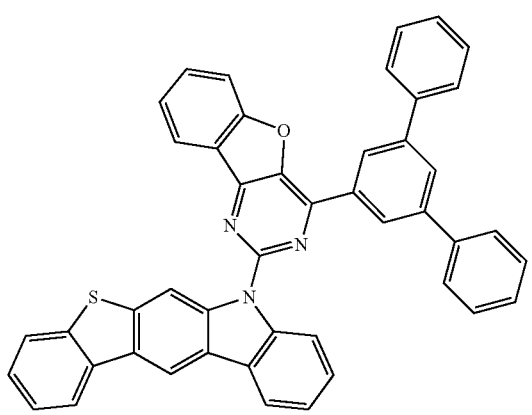
16-8
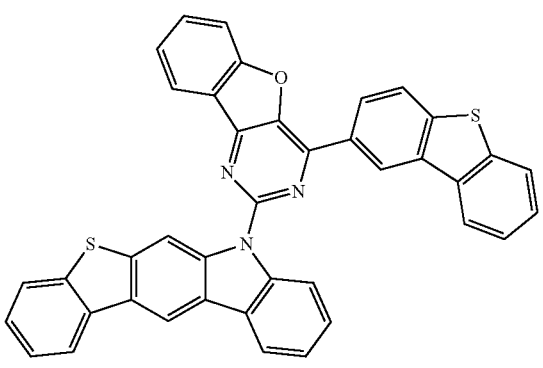
16-5
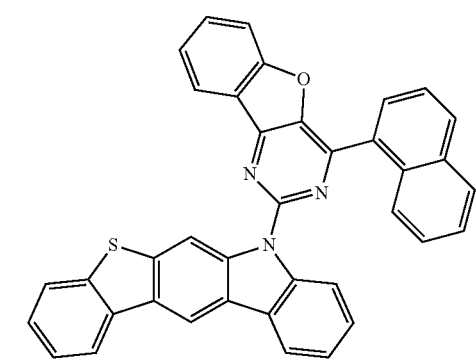
16-9
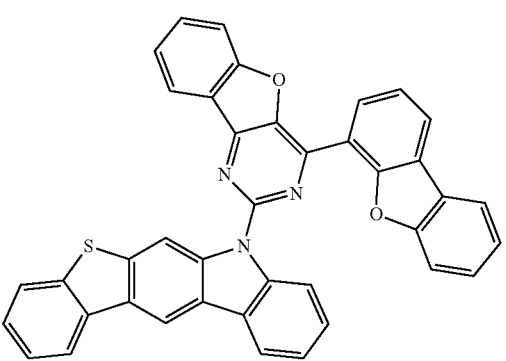
16-6
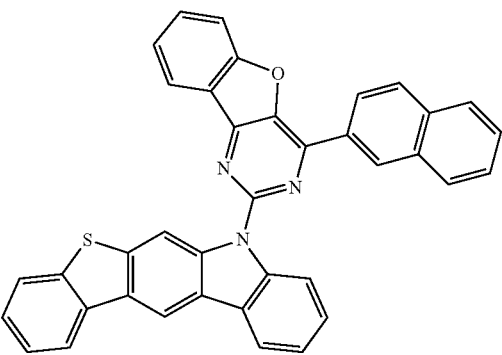
16-10
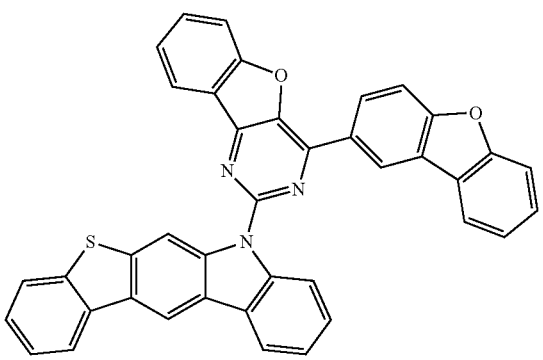

-continued
16-11
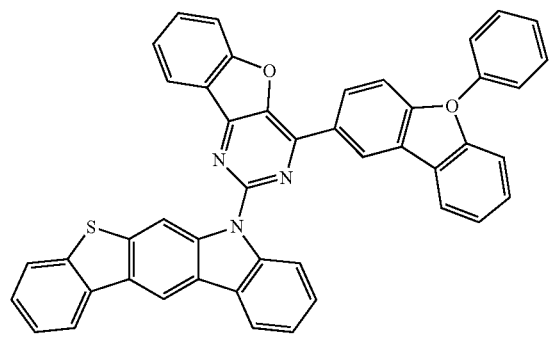
16-12
17-1
17-2
-continued
17-3
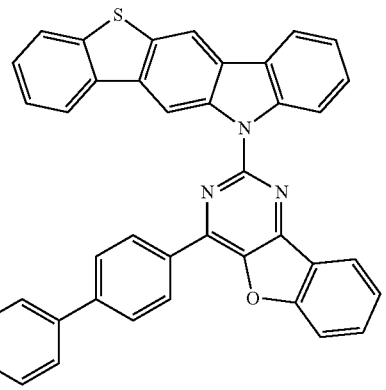
17-4
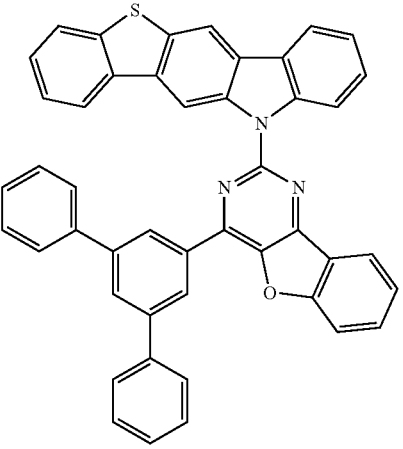
17-5
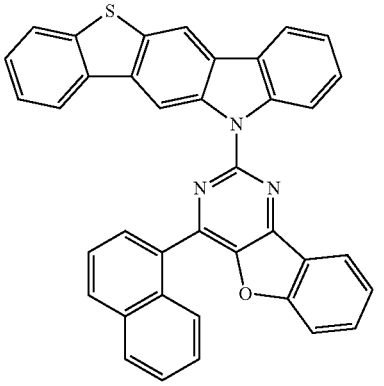
17-6
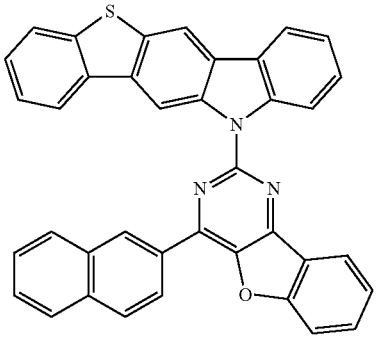

17-7
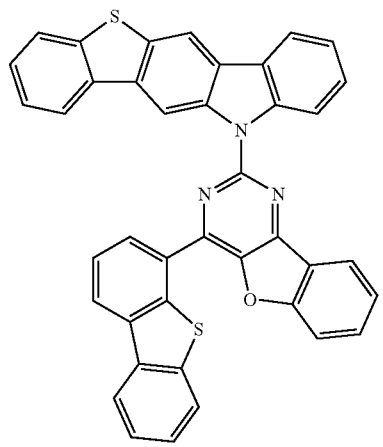
17-8
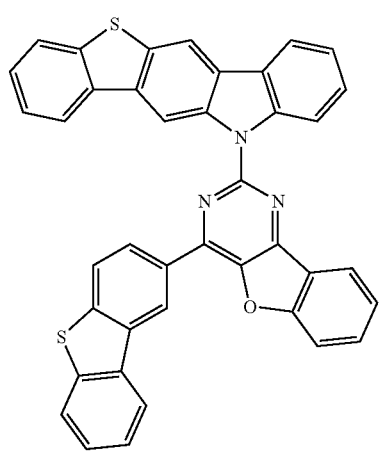
17-9
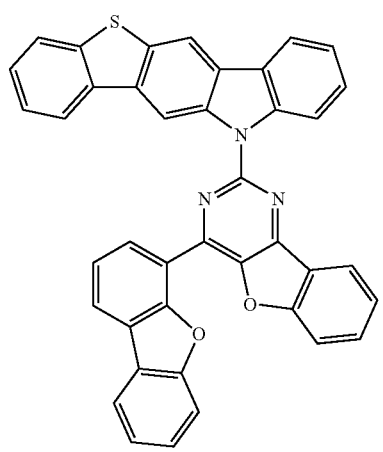
17-10
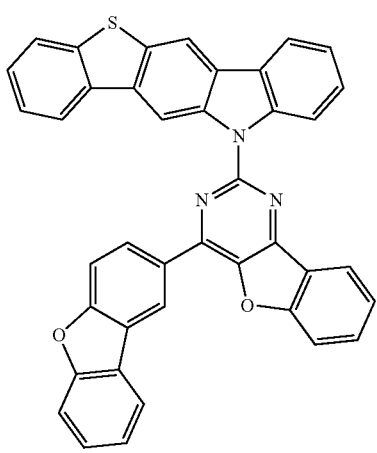
17-11
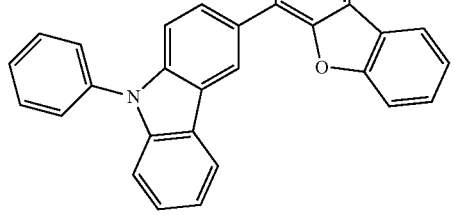
17-12
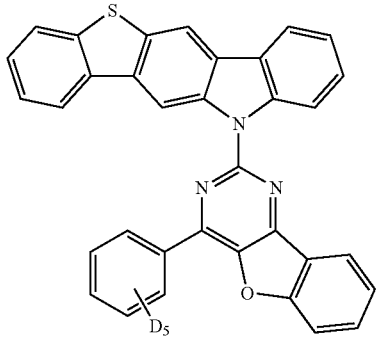
18-1
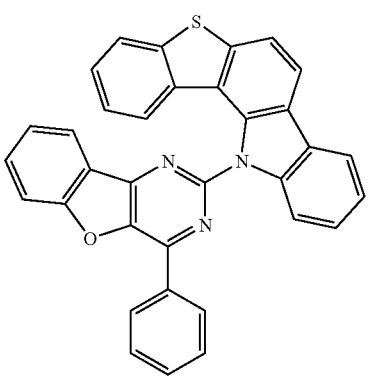

-continued
18-2
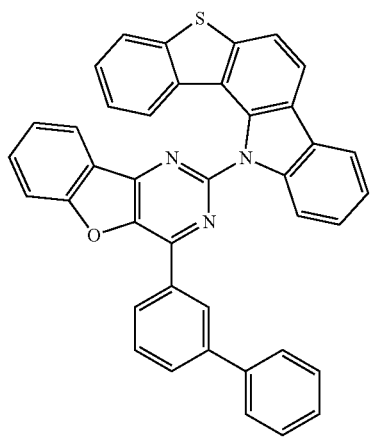
18-3
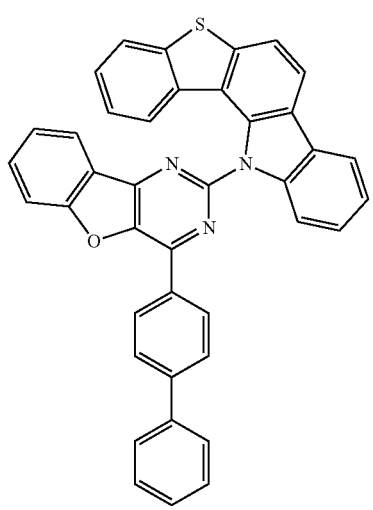
18-4
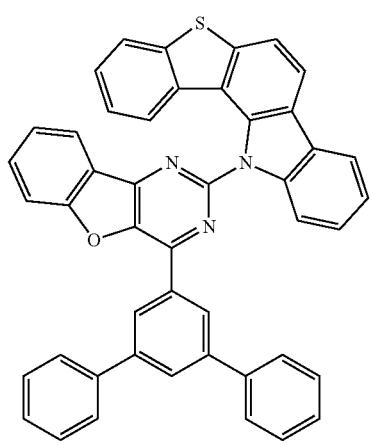
-continued
18-5
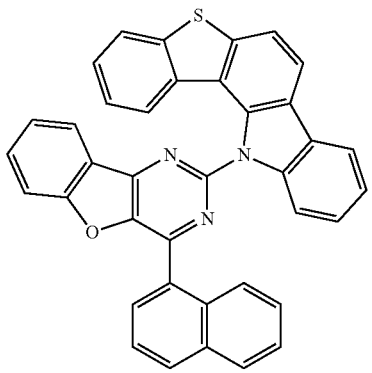
18-6
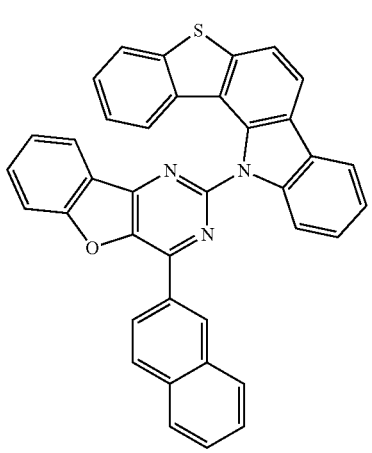
18-7
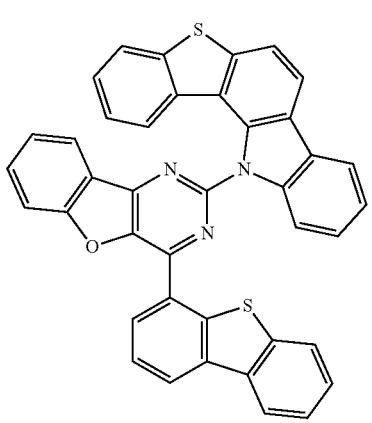

18-8
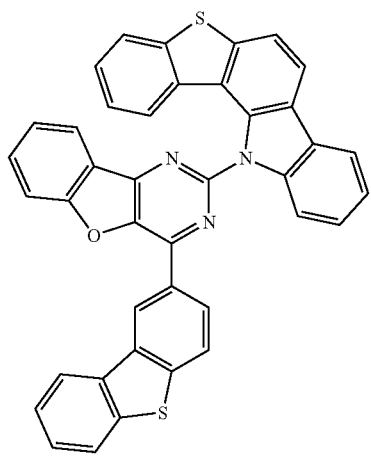
18-9
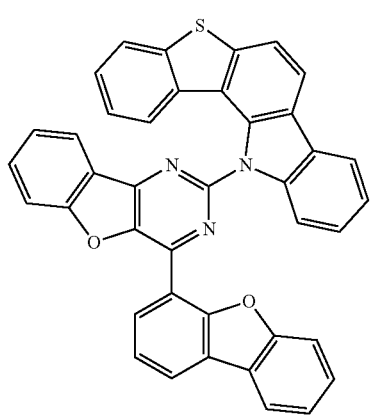
18-10
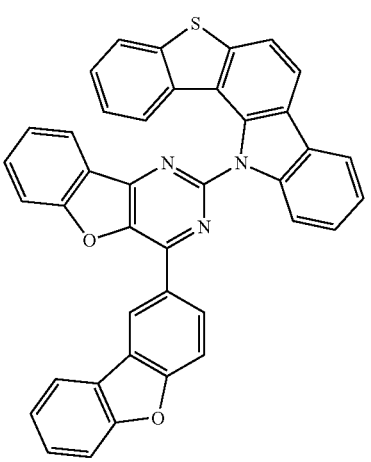
18-11
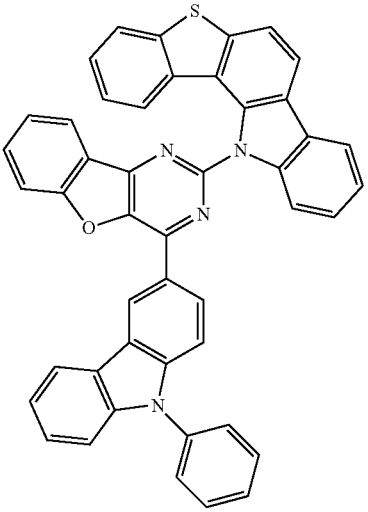
18-12
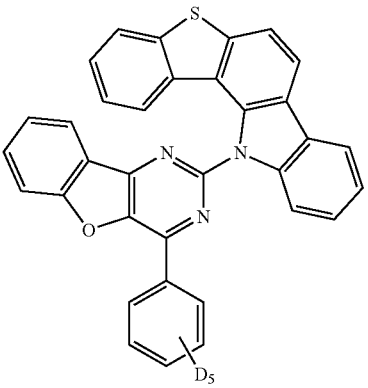
19-1
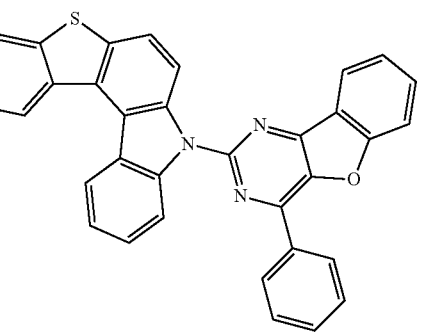
19-2
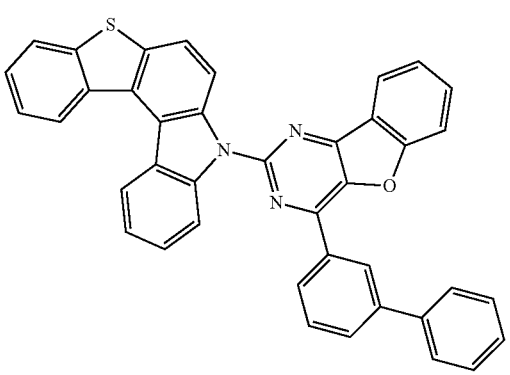

-continued
19-3
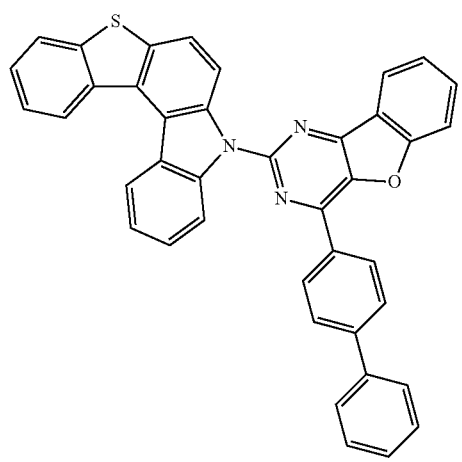
19-4
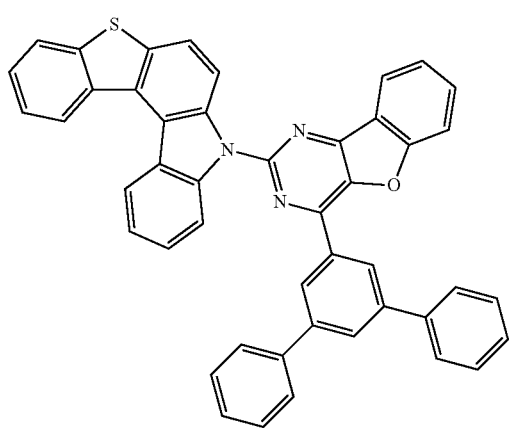
19-5
19-6
-continued
19-7
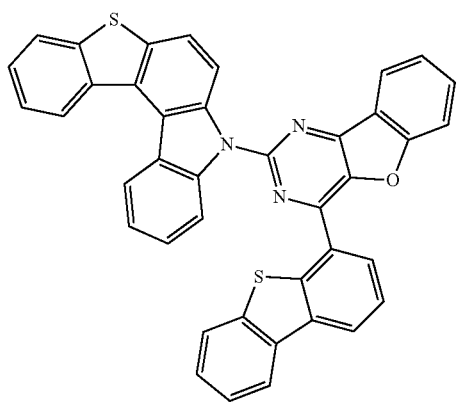
19-8
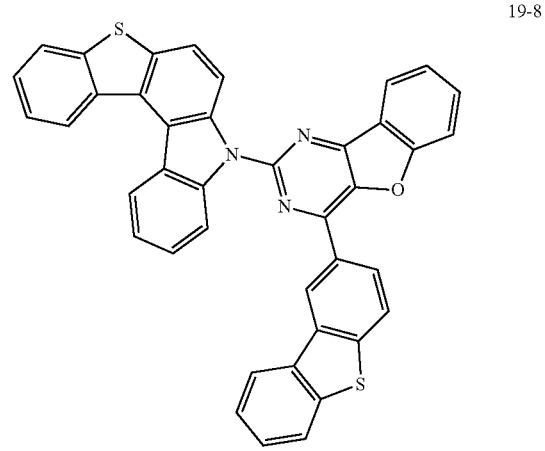
19-9
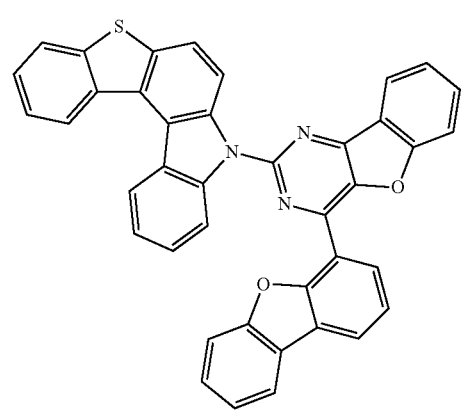

19-10
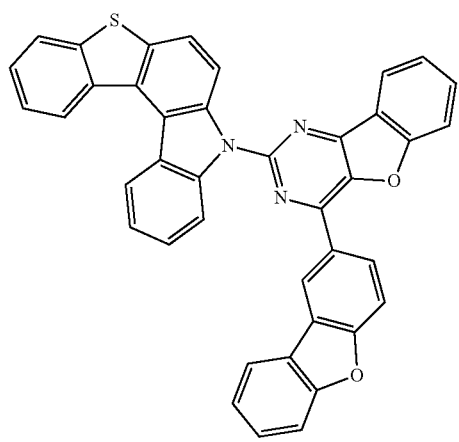
19-11
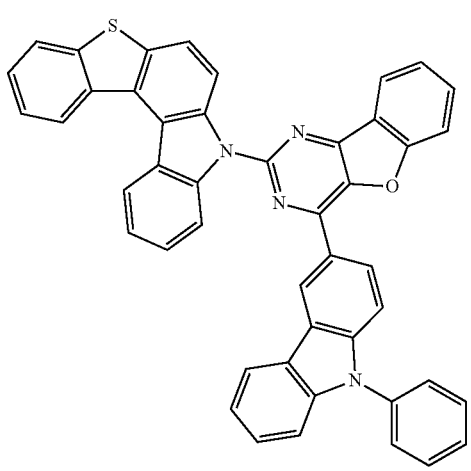
19-12
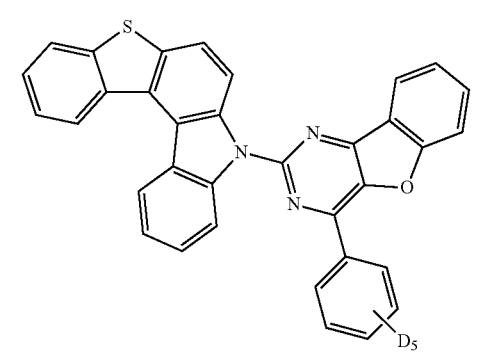
20-1
20-2
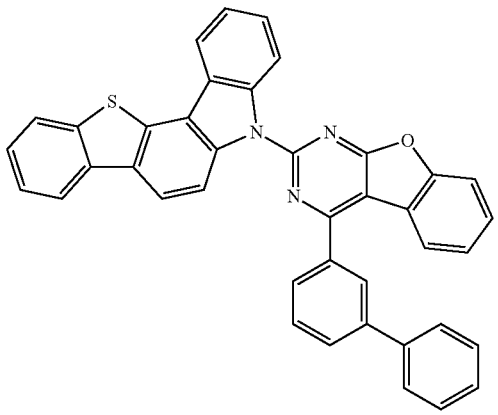
20-3
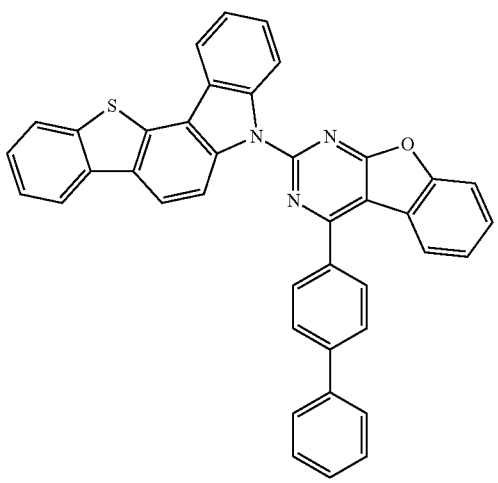
20-4
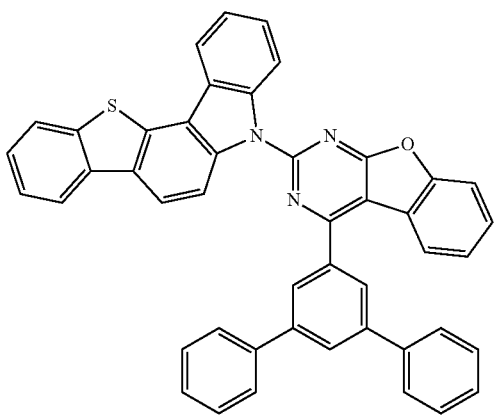

-continued
20-5
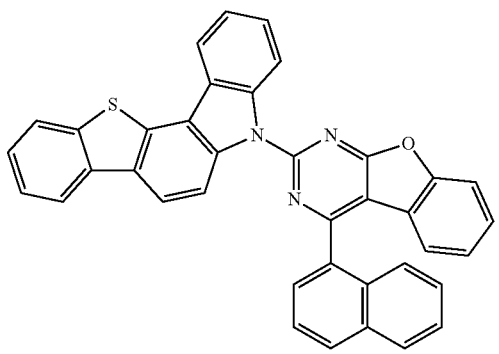
20-6
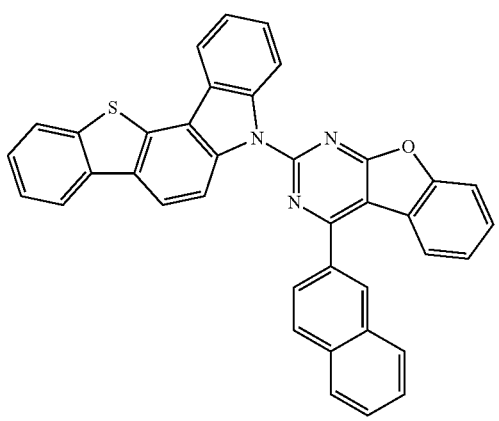
20-7
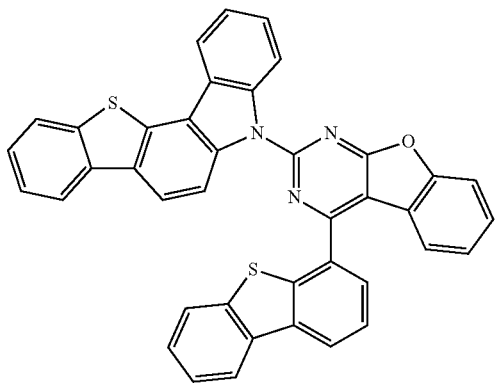
20-9
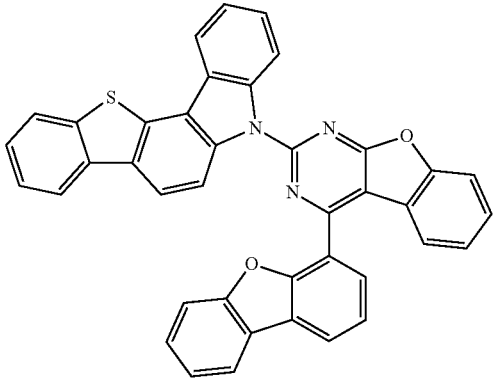
20-10
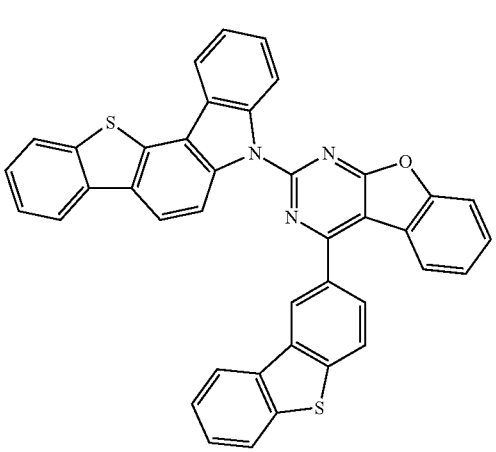
20-11
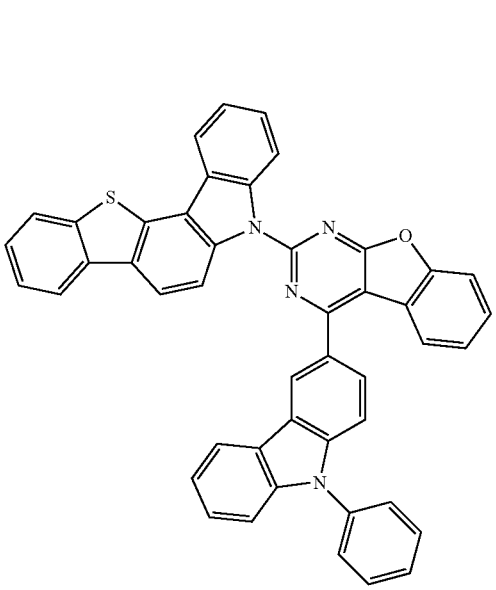

20-12
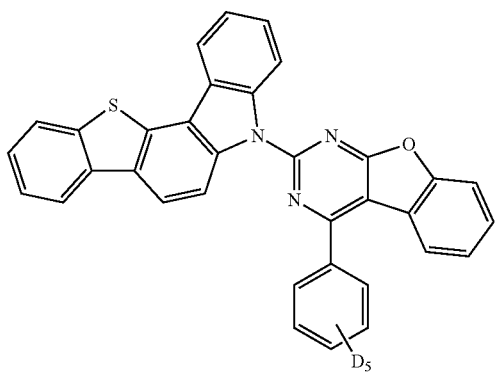
21-1
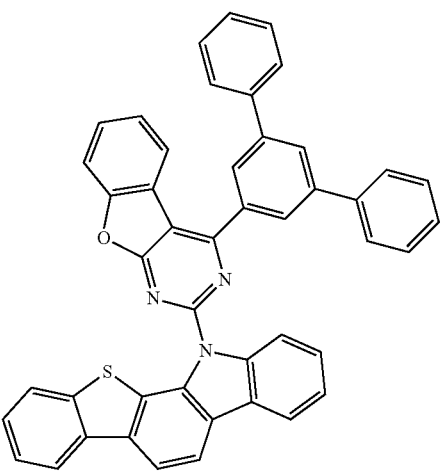
21-2
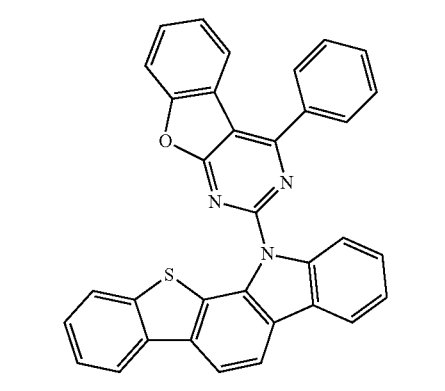
21-4
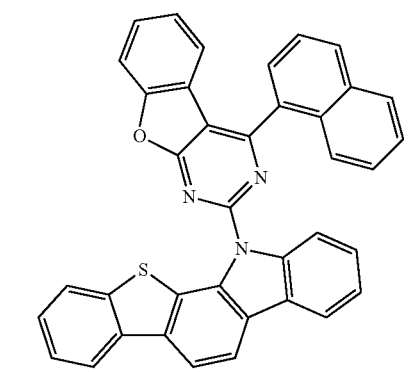
21-5
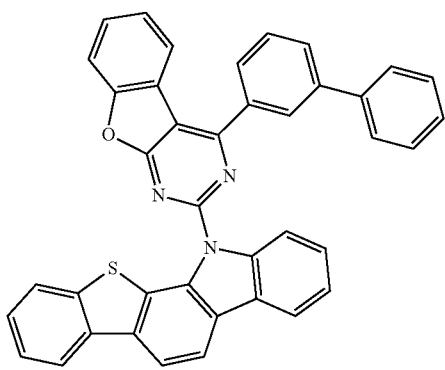
21-3
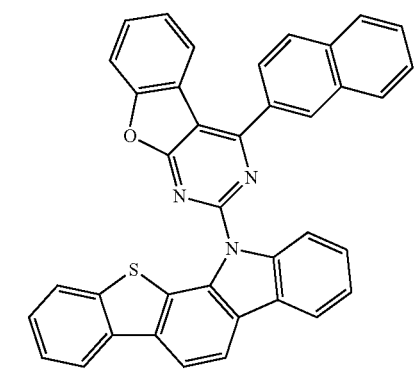
21-6
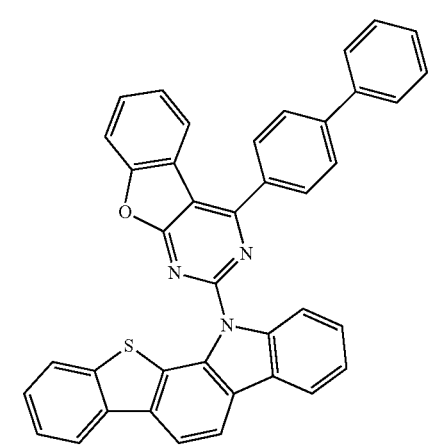
21-7
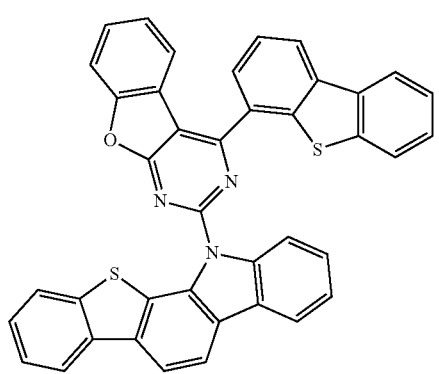

205
-continued
21-8
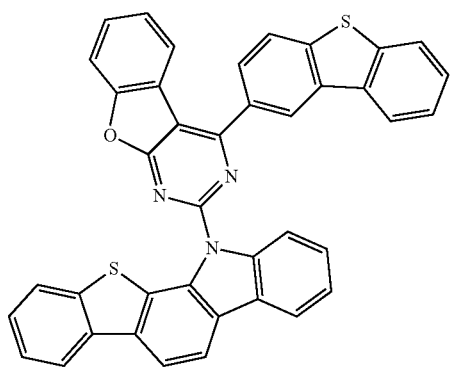
21-9
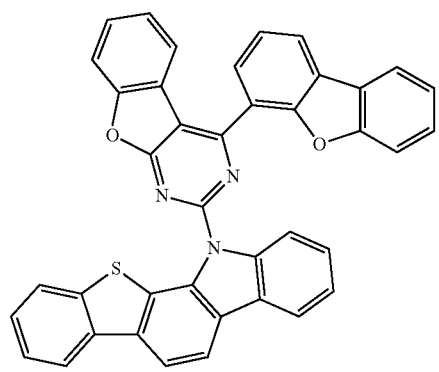
21-10
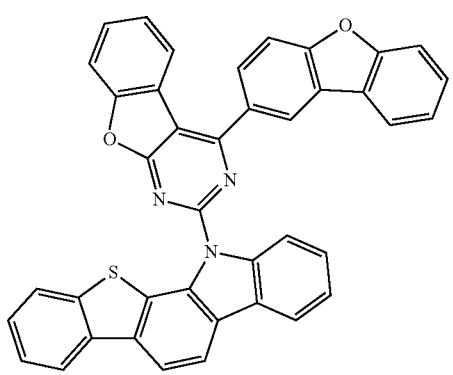
21-11
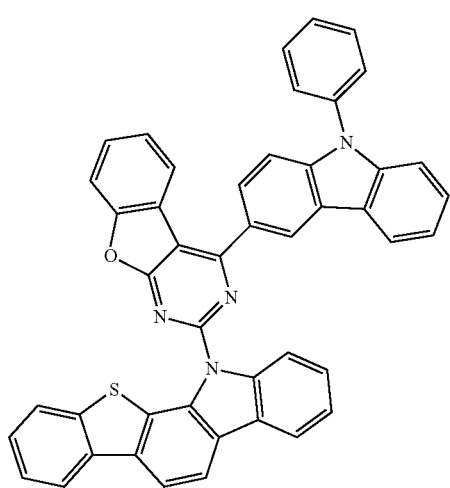
206
-continued
21-12
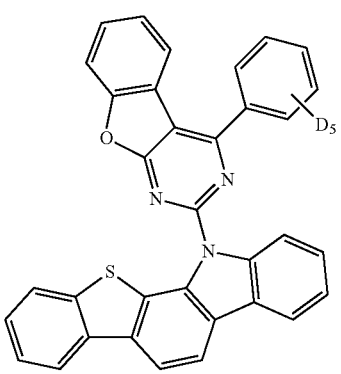
22-1
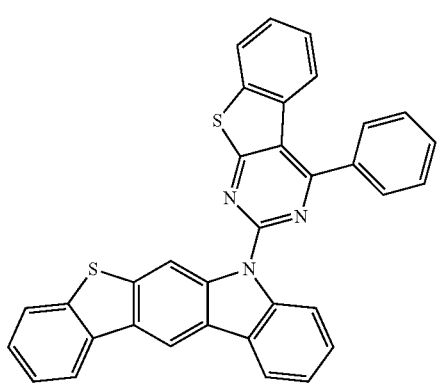
22-2
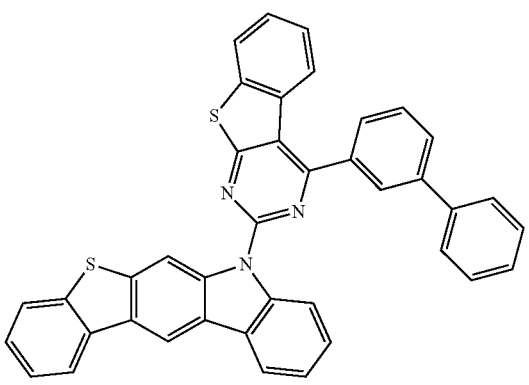
22-3
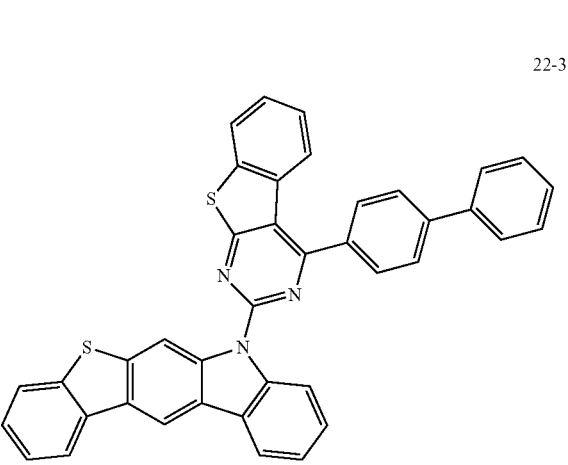

22-4
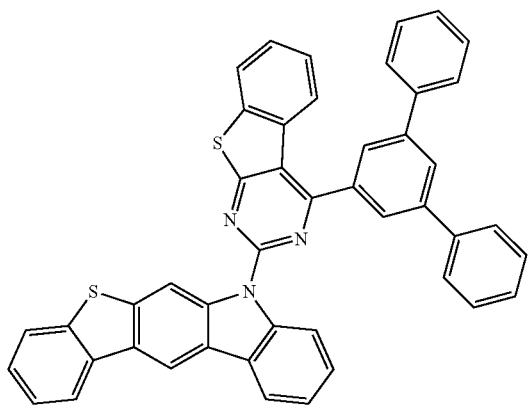
22-5
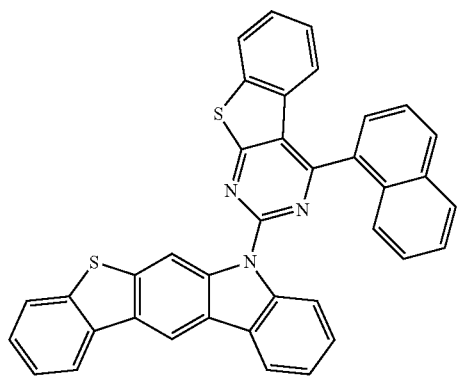
22-6
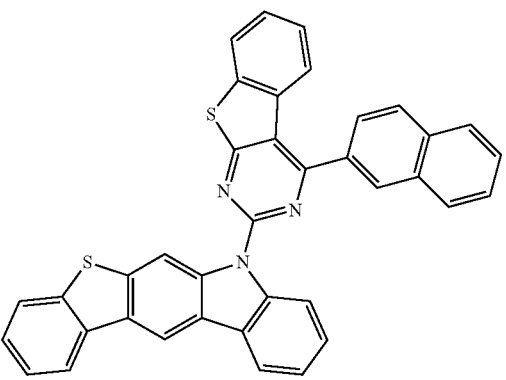
22-7
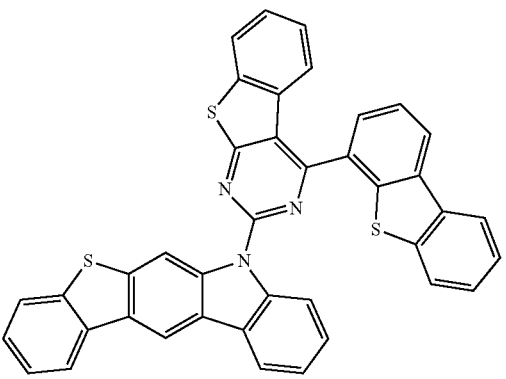
22-8
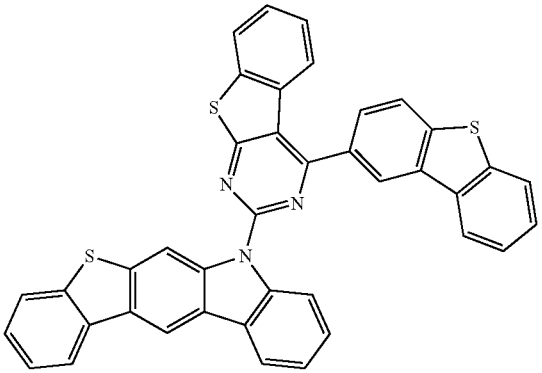
22-9
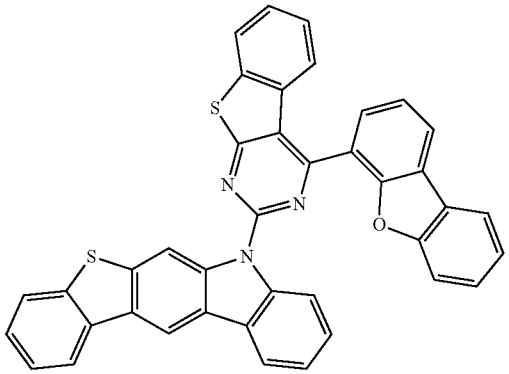
22-10
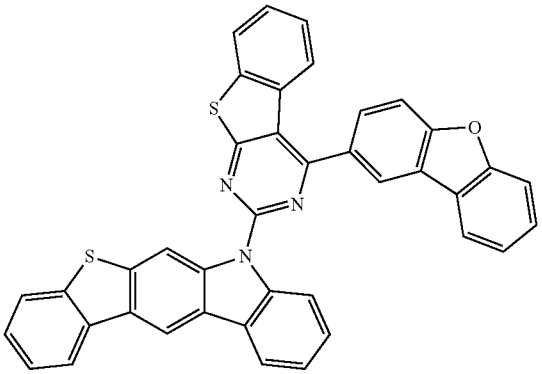
22-11
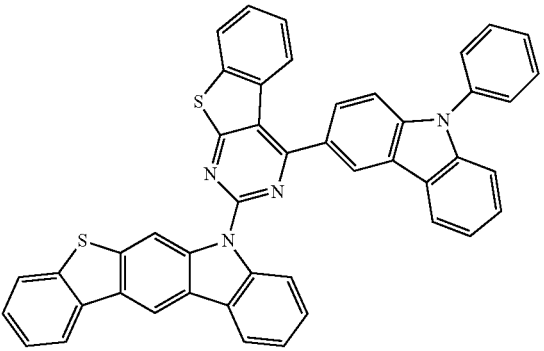

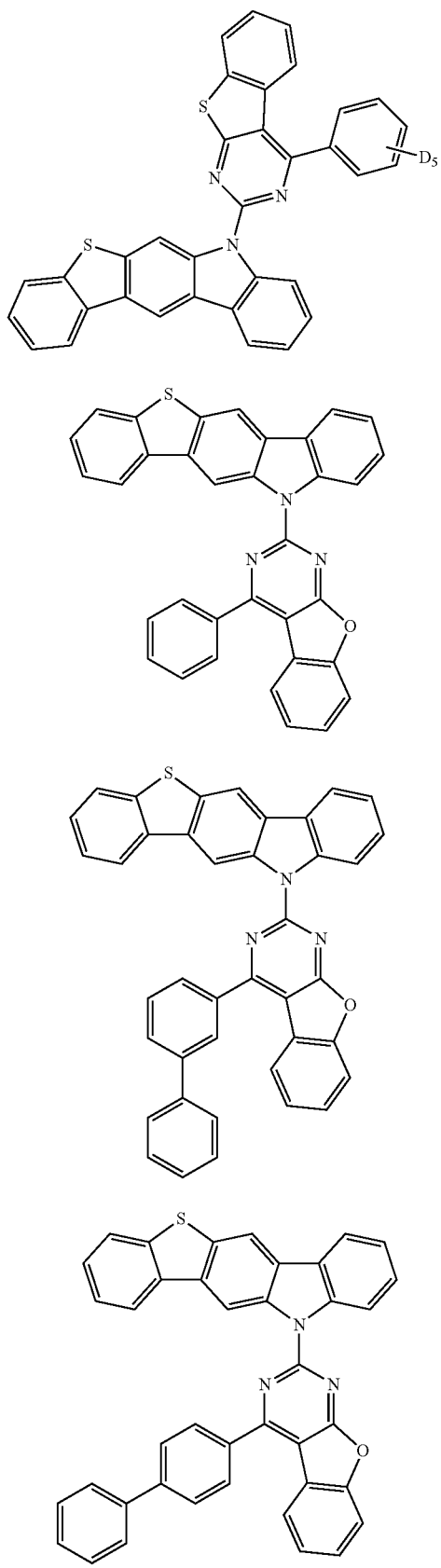
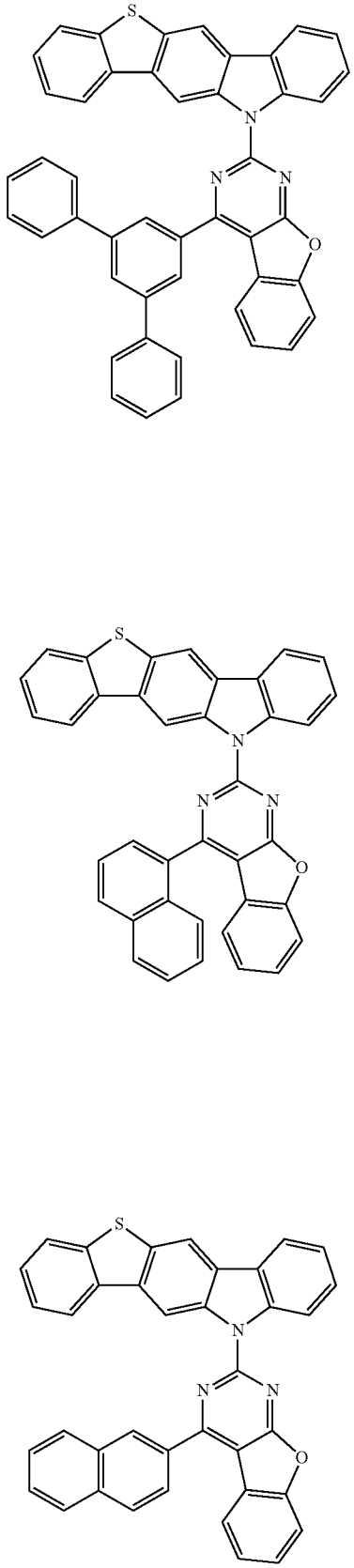

-continued
23-7
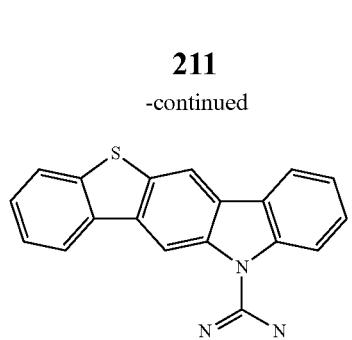
23-8
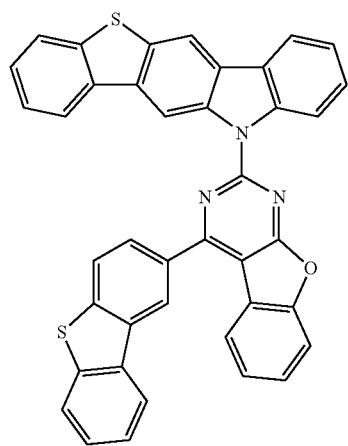
23-9
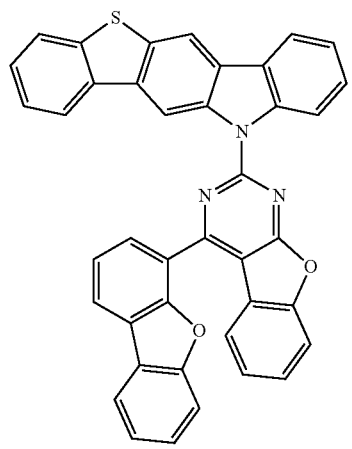
-continued
23-10
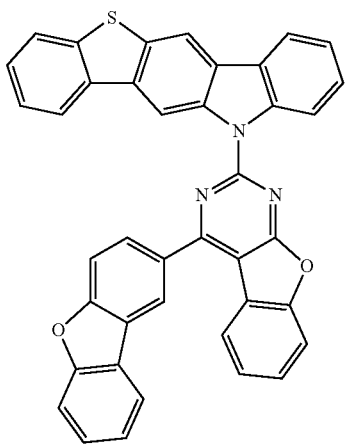
23-11
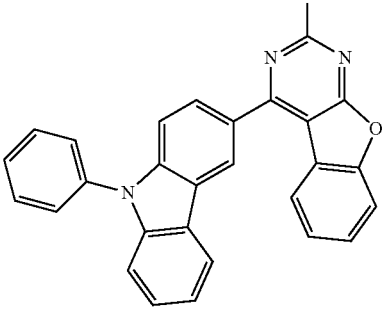
23-12
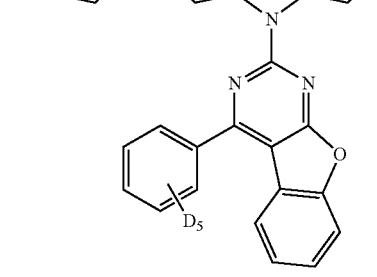
24-1
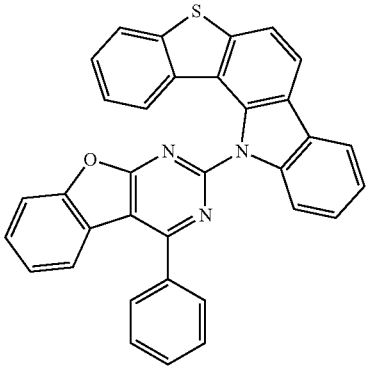

24-2
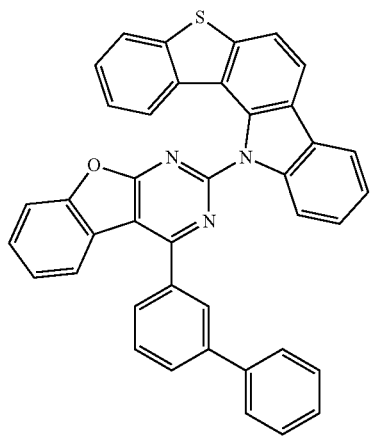
24-3
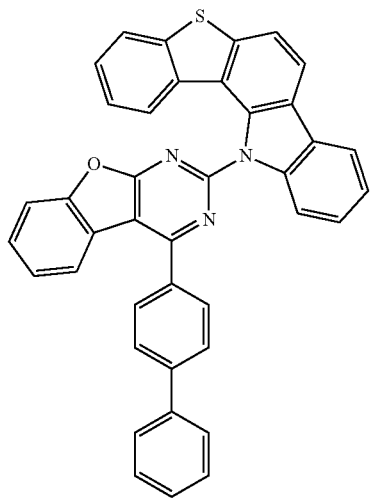
24-4
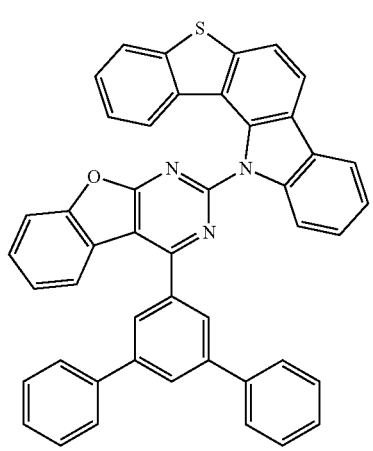
24-5
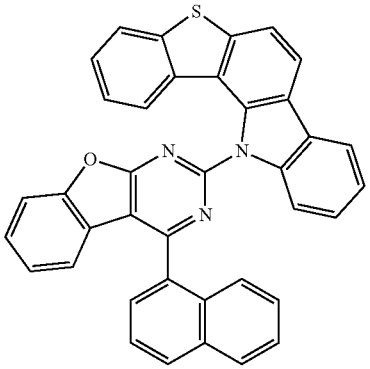
24-6
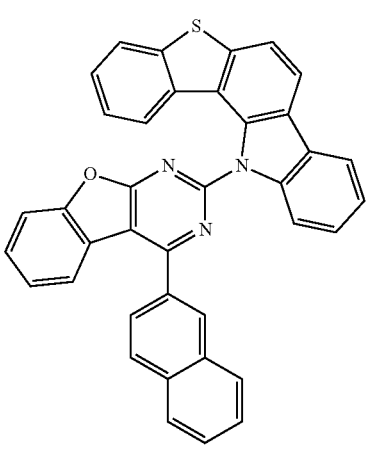
24-7
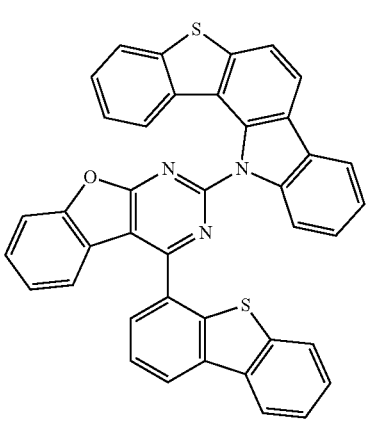

-continued
24-8
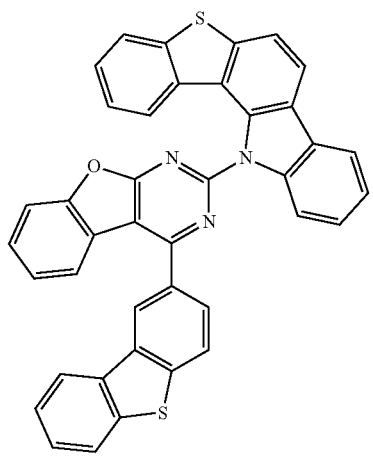
24-9
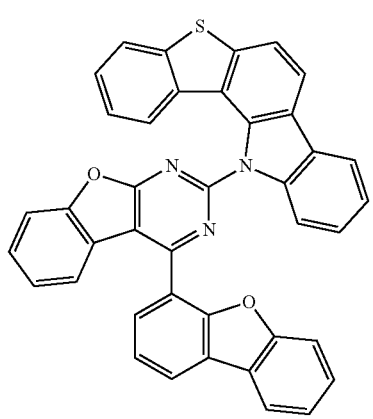
24-10
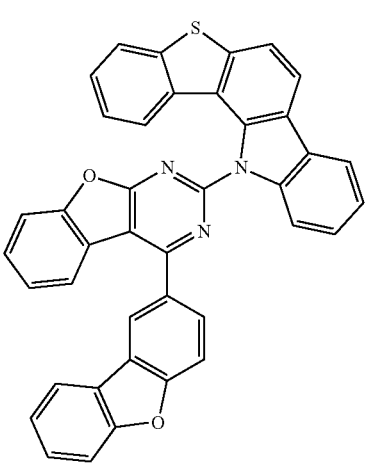
-continued
24-11
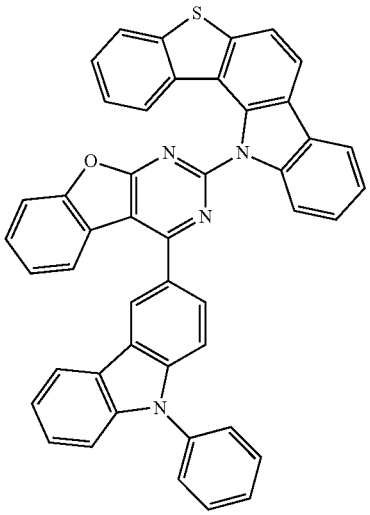
24-12
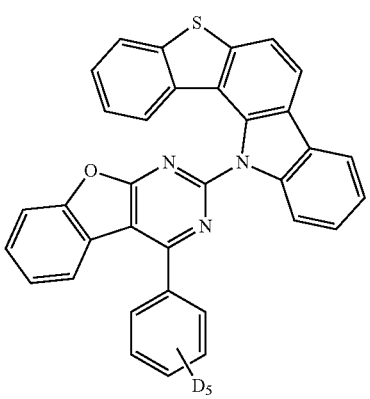
25-1
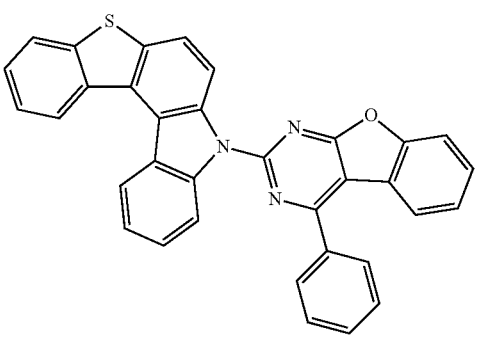
25-2
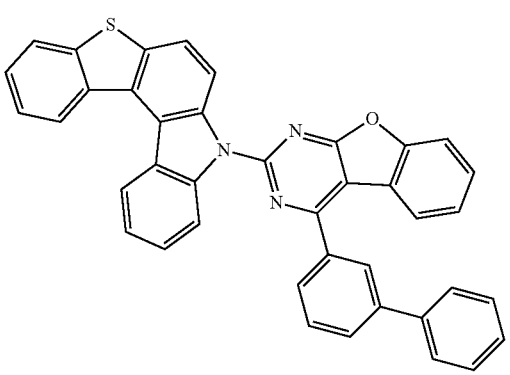

25-3
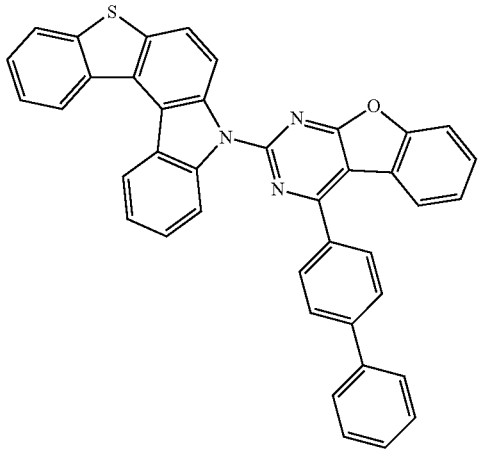
25-4
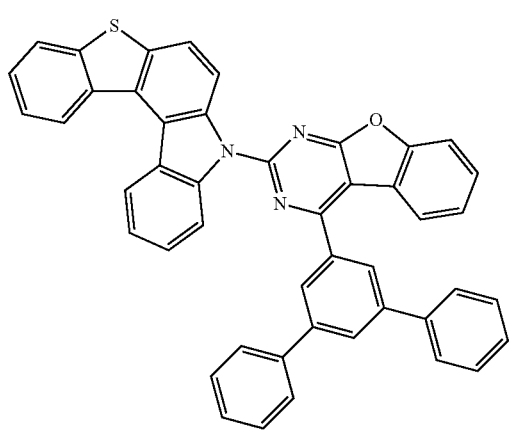
25-5
25-6
25-7
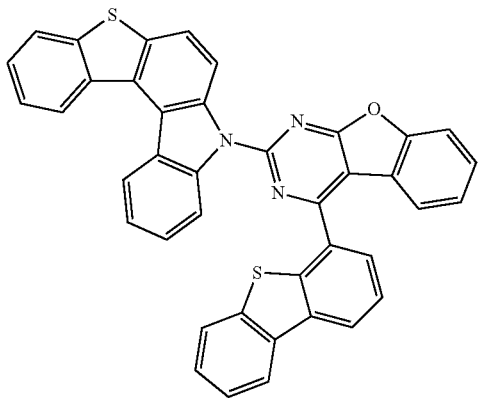
25-8
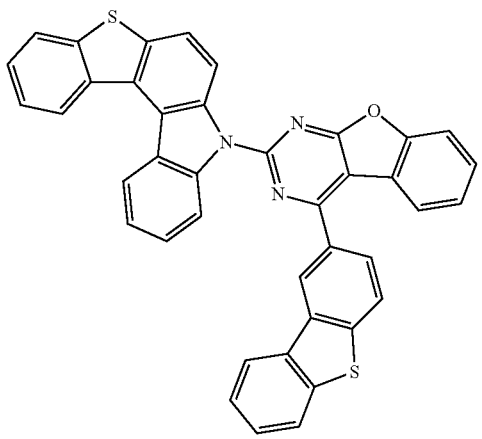
25-9
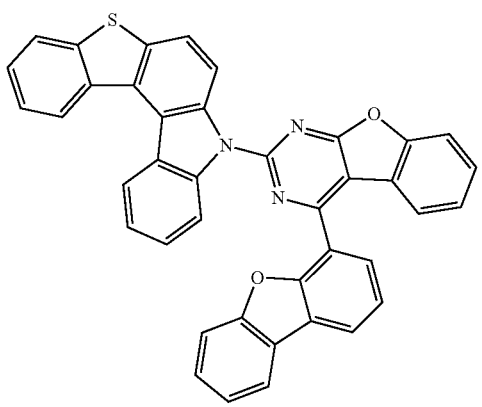

25-10

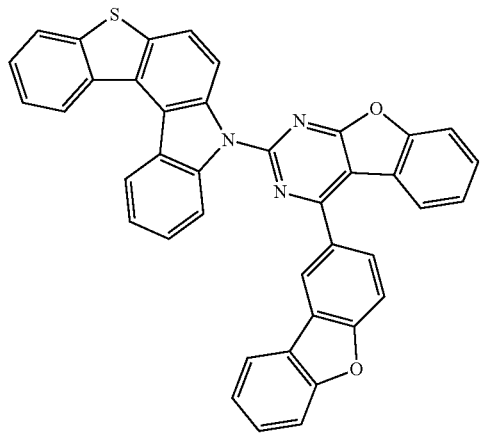

25-11

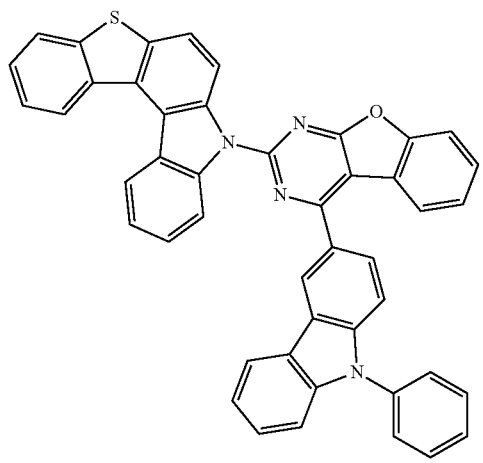

25-12

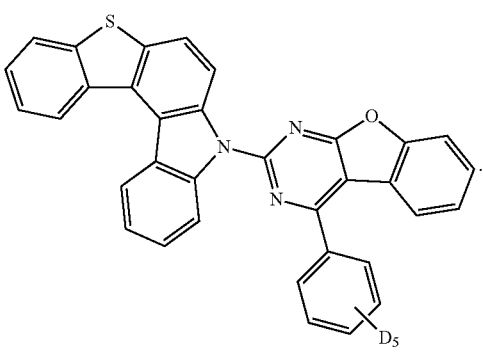

5. An organic electric element comprising a first electrode, a second electrode, and an organic material layer disposed between the first electrode and the second electrode, wherein the organic material layer comprises the compound of claim 1.

6. The organic electric element of claim 5, wherein the compound is comprised in at least one of a hole injection layer, a hole transport layer, an emission-auxiliary layer and an light emitting layer, and the compound is a single compound or a mixture of two or more different kinds.

7. The organic electric element of claim 6, wherein the compound is used as phosphorescent host material of the light emitting layer.

8. The organic electric element as claimed in claim 5, wherein the organic electric element further including at least a layer to improve luminous efficiency which is formed on at least one of the sides the first and second electrodes, which is opposite to the organic material layer.

9. The organic electric element of claim 5, wherein the organic material layer is formed by the processes of spin coating, nozzle printing, inkjet printing, slot coating, dip coating or roll-to-roll.

10. An electronic device comprising:
a display device comprising the organic electric element of claim 5, and
a control unit for driving the display device.

11. The electronic device of claim 10, wherein the organic electric element comprises at least one of an organic light emitting diode, an organic solar cell, an organic photo conductor, an organic transistor, and an element for monochromatic or white illumination.

* * * * *